United States Patent
Nguyen et al.

(10) Patent No.: US 10,064,880 B2
(45) Date of Patent: Sep. 4, 2018

(54) SILANOL BASED THERAPEUTIC PAYLOADS

(71) Applicant: BlinkBio, Inc., Jupiter, FL (US)

(72) Inventors: Hanh N. Nguyen, Jupiter, FL (US); Leslie O. Ofori, Jupiter, FL (US); Jutta Wanner, Palm Beach, FL (US); Douglas S. Werner, West Palm Beach, FL (US)

(73) Assignee: BlinkBio, Inc., Jupiter, FL (US)

( * ) Notice: Subject to any disclaimer, the term of this patent is extended or adjusted under 35 U.S.C. 154(b) by 0 days.

(21) Appl. No.: 15/922,264

(22) Filed: Mar. 15, 2018

(65) Prior Publication Data

US 2018/0200273 A1    Jul. 19, 2018

Related U.S. Application Data

(63) Continuation of application No. PCT/US2017/036728, filed on Jun. 9, 2017.

(60) Provisional application No. 62/477,695, filed on Mar. 28, 2017, provisional application No. 62/349,274, filed on Jun. 13, 2016, provisional application No. 62/347,700, filed on Jun. 9, 2016.

(51) Int. Cl.
*C07F 7/08* (2006.01)
*A61K 31/695* (2006.01)
*A61K 47/54* (2017.01)

(52) U.S. Cl.
CPC .......... *A61K 31/695* (2013.01); *A61K 47/545* (2017.08); *A61K 47/555* (2017.08); *C07F 7/0836* (2013.01)

(58) Field of Classification Search
None
See application file for complete search history.

(56) References Cited

U.S. PATENT DOCUMENTS

| | | | |
|---|---|---|---|
| 6,326,011 B1 | 12/2001 | Miyazawa et al. | |
| 7,687,496 B2 | 3/2010 | Narkunan et al. | |
| 8,575,188 B2 | 11/2013 | Cai et al. | |
| 2004/0161403 A1 | 8/2004 | Zhao et al. | |
| 2009/0149399 A1 | 6/2009 | Tung | |
| 2010/0159446 A1 | 6/2010 | Haff et al. | |
| 2011/0263688 A1 | 10/2011 | Barany et al. | |
| 2012/0045396 A1 | 2/2012 | Godin-Vilentchouk et al. | |
| 2012/0295874 A1 | 11/2012 | Barany et al. | |
| 2013/0296285 A1 | 11/2013 | Alferiev et al. | |
| 2014/0161729 A1 | 6/2014 | Barany et al. | |
| 2014/0163229 A1 | 6/2014 | Barany et al. | |
| 2014/0193437 A1 | 7/2014 | Lin et al. | |
| 2014/0194383 A1 | 7/2014 | Barany et al. | |
| 2014/0243286 A1 | 8/2014 | Arnold et al. | |
| 2014/0243321 A1 | 8/2014 | Arnold et al. | |
| 2014/0243322 A1 | 8/2014 | Arnold et al. | |
| 2014/0274951 A1 | 9/2014 | Guzzo et al. | |
| 2014/0296181 A1 | 10/2014 | Arnold et al. | |
| 2015/0080570 A1 | 3/2015 | Arnold et al. | |
| 2015/0087043 A1 | 3/2015 | Arnold et al. | |
| 2015/0105553 A1 | 4/2015 | Barany et al. | |
| 2017/0080001 A1 | 3/2017 | Barany et al. | |
| 2017/0202970 A1 | 7/2017 | Foreman et al. | |

FOREIGN PATENT DOCUMENTS

| | | |
|---|---|---|
| WO | 2009126290 A2 | 10/2009 |
| WO | 2016183359 A1 | 11/2016 |

OTHER PUBLICATIONS

U.S. Appl. No. 15/477,721, published as US 2017-0202970 A1 on Jul. 20, 2017; U.S. Pat. No. 9,931,407, Silicon Based Drug Conjugates and Methods of Using Same, filed Apr. 3, 2017/Apr. 3, 2018.
U.S. Appl. No. 15/889,638, Silicon Based Drug Conjugates and Methods of Using Same, filed Feb. 6, 2018.
International Search Report and Written Opinion for International Application No. PCT/US2016/032177, dated Aug. 18, 2016.
International Search Report and Written Opinion for International Application No. PCT/US2017/036728, dated Sep. 8, 2017.

*Primary Examiner* — Samantha L Shterengarts

(74) *Attorney, Agent, or Firm* — Goodwin Procter LLP

(57) ABSTRACT

Described herein in part are silanol based therapeutic payloads comprising a silanol terminus, a divalent spacer moiety, and a drug moiety capable of effecting a target cell or tissue.

2 Claims, No Drawings

SILANOL BASED THERAPEUTIC PAYLOADS

CROSS REFERENCE TO RELATED APPLICATION

This application is a continuation of PCT/US2017/036728 filed Jun. 9, 2017, which claims the benefit of, and priority to, U.S. provisional application Ser. No. 62/477,695, filed on Mar. 28, 2017; 62/349,274, filed on Jun. 13, 2016; and 62/347,700, filed on Jun. 9, 2016; the contents of each of which are hereby incorporated by reference herein in their entirety.

BACKGROUND

Devices and methods for delivery of desired components to a site of interest remain a growing need. A variety of methods and routes of administration have been developed to deliver pharmaceuticals or diagnostics, such as small molecular drugs, imaging agents and/or other biologically active compounds (e.g., peptides, hormones, proteins, and enzymes) and many routes of administration are known for delivering desired pharmaceuticals to a patient. However, as greater knowledge is learned regarding toxicity of drugs and the ability to elicit specific responses by delivery of a pharmaceutical only to a specific portion of the body, controlled release of pharmaceuticals after their administration has become a highly important area of research.

For example, the therapeutic efficacy of active agents is often limited by the inability to selectively deliver the drugs to the cell, e.g., most of the currently available anticancer drugs are highly cytotoxic and can kill normal cells along with cancerous cells. Thus, when high doses of drugs are used, there can be severe side effects. As a result, most of the currently used anticancer drugs have a rather limited therapeutic index. Such a limit on dosage can prevent complete eradication of cancer cells in a patient, and may lead to recurrence of the cancer in many patients. The limit in dosage can also predispose the recurring cancer to drug resistance, thus worsening the prognosis for the patient.

More generally, technologies which can specifically deliver drugs to affected tissues in diseases involving viral, bacterial, inflammatory, metabolic, and neurologic imbalances represent an important therapeutic breakthrough. Often, therapeutics for these diseases very strictly requires a large therapeutic window to be considered for clinical study. Introduction of moieties which deliver these therapeutics directly and specifically to the diseased tissues or to the disease-causing agents lowers the specificity requirements of the therapeutic itself. Accordingly, there is an ongoing need for new therapeutic approaches that permit the selective delivery of active agents to diseased cells, thereby providing improved therapeutic indices.

SUMMARY

The present disclosure provides, for example, a method of delivering a therapeutically effective amount of a silanol drug moiety to a patient in need thereof, comprising administering to the patient a drug conjugate represented by:

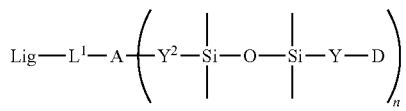

wherein Lig, $L^1$, A, $Y^2$, Y, D, and n are defined herein. For example, the drug conjugate may release the silanol drug moiety in a pH dependent fashion.

In some embodiments, for example, a disclosed drug conjugate may represented by:

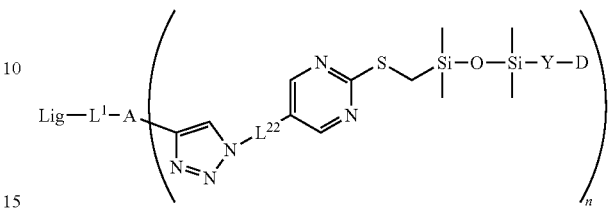

wherein Lig, $L^1$, A, $L^{22}$, Y, D and n are defined herein.

The present disclosure also provides, for example, silanol based therapeutics (e.g., a therapeutic payload) that may be used, for example, as part of a drug conjugate that can include for example, a targeting moiety, and a disclosed silanol based compound. For example, provided herein are compounds that include a silanol moiety (e.g., a silanol terminus that may be used as a basis of a drug-target conjugate) and a therapeutic or drug moiety. In an embodiment, provided herein is a therapeutic agent that includes a) a silanol moiety bound directly or via a linker, to a drug moiety (e.g., capable of effecting a target cell or tissue) and/or b) a silanol moiety that replaces one or more carbons or heteroatoms of an existing therapeutic agent, thereby facilitating e.g., a drug conjugate.

For example, provided herein is a therapeutic agent that includes a silanol terminus, and optionally divalent spacer moiety, and a drug moiety, for example, a silanol based payload represented by the formula:

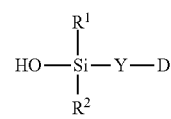

and pharmaceutically acceptable salts, cocrystals, stereoisomers, metabolites, tautomers, solvates, and hydrates thereof, wherein $R^1$, $R^2$, Y, and D are defined herein.

DETAILED DESCRIPTION

The present disclosure is directed, at least in part, toward methods of delivering a therapeutically effective amount of a silanol drug moiety to a patient in need thereof, comprising administering to the patient a drug conjugate represented by:

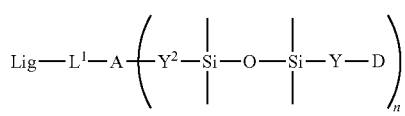

wherein

Lig is a targeting moiety;

$L^1$ is a linker moiety;

A is an adaptor moiety or a bond;

$Y^2$ is represented by $L^{22}$ or —BO-$L^{22}$-SL-, wherein BO is a bond or is a fused biorthogonal linker moiety, $L^{22}$ is a second linker moiety, and SL is an optional catalytic moiety;

n is 1, 2, 3, 4, 5, 6 or 7;

Y is a divalent spacer moiety; and

D, for each occurrence, is a drug moiety that effects a target cell or tissue.

In some embodiments, Lig, for example, may be for example, a small molecule moiety, a peptide, an antibody, an antibody fragment, a peptide and/or a carbohydrate.

In some embodiments, the drug conjugate may release the silanol drug moiety in a pH dependent fashion.

In certain embodiments, the silanol drug moiety may, for example, be represented by:

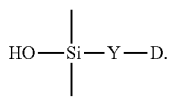

In an embodiment, SL may be chosen to release the silanol drug moiety from the conjugated at pH less than about 7 or greater than about 7.5 at 25° C. or 37° C.

In certain embodiments, A may be selected, for example, from the group consisting of a bond,

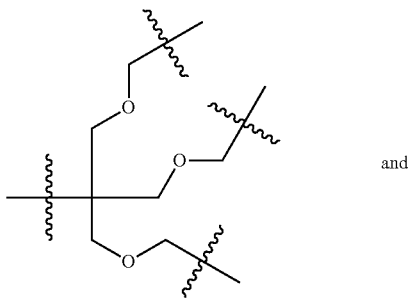 and

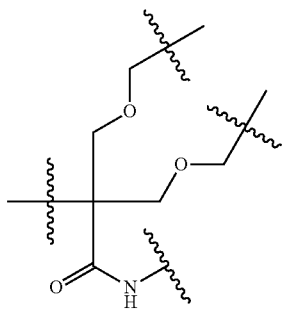

In certain other embodiments, BO may be selected, for example, from the group consisting of:

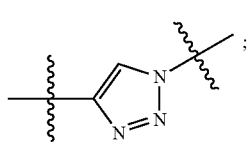 [SMILES: *c1cn(*)nn1] ; 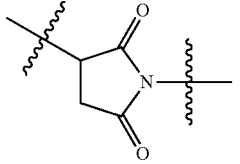 ;

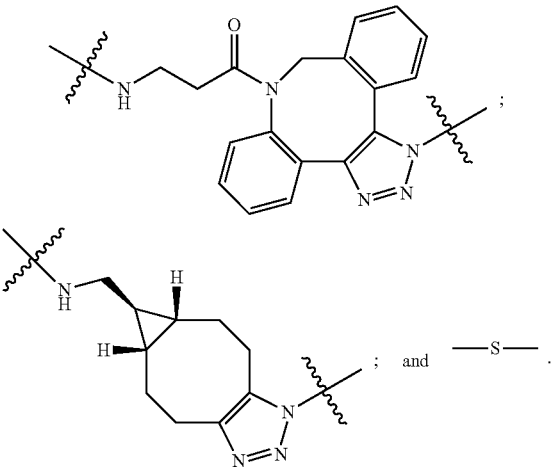

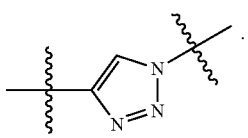 ; and —S—.

For example, BO may be:

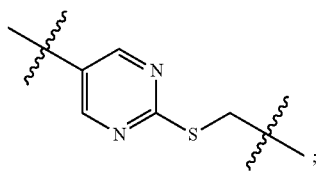

In some embodiments, $L^{22}$ may be selected, for example, from the group consisting of: —(CH$_2$—CH$_2$—O)$_s$—, —(OCH$_2$—CH$_2$)$_s$—, —(CH$_2$—CH$_2$—O)$_s$—(CH$_2$)$_i$—, —(CH$_2$)$_i$—(OCH$_2$—CH$_2$)$_s$—, and C$_{1-6}$alkylene; wherein s is 0 to 10 for each occurrence; and i is 1, 2, or 3.

In certain embodiments, SL may be selected, for example, from the group consisting of —NR$^Y$—C(O)—(CH$_2$)$_j$-phenyl-(CH$_2$)$_q$— (wherein R$^Y$ is hydrogen or C$_{1-3}$alkyl; j is 0, 1, 2, 3 or 4; and q is 0, 1 or 2); 5-6 membered heteroaryl-S—(CH$_2$)$_p$— (wherein p is 0, 1, 2, or 3), a bond, and —NR$^Y$—C(O)—C$_{1-4}$alkylene (wherein R$^Y$ is hydrogen or C$_{1-3}$alkyl).

For example, SL may be selected from the group consisting of:

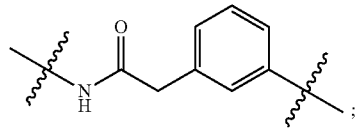

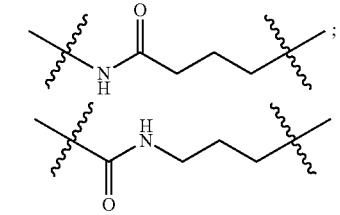

-continued

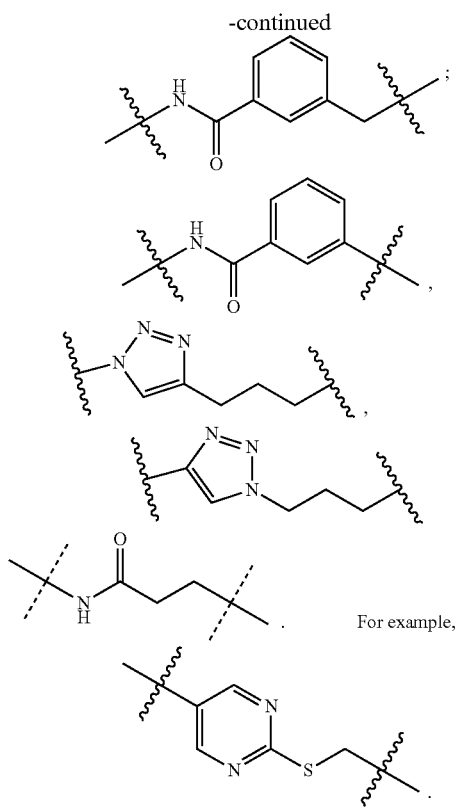

For example, SL may be:

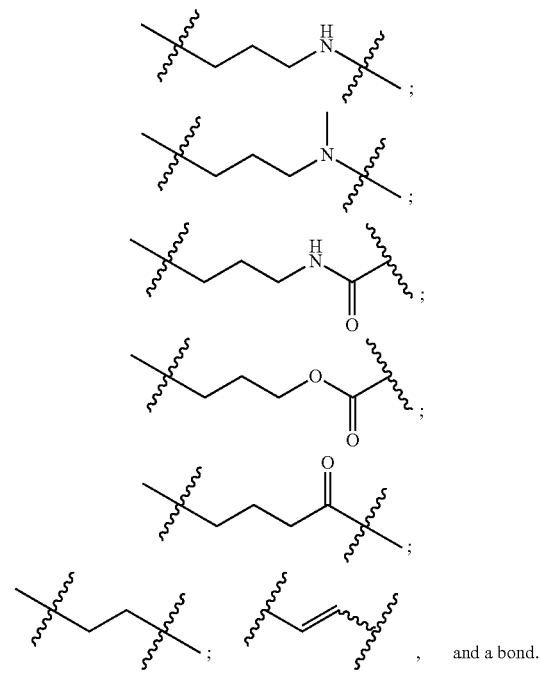

In certain embodiments, Y may be selected, for example, from the group consisting of a bond, $C_{1-4}$alkylene, $C_{1-4}$alkylene-C(O)—, and $C_{1-4}$alkylene-C(O)—NR$^Y$—, wherein R$^Y$ is hydrogen or $C_{1-3}$alkyl.

For example, wherein Y may be selected from the group consisting of:

In certain embodiments, L$^1$ may be, for example $C_{1-30}$alkylene; wherein one, two, three, four, five, six, seven or eight methylene units of L$^1$ are optionally and independently replaced by a substituent each selected from the group consisting of phenyl, heteroaryl, —N(R$^1$)—, C(O)N(R$^1$)—, —N(R$^1$)C(O))—, —O—, (—O—CH$_2$—CH$_2$)$_s$—, and (CH$_2$—CH$_2$—O)$_s$—, wherein s is an integer from 3-10; and R$^{1Y}$ is independently selected for each occurrence from the group consisting of hydrogen and $C_{1-3}$alkyl.

In some embodiments, D may be selected, for example, from the group consisting of a vinca alkaloid, an auristatin, maytansine, a pyrrolobenzodiazepine dimer, a camptothecin, SN38, a PARP inhibitor, salinomycin, a kinase inhibitor, siRNA, and a nuclear hormone regulator.

For example, a disclosed drug conjugate may represented by

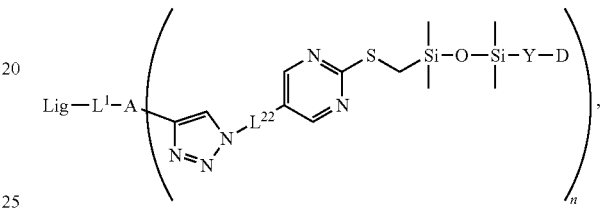

wherein Lig, L$_1$, A, L$^{22}$, Y and D are defined herein.

It can be appreciated that Lig is a targeting moiety that may include one or more ligands that selectively bind or recognize at least one of Folate Receptors, prostate specific membrane antigen (PSMA), surface antigen in leukemia SAIL, intergrin $\alpha_v\beta_3$, asialoglycoprotein receptor, hydroxyapatite, delta-like protein-3 DLL3 receptor, receptor dystroglycan, cholescystokinin receptors, somatostatin receptor, onco fetal antigens, receptor tyrosine kinases, GPCRs, GPCRmAB targets, sigma-receptor, transferrin receptor, mannose receptor vitamin receptors, Trop-2, Notch receptor, CD33, CD44, and CD206. For example, a targeting moiety may be selected from the group consisting of: folic acid its derivatives, DUPA its derivatives, RGD and its derivatives, GPCR mABs, transferrin, G11 and analogs thereof which target EGFR, carbohydrates, aptamers, somatostatin analogs, and extracellular ligands that induce receptor internalization upon binding. For example, targeting moieties may be selected from the group consisting of: small molecules, peptides, peptidomimetics, aptamers, antibodies, and carbohydrates and derivatives thereof. A targeting moiety in certain embodiments is a protein (e.g., an antibody or antibody fragment), nucleic acid, lipid, oligomer, glycopeptide, polysaccharide, polymer (e.g., a dendrimer), nanoparticle, or any combination thereof. For example, a viral coat protein is contemplated, as e.g., a cognate ligand of certain cell surface receptors.

Therapeutic Payloads

The present disclosure further provides, for example, silanol containing therapeutic payloads, such as a payload comprising a silanol terminus, an optional divalent spacer moiety, and a drug moiety capable of effecting a target cell or tissue. For example, disclosed herein is a silanol based payload represented by the formula:

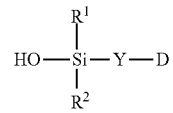

and pharmaceutically acceptable salts, cocrystals, stereoisomers, metabolites, tautomers, solvates, and hydrates thereof, wherein:

D is a drug moiety capable of effecting a target cell or tissue;

Y is a divalent spacer moiety selected from the group consisting of a bond and $C_{1-20}$alkylene, wherein one, two, three or four methylene units of $C_{1-20}$alkylene are optionally and independently replaced by $C_{3-8}$cycloalkylene, $C_{2-10}$alkenylene, $C_{2-10}$alkynylene, aryl, spirocyclic, heteroaryl, —$NR^{1Y}$—, —$N(R^{1Y})C(O)$—, —$C(O)N(R^{1Y})$—, —O—, —C(O)—, —OC(O)—, —C(O)O—, —S—, —SO—, —$SO_2$—, —C(=S)—, —C(=$NR^{1Y}$)—, —$NR^{1Y}$—$C_{1-15}$alkyl-$NR^{1Y}$—C(O)—; —($CH_2$—$CH_2$—O)$_s$—, —(O—$CH_2$—$CH_2$)$_s$—, —$NR^{1Y}$—($CH_2$—$CH_2$—O)$_s$—$C_{1-6}$alkyl-$NR^{1Y}$—C(O)—; —(O—$CH_2$—$CH_2$)$_s$—$NR^{1Y}$—C(O)—; —S—$C_{0-6}$alkyl-; —$NR^{1Y}$—$C_{1-6}$alkyl-; —N($C_{1-3}$alkyl)-$C_{1-6}$alkyl-NH—C(O)—; —NH—$C_{1-6}$alkyl-N($C_{1-3}$alkyl)-C(O)—; —$SO_2$—$NR^{1Y}$—$C_{0-6}$alkyl-; —$N(R^{1Y})SO_2$—$C_{0-6}$alkyl-; —$SO_2$-heterocyclyl-$C_{0-6}$alkyl-; -heterocyclyl-C(O)—; -heterocyclyl-$C_{0-6}$alkyl-$NR^{1Y}$—C(O)—; —$NR^{1Y}$—$C_{0-6}$alkylene-heterocyclyl-C(O)—; —O—$C_{1-6}$alkylene-C(O)—; —O—$C_{1-15}$alkylene-$NR^{1Y}$—C(O)—; and —O—$C_{1-15}$alkylene-C(O)—$NR^{1Y}$—; —O—$C_{1-6}$alkylene-; wherein Y is optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, carbonyl, oxime, hydrazide, hydrazone, urea, thiourea, amidine, guanidine, sulfonamide, acylsulfonamide, and sulfonyl amide;

s is an integer from 1-15;

$R^1$ and $R^2$ are each selected independently from the group consisting of —OH, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, phenyl, heterocyclyl, and heteroaryl; wherein $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, phenyl, heterocyclyl, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$alkyl, —O—C(O)—$C_{1-6}$alkyl, —NHC(O)$C_{1-6}$alkyl, —C(O)$NH_2$, —C(O)NH$C_{1-6}$alkyl, —C(O)N($C_{1-6}$alkyl)$_2$, —NHC(O)$CF_3$, $PO_3H$, $OPO_3H$, —C(O)—$NR^a$—$SO_2$—$C_{1-6}$alkyl, —$SO_3H$, —$SO_2$—$NR^aR^b$, —$NR^a$—$SO_2$—$C_{1-6}$alkyl, and —$SO_2$—$NR^a$—$C_{1-6}$alkyl;

or any pairwise combination of $R^1$, $R^2$, Y, and D may, independently, together with the atoms to which they are attached, each form a 4-10 membered carbocyclic or heterocyclic or spirocyclic ring, wherein the 4-10 membered heterocyclic ring may optionally contain one or more additional heteroatoms selected from O, S, SO, $SO_2$, or N; wherein the 4-10 membered carbocyclic or heterocyclic ring is optionally substituted; each ring formed may optionally be fused to another through a single shared atom or single shared bond; and $R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted; or $R^a$ and $R^b$, together with the nitrogen to which they are attached, form a 4-8 membered heterocyclic ring, optionally containing an additional heteroatom selected from O, S, SO, $SO_2$, or N; wherein the 4-8 membered heterocyclic ring is optionally substituted.

In certain embodiments, $R^1$ and $R^2$ each may be the same or different.

In some embodiments, $R^1$ and $R^2$ may be each independently selected from $C_{1-6}$alkyl. For example, $R^1$ and $R^2$ may be methyl.

In certain embodiments, silanol based payloads disclosed herein may be a silanol based analog of a disease-modifying agent, e.g., selected from the group consisting of antigens, proteins, cytotoxic agents, metabolic modulators, anti-inflammatory agents, anti-viral agents, antibiotics, pathway modulators, siRNA, mRNA, miRNA, and endosomal escape enhancers. For example, a silanol based payload disclosed herein may be a silanol based analog of a therapeutic agent selected from the group consisting of check-point inhibitors, kinase inhibitors, proteasome inhibitors, topoisomerase inhibitors, tubulin inhibitors, rapamycin analogs, auristatin F analogs, maytansinoid analogs, duocarmycin analogs, calicheamicin analogs, and DM4 analogs, for example, selected from camptothecin analogs, doxorubicin analogs, vinca alkaloid analogs, taxane analogs (docetaxel, paclitaxel), rapamycin analogs, platinum based chemotherapeutics, and tubulysin analogs. The silanol based payload, in some cases, may be a molecule that is, e.g., modulating cellular pathways by binding to a biomolecule, such as, for example, a protein or a specific protein domain, a component of a biological cell such as ribosome (composed of proteins and nucleic acids), or an enzyme active site. For example, a disclosed silicon based payload may be capable of binding to an intracellular biomolecular target.

In various embodiments, a disclosed silanol based payload may be a therapeutic moiety. The therapeutic moiety can be, for example, a cytotoxic moiety. A cytotoxic moiety may be an analog of SN-38, bendamustine, a VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or (a) fragment(s) thereof.

In various embodiments, a disclosed silanol based payload may be an analog of an DNA alkylating agent or a fragment thereof (e.g., temozolomide, mitozolomide, nitrogen mustards, estramustine, or chloromethine).

In various embodiments, a disclosed silanol based payload may be an analog of a therapeutic agent selected from the group consisting of peptidyl-prolyl isomerase ligands, e.g., FK506 (tacrolimus), rapamycin and cyclosporin A; steroid hormone receptor ligands, e.g., naturally occurring steroid hormones such as estrogen, progestin, testosterone, as well as synthetic derivatives and mimetics thereof; small molecules that bind to cytoskeletal proteins, e.g., antimitotic agents, such as taxanes, colchicine, colcemid, nocadozole, vinblastine, and vincristine, actin binding agents, such as cytochalasin, latrunculin, halloidin; lenalidomide, pomalidomide, camptothecins including SN-38, topotecan, combretastatins, capecitabine, gemcitabine, vinca alkaloids, platinum-containing compounds, metformin, HDAC inhibitors (e.g., suberoylanilidehydroxamic acid (SAHA)), thymidylate synthase inhibitors such as methotrexate, pemetrexed, and raltitrexed; nitrogen mustards such as bendamustine and melphalan; 5-fluorouracil (5-FU) and its derivatives; and agents used in ADC drugs, such as brentuximab, vedotin, trastuzumab emtansine (T-DM1), and gemtuzumab ozogamicin (Mylotarg).

In various embodiments, a disclosed silanol based payload may an analog of a therapeutic agent selected from the group consisting of central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs), analgesics (morphine and derivatives, oripavine derivatives, morphinan derivatives, phenylpiperidines, 2,6-methane-3-benzazocaine derivatives, diphenylpropylamines and isosteres, salicylates, 7-aminophenol derivatives, 5-pyrazolone derivatives, arylacetic acid derivatives, fenamates and isosteres) and antiemetics (anticholinergics, antihistamines, antidopaminergics); central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics; psychopharmacological/psychotropics, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives), antidepressants (tricyclic compounds, MAO inhibitors).

In various embodiments, a disclosed silanol based payload may be an analog of a therapeutic agent selected from the group consisting of respiratory tract drugs, e.g., central antitussives (opium alkaloids and their derivatives); immunosuppressive agents; pharmacodynamic agents, such as peripheral nervous system drugs, e.g., local anesthetics (ester derivatives, amide derivatives); drugs acting at synaptic or neuroeffector junctional sites, e.g., cholinergic agents, cholinergic blocking agents, neuromuscular blocking agents, adrenergic agents, antiadrenergic agents; smooth muscle active drugs, e.g., spasmolytics (anticholinergics, musculotropic spasmolytics), vasodilators, smooth muscle stimulants; histamines and antihistamines, e.g., histamine and derivative thereof (betazole), antihistamines (H1-antagonists, H2-antagonists), histamine metabolism drugs; cardiovascular drugs, e.g., cardiotonics (plant extracts, butenolides, pentadienolids, alkaloids from erythrophleum species, ionophores, -adrenoceptor stimulants), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemo styptics; chemo therapeutic agents, such as anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, and cytostatics, i.e., antineoplastic agents or cytotoxic drugs, such as alkylating agents, e.g., mechlorethamine hydrochloride (nitrogen mustard, mustargen, HN2), cyclophosphamide (Cytovan, Endoxana), ifosfamide (IFEX), chlorambucil (Leukeran), Melphalan (phenylalanine mustard, L-sarcolysin, Alkeran, L-PAM), busulfan (Myleran), Thiotepa (triethylenethiophosphoramide), carmustine (BiCNU, BCNU), lomustine (CeeNU, CCNU), streptozocin (Zanosar); plant alkaloids, e.g., vincristine (Oncovin), vinblastine (Velban, Velbe), paclitaxel (Taxol); antimetabolites, e.g., methotrexate (MTX), mercaptopurine (Purinethol, 6-MP), thioguanine (6-TG), fluorouracil (5-FU), cytarabine (Cytosar-U, Ara-C), azacitidine (Mylosar, 5-AZA); antibiotics, e.g., dactinomycin (Actinomycin D, Cosmegen), doxorubicin (Adriamycin), daunorubicin (duanomycin, Cerubidine), idarubicin (Idamycin), bleomycin (Blenoxane), picamycin (Mithramycin, Mithracin), mitomycin (Mutamycin), and other anticellular proliferative agents, e.g., hydroxyurea (Hydrea), procarbazine (Mutalane), dacarbazine (DTIC-Dome), cisplatin (Platinol) carboplatin (Paraplatin), asparaginase (Elspar), etoposide (VePesid, VP-16-213), amsarcrine (AMSA, m-AMSA), mitotane (Lysodren), or mitoxantrone (Novatrone).

In various embodiments, a disclosed silanol based payload may be an analog of a therapeutic agent selected from the group consisting of anti-inflammatory agents; antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin; polypeptides, e.g., amphomycin, bacitracin, capreomycin; tetracyclines, e.g., apicycline, chlortetracycline, clomocycline; synthetic antibacterial agents, such as 2,4-diaminopyrimidines, nitrofurans, quinolones and analogs thereof, sulfonamides, or sulfones.

In various embodiments, a disclosed silanol based payload may be an analog of a therapeutic agent selected from the group consisting of antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, thiocarbamates, e.g., tolciclate, triazoles, e.g., fluconazole, itraconazole, or terconazole.

In various embodiments, a disclosed silanol based payload may be an analog of a therapeutic agent selected from the group consisting of anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, or diethylcarbamazine.

In various embodiments, a disclosed silanol based payload may be an analog of a therapeutic agent selected from the group consisting of antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, or dibasic sodium arsenate.

In various embodiments, a disclosed silanol based payload may be an analog of a therapeutic agent selected from the group consisting of antiprotozoan agents, such as: acranil, tinidazole, ipronidazole, ethylstibamine, pentamidine, acetarsone, aminitrozole, anisomycin, nifuratel, tinidazole, benzidazole, or suramin.

In various embodiments, a disclosed silanol based payload may be an analog of a therapeutic agent selected from the group consisting of docetaxel or paclitaxel; BEZ235; temsirolimus; PLX4032; cisplatin; AZD8055; and crizotinib.

In various embodiments, a disclosed silanol based payload may be an analog of topotecan or irinotecan.

In various embodiments, a disclosed silanol based payload may be an analog of siRNA, mRNA or miRNA optionally in combination with endosomal escape enhancers.

In various embodiments, a disclosed silanol based payload may be an analog of an antigen.

In various embodiments, a disclosed silanol based payload may be an analog of a therapeutic agent selected from the group consisting of mechanistic target of rapamycin (mTOR) inhibitors, e.g., apitolisib and everolimus; BCR-ABL fusion gene agents, e.g., dasatinib, potanibib and gleevec; pan-cyclin-dependent kinase (pan-CDK) inhibitors, e.g., (R)-roscovitine and (S)-CR8; selective cyclin-dependent kinase (CDK) inhibitors, e.g., palbociclib, abemaciclib, ribociclib and SNS-032; Bruton tyrosine kinase (BTK) inhibitors, e.g., ibrutinib, Janus kinase (JAK) inhibitors; Aurora kinase inhibitors, e.g., VX-680; tyrosine kinase inhibitors, e.g., axitinib; MET proto-oncogene/receptor tyrosine kinase (c-MET) inhibitors, e.g., AMG458; vascular endothelial growth factor (VEGF) agents, e.g., motesanib; epidermal growth factor receptor (EGFR) agents, e.g., IRESSA, tykerb and sunitinib; EFGR T790M agents, e.g., WZ4002, AZD9291 and CO-1686; B-Raf proto-oncogene (serine/threonine kinase) agents, e.g., sorafenib; Rho-associated protein kinase (Rho/ROCK) inhibitors, e.g., fasudil; Wee1 kinase agents, e.g., AZD1775; poly ADP ribose polymerase (PARP) inhibitors, e.g., olaparib and rucaparib; B-cell lymphoma 2 (Bcl-2) agents, e.g., navitoclax and venetoclax; tubulin-effecting agents, e.g., paclitaxel, vinblastine, deacetyl vinblastine, tubulysin B, auristatine (e.g., monomethylauristatine E), colchicine, combretastatin and eribulin; DNA-crosslinking agents, e.g., cyclophosphamide, oxaliplatin, carboplatin, chlorambucil, mechloethamine, melphalan, mytomycin C, pyrrolobenzodiazepines, cisplatin and derivatives, and bulsafan; DNA-intercalating agents, e.g., doxorubicin; topoisomerase I inhibitors, e.g., camptothecin, SN-38 and exatecan (DX-8951f); estrogen receptor antagonists, e.g., tamoxifen; BRD4/cMYC inhibitors; HSP70/HSP90 inhibitors, e.g., triptolide and ganetinib; proteosome inhibitors, e.g, epoxomicin, carfilzomib, velcade and salinosporamide; peroxisome proliferator-activated receptor gamma (PPAR-γ) agonists, e.g., pioglitazone; proprotein convertase subtilisin/kexin type 9 (PCSK9) RNAi analogs; zetia analogs; TGR5 (non-systemic takeda G-protein receptor 5) agents; non-systemic μ-opioid antagonists, e.g., naloxol; and bisphosphonate analogs, e.g., zoledronate, triazole zoledronate, ibandronate and risedronate.

In an embodiment, a disclosed silanol based payload may be represented by:

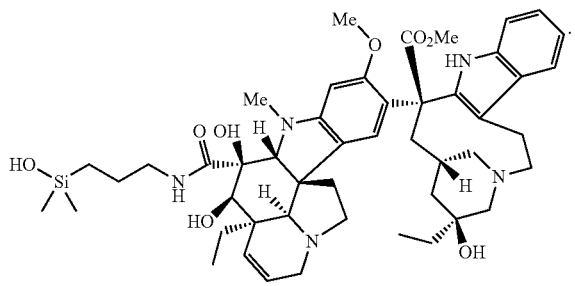

In various embodiments a disclosed silanol based payload may be combined with a second disclosed silanol based payload, and the resulting silanol based payload combination may act as a synthetic lethal combination or as a synergistic combination.

In various embodiments a disclosed silanol based payload may be a conditionally activated payload (CAP): this conditionally activated payload will be charged at pH7.4 resulting in poor cellular effects; however, targeted delivery, and endosomal or microenvironmental release will activate the payload and result in potent cell kill.

In some embodiments the targeted delivery of these conditionally activated payloads will result of a cellular EC50 of <80 nM, in some embodiments the targeted delivery of these conditionally activated payloads will result of a cellular EC50 of <20 nM, the targeted delivery of these conditionally activated payloads will result of a cellular EC50 of <10 nM, the targeted delivery of these conditionally activated payloads will result of a cellular EC50 of <1 nM, the targeted delivery of these conditionally activated payloads will result of a cellular EC50 of <0.1 nM. In certain embodiments, targeted delivery of a disclosed silanol based payload may result in improved intracellular concentrations and, for example, may overcome exposure challenges. In some embodiments, the presence of the silanol moiety, i.e., HO—Si($R^1$)($R^2$)—, may not negate the potency of the drug moiety, D. In an embodiment, a disclosed silanol based payload may have improved cell permeability and, for example, may permeate to neighboring cells.

Methods

Also provided herein are methods of delivering a disclosed silanol based payload to a cell or to a tissue, comprising contacting the cell or tissue with a drug conjugate represented by:

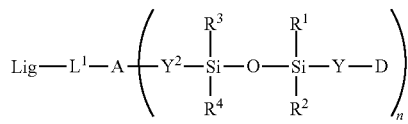

wherein
  Lig is a targeting moiety;
  $L^1$ is a linker moiety;
  A is an adaptor moiety or a bond;
  $Y^2$ is represented by $L^{22}$ or —BO-$L^{22}$-SL-, wherein BO is a bond or is a fused biorthogonal linker moiety, $L^{22}$ is a second linker moiety, and SL is an optional catalytic moiety;
  $R^1$, $R^2$, $R^3$ and $R^4$ are each independently selected from $C_{1-6}$alkyl;
  n is 1, 2, 3, 4, 5, 6 or 7;
  Y is the divalent spacer moiety; and
  D, for each occurrence, is a drug moiety.

In certain embodiments, Lig, for example, may be, e.g., a small molecule moiety, a peptide, an antibody, an antibody fragment, a peptide and/or a carbohydrate.

In some embodiments, a therapeutically effective amount of a contemplated silanol based payload may be administered (e.g., by administering a contemplated drug conjugate) to a patient in need thereof. In some embodiments, a disclosed silanol based payload may have a molecular weight between 50 Da and 2000 Da, in some embodiments between 50 Da and 1500 Da, in some embodiments, between 50 Da and 1000 Da, and in some embodiments, between 50 Da and 500 Da. In certain embodiments, a targeting moiety may have a molecular weight of less than 2000 Da, in some embodiments, less than 1000 Da, and in some embodiments less than 500 Da.

Disclosed silanol based payloads may be administered (e.g., by administering a contemplated drug conjugate) to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound (e.g., a contemplated silicon based payload and/or drug conjugate) may be administered orally, subcutaneously, topically, parenterally, by inhalation spray or rectally in dosage unit formulations containing conventional non-toxic pharmaceutically acceptable carriers, adjuvants, and vehicles. Parenteral administration may include subcutaneous injections, intravenous or intramuscular injections, or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a partial or total alleviation of symptoms, is achieved.

In another aspect, silanol based payloads and/or drug conjugated disclosed herein may be formulated together with a pharmaceutically acceptable carrier provided. In particular, the present disclosure provides silanol based payloads and/or drug conjugates disclosed herein formulated together with one or more pharmaceutically acceptable carriers. These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral, i.v., or subcutaneous administration.

Exemplary pharmaceutical compositions may be used in the form of a pharmaceutical preparation, for example, in solid, semisolid, spray-dried, dispersion, or liquid form, which contains one or more of the compounds, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants.

In another aspect, enteral pharmaceutical formulations including a disclosed silanol based payload, an enteric material, and a pharmaceutically acceptable carrier or excipient thereof are provided. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that may be used.

Certain terms employed in the specification, examples, and appended claims are collected here. These definitions should be read in light of the entirety of the disclosure and understood as by a person of skill in the art. Unless defined otherwise, all technical and scientific terms used herein have the same meaning as commonly understood by a person of ordinary skill in the art.

Definitions

In some embodiments, a silanol based payload, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "acyl," as used herein, refers to a moiety that includes a carbonyl group. In some embodiments, an acyl group may have a general formula selected from —C(O)R$_x$; —CO$_2$(R$_x$); —C(O)N(R$_x$)$_2$; —OC(O)R$_x$; —OCO$_2$R$_x$; and —OC(O)N(R$_x$)$_2$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments, aryl refers to a mono- or bicyclic carbocyclic ring system having one or two aromatic rings including, but not limited to, phenyl, naphthyl, tetrahydronaphthyl, indanyl, indenyl, and the like. In certain embodiments, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. In certain embodiments, any of the above aryl or heteroaryl rings may be fused to a heterocyclic ring.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heterocyclic," as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term "alkenyl" as used herein refers to an unsaturated straight or branched hydrocarbon having at least one carbon-carbon double bond, such as a straight or branched group of 2-6 or 3-4 carbon atoms, referred to herein for example as C$_{2-6}$alkenyl, and C$_{3-4}$alkenyl, respectively. Exemplary alkenyl groups include, but are not limited to, vinyl, allyl, butenyl, pentenyl, etc.

The term "alkenyloxy" used herein refers to a straight or branched alkenyl group attached to an oxygen (alkenyl-0). Exemplary alkenoxy groups include, but are not limited to, groups with an alkenyl group of 3-6 carbon atoms referred to herein as C$_{3-6}$alkenyloxy. Exemplary "alkenyloxy" groups include, but are not limited to allyloxy, butenyloxy, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as C$_{1-6}$alkoxy, and C$_2$-C$_6$alkoxy, respectively. Exemplary alkoxy groups include, but are not limited to methoxy, ethoxy, isopropoxy, etc.

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as C$_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "carboxylic acid" as used herein refers to a group of formula —$CO_2H$.

The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" as used herein refer to F, Cl, Br, or I.

The term "heterocyclylalkoxy" as used herein refers to a heterocyclyl-alkyl-O— group.

The term "heterocyclyloxyalkyl" refers to a heterocyclyl-O-alkyl- group.

The term "heterocyclyloxy" refers to a heterocyclyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "connector" as used herein to refers to an atom or a collection of atoms optionally used to link interconnecting moieties, such as a disclosed linker and a pharmacophore. Contemplated connectors are generally hydrolytically stable.

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic, or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal, or human that is being sought by the researcher, veterinarian, medical doctor, or other clinician. The compounds are administered in therapeutically effective amounts to treat a disease. Alternatively, a therapeutically effective amount of a compound is the quantity required to achieve a desired therapeutic and/or prophylactic effect.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The silanol based payloads of the disclosure may contain one or more chiral centers and/or double bonds and, therefore, exist as stereoisomers, such as geometric isomers, enantiomers, atropisomers, or diastereomers. The term "stereoisomers" when used herein consist of all geometric isomers, enantiomers or diastereomers. These compounds may be designated by the symbols "R" or "S," depending on the configuration of substituents around the stereogenic carbon atom. Various stereoisomers of these compounds and mixtures thereof are encompassed by this disclosure. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers, atropisomers, or diastereomers. The enantiomers and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds. The symbol ════ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of the compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, Classics in Stereoselective Synthesis, Wiley-VCH: Weinheim, 2009.

The compounds disclosed herein can exist in solvated as well as unsolvated forms with pharmaceutically acceptable solvents such as water, ethanol, and the like. In one embodiment, the compound is amorphous. In one embodiment, the compound is a polymorph. In another embodiment, the compound is in a crystalline form.

Also embraced are isotopically labeled compounds which are identical to those recited herein, except that one or more atoms are replaced by an atom having an atomic mass or mass number different from the atomic mass or mass number usually found in nature. Examples of isotopes that can be incorporated into the compounds include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{10}$B, and $^{36}$Cl, respectively. For example, a compound may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood, or liver). Prodrugs are well known in the art (for example, see Rautio, Kumpulainen, et al, Nature Reviews Drug Discovery 2008, 7, 255). For example, if a compound or a pharmaceutically acceptable salt, hydrate, or solvate of the compound contains a carboxylic acid functional group, a prodrug can comprise an ester formed by the replacement of the hydrogen atom of the acid group with a group such as ($C_{1-8}$)alkyl, ($C_{2-12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl ($C_{1-6}$)alkoxycarbonyloxymethyl, N—($C_{1-6}$)alkoxycarbonylaminomethyl, succinoyl, ($C_{1-6}$)alkanoyl, α-amino($C_{1-4}$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O(C$_1$-C$_6$)alkyl)$_2$ or glycosyl (the radical resulting from the removal of a hydroxyl group of the hemiacetal form of a carbohydrate).

If a compound incorporates an amine functional group, a prodrug can be formed, for example, by creation of an amide or carbamate, an N-acyloxyalkyl derivative, an (oxodioxolenyl)methyl derivative, an N-Mannich base, imine, or enamine. In addition, a secondary amine can be metabolically cleaved to generate a bioactive primary amine, or a tertiary amine can be metabolically cleaved to generate a bioactive primary or secondary amine. For examples, see Simplício et al., *Molecules* 2008, 13, 519 and references therein.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Liquid Chromatography Mass Spectrometry (LCMS) was performed on a Waters Acquity UPLC/SQD2 mass spectrometer under the following parameters: Column: ACE Excel 2 SuperC18; Length: 100 mm; Diameter: 2.1 mm; pore size: 2.0 μm; Column temp: 40° C., Sample temp: 25° C. or 37° C. Gradient elution methods and mobile phase eluents are shown below.

| polar_3 min_0_1500 (0.8 mL/min flow) | | |
|---|---|---|
| Time (min) | Solvent A (%) | Solvent B (%) |
| 0 | 95 | 5 |
| 0.2 | 95 | 5 |
| 1.50 | 10 | 90 |
| 2.00 | 10 | 90 |
| 2.20 | 95 | 5 |
| 3.00 | 95 | 5 |

| polar_3 min_0_1500 (0.6 mL/min flow) | | |
|---|---|---|
| Time (min) | Solvent A (%) | Solvent B (%) |
| 0 | 95 | 5 |
| 0.2 | 95 | 5 |
| 1.50 | 10 | 90 |
| 2.00 | 10 | 90 |
| 2.20 | 95 | 5 |
| 3.00 | 95 | 5 |

| non_polar_3 min (0.8 mL/min flow) | | |
|---|---|---|
| Time (min) | Solvent A (%) | Solvent B (%) |
| 0 | 85 | 15 |
| 0.2 | 85 | 15 |
| 1.60 | 1 | 99 |
| 2.20 | 1 | 99 |
| 2.80 | 85 | 15 |
| 3.00 | 85 | 15 |

| nonpolar_3 min_1500 (0.6 mL/min flow) | | |
|---|---|---|
| Time (min) | Solvent A (%) | Solvent B (%) |
| 0 | 85 | 15 |
| 0.2 | 85 | 15 |
| 1.60 | 1 | 99 |
| 2.20 | 1 | 99 |
| 2.80 | 85 | 15 |
| 3.00 | 85 | 15 |

Acidic Mobile Phase

Solvent A (0.1% formic acid in water, pH=2.3)

Solvent B (0.1% formic acid in acetonitrile)

Basic Mobile Phase

Solvent A (0.1% NH$_4$OH in water, pH=10.63)

Solvent B (100% acetonitrile)

Neutral Mobile Phase A

Solvent A (5 mM ammonium formate in water, pH=7.7)

Solvent B (100% acetonitrile)

Neutral Mobile Phase B

Solvent A (10 mM ammonium bicarbonate in water, pH=7.4)

Solvent B (100% acetonitrile)

Slightly Acidic Mobile Phase

Solvent A (10 mM ammonium acetate in water, pH=6.33)

Solvent B (100% acetonitrile)

Preparative High-performance liquid chromatography (HPLC) was performed on a Waters 2489 HPLC equipped with a UV/Vis detector, 2545 Binary Gradient Module, and Waters Fraction Collector III using ChromScope software and under the following conditions: Preparative column: XBridge Prep C18 5 mm; OBD 19×250 mm column; Column temp: 25° C.; Sample temp: 25° C. Neutral mobile phase eluents were Solvent A (10 mM Ammonium bicarbonate in water, 5% acetonitrile, pH=7.4, degassed) and Solvent B (100% acetonitrile, degassed). Gradient elution methods and mobile phase eluents are shown below.

| Preparative HPLC gradient 1 | | | |
|---|---|---|---|
| Time (min) | Flow (mL/min) | Solvent A (%) | Solvent B (%) |
| Initial | 18 | 95 | 5 |
| 5 | 18 | 90 | 10 |
| 20 | 18 | 40 | 60 |
| 25 | 18 | 20 | 80 |
| 30 | 18 | 10 | 90 |
| 35 | 18 | 5 | 95 |
| 40 | 18 | 95 | 5 |

| Preparative HPLC gradient 2 | | | |
|---|---|---|---|
| Time (min) | Flow (mL/min) | Solvent A (%) | Solvent B (%) |
| Initial | 20 | 80 | 20 |
| 2 | 20 | 60 | 40 |
| 5 | 20 | 50 | 50 |
| 10 | 20 | 40 | 60 |
| 20 | 20 | 20 | 80 |
| 35 | 20 | 20 | 80 |
| 45 | 20 | 20 | 80 |
| 50 | 20 | 15 | 85 |
| 60 | 20 | 5 | 95 |
| 65 | 20 | 5 | 95 |
| 80 | 20 | 5 | 95 |
| 100 | 20 | 90 | 10 |

Silicon Based Payloads:

Examples of silanol based payloads contemplated in the present disclosure, as well as selected physiochemical properties, are shown in Table 1.

TABLE 1

| Example | Silanol Compound | cLogP[a] Silanol | RT (min) Silanol |
|---|---|---|---|
| 1 | | 4.234 | 2.37[c] |
| 2 | | 4.156 | 2.16[d] |
| 3 | | 3.977 | 2.10[d] |
| 4 | | 5.138 | |
| 5 | | 4.823 | 1.88[e] |
| 6 | | 3.944 | 2.23[e] |

TABLE 1-continued

| Example | Silanol Compound | cLogP[a] Silanol | RT (min) Silanol |
|---|---|---|---|
| 7 | | 2.295 | 1.98[b] |
| 8 | | 1.886 | |
| 9 | | 2.146 | |
| 10 | | 1.551 | |

TABLE 1-continued

| Example | Silanol Compound | cLogP[a] Silanol | RT (min) Silanol |
|---|---|---|---|
| 11 | | 1.547 | |
| 12 | | 3.742 | |
| 13 | | 5.969 | 1.83[b] |
| 14 | | 6.104 | |
| 15 | | 4.442 | |

TABLE 1-continued

| Example | Silanol Compound | cLogP[a] Silanol | RT (min) Silanol |
|---|---|---|---|
| 16 | | | 5.367 |
| 17 | | | 4.055 |
| 18 | | | 4.237 |
| 19 | | | 4.958 |

TABLE 1-continued

| Example | Silanol Compound | cLogP[a] Silanol | RT (min) Silanol |
|---|---|---|---|
| 20 | 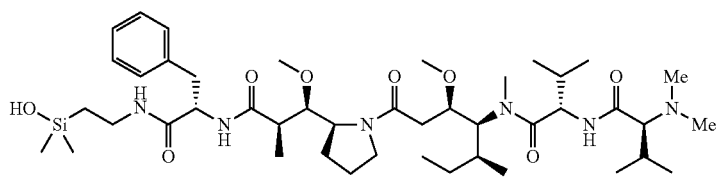 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCC[Si](C)(C)O)OC)N(C)C(=O)[C@@H](NC(=O)[C@H](C(C)C)N(C)C)C(C)C] | 3.786 | |

[a] Calculated cLogP.
[b] LCMS retention time from polar_3 min_1500 method.
[c] LCMS retention time from nonpolar_3 min_1500 method.
[d] LCMS retention time from nonpolar_3 min_neutral method (0.6 mL/min flow rate)

Table 2 shows the parent compounds of the silanol based payloads of Table 1, respectively, as well as selected physiochemical properties and the difference in values of the physiological properties of silanol based payloads from the parent compounds. As shown in Table 2, an increase in lipophilicity is observed by incorporation of the silanol moieties.

TABLE 2

| Parent Compound of Example No.: | Structure | cLogP[a] Parent | RT (min) Parent | Δ[d] cLogP | Δ[d] RT (min) |
|---|---|---|---|---|---|
| 1 | 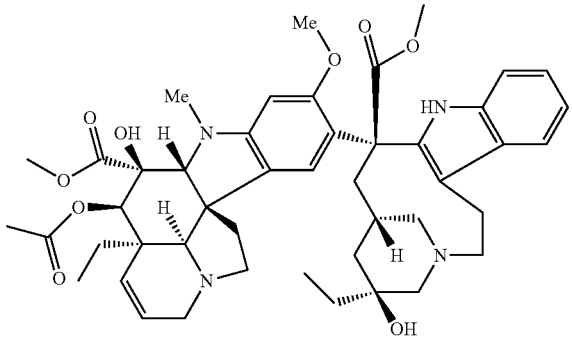 | 3.925 | 2.30[c] | 0.309 | 0.07[c] |
| 2 | 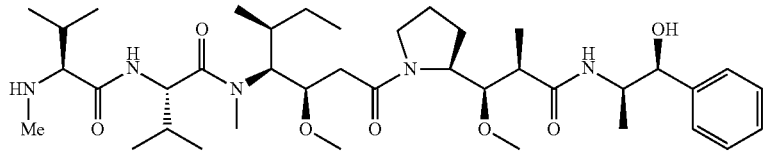 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] | 3.162 | 2.03[d] | 0.994 | 0.13 |
| 3 | 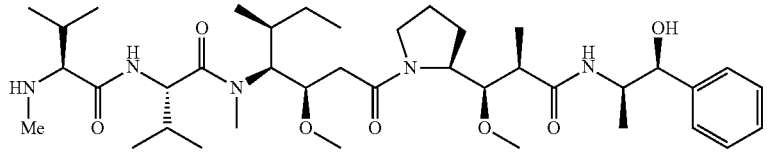 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] | 3.162 | 2.03[d] | 0.815 | 0.07 |
| 4 | 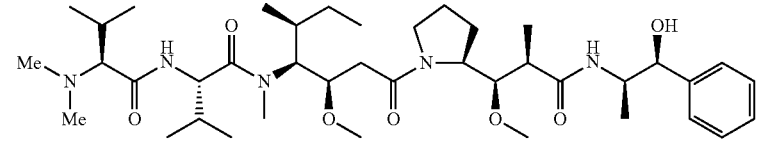 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)C(C)C] | 3.411 | | 1.727 | |

TABLE 2-continued

| Parent Compound of Example-No.: | Structure | cLogP[a] Parent | RT (min) Parent | Δ[d] cLogP | Δ[d] RT (min) |
|---|---|---|---|---|---|
| 5 | 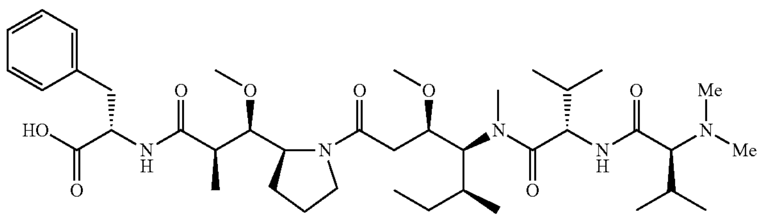 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C)C(C)C] | 3.896 | 1.82[c] | 0.927 | 0.41 |
| 6 | 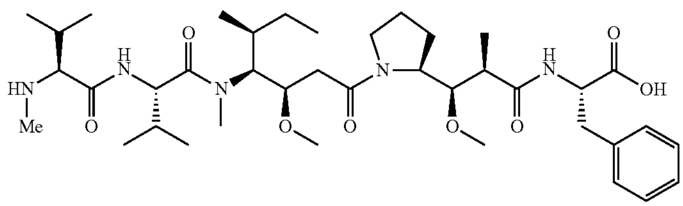 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C] | 2.950 | 1.74[c] | 0.994 | 0.14 |
| 7 | 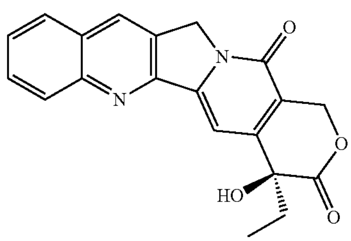 [SMILES: CC[C@@]1(O)C(=O)OCc2c1cc1n(c2=O)Cc2cc3ccccc3nc2-1] | 1.423 | 1.83[b] | 0.872 | 0.15 |
| 8 | 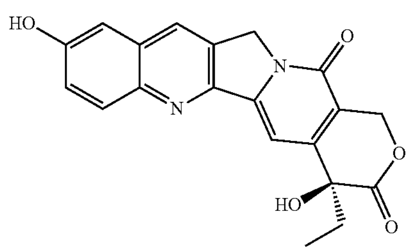 [SMILES: CC[C@@]1(O)C(=O)OCc2c1cc1n(c2=O)Cc2cc3cc(O)ccc3nc2-1] | 1.014 | 1.69[b] | 0.872 | |
| 9 | 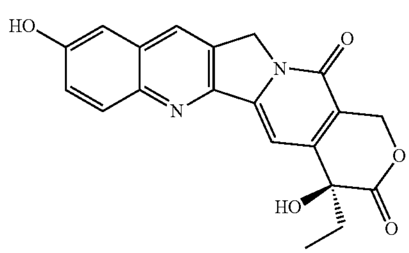 [SMILES: CC[C@@]1(O)C(=O)OCc2c1cc1n(c2=O)Cc2cc3cc(O)ccc3nc2-1] | 1.014 | 1.69[b] | 1.132 | |
| 10 | 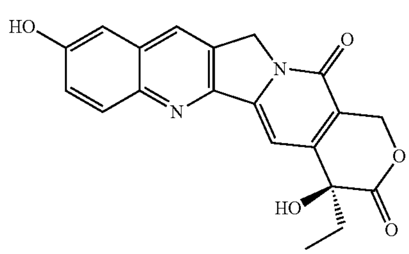 [SMILES: CC[C@@]1(O)C(=O)OCc2c1cc1n(c2=O)Cc2cc3cc(O)ccc3nc2-1] | 1.014 | 1.69[b] | 0.537 | |

TABLE 2-continued

| Parent Compound of Example-No.: | Structure | cLogP[a] Parent | RT (min) Parent | Δ[d] cLogP | Δ[d] RT (min) |
|---|---|---|---|---|---|
| 11 | 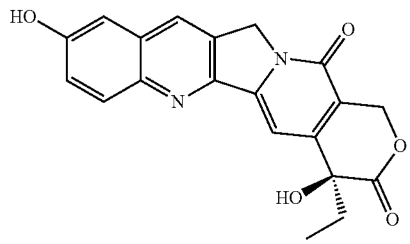 [SMILES: CC[C@@]1(O)C(=O)OCc2c1cc1n(c2=O)Cc2cc3cc(O)ccc3nc2-1] | 1.014 | 1.69[b] | 0.533 | |
| 12 | 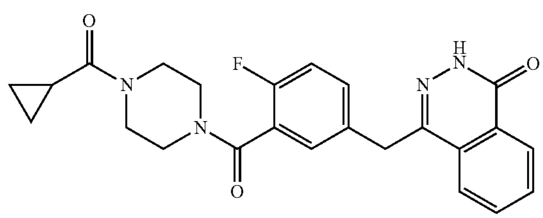 [SMILES: O=C(c1cc(Cc2n[nH]c(=O)c3ccccc23)ccc1F)N1CCN(C(=O)C2CC2)CC1] | 2.753 | | 0.989 | |
| 13 | 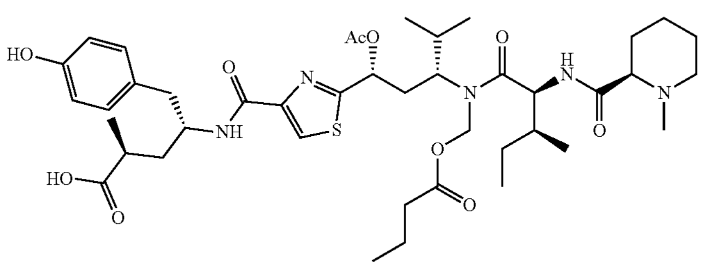 [SMILES: CCCC(=O)OCN(C(=O)[C@@H](NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)O)cs1)C(C)C] | 5.042 | 1.80[b] | 0.927 | 0.03 |
| 14 | 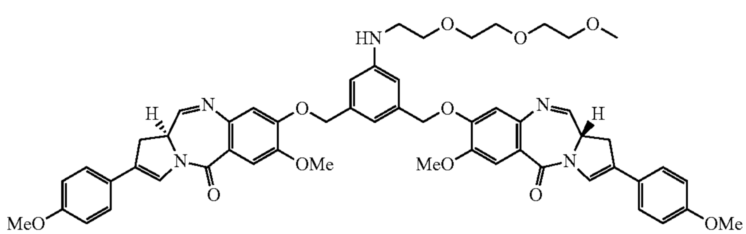 [SMILES: COCCOCCOCCNc1cc(COc2cc3c(cc2OC)C(=O)N2C=C(c4ccc(OC)cc4)C[C@H]2C=N3)cc(COc2cc3c(cc2OC)C(=O)N2C=C(c4ccc(OC)cc4)C[C@H]2C=N3)c1] | 5.392 | | 0.712 | |
| 15 | 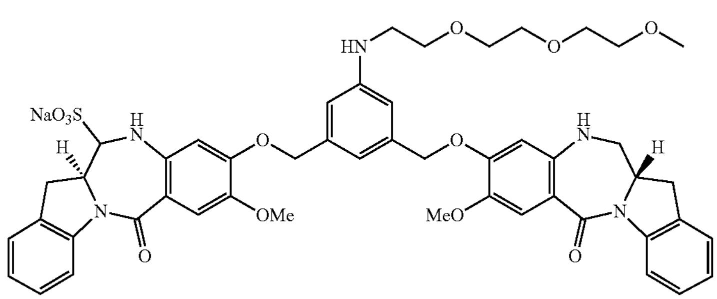 | 3.730 | | 0.712 | |

TABLE 2-continued

| Parent Compound of Example No.: | Structure | cLogP[a] Parent | RT (min) Parent | Δ[d] cLogP | Δ[d] RT (min) |
|---|---|---|---|---|---|
| 16 | 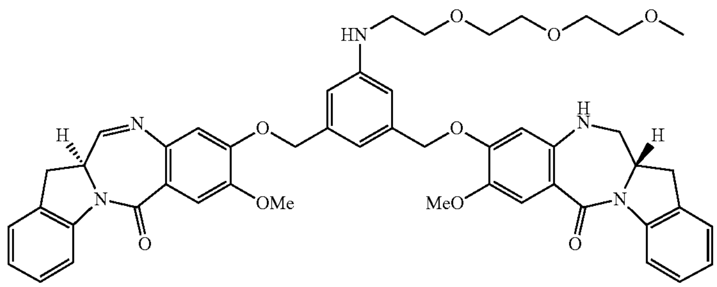 [SMILES: COCCOCCOCCNc1cc(COc2cc3c(cc2OC)C(=O)N2c4ccccc4C[C@H]2C=N3)cc(COc2cc3c(cc2OC)C(=O)N2c4ccccc4C[C@H]2CN3)c1] | 4.655 | | 0.712 | |
| 17 | 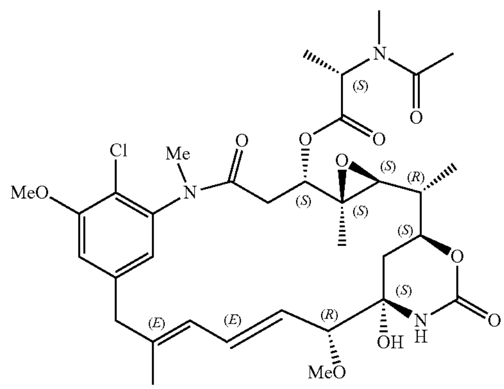 | 3.067 | | 0.988 | |
| 18 | 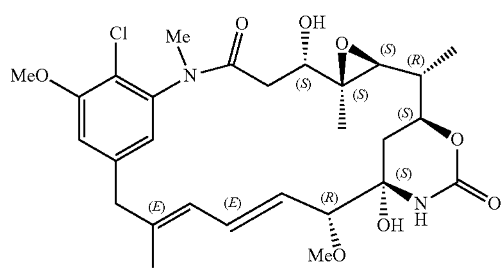 | 2.510 | | 1.727 | |
| 19 | 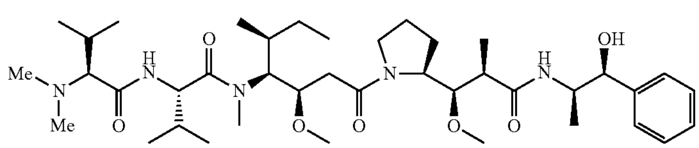 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)C(C)C] | 3.411 | | 1.547 | |
| 20 | 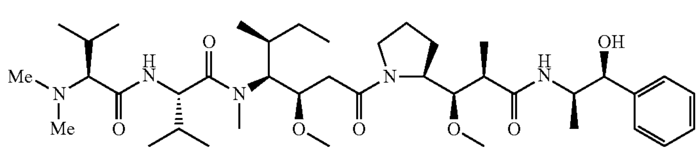 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C)C(C)C] | 3.411 | | 0.375 | |

[a] Calculated cLogP.
[b] LCMS retention time from polar_3 min_1500 method.
[c] LCMS retention time from nonpolar_3 min_1500 method.
[d] Δ is the value difference of silanol from the parent compound.

Syntheses

Example 1: Scheme for the Preparation of Example 1

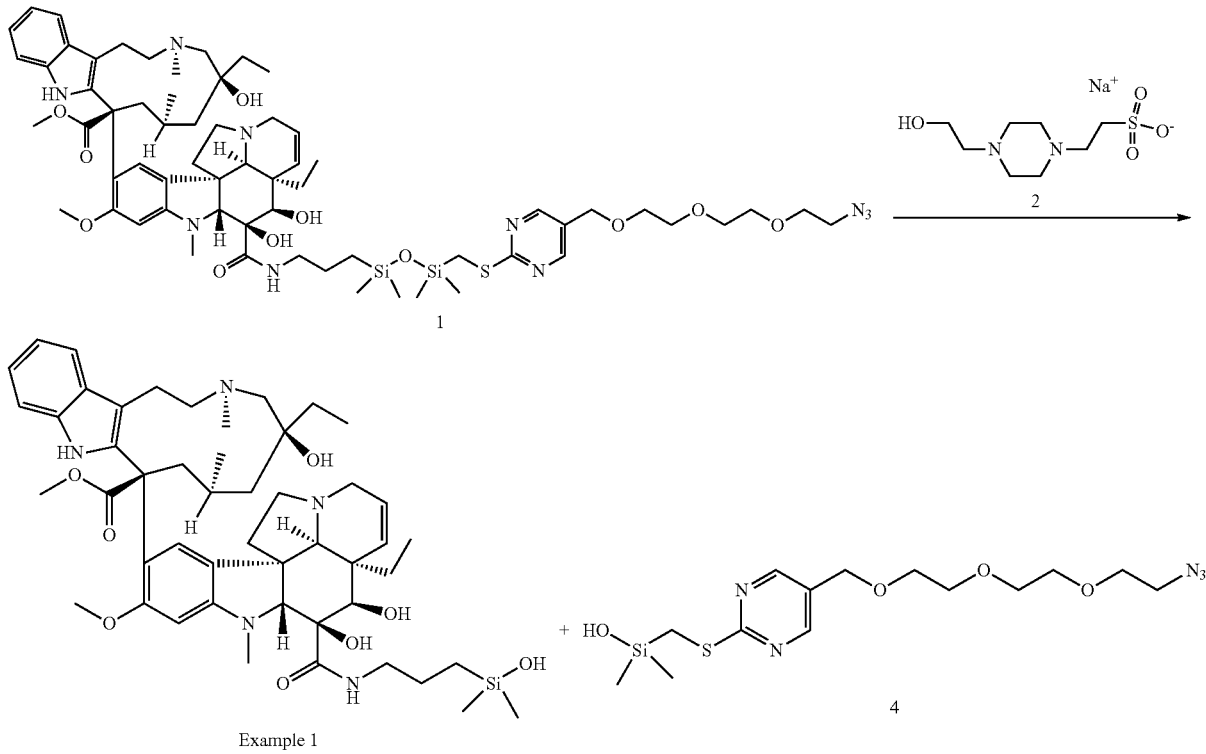

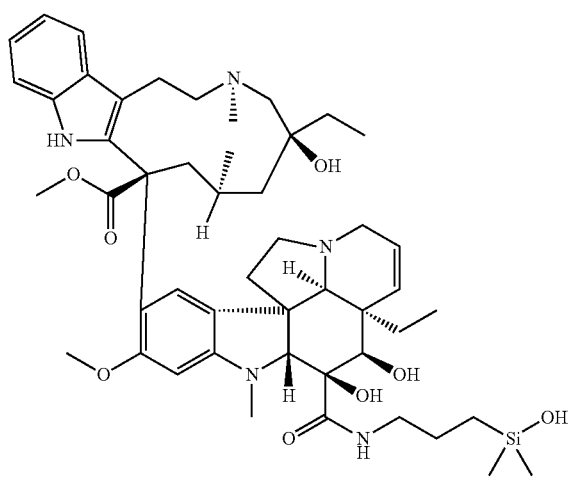

Example 1

Methyl (3R,5S,7R,9S)-5-ethyl-9-((3aR,3a1R,4R,5S, 5aR,10bR)-3a-ethyl-4,5-dihydroxy-5-((3-(hydroxy-dimethylsilyl)propyl)carbamoyl)-8-methoxy-6-methyl-3a,3a1,4,5,5a,6,11,12-octahydro-1H-indolizino[8,1-cd]carbazol-9-yl)-5-hydroxy-1,4,5,6,7,8,9,10-octahydro-2H-3,7-methano[1]azacycloundecino[5,4-b]indole-9-carboxylate [Example 1]

A solution of (3R,5S,7R,9S)-methyl 9-((3aR,3a1R,4R,5S, 5aR,10bR)-5-((3-(3-(((5-((2-(2-(2-azidoethoxy)ethoxy)ethoxy)methyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (50 mg, 0.040 mmol) in DMSO (2.0 ml) was charged with 50 mM HEPES Buffer (pH 5.0) (2.0 ml, 0.100 mmol) (Note: upon addition of HEPES buffer the sample crashed out of solution). The reaction mixture was charged with 1 drop of 6N HCl and heated to 40° C. for 16 h with stirring. (Note upon addition of HCl the solution went homogeneous again) The reaction was purified by reverse phase preparative HPLC [Prep_AmmBicarb-pH7.4_Method1B] resulting in 18 mg, 20.3% yield of the title compound as a white solid after lyophilization. $^1$H NMR (DMSO-$d_6$, 400 MHz): δ (ppm) 9.33 (s, 1H), 8.50 (s, 1H), 7.75 (br t, J=5.9 Hz, 1H), 7.37 (d, J=8.1 Hz, 1H), 7.26 (d, J=8.1 Hz, 1H), 6.97-7.04 (m, 1H), 6.88-6.95 (m, 1H), 6.45 (s, 1H), 6.20 (s, 1H), 5.69 (br dd, J=10.6, 4.8 Hz, 1H), 5.56-5.62 (m, 1H), 5.23-5.53 (m, 1H), 4.00-4.11 (m, 1H), 3.96 (br s, 2H), 3.83 (br s, 1H), 3.67-3.78 (m, 5H), 3.54 (s, 4H), 3.34 (br s, 4H), 3.27 (br d, J=14.1 Hz, 1H), 3.02-3.22 (m, 7H), 2.83-2.93 (m, 2H), 2.61-2.78 (m, 8H), 2.28-2.41 (m, 2H), 1.90-2.06 (m, 2H), 1.43-1.67 (m, 5H), 1.25-1.39 (m, 2H), 1.12-1.23 (m, 3H), 0.71-0.84 (m, 6H), 0.57-0.67 (m, 1H), 0.42-0.50 (m, 2H), 0.00 (s, 6H); MS (ES$^+$): m/z=870.55 [M+H]$^+$; LCMS: $t_R$=1.66 min [polar_3 min_1500].

Methyl (3R,5S,7R,9S)-9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyldisiloxaneyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate [1]

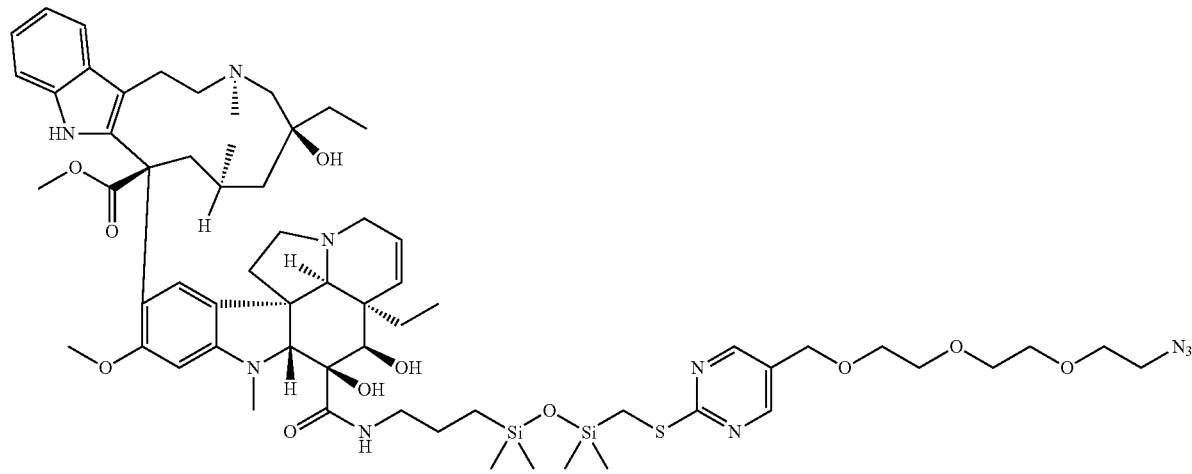

The synthesis of compound 1 can be found in WO2016183359.

Example 2: Scheme for the Preparation of Example 2

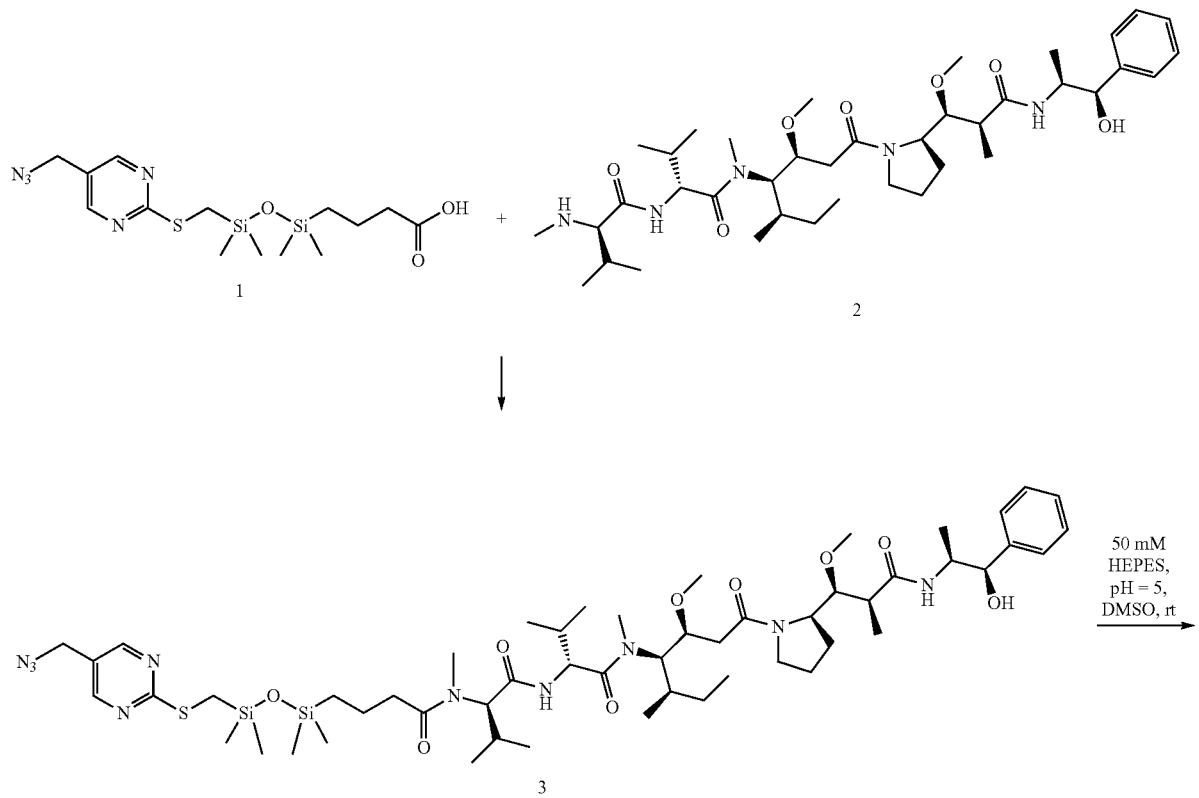

-continued

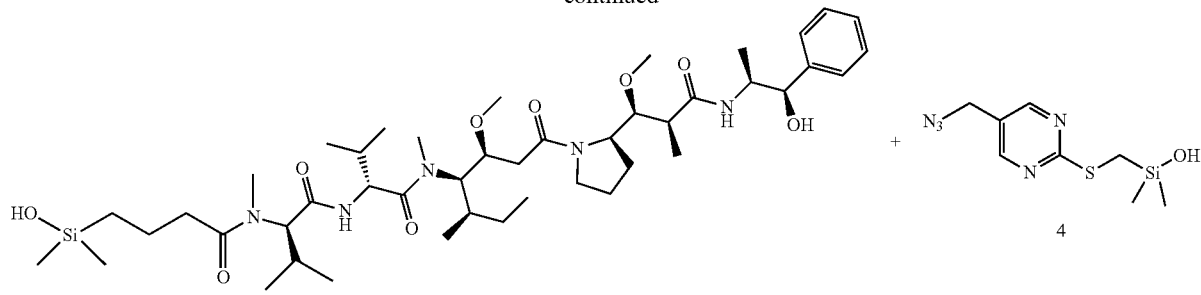

Example2

(R)—N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-2-((R)-2-(4-(hydroxydimethylsilyl)-N-methylbutanamido)-3-methylbutanamido)-N,3-dimethylbutanamide
[Example 2]

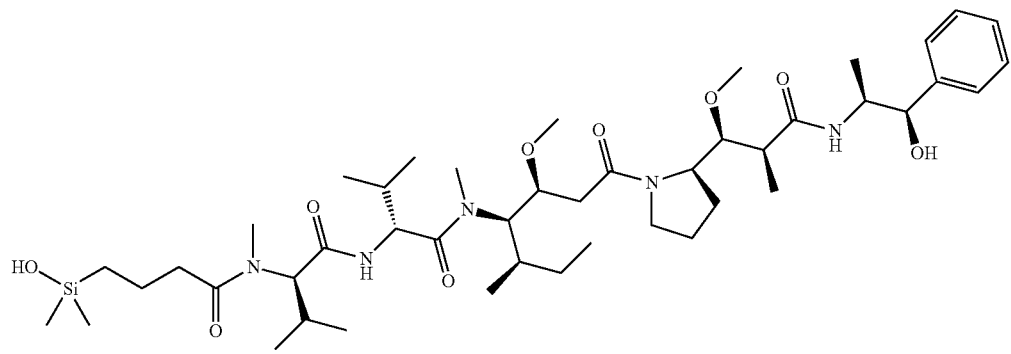 [SMILES: CC[C@@H](C)[C@H]([C@H](CC(=O)N1CCC[C@@H]1[C@@H](OC)[C@H](C)C(=O)N[C@@H](C)[C@H](O)c1ccccc1)OC)N(C)C(=O)[C@H](NC(=O)[C@@H](C(C)C)N(C)C(=O)CCC[Si](C)(C)O)C(C)C]

A solution of (R)-2-((R)-2-(4-(3-(((5-(azidomethyl)pyrimidin-2-yl)thio)methyl)-1,1,3,3-tetramethyldisiloxanyl)-N-methylbutanamido)-3-methylbutanamido)-N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide (15 mg, 0.014 mmol) in DMSO (700 µl) was charged with 50 mM HEPES Buffer (pH 5.0) (273 µl, 0.014 mmol) and 1 drop of 6N HCl and stirred at rt for 2 hr. From LCMS, the reaction looked complete therefore the reaction was purified by Prep HPLC [Prep_AmmBicarb_pH7.4_Method1B] resulting in 5.3 mg, 45% yield of the title compound as a white solid. $^1$H NMR (DMSO-$d_6$, 400 MHz): δ (ppm) 7.90 (br dd, J=8.6, 4.0 Hz, 1H), 7.85-8.60 (m, 1H), 7.60-7.75 (m, 1H), 7.23-7.36 (m, 4H), 7.12-7.21 (m, 1H), 5.28-5.46 (m, 2H), 4.74 (br d, J=4.3 Hz, 1H), 4.37-4.67 (m, 3H), 3.82-4.06 (m, 2H), 3.73-3.82 (m, 1H), 3.52-3.64 (m, 1H), 3.23 (dd, J=7.5, 1.1 Hz, 4H), 3.16-3.21 (m, 3H), 3.12 (d, J=8.3 Hz, 2H), 2.95-3.00 (m, 1H), 2.89-3.00 (m, 2H), 2.84 (d, J=17.4 Hz, 2H), 2.21-2.46 (m, 5H), 2.07-2.19 (m, 2H), 1.90-2.05 (m, 1H), 1.65-1.86 (m, 3H), 1.43-1.61 (m, 4H), 1.29 (br dd, J=10.7, 2.7 Hz, 1H), 0.95-1.07 (m, 7H), 0.70-0.92 (m, 20H), 0.45-0.54 (m, 2H), −0.03-0.01 (m, 6H); MS (ES$^+$): m/z=844.67 [M−18]$^+$; LCMS: $t_R$=2.21 min [polar_3 min_1500].

(R)-2-((R)-2-(4-(3-(((5-(azidomethyl)pyrimidin-2-yl)thio)methyl)-1,1,3,3-tetramethyldisiloxaneyl)-N-methylbutanamido)-3-methylbutanamido)-N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide [3]

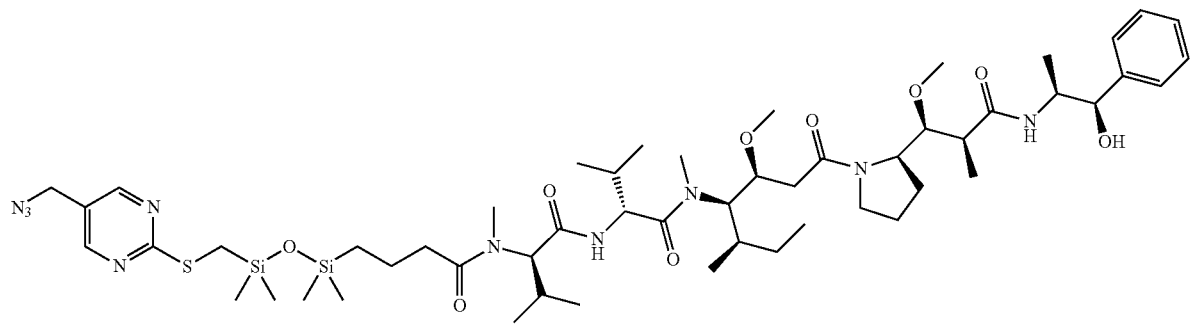 [SMILES: CC[C@@H](C)[C@H]([C@H](CC(=O)N1CCC[C@@H]1[C@@H](OC)[C@H](C)C(=O)N[C@@H](C)[C@H](O)c1ccccc1)OC)N(C)C(=O)[C@H](NC(=O)[C@@H](C(C)C)N(C)C(=O)CCC[Si](C)(C)O[Si](C)(C)CSc1ncc(CN=[N+]=[N-])cn1)C(C)C]

A solution of 2,5-dioxopyrrolidin-1-yl 4-(3-(((5-(azidomethyl)pyrimidin-2-yl)thio)methyl)-1,1,3,3-tetramethyldisiloxanyl)butanoate (22.83 mg, 0.046 mmol) and (R)—N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((R)-3-methyl-2-(methylamino)butanamido)butanamide (30 mg, 0.042 mmol) in DCM (0.500 ml) was charged with DIEA (0.015 ml, 0.084 mmol) and stirred at rt for 48 h. From LCMS very little reaction had taken place therefore the reaction was heated to 40° C. for 3 or 4 days periodically checking the reaction mixture by LCMS for progress. The reaction mixture had progressed but there was still low conversion. The reaction mixture was heated to 70° C. for multiple days checking periodically by LCMS for reaction progress. The reaction was stopped after ~65% was converted to product. There crude reaction mixture was purified by ISCO column chromatography on silica gel eluting with [0% (10% 7N ammonia in methanol) in DCM to 8% (10% 7N ammonia in methanol) in DCM resulting in 22 mg, 47.9% yield of the title compound as a clear colorless oil. $^1$H NMR (CDCl$_3$, 400 MHz): δ (ppm) 8.24-8.30 (m, 2H), 7.09-7.21 (m, 5H), 7.00-7.08 (m, 1H), 6.30-6.42 (m, 2H), 4.74 (br d, J=2.3 Hz, 1H), 4.48-4.57 (m, 1H), 4.37-4.47 (m, 2H), 4.12 (s, 2H), 4.05 (td, J=7.1, 2.8 Hz, 1H), 3.91-3.99 (m, 2H), 3.85 (br s, 1H), 3.63 (br dd, J=8.6, 1.5 Hz, 1H), 3.26-3.57 (m, 3H), 3.16-3.24 (m, 5H), 3.07-3.14 (m, 4H), 2.91 (s, 1H), 2.74-2.84 (m, 6H), 2.65-2.73 (m, 1H), 2.52-2.57 (m, 1H), 2.10-2.30 (m, 8H), 1.98-2.08 (m, 2H), 1.72-1.95 (m, 7H), 1.64 (br d, J=8.3 Hz, 3H), 1.41-1.52 (m, 3H), 1.11-1.24 (m, 2H), 0.99-1.10 (m, 6H), 0.52-0.89 (m, 32H), 0.35-0.44 (m, 2H), 0.00 (s, 6H), −0.11 (s, 6H); MS (ES$^+$): m/z=1099.69 [M+H]$^+$, 859.61 [M−18]$^+$; LCMS: t$_R$=2.78 min [nonpolar_3 min].

4-(3-(((5-(azidomethyl)pyrimidin-2-yl)thio)methyl)-1,1,3,3-tetramethyldisiloxaneyl) butanoic acid [1]

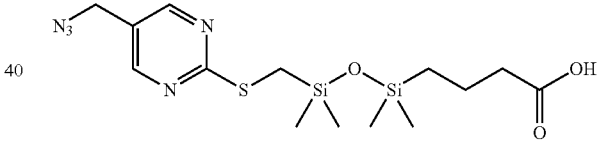

The synthesis of compound [1] can be found in WO2016183359.

Example 3: Scheme for the Preparation of Example 3

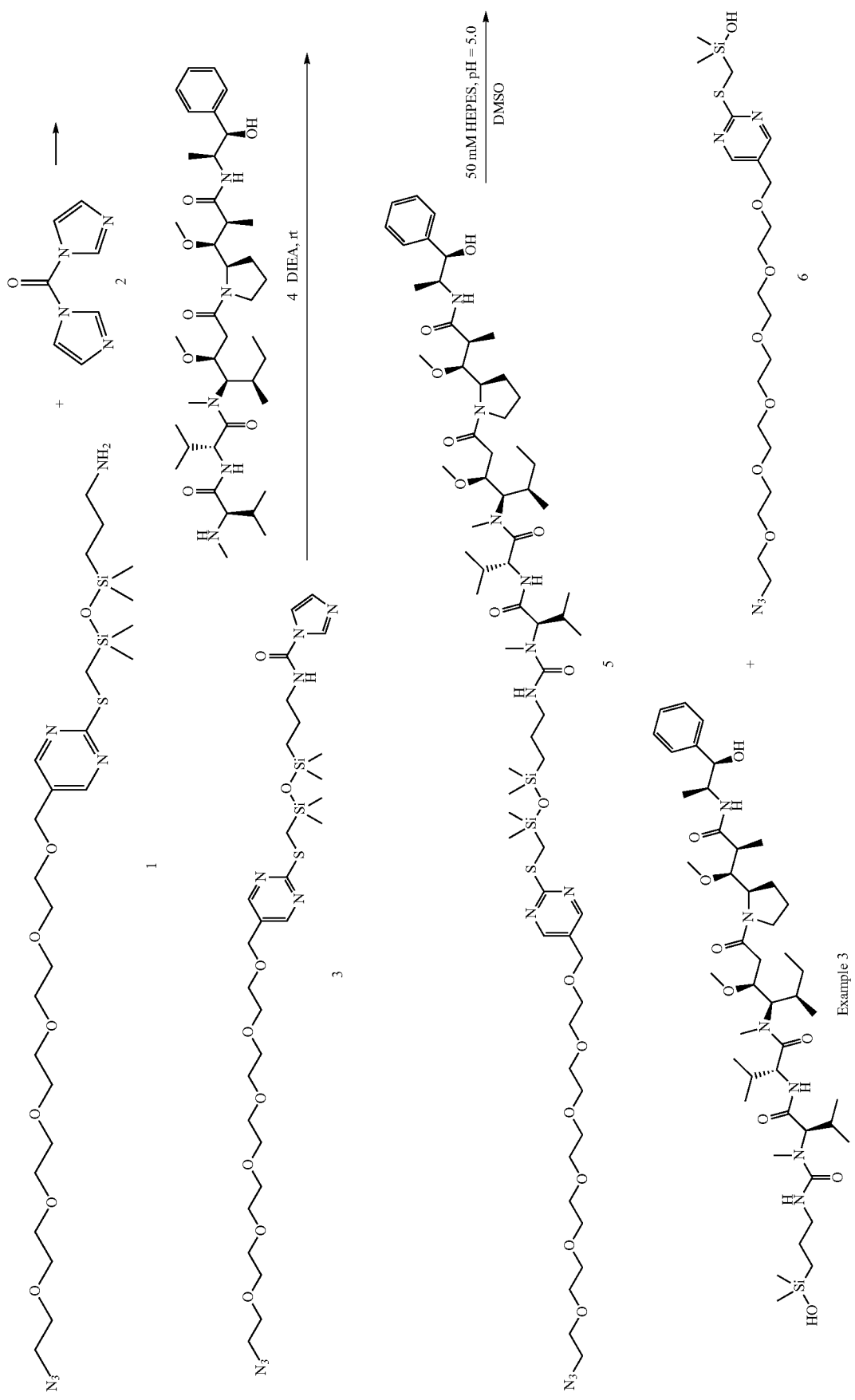

(R)—N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-2-((R)-2-(3-(3-(hydroxydimethylsilyl)propyl)-1-methylureido)-3-methylbutanamido)-N,3-dimethylbutanamide [Example 3]

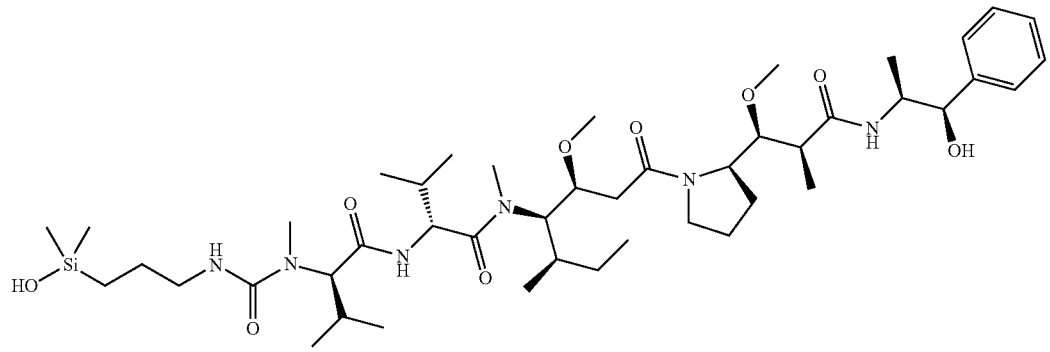 [SMILES: CC[C@@H](C)[C@H]([C@H](CC(=O)N1CCC[C@@H]1[C@@H](OC)[C@H](C)C(=O)N[C@@H](C)[C@H](O)c1ccccc1)OC)N(C)C(=O)[C@H](NC(=O)[C@@H](C(C)C)N(C)C(=O)NCCC[Si](C)(C)O)C(C)C]

A solution of (R)-2-((R)-2-(3-(3-(3-(((5-(19-azido-2,5,8,11,14,17-hexaoxanonadecyl)pyrimidin-2-yl)thio)methyl)-1,1,3,3-tetramethyldisiloxanyl)propyl)-1-methylureido)-3-methylbutanamido)-N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide (27 mg, 0.020 mmol) in DMSO (1 mL) was charged with 50 mM HEPES Buffer (pH 5.0) (0.392 mL, 0.020 mmol) and 2 drops of 6N HCl. This was stirred at rt for 2 hr. and the crude was directly purified by prep HPLC [Method: PREP_AmmBicarb_pH7.4_Method1B] resulting in 7 mg, 40.8% yield of the title compound as a white solid. $^1$H NMR (DMSO-$d_6$, 400 MHz): δ (ppm) 7.85-7.94 (m, 1H), 7.63 (d, J=8.6 Hz, 1H), 7.23-7.35 (m, 4H), 7.13-7.19 (m, 1H), 6.44-6.58 (m, 1H), 5.24-5.47 (m, 2H), 4.69-4.79 (m, 1H), 4.57 (br t, J=8.8 Hz, 1H), 4.39-4.50 (m, 1H), 3.89-4.07 (m, 3H), 3.78 (dd, J=9.5, 2.1 Hz, 1H), 3.51-3.62 (m, 1H), 3.40-3.50 (m, 1H), 3.24 (d, J=7.8 Hz, 4H), 3.17-3.21 (m, 3H), 3.10 (s, 2H), 2.97-3.07 (m, 2H), 2.95 (s, 2H), 2.74 (d, J=14.7 Hz, 2H), 2.64-2.78 (m, 1H), 2.36-2.45 (m, 1H), 2.06-2.34 (m, 3H), 1.87-2.03 (m, 1H), 1.65-1.85 (m, 3H), 1.36-1.60 (m, 4H), 1.24-1.35 (m, 1H), 0.95-1.08 (m, 6H), 0.66-0.91 (m, 18H), 0.42 (td, J=8.5, 2.8 Hz, 2H), −0.02 (s, 6H); MS (ES$^+$): m/z=877.59 [M+H]$^+$, 859.61 [M−18]$^+$; LCMS: $t_R$=2.23 min [polar_3 min_1500].

(R)-2-((R)-2-(3-(3-(3-(((5-(19-azido-2,5,8,11,14,17-hexaoxanonadecyl)pyrimidin-2-yl)thio)methyl)-1,1,3,3-tetramethyldisiloxaneyl)propyl)-1-methylureido)-3-methylbutanamido)-N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide [5]

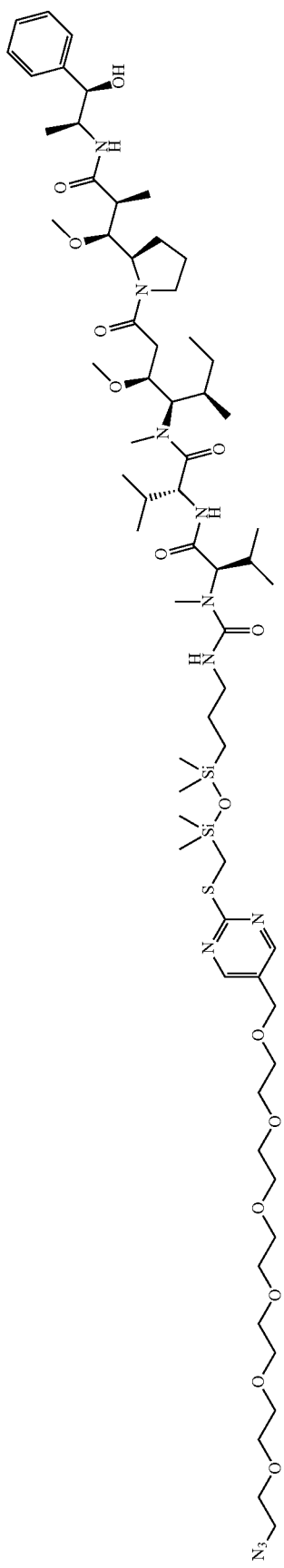

A solution of N-(3-(3-(((5-(19-azido-2,5,8,11,14,17-hexaoxanonadecyl)pyrimidin-2-yl)thio)methyl)-1,1,3,3-tetramethyldisiloxanyl)propyl)-1H-imidazole-1-carboxamide (20.31 mg, 0.028 mmol) in anhydrous Acetonitrile (0.250 ml) was charged with TEA (7.77 µl, 0.056 mmol) and cooled to 0° C. and dropwise charged with a solution of (R)—N-((3S,4R,5R)-1-((R)-2-((1S,2S)-3-(((1R,2S)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((R)-3-methyl-2-(methylamino) butanamido)butanamide (20.0 mg, 0.028 mmol) in Acetonitrile (0.250 ml) over a 2 min period and stirred at 0° C. for 30 min then allowed to warm to rt and stirred for an additional 48 h at rt. From TLC, looks like all the sm material amine has been consumed therefore the reaction mixture was worked up. The reaction was partitioned between DCM and water and separated. The aqueous was extracted with DCM (3×) and the combined DCM fractions were dried over $Na_2SO_4$, filtered and concentrated in vacuo and purified ISCO CombiFlash chromatography on silica gel, 4 g Gold cartridge eluting with 8% (10% 7N ammonia in methanol) in DCM]. resulting in 27 mg, 70% yield of the title compound as clear colorless oil. $^1$H NMR (CHLOROFORM-d, 400 MHz): δ (ppm) 8.46-8.52 (m, 2H), 7.30-7.42 (m, 4H), 7.21-7.27 (m, 1H), 6.66-6.95 (m, 1H), 6.50-6.63 (m, 1H), 4.92-4.99 (m, 1H), 4.58-4.78 (m, 3H), 4.50 (s, 2H), 4.22-4.34 (m, 2H), 4.16 (br d, J=4.8 Hz, 1H), 4.05 (br s, 1H), 3.84 (br dd, J=8.6, 1.8 Hz, 1H), 3.60-3.71 (m, 22H), 3.47-3.56 (m, 1H), 3.37-3.45 (m, 6H), 3.30-3.35 (m, 3H), 3.09-3.29 (m, 3H), 2.97-3.05 (m, 2H), 2.80-2.86 (m, 2H), 2.72-2.79 (m, 1H), 2.31-2.51 (m, 5H), 2.15-2.26 (m, 1H), 1.97-2.12 (m, 4H), 1.78-1.92 (m, 4H), 1.46-1.57 (m, 2H), 1.31-1.43 (m, 1H), 1.21-1.29 (m, 4H), 0.76-1.08 (m, 25H), 0.53 (dd, J=10.9, 6.3 Hz, 2H), 0.17-0.25 (m, 6H), 0.04-0.12 (m, 6H); MS (ES$^+$): m/z=1378.82 [M+H]$^+$; LCMS: $t_R$=2.30 min [polar_3 min_1500].

N-(3-(3-(((5-(19-azido-2,5,8,11,14,17-hexaoxanonadecyl)pyrimidin-2-yl)thio)methyl)-1,1,3,3-tetramethyldisiloxaneyl)propyl)-1H-imidazole-1-carboxamide [3]

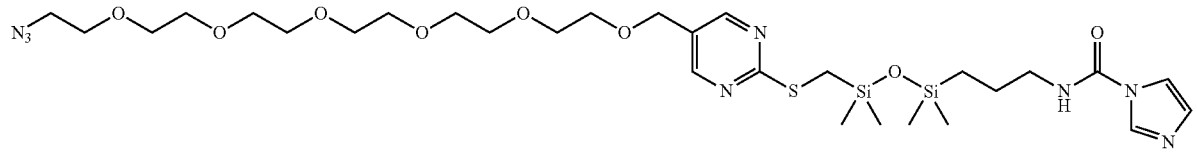 [SMILES: C[Si](C)(CCCNC(=O)n1ccnc1)O[Si](C)(C)CSc1ncc(COCCOCCOCCOCCOCCOCCN=[N+]=[N-])cn1]

A solution of di(1H-imidazol-1-yl)methanone (192 mg, 1.181 mmol) in anhydrous THF (14.00 mL) was cooled to 0° C. and dropwise charged with a solution of 3-(3-(((5-(19-azido-2,5,8,11,14,17-hexaoxanonadecyl)pyrimidin-2-yl)thio)methyl)-1,1,3,3-tetramethyldisiloxanyl) propan-1-amine (500 mg, 0.787 mmol) in THF (1.50 mL) over a 5 min period and stirred at 0° C. for 30 min then allowed to warm to rt. From TLC, looks like all the sm material amine has been consumed [8% (10% 7N ammonia in methanol) in DCM]. The reaction mixture was partitioned between DCM and $H_2O$ and separated. The aqueous was extracted with DCM (3×) and the combined organic fractions were washed with brine (1×), dried over $Na_2SO_4$, filtered and concentrated in vacuo and the crude was purified by chromatography on silica gel eluting with 0% (10% 7N NH$_3$ in MeOH) in DCM to 5% solution of (10% 7N NH$_3$ in MeOH) in DCM resulting in 350 mg, 60% yield of the title compound as a clear colorless thick oil. $^1$H NMR (CHLOROFORM-d, 400 MHz): δ (ppm) 8.48 (s, 2H), 8.20 (s, 1H), 7.46 (s, 1H), 7.04-7.12 (m, 1H), 6.45-6.55 (m, 1H), 5.30 (s, 5H), 4.49 (s, 2H), 3.62-3.70 (m, 24H), 3.35-3.42 (m, 4H), 2.43 (s, 2H), 1.81-1.89 (m, 2H), 1.64-1.75 (m, 2H), 0.54-0.62 (m, 2H), 0.22 (s, 6H), 0.10 (s, 6H); MS (ES$^+$): m/z=729.19, 730.48 [M+H]$^+$; LCMS: $t_R$=1.88 min [nonpolar_3 min].

Example 5: (S)—N-((3R,4S,5S)-1-((S)-2-((3R,4R,7S)-7-benzyl-13-hydroxy-4,13-dimethyl-5,8-dioxo-2-oxa-6,9-diaza-13-silatetradecan-3-yl)pyrrolidin-1-yl)-3-methoxy-5-methyl-1-oxoheptan-4-yl)-2-0S)-2-(dimethylamino)-3-methylbutanamido)-N,3-dimethylbutanamide The title compound was prepared according to the scheme shown below.

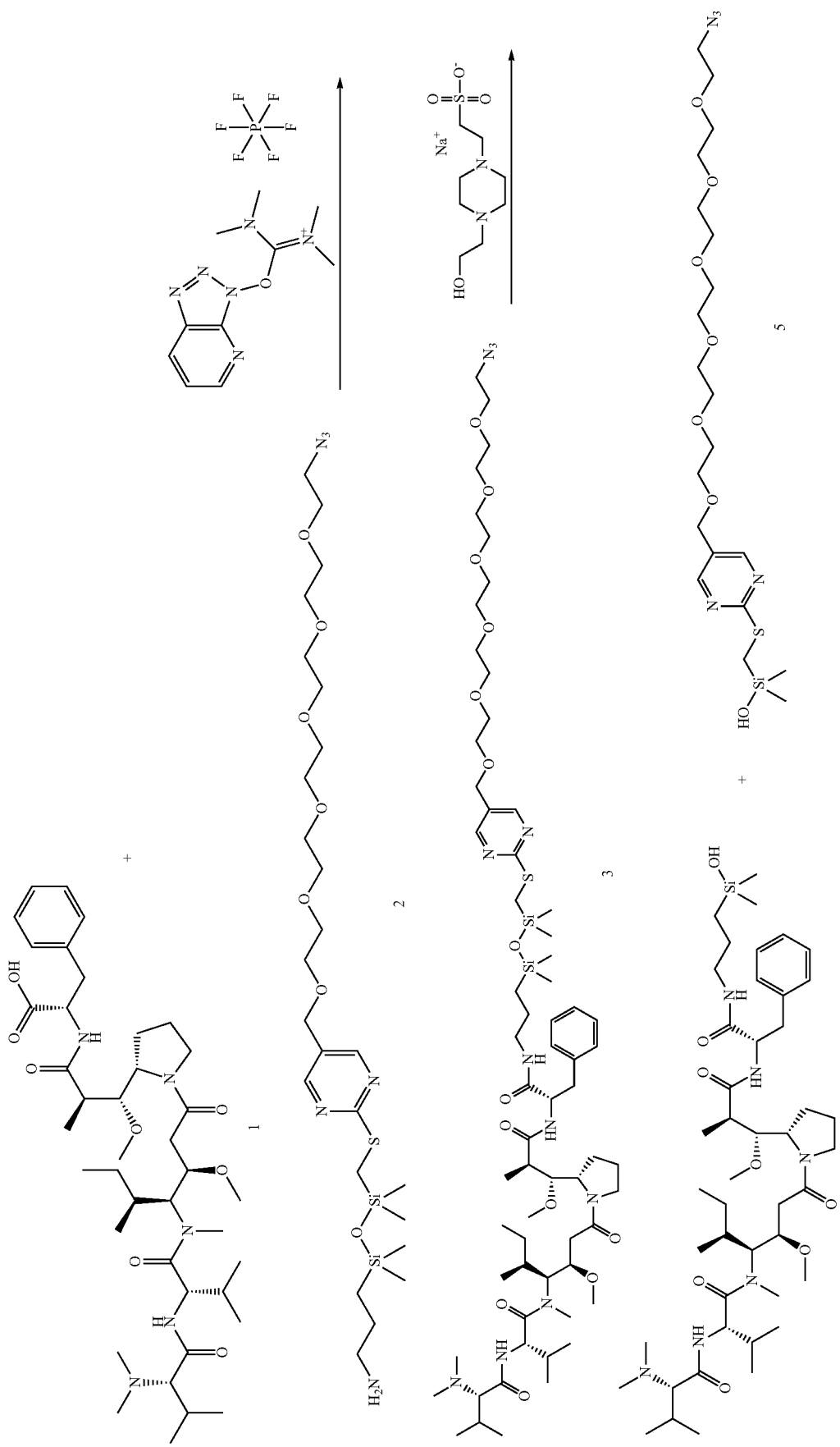

(S)—N-((3R,4S,5S)-1-((S)-2-((3R,4R,7S)-7-benzyl-13-hydroxy-4,13-dimethyl-5,8-dioxo-2-oxa-6,9-diaza-13-silatetradecan-3-yl)pyrrolidin-1-yl)-3-methoxy-5-methyl-1-oxoheptan-4-yl)-2-((S)-2-(dimethylamino)-3-methylbutanamido)-N,3-dimethylbutanamide [Example 5]

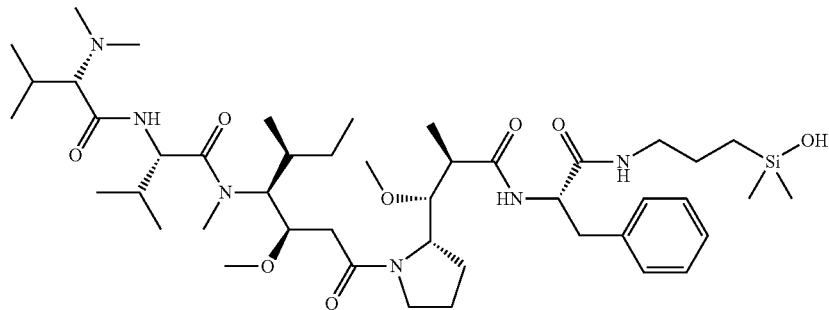

A solution of (S)—N-((3R,4S,5S)-1-((S)-2-((10S,13R,14R)-1-((5-(19-azido-2,5,8,11,14,17-hexaoxanonadecyl)pyrimidin-2-yl)thio)-10-benzyl-2,2,4,4,13-pentamethyl-9,12-dioxo-3,15-dioxa-8,11-diaza-2,4-disilahexadecan-14-yl)pyrrolidin-1-yl)-3-methoxy-5-methyl-1-oxoheptan-4-yl)-2-((S)-2-(dimethylamino)-3-methylbutanamide (26 mg, 0.019 mmol) in DMSO (1.00 ml) was charged with 50 mM HEPES Buffer (pH 5.0) (0.500 ml, 0.025 mmol) and 1 drop of 6 N HCl and stirred at rt for 3 h. The crude was directly injected onto the HPLC resulting in 7 mg, 32.5% yield of the title compound as a white solid.
$^1$H NMR (DMSO-d$_6$, 400 MHz): δ (ppm) 8.29 (br d, J=9.1 Hz, 1H), 8.02-8.33 (m, 1H), 7.95 (br t, J=5.7 Hz, 1H), 7.88 (br t, J=5.7 Hz, 1H), 7.18-7.30 (m, 4H), 7.09-7.17 (m, 1H), 4.63-4.75 (m, 1H), 4.49-4.62 (m, 1H), 4.42-4.48 (m, 1H), 3.80 (dd, J=9.9, 2.0 Hz, 1H), 3.97 (br s, 1H), 3.42-3.58 (m, 3H), 3.22 (s, 3H), 3.18 (d, J=6.8 Hz, 3H), 2.95-3.11 (m, 7H), 2.76 (br dd, J=13.5, 10.7 Hz, 1H), 2.61-2.68 (m, 2H), 2.36-2.46 (m, 1H), 2.24-2.34 (m, 2H), 2.20 (d, J=8.8 Hz, 6H), 1.64-2.05 (m, 6H), 1.24-1.56 (m, 6H), 1.03 (br d, J=6.6 Hz, 2H), 0.80-0.99 (m, 16H), 0.66-0.79 (m, 6H), 0.41 (dt, J=12.4, 4.4 Hz, 2H), −0.02 (s, 6H); MS (ES$^+$): m/z=861.52, 862.65 [M+H]$^+$; LCMS: t$_R$=1.68 min [polar_3 min_1500].

(S)—N-((3R,4S,5S)-1-((S)-2-((3R,4R,7S)-7-benzyl-13-hydroxy-4,13-dimethyl-5,8-dioxo-2-oxa-6,9-diaza-13-silatetradecan-3-yl)pyrrolidin-1-yl)-3-methoxy-5-methyl-1-oxoheptan-4-yl)-2-((S)-2-(dimethylamino)-3-methylbutanamido)-N,3-dimethylbutanamide [3]

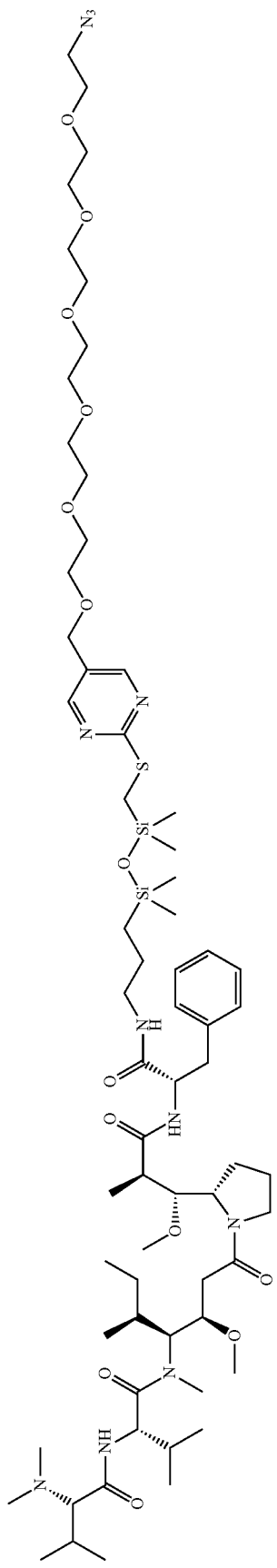

A solution of (S)-1-(((S)-1-(((3R,4S,5S)-1-((S)-2-((1R,2R)-3-(((S)-1-carboxy-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-N,N,3-trimethyl-1-oxobutan-2-aminium, 2,2,2-trifluoroacetate salt (387 mg, 0.450 mmol) in DMF (5.00 ml) was cooled to 0° C. and charged with DIEA (0.327 ml, 1.873 mmol) and a solution of HATU (171 mg, 0.450 mmol) in DMF (2.00 ml) and stirred at 0° C. for 30 min. The reaction mixture was charged with a solution of 2-(4-(3-(3-aminopropyl)-1,1,3,3-tetramethyldisiloxanyl)phenyl)-N-(17-azido-3,6,9,12,15-pentaoxaheptadecyl)acetamide (230 mg, 0.375 mmol) in DMF (2.00 ml) then allowed to warm to rt and stirred at rt for an additional 16 h. The reaction mixture was partitioned between DCM (30 mL) and H$_2$O (20 mL) and separated. The aqueous was extracted with DCM (5×15 mL) and the combined organic was washed with water (2×20 mL) brine (1×30 mL), dried over Na$_2$SO$_4$, filtered and concentrated in vacuo resulting in a crude oil which was purified by chromatography on silica gel [ISCO Combi-Flash, eluting with 100% DCM to 8% of a 10% solution of 7N NH$_3$ in MeOH in methanol] resulting in 420 mg, 84% yield of the title compound as a white foam solid. $^1$H NMR (CDCl$_3$, 400 MHz): δ (ppm) 7.32-7.43 (m, 2H), 7.06-7.30 (m, 8H), 6.78-6.96 (m, 1H), 6.71 (br d, J=4.8 Hz, 1H), 6.58 (br d, J=7.8 Hz, 1H), 6.31-6.47 (m, 1H), 4.74 (br dd, J=9.0, 6.9 Hz, 1H), 4.56-4.68 (m, 1H), 3.99 (br d, J=5.6 Hz, 1H), 3.80 (br d, J=8.6 Hz, 1H), 3.45-3.65 (m, 23H), 3.36 (dt, J=17.3, 5.1 Hz, 6H), 3.27 (d, J=18.2 Hz, 5H), 2.94-3.13 (m, 7H), 2.18-2.31 (m, 7H), 1.85-2.11 (m, 4H), 1.71-1.83 (m, 2H), 1.24-1.38 (m, 3H), 1.04-1.16 (m, 3H), 0.84-1.00 (m, 16H), 0.71-0.81 (m, 4H), 0.33-0.41 (m, 2H), 0.26 (s, 6H), −0.05-0.04 (m, 6H); MS (ES$^+$): m/z=1341.95 [M+H]$^+$; LCMS: t$_R$=2.03 min [nonpolar_3 min].

Example 6: ((2R,3R)-3-((S)-1-((3R,4S,5S)-4-((S)-2-((S)-2-(4-(hydroxydimethylsilyl)-N-methylbutanamido)-3-methylbutanamido)-N,3-dimethylbutanamido)-3-methoxy-5-methylheptanoyl)pyrrolidin-2-yl)-3-methoxy-2-methylpropanoyl)-L-phenylalanine The title compound was prepared according to the scheme shown below.

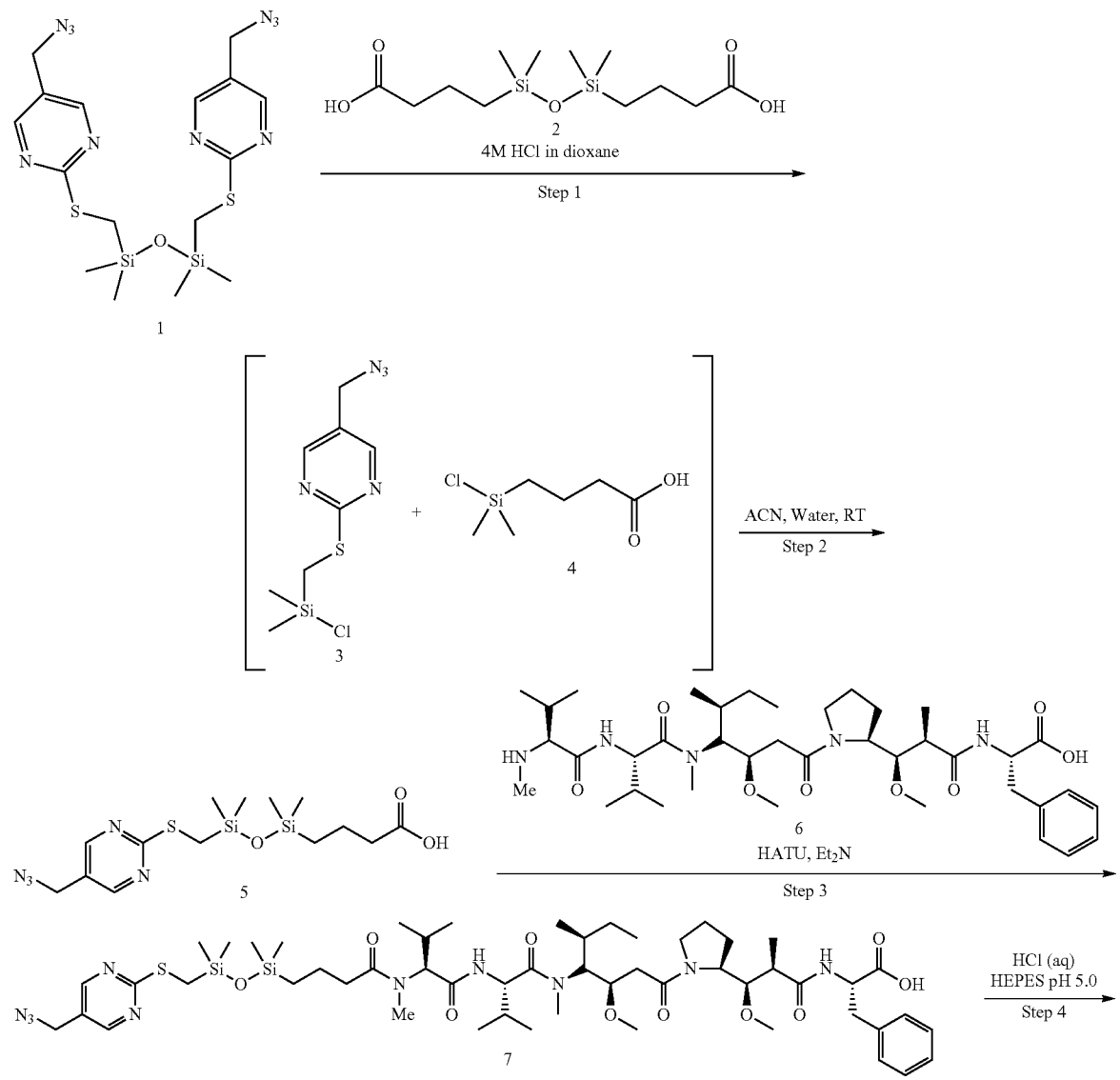

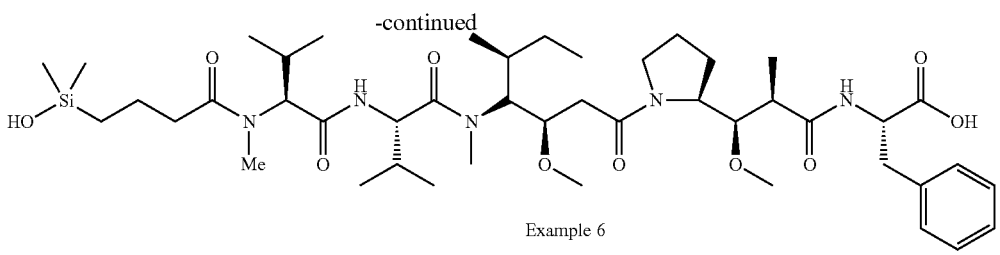

Example 6

Steps 1 and 2. Synthesis of 4-(3-(((5-(Azidomethyl)pyrimidin-2-yl)thio)methyl)-1,1,3,3-tetramethyldisiloxanyl)butanoic acid [5]

A solution of 1,3-bis(((5-(azidomethyl)pyrimidin-2-yl)thio)methyl)-1,1,3,3-tetramethyldisiloxane 1 (1.5 g, 3.048 mmol; WO2016183359) and 4,4'-(1,1,3,3-tetramethyldisiloxane-1,3-diyl)dibutyric acid 2 (932 mg, 3.048 mmol) in 4M HCl in dioxane (30 mL) was stirred at room temperature for 1 h. The reaction mixture was concentrated in vacuo resulting in the crude intermediate 3 and 4. The intermediate 3 and 4 was dissolved in acetonitrile (200 mL) and followed by addition of water (0.11 mL, 6.097 mmol) and DIPEA (3.09 mL, 18.29 mmol) and stirred at room temperature for another 1 h. The reaction mixture was concentrated in vacuo resulting in the crude compound which was purified by CombiFlash column chromatography eluting with 10-30% ethyl acetate in n-hexane to afford 1.2 g (50% yield) of the title compound as colourless oil. $^1$H NMR (400 MHz, DMSO-d$_6$) δ=11.95 (s, 1H), 8.67 (s, 2H), 4.50 (s, 2H), 2.39-2.44 (m, 2H), 2.22 (dt, J=3.67, 7.21 Hz, 2H), 1.48-1.60 (m, 2H), 0.52 (td, J=4.59, 12.35 Hz, 2H), 0.18 (s, 6H), 0.06 (s, 6H).

Step 3. Synthesis of ((2R,3R)-3-((S)-1-((3R,4S,5S)-4-((S)-2-((S)-2-(4-(3-(((5-(azidomethyl)pyrimidin-2-yl)thio)methyl)-1,1,3,3-tetramethyldisiloxaneyl)-N-methylbutanamido)-3-methylbutanamido)-N,3-dimethylbutanamido)-3-methoxy-5-methylheptanoyl)pyrrolidin-2-yl)-3-methoxy-2-methylpropanoyl)-L-phenylalanine A solution of 4-(3-(((5-(azidomethyl)pyrimidin-2-yl)thio)methyl)-1,1,3,3-tetramethyldisiloxanyl)butanoic acid (16.38 mg, 0.041 mmol) and HATU (15.58 mg, 0.041 mmol) in DMF (1997 µl) was stirred for 15 min then charged with a solution of (S)-2-((2R,3R)-3-((S)-1-(3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid (20 mg, 0.027 mmol) and TEA (6.47 µL, 0.046 mmol) in DMF (1331 µL). After stirring at rt for 7 hrs, the reaction was diluted with DCM (20 mL) and washed with water (2×10 mL). The filtrate was washed with brine, dried over MgSO$_4$, filtered, and concentrated. This material was carried on to the hydrolysis step. MS (ES$^+$): m/z=1,113.74 [M+H]$^+$; LCMS: t$_R$=2.77 min.

Step 4. ((2R,3R)-3-((S)-1-((3R,4S,5S)-4-((S)-2-((S)-2-(4-(hydroxydimethylsilyl)-N-methylbutanamido)-3-methylbutanamido)-N,3-dimethylbutanamido)-3-methoxy-5-methylheptanoyl)pyrrolidin-2-yl)-3-methoxy-2-methylpropanoyl)-L-phenylalanine The crude product from Step 3 was dissolved in DMSO (0.500 mL) to give a white suspension. Then 2 drops of 6N aq HCl (4.55 µL, 0.027 mmol) was added. The reaction became clear in 5 min. The reaction was monitored by LCMS at 254 and 230 nm. After 1 hr and 30 min, the reaction was diluted with 0.5 mL of DMSO and passed through an ISCO solid loading cartridge. The filtrate was injected onto the prep HPLC. Using Prep HPLC with Gradient 1, (S)-2-((2R,3R)-3-((S)-1-((8S,11S,14S,15R)-14-((S)-sec-butyl)-2-hydroxy-8,11-diisopropyl-15-methoxy-2,7,13-trimethyl-6,9,12-trioxo-7,10,13-triaza-2-silaheptadecan-17-oyl)pyrrolidin-2-yl)-3-methoxy-2-methylpropanamido)-3-phenylpropanoic acid (8.00 mg, 9.13 µmol, 33.4% yield) was obtained as a white solid. MS (ES$^+$): m/z=858.63 [M−OH]$^+$; LCMS: t$_R$=2.27 min [polar_3 min_1500, detection at 230 nm]. $^1$H NMR (400 MHz, DMSO-d$_6$) δ ppm 7.09-7.33 (m, 5H) 5.26-5.38 (m, 1H) 4.29-4.78 (m, 3H) 3.69-4.05 (m, 2H) 3.40-3.62 (m, 2H) 3.12-3.30 (m, 10H) 2.63-3.12 (m, 9H) 2.09-2.46 (m, 7H) 1.70-2.01 (m, 4H) 1.40-1.62 (m, 3H) 1.17-1.39 (m, 3H) 0.97-1.11 (m, 2H) 0.67-0.96 (m, 21H) 0.44-0.56 (m, 2H) 0.01-0.07 (m, 2H) −0.06-0.01 (m, 4H). Rotamers were observed in $^1$H NMR.

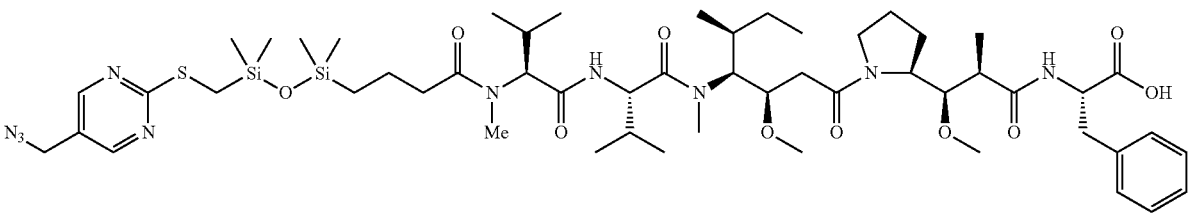 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCC[Si](C)(C)O[Si](C)(C)CSc1ncc(CN=[N+]=[N-])cn1)C(C)C]

Example 7: (S)-4-Ethyl-4-hydroxy-11-(2-(hydroxy-dimethylsilyl)ethyl)-1,12-dihydro-14H-pyrano[3',4':6,7]indolizino[1,2-b]quinoline-3,14(4H)-dione

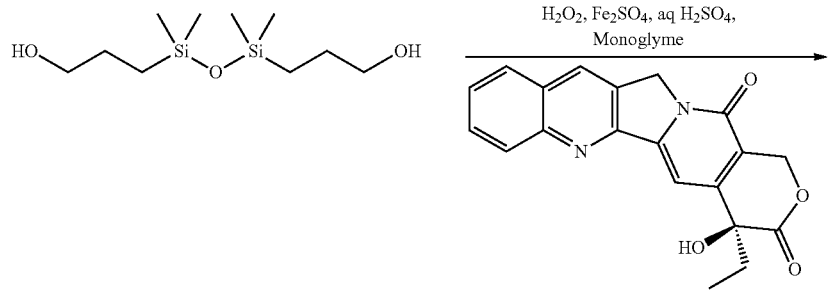

Iron (II) sulfate heptahydrate (24.0 mg, 0.055 mmol) was dissolved in 30% aqueous sulfuric acid (148 μl, 0.086 mmol) at rt. After stirring for 20 minutes at room temperature, a solution of 3,3'-(1,1,3,3-tetramethyldisiloxane-1,3-diyl)bis(propan-1-ol) (53.9 mg, 0.215 mmol; prepared according to Frampton, Mark B., Izabela Subczynska, and Paul M. Zelisko. "Biocatalytic synthesis of silicone polyesters." *Biomacromolecules* 11.7 (2010): 1818-1825) in 1,2-dimethoxyethane (598 μl) was then added dropwise into the flask and the whole was stirred for 15 minutes. To the above mixture was slowly added over a 30 minute time period a solution containing camptothecin (30.0 mg, 0.086 mmol), 30% aqueous sulfuric acid (1656 μl, 0.086 mmol), and 30% aqueous hydrogen peroxide (77 μl, 0.689 mmol). The solution was stirred for one hour at room temperature and another 231 uL of 30% aqueous hydrogen peroxide was added over a 30 minute time period. After 5 hrs, LCMS showed product formation. After 22 hrs, the reaction mixture was cooled to 0° C. and neutralized with saturated aq NaHCO$_3$. The mixture was filtered through an ISCO silica gel dry loading cartridge. The filtrate was spun down and the supernatant was injected onto the prep-HPLC (7×5 mL, HPLC method 1B). Fractions containing the product were collected and the solvent was removed on the lyophilizer to give (S)-4-ethyl-4-hydroxy-11-(2-(hydroxydimethylsilyl)ethyl)-1H-pyrano[3',4':6,7]indolizino[1,2-b]quinoline-3,14(4H,12H)-dione (3 mg, 6.66 μmol, 7.73% yield) as a white solid. $^1$H NMR (400 MHz, DMSO-d$_6$) δ ppm 8.16-8.25 (m, 2H) 7.86 (t, J=7.30 Hz, 1H) 7.75 (ddd, J=8.40, 7.01, 1.26 Hz, 1H) 7.33 (s, 1H) 6.53 (s, 1H) 5.68 (s, 1H) 5.44 (s, 2H) 5.33 (s, 2H) 3.37-3.50 (m, 1H) 3.26-3.30 (m, 1H) 3.14-3.24 (m, 2H) 2.52-2.60 (m, 2H) 1.82-1.93 (m, 2H) 1.23 (s, 1H) 0.84-0.96 (m, 5H) 0.06-0.15 (m, 6H). 2D NMRs confirmed the title compound; MS (ES$^+$): m/z=[M+1]=451.01; LCMS: t$_R$=1.98 min [polar_3 min_1500].

Example 8: (S)-4-Ethyl-4,9-dihydroxy-11-(2-(hydroxydimethylsilyl)ethyl)-1,12-dihydro-14H-pyrano[3',4':6,7]indolizino[1,2-b]quinoline-3,14(4H)-dione The title compound can be prepared according to the scheme shown below.

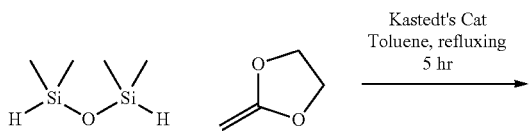

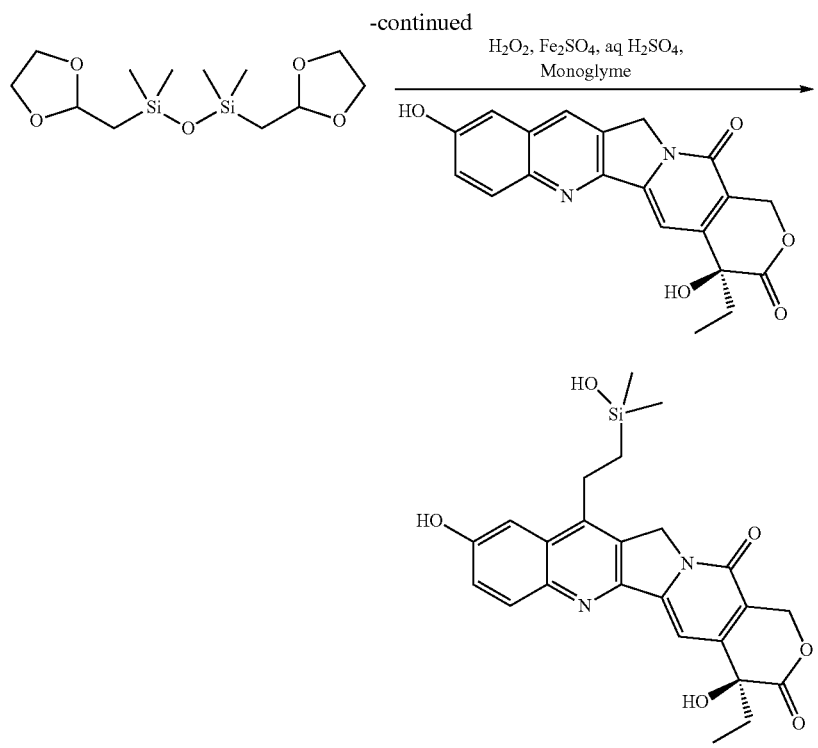
Example 9: (S,E)-4-ethyl-4,9-dihydroxy-11-(2-(hydroxydimethylsilyl)vinyl)-1,12-dihydro-14H-pyrano[3',4':6,7]indolizino[1,2-b]quinoline-3,14(4H)-dione
The title compound can be prepared according to the scheme shown below.
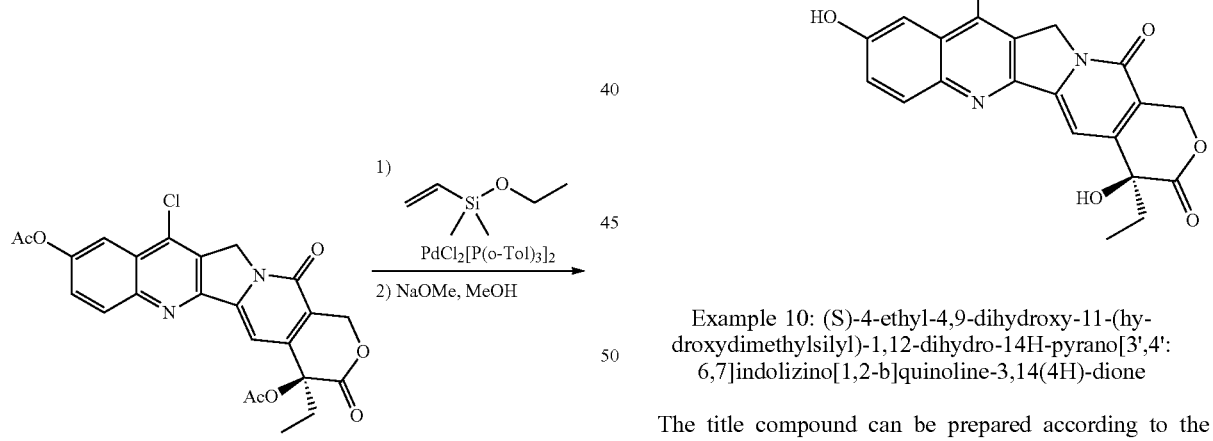
Example 10: (S)-4-ethyl-4,9-dihydroxy-11-(hydroxydimethylsilyl)-1,12-dihydro-14H-pyrano[3',4':6,7]indolizino[1,2-b]quinoline-3,14(4H)-dione
The title compound can be prepared according to the scheme shown below.
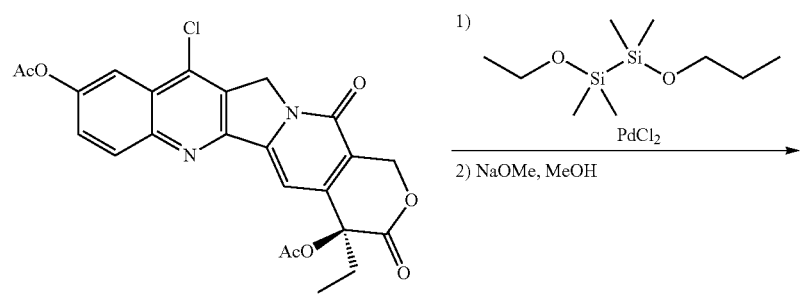

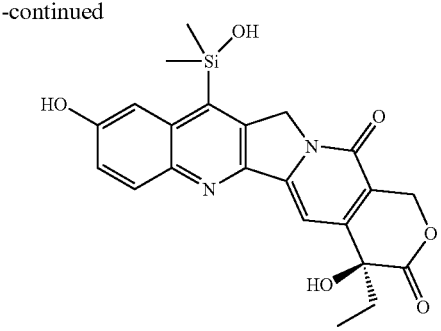

Example 12: Scheme for the Preparation of Example 12

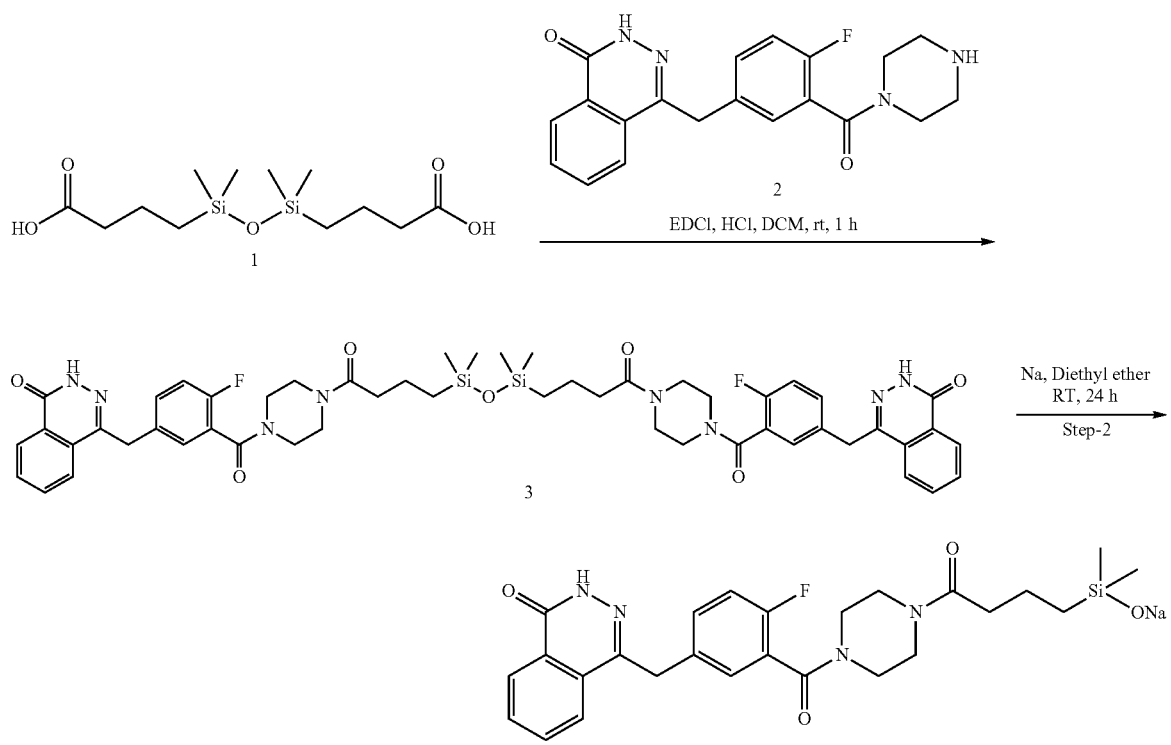

Sodium (4-(4-(2-fluoro-5-((4-oxo-3,4-dihydrophthalazin-1-yl)methyl)benzoyl)piperazin-1-yl)-4-oxobutyl)dimethylsilanolate [Example 12]

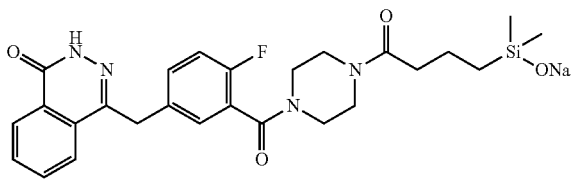

A solution of 4,4'-(((4,4'-(4,4'-(1,1,3,3-tetramethyldisiloxane-1,3-diyl)bis(butanoyl)bis(piperazine-4,1-diyl-1-carbonyl)bis(4-fluoro-3,1-phenylene))bis(methylene))bis (phthalazin-1(2H)-one) (200 mg, 0.1993 mmol) in diethyl ether (5 mL) was charged with sodium metal (5 mg, 0.1993 mmol) at room temperature and stirred for 24 h. The diethyl ether layer was decanted and the resulting solution was diluted with water. The precipitate was filtered and the collected filtrate was lyophilized to afford 100 mg, 94% yield of the title compound as an off white solid. $^1$H NMR (400 MHz, DMSO-d$_6$) δ=8.07 (d, J=6.48 Hz, 1H), 7.97-8.04 (m, 1H), 7.57-7.64 (m, 1H), 7.41-7.52 (m, 3H), 7.34-7.39 (m, 1H), 7.13 (d, J=7.58 Hz, 1H), 4.22 (d, J=8.68 Hz, 2H), 3.37-3.51 (m, 4H), 3.17-3.33 (m, 4H), 2.24-3.00 (m, 2H), 1.44-1.55 (m, 2H), 0.18-0.25 (m, 2H), −0.28 (br. s, 6H); $^1$H NMR (400 MHz, D$_2$O) δ 8.11-8.15 (m, 1H), 7.63-7.74 (m, 3H), 7.34-7.42 (m, 1H), 7.02-7.11 (m, 2H), 4.36 (s, 2H), 3.50-3.67 (m, 4H), 3.07-3.25 (m, 4H), 2.38 (t, J=7.09 Hz, 1H), 2.29 (t, J=7.34 Hz, 1H), 1.45-1.58 (m, 2H), 0.44-0.52 (m, 2H), −0.02 (s, 3H), −0.02 (s, 3H); MS (ES$^+$): m/z=533.00 [M+H]$^+$; LCMS: t$_R$=1.75 min.

4,4'-(((4,4'-(4,4'-(1,1,3,3-tetramethyldisiloxane-1,3-diyl)bis(butanoyl))bis(piperazine-4,1-diyl-1-carbonyl))bis(4-fluoro-3,1-phenylene))bis(methylene))bis(phthalazin-1(2H)-one): [3]

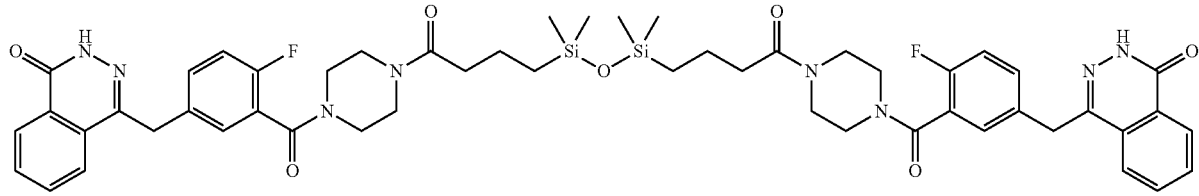 [SMILES: C[Si](C)(CCCC(=O)N1CCN(C(=O)c2cc(Cc3n[nH]c(=O)c4ccccc34)ccc2F)CC1)O[Si](C)(C)CCCC(=O)N1CCN(C(=O)c2cc(Cc3n[nH]c(=O)c4ccccc34)ccc2F)CC1]

A solution of 4,4'-(1,1,3,3-tetramethyldisiloxane-1,3-diyl) dibutyric acid (250 mg, 0.816 mmol) in dichlormethane (5 mL) was charged EDCI-HCl (396 mg, 2.042 mmol) and 4-(4-fluoro-3-(piperazine-1-carbonyl)benzyl)phthalazin-1 (2H)-one (598 mg, 1.633 mmol) at room temperature and stirred for 1 h. After completion of the reaction (monitored by TLC), water (5 mL) was added in the reaction mixture and organic layer was separated to obtain crude compound. The crude compound was purified by CombiFlash chromatography using 1-10% MeOH in DCM to obtain 286 mg, 38% yield of the title compound as an off white solid. $^1$H NMR (400 MHz, DMSO-d$_6$): δ 12.57 (s, 2H), 8.55 (d, J=10.27 Hz, 2H), 8.23 (d, J=7.83 Hz, 1H), 7.92-7.96 (m, 1H), 7.84-7.89 (m, 2H), 7.78-7.83 (m, 2H), 7.38-7.44 (m, 2H), 7.33 (br. s, 2H), 7.21 (t, J=8.80 Hz, 2H), 4.44 (s, 2H), 4.30 (s, 2H), 3.49-3.62 (m, 14H), 3.33-3.38 (m, 4H), 3.08-3.18 (m, 2H), 2.25-2.38 (m, 4H), 1.44-1.55 (m, 2H), 0.46-0.54 (m, 2H), 0.14 (br. s, 3H), 0.13 (br. s, 3H), 0.04 (br. s, 3H), 0.03 (br. s, 3H); MS (ES$^+$): =493.20 [Monomer M−18]$^+$; LCMS: t$_R$=0.792 min.

Example 13: Scheme for the Preparation of Example 13

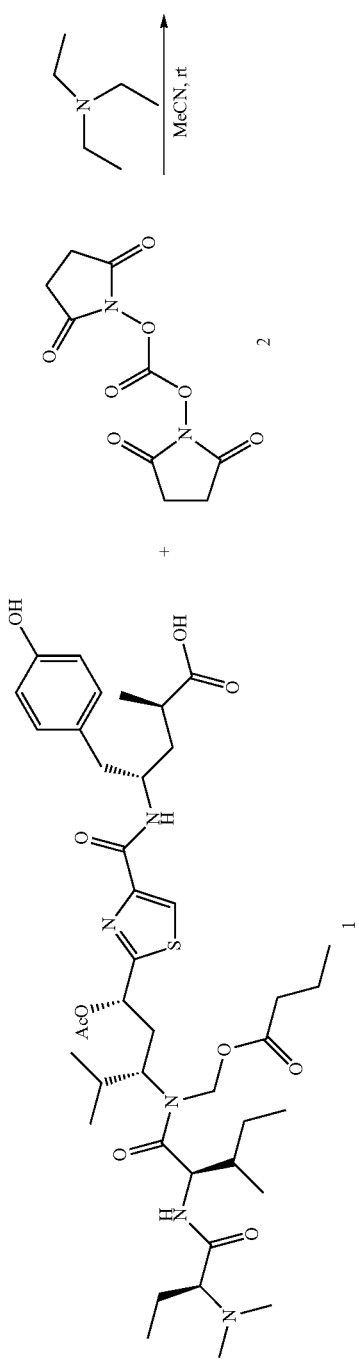

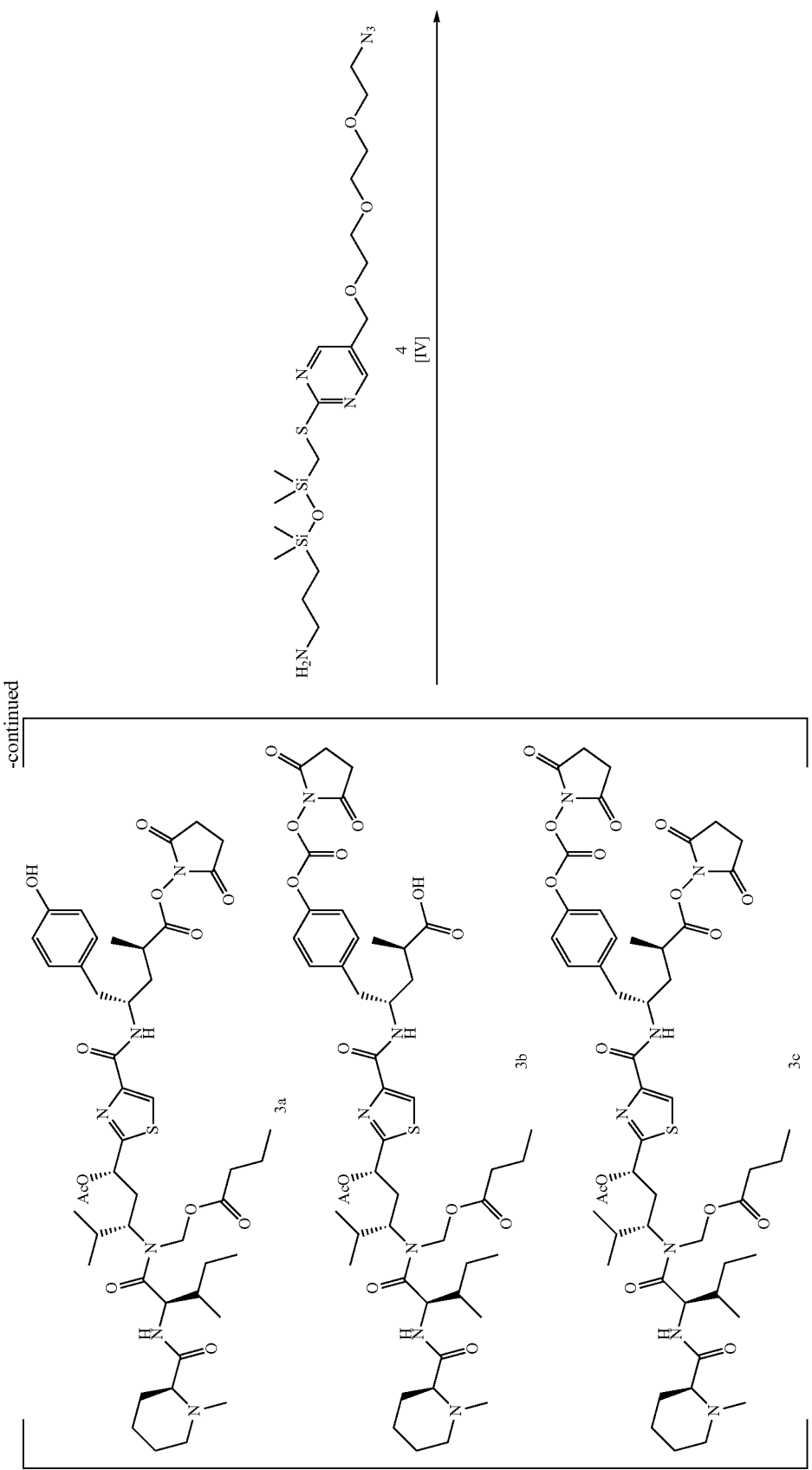

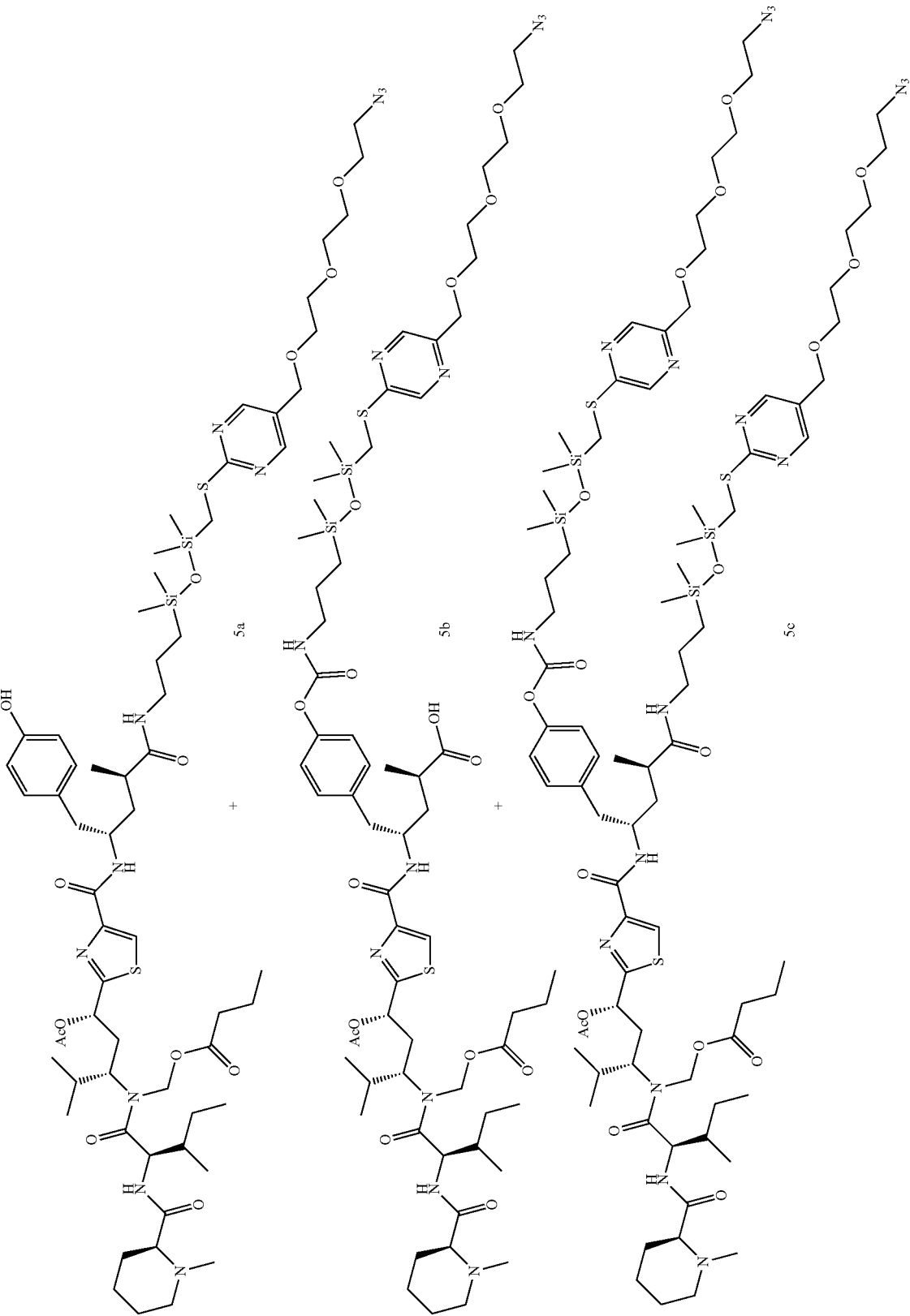

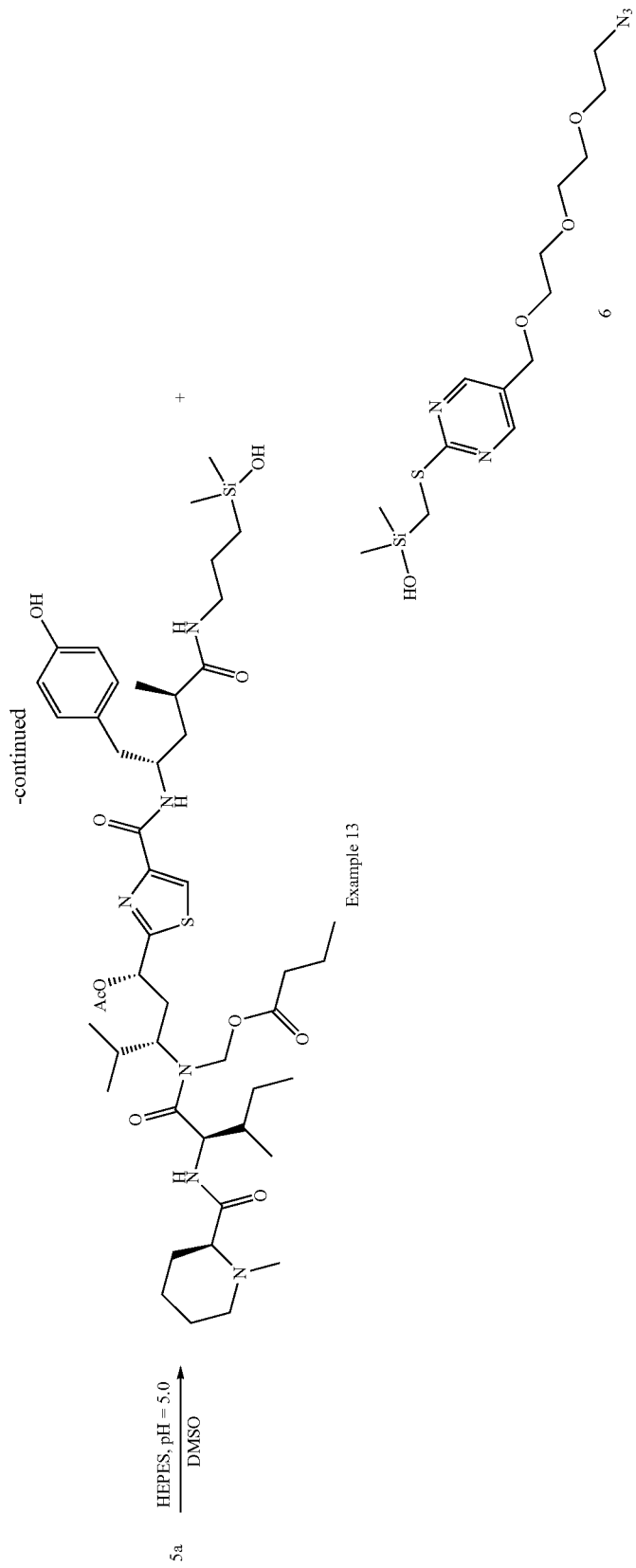

((2R,3S)—N-((1S,3S)-1-acetoxy-1-(4-(((2S,4R)-5-((3-(hydroxydimethylsilyl)propyl)amino)-1-(4-hydroxyphenyl)-4-methyl-5-oxopentan-2-yl)carbamoyl)thiazol-2-yl)-4-methylpentan-3-yl)-3-methyl-2-((S)-1-methylpiperidine-2-carboxamido)pentanamido)methyl butyrate [Example 13]

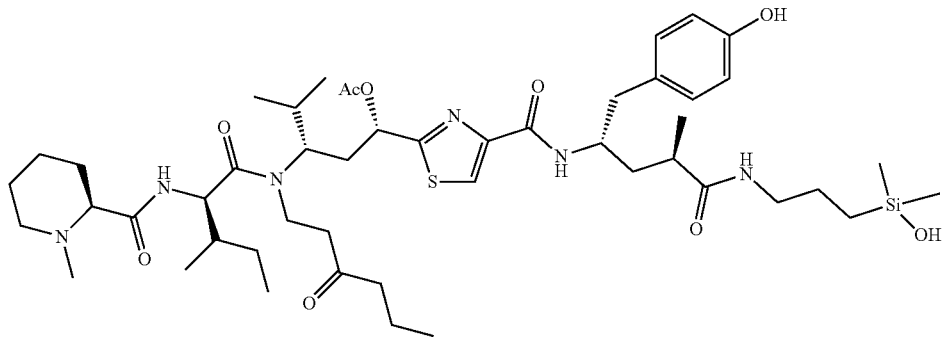 [SMILES: CCCC(=O)CCN(C(=O)[C@H](NC(=O)[C@@H]1CCCCN1C)C(C)CC)[C@@H](C[C@H](OC(C)=O)c1nc(C(=O)N[C@H](Cc2ccc(O)cc2)C[C@@H](C)C(=O)NCCC[Si](C)(C)O)cs1)C(C)C]

A solution of ((2R,3S)—N-((1S,3S)-1-acetoxy-1-(4-(((2S,4R)-5-((3-(3-(((5-((2-(2-(2-azidoethoxy)ethoxy)ethoxy)methyl)pyrimidin-2-yl)thio)methyl)-1,1,3,3-tetramethyldisiloxanyl)propyl)amino)-1-(4-hydroxyphenyl)-4-methyl-5-oxopentan-2-yl)carbamoyl)thiazol-2-yl)-4-methylpentan-3-yl)-3-methyl-2-((S)-1-methylpiperidine-2-carboxamido)pentanamido)methyl butyrate (8.00 mg, 6.08 μmol) in DMSO (500 μL) and was charged with 50 mM HEPES Buffer (pH 5.0) (122 μL, 6.08 μmol) and 10 uL of 6N HCl and stirred at rt for 2 h. The crude reaction mixture was then purified by Prep HPLC [PREP2_AmmBicarb_pH7.4_Method1B] resulting in 5.1 mg, 89% yield of the title compound as a white solid. $^1$H NMR (DMSO-$d_6$, 700 MHz): δ (ppm) 8.19 (s, 1H), 7.93 (br d, J=8.6 Hz, 1H), 7.80 (br d, J=9.0 Hz, 1H), 7.77 (br t, J=5.8 Hz, 1H), 6.96 (d, J=8.4 Hz, 2H), 6.61 (d, J=8.4 Hz, 2H), 6.19-6.30 (m, 1H), 5.74 (dd, J=11.5, 1.8 Hz, 1H), 5.27 (d, J=12.0 Hz, 1H), 4.42 (br t, J=9.0 Hz, 1H), 3.99-4.06 (m, 1H), 3.01-3.07 (m, 1H), 2.94 (br d, J=4.1 Hz, 1H), 2.80-2.85 (m, 1H), 2.69-2.74 (m, 3H), 2.66 (br dd, J=13.7, 6.1 Hz, 4H), 2.30-2.39 (m, 1H), 2.18-2.29 (m, 1H), 2.12 (s, 3H), 2.05 (s, 3H), 1.90-1.97 (m, 1H), 1.69-1.84 (m, 1H), 1.34-1.46 (m, 5H), 1.34-1.67 (m, 10H), 1.24 (br s, 2H), 1.15 (s, 4H), 1.04-1.14 (m, 1H), 0.97 (t, J=6.2 Hz, 6H), 0.84-0.88 (m, 1H), 0.78-0.84 (m, 10H), 0.68 (br d, J=6.5 Hz, 2H), 0.41-0.48 (m, 1H), 0.07 (d, J=1.3 Hz, 3H), −0.03-0.01 (m, 6H); MS (ES$^+$): m/z=945.92 [M+H]$^+$; LCMS: $t_R$=1.84 min [polar_3 min_1500].

((2R,3S)—N-((1S,3S)-1-acetoxy-1-(4-(((2S,4R)-5-((3-(3-(((5-((2-(2-(2-azidoethoxy)ethoxy) ethoxy)methyl)pyrimidin-2-yl)thio)methyl)-1,1,3,3-tetramethyldisiloxaneyl)propyl)amino)-1-(4-hydroxyphenyl)-4-methyl-5-oxopentan-2-yl)carbamoyl)thiazol-2-yl)-4-methylpentan-3-yl)-3-methyl-2-((S)-1-methylpiperidine-2-carboxamido)pentanamido)methyl butyrate [5a]

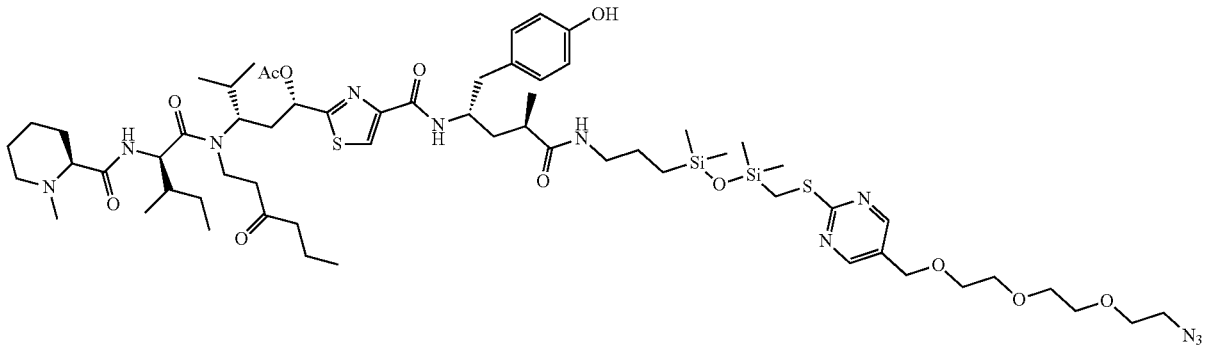 [SMILES: CCCC(=O)CCN(C(=O)[C@H](NC(=O)[C@@H]1CCCCN1C)C(C)CC)[C@@H](C[C@H](OC(C)=O)c1nc(C(=O)N[C@H](Cc2ccc(O)cc2)C[C@@H](C)C(=O)NCCC[Si](C)(C)O[Si](C)(C)CSc2ncc(COCCOCCOCCN=[N+]=[N-])cn2)cs1)C(C)C]

A solution of (2R,4S)-4-(2-((1S,3S)-1-acetoxy-3-((2R,3S)—N-((butyryloxy)methyl)-3-methyl-2-((S)-1-methylpiperidine-2-carboxamido)pentanamido)-4-methylpentyl)thiazole-4-carboxamido)-5-(4-hydroxyphenyl)-2-methylpentanoic acid (8.00 mg, 9.64 μmol) in MeCN (200

μL) was charged with bis(2,5-dioxopyrrolidin-1-yl) carbonate (3.70 mg, 0.014 mmol) and 100 mM TEA in MeCN (116 μL, 0.012 mmol) and stirred for 30 min. From LCMS there was a mixture of active ester and carbonate and bis activated. The reaction was then charged with ((2R,3S)—N-((1S,3S)-1-acetoxy-1-(4-(((2S,4R)-5-((3-(3-(((5-((2-(2-(2-azidoethoxy)ethoxy)ethoxy) methyl)pyrimidin-2-yl)thio) methyl)-1,1,3,3-tetramethyldisiloxanyl)propyl)amino)-1-(4-hydroxyphenyl)-4-methyl-5-oxopentan-2-yl)carbamoyl) thiazol-2-yl)-4-methylpentan-3-yl)-3-methyl-2-((S)-1-methylpiperidine-2-carboxamido)pentanamido)methyl butyrate (8 mg, 6.08 μmol, 63.1% yield) in MeCN (200 μL) and stirred at rt for 16 h. From LCMS the reaction was complete therefore the reaction was purified by HPLC [PREP2_AmmBicarb_pH7.4_Method1B], resulting in 8 mg, 63% yield of the title compound (product P1) as an off white foam solid.

Example 17: (14S,16S,32S,33S,2R,4S,10E,12E, 14R)-86-Chloro-14-hydroxy-85,14-dimethoxy-33,2, 7,10-tetramethyl-12,6-dioxo-7-aza-1(6,4)-oxazinana-3(2,3)-oxirana-8(1,3)-benzenacyclotetradecaphane-10,12-dien-4-yl N-(4-(hydroxydimethylsilyl) butanoyl)-N-methyl-L-alaninate

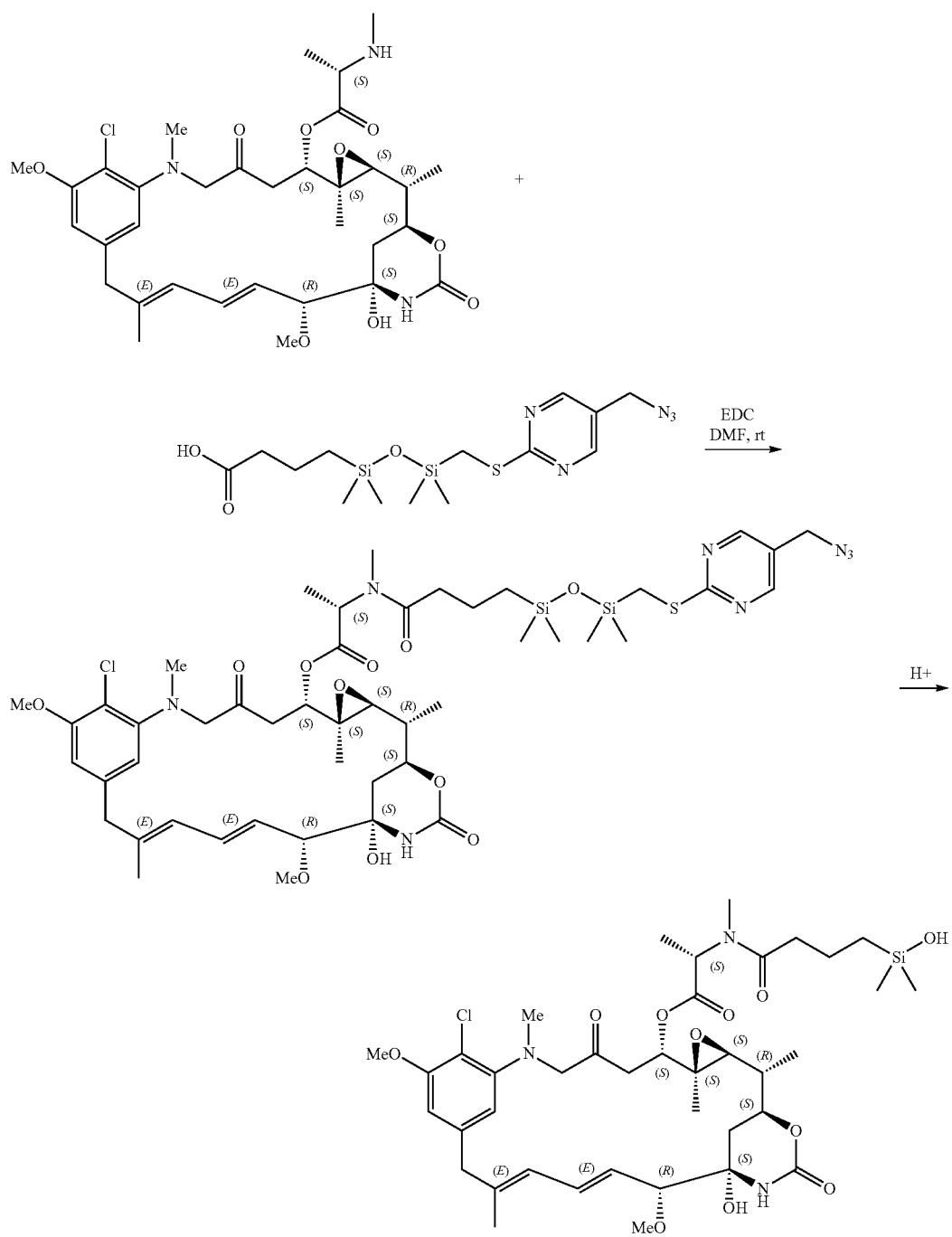

Step 1. Synthesis of (14S,16S,32S,33S,2R,4S,10E, 12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-(3-(((5-(azidomethyl)pyrimidin-2-yl)thio)methyl)-1,1,3,3-tetramethyldisiloxaneyl)butanoyl)-N-methyl-L-alaninate The title compound can be prepared with crude (14S,16S, 32S,33S,2R,4S,10E,12E,14R)-86-chloro-14-hydroxy-85, 14-dimethoxy-33,2,7,10-tetramethyl-12,6-dioxo-7-aza-1(6, 4)-oxazinana-3(2,3)-oxirana-8(1,3)-benzenacyclotetradecaphane-10,12-dien-4-ylmethyl-L-alaninate) (prepared according to CN103333179A) dissolved in DMF (1261 µL), cooled to 0° C. Addition of EDC (19.34 mg, 0.101 mmol) at 0° C. and allowing the mixture to warm to rt overnight, quenching the reaction with water, and extracting with EtOAc.

Step 2. Synthesis of (14S,16S,32S,33S,2R,4S,10E, 12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-(hydroxydimethylsilyl)butanoyl)-N-methyl-L-alaninate A solution of (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8 (1,3)-benzenacyclotetradecaphane-10,12-dien-4-yl N-(4-(3-(((5-(azidomethyl)pyrimidin-2-yl)thio)methyl)-1,1,3,3-tetramethyldisiloxaneyl)butanoyl)-N-methyl-L-alaninate (26 mg, 0.019 mmol) in DMSO (1.00 mL) was charged with 50 mM HEPES Buffer (pH 5.0) (0.500 mL, 0.025 mmol) and 1 drop of 6 N HCl and stirred at rt for 3 h. (Note upon addition of HEPES the reaction mixture became slightly cloudy but upon addition of the 1 drop of 6N HCl the reaction went homogeneous). The reaction was monitored by LCMS. Purified with HPLC.

Example 18: (14S,16S,32S,33S,2R,4S,10E,12E, 14R)-86-chloro-14-hydroxy-85,14-dimethoxy-33,2, 7,10-tetramethyl-12,6-dioxo-7-aza-1(6,4)-oxazinana-3(2,3)-oxirana-8(1,3)-benzenacyclotetradecaphane-10,12-dien-4-yl 4-(hydroxydimethylsilyl)butanoate The title compound can be prepared according to the scheme shown below.

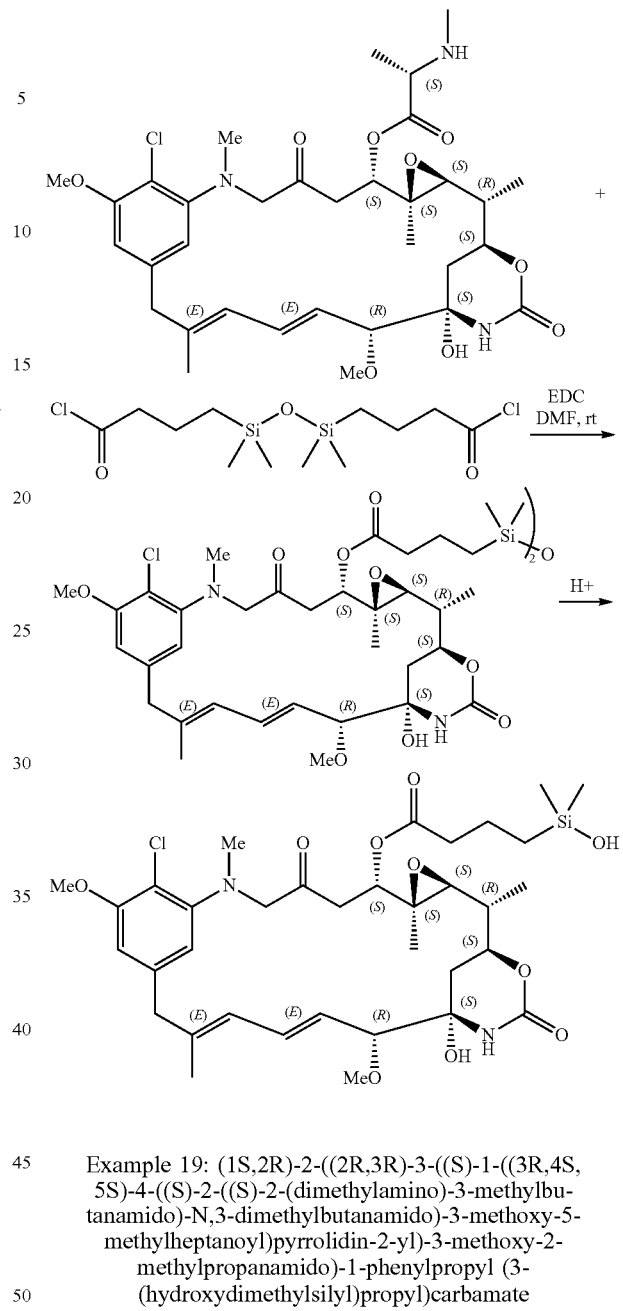

Example 19: (1S,2R)-2-((2R,3R)-3-((S)-1-((3R,4S, 5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanamido)-1-phenylpropyl (3-(hydroxydimethylsilyl)propyl)carbamate The title compound can be prepared according to the scheme shown below.

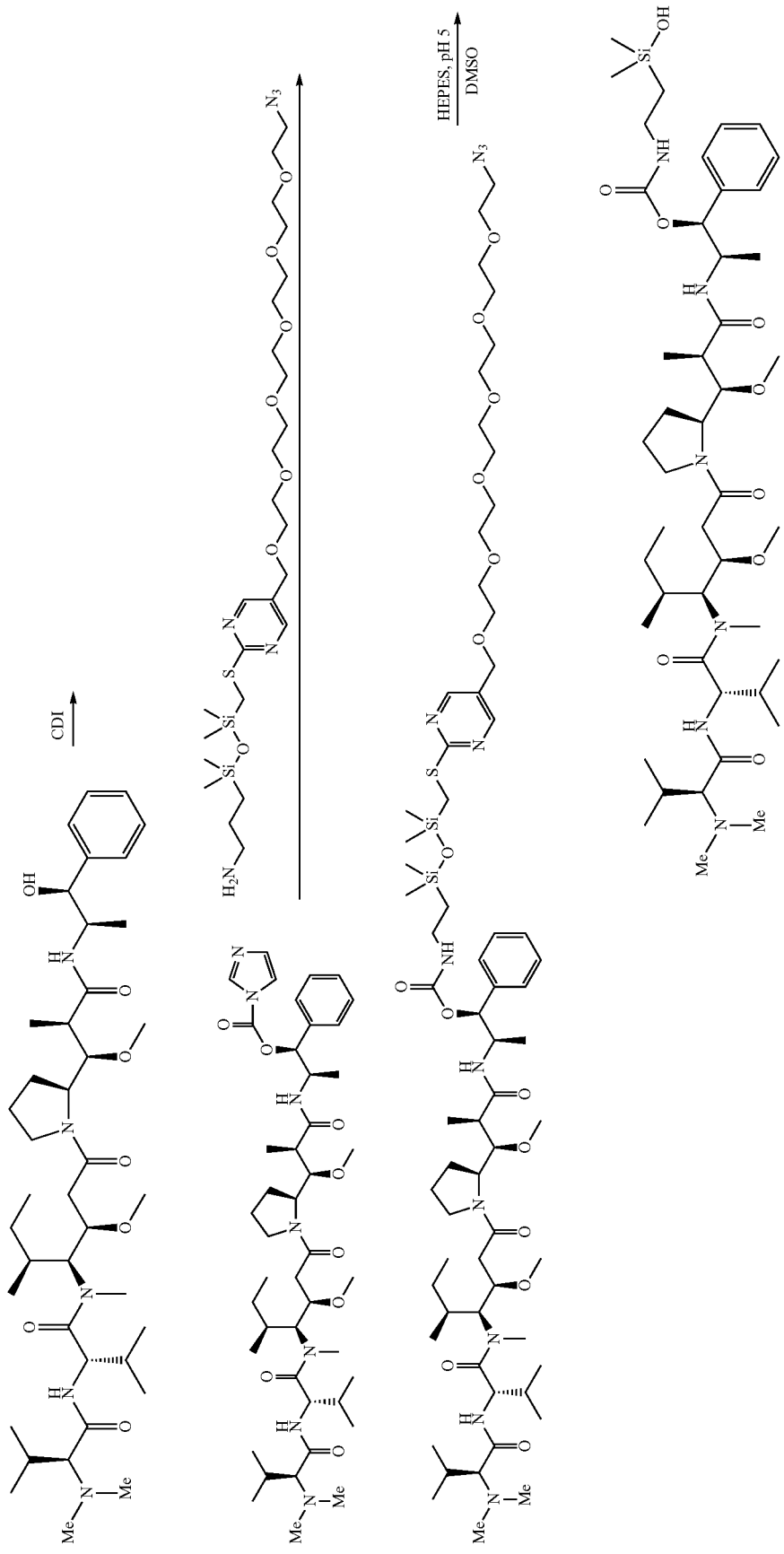

Example 20: (S)—N-((3R,4S,5S)-1-((S)-2-((7S,10R,11R)-7-benzyl-2-hydroxy-2,10-dimethyl-6,9-dioxo-12-oxa-5,8-diaza-2-silatridecan-11-yl)pyrrolidin-1-yl)-3-methoxy-5-methyl-1-oxoheptan-4-yl)-2-((S)-2-(dimethylamino)-3-methylbutanamido)-N,3-dimethylbutanamide The title compound can be prepared according to the scheme shown below.

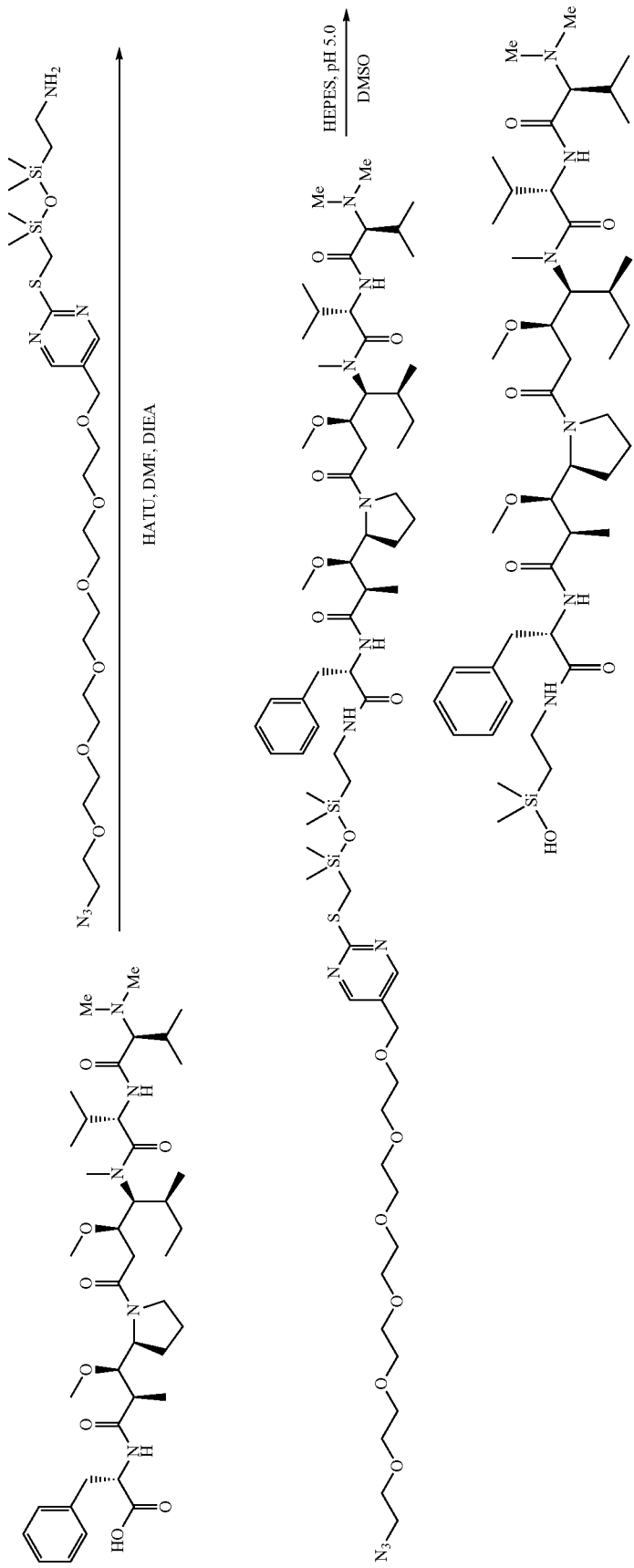

Further non-limiting silanol based payloads of the present disclosure and their mechanism of action are shown below.
mTOR Silanols:
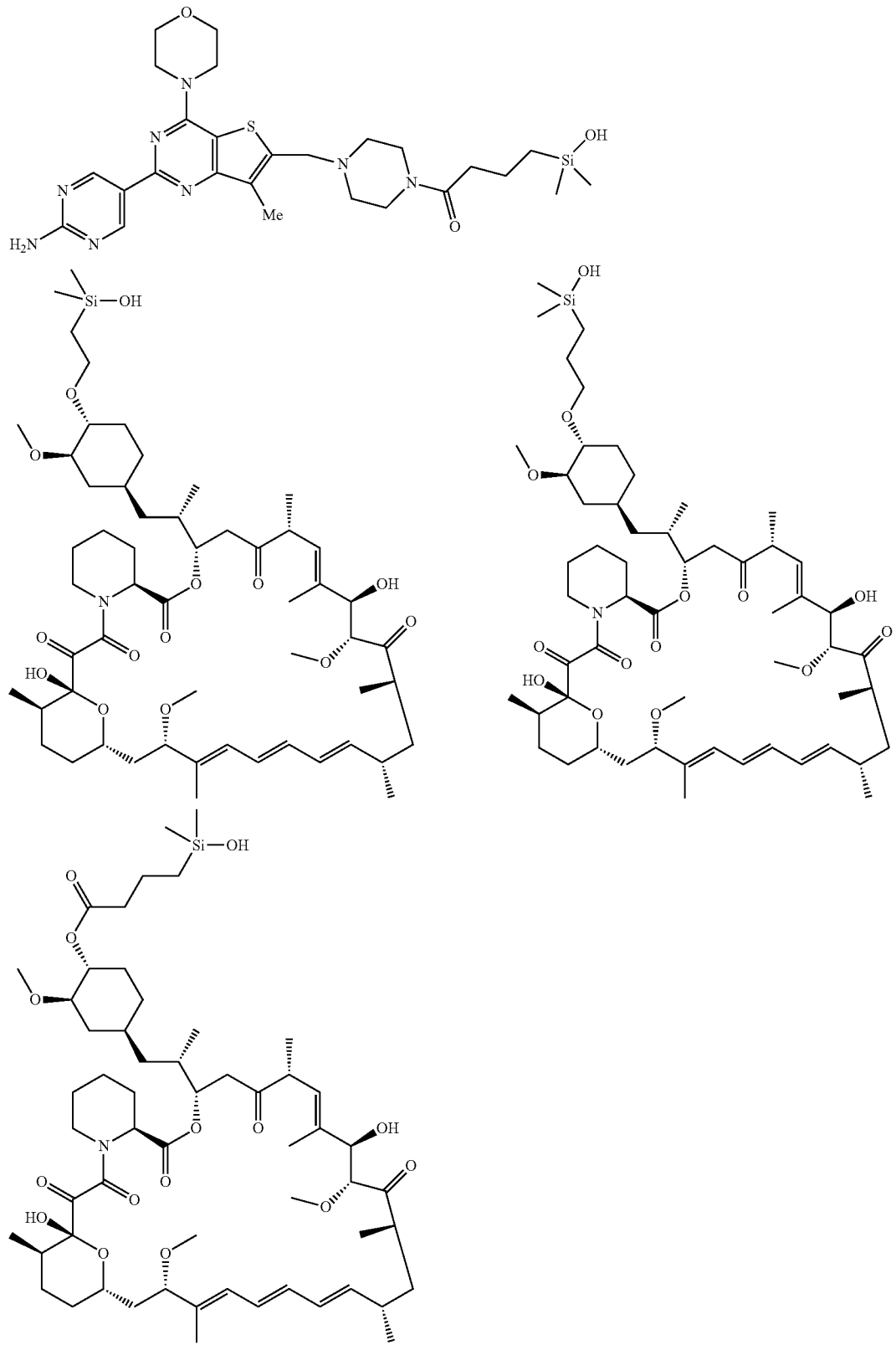

-continued
BCR-Abl Silanols:
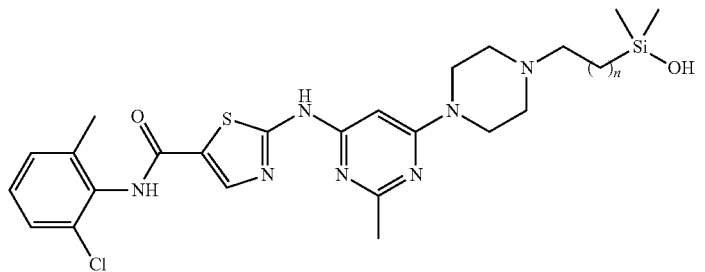
n = 0, 1
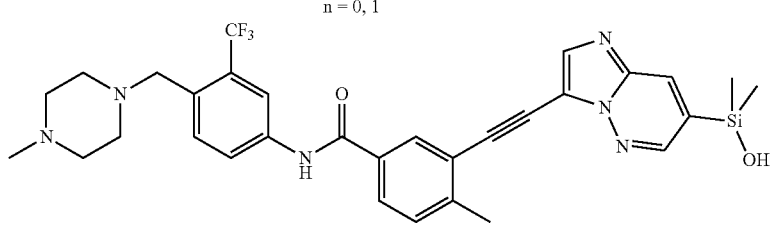
CDK Inhibitor Silanols
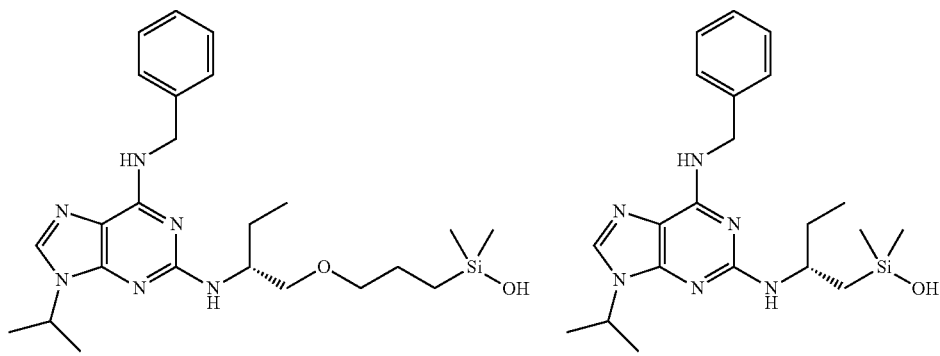
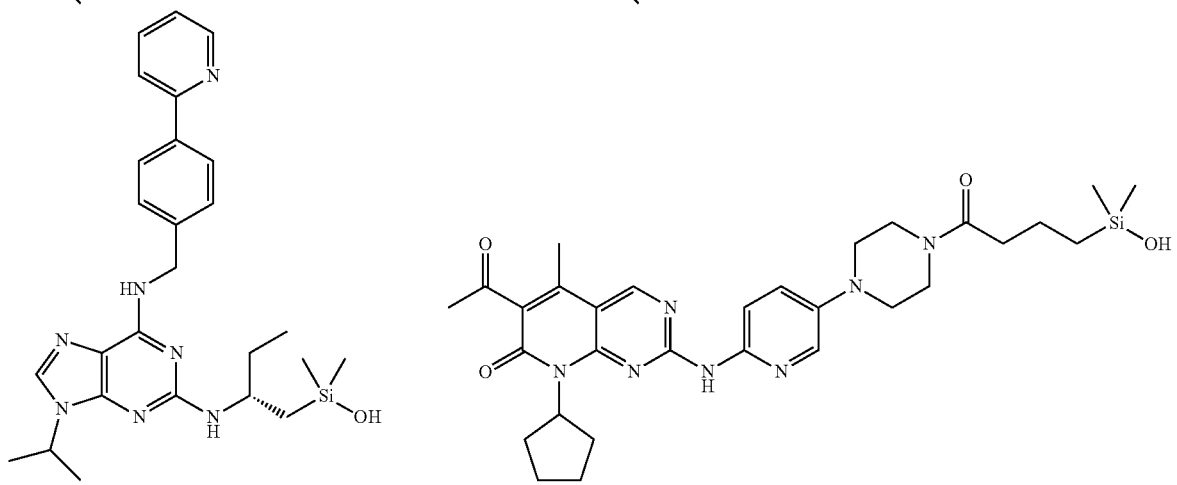
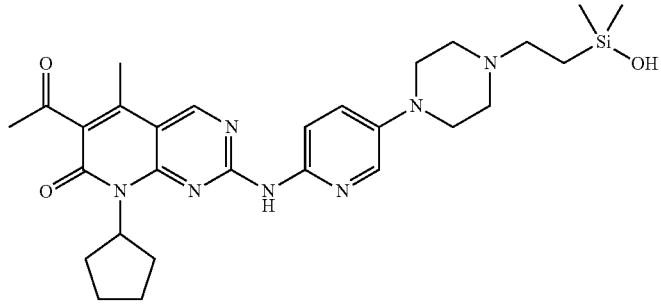

-continued
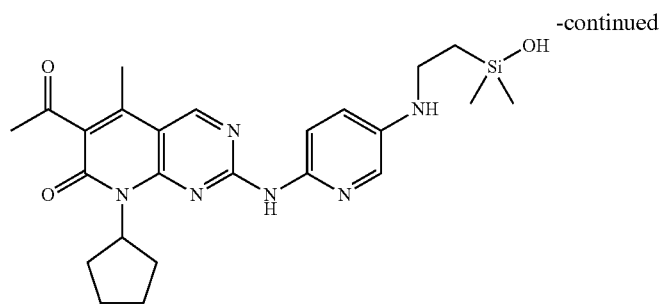
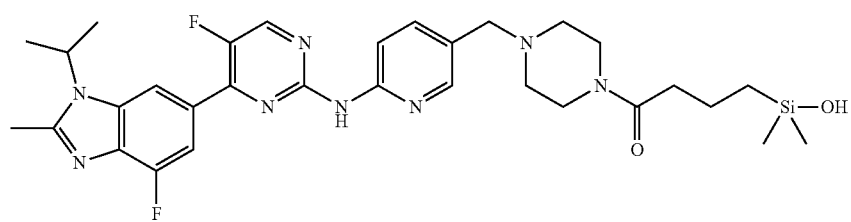
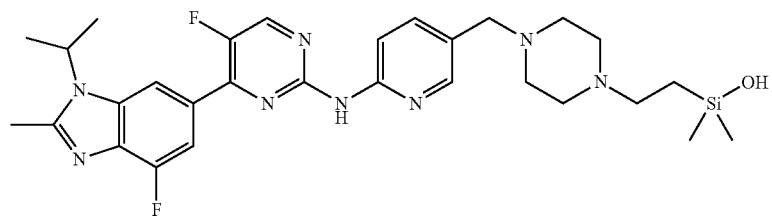
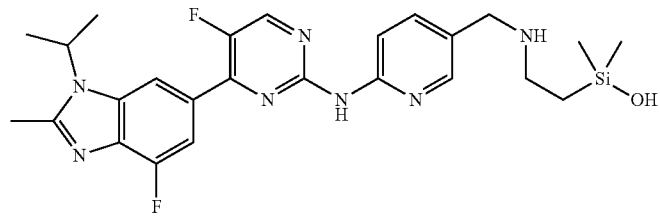
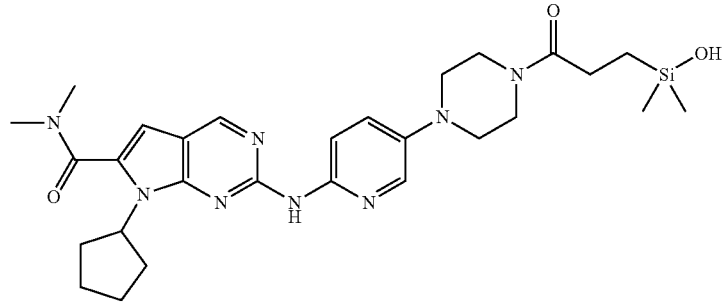
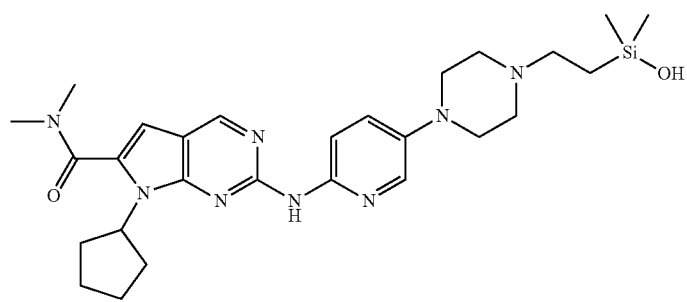

-continued
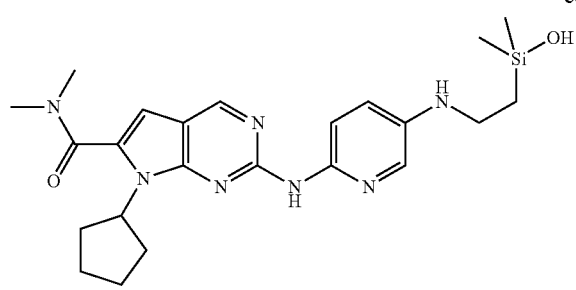
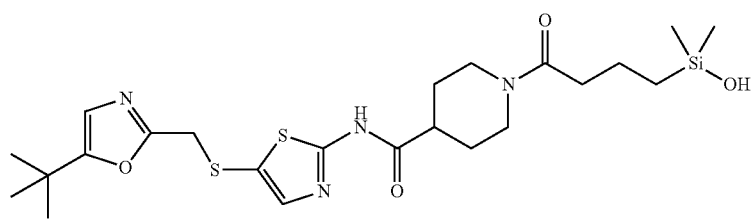
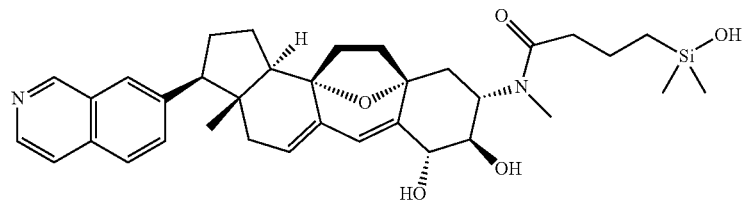
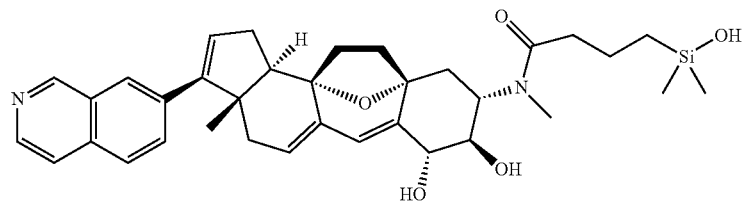
BTK Inhibitor Silanols:
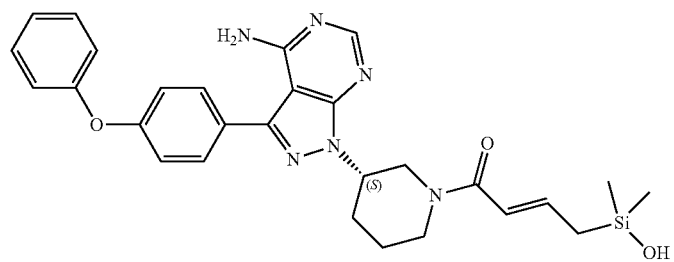
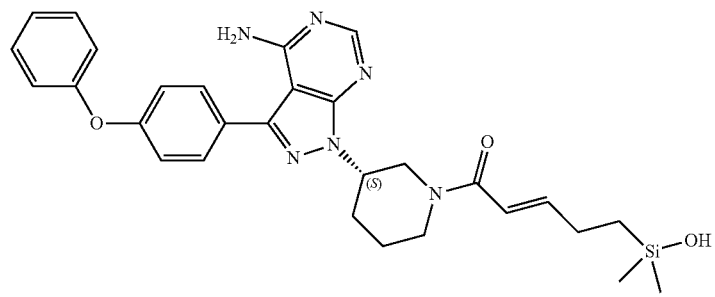

-continued
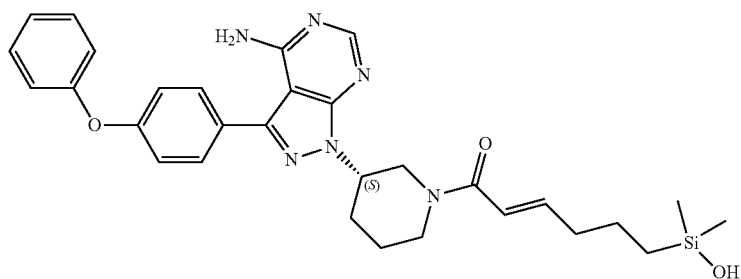
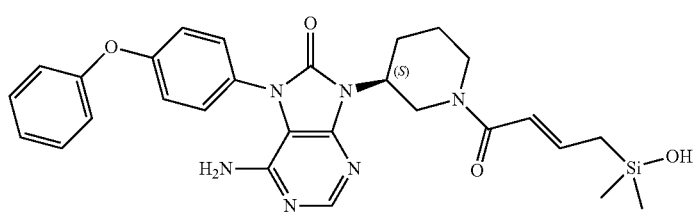
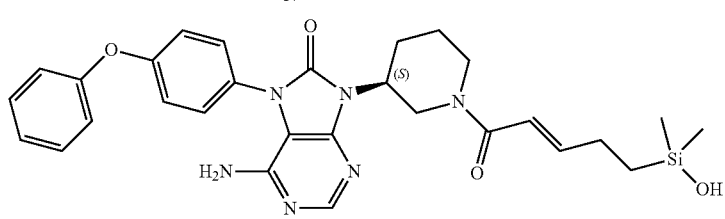
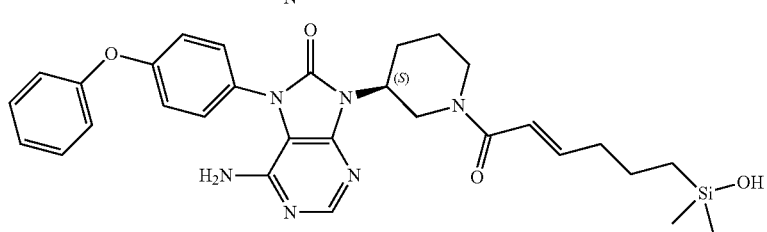
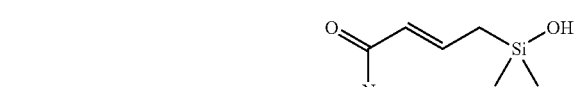
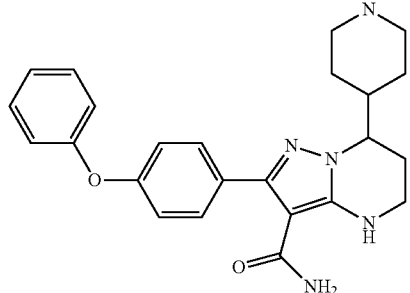
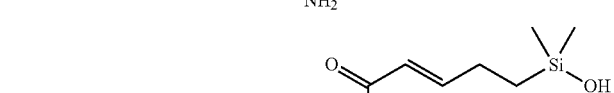
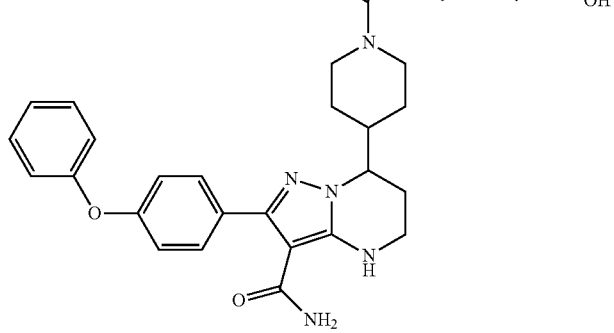

-continued
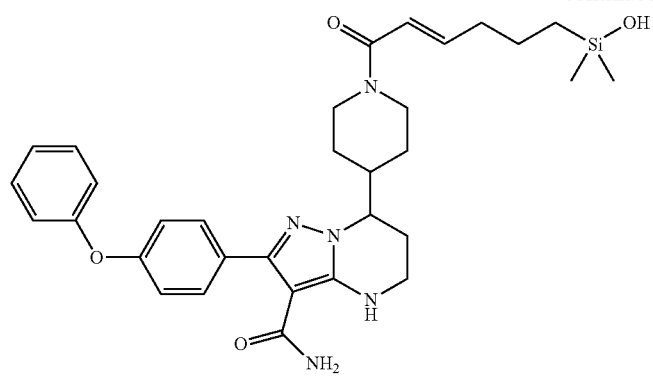
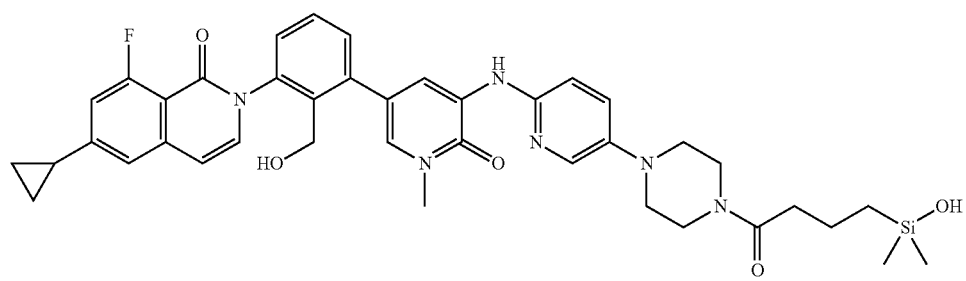
Aurora Inhibitor Silanols:
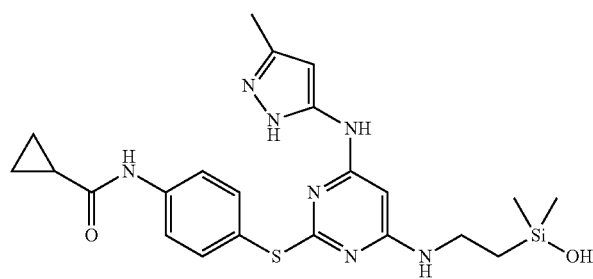
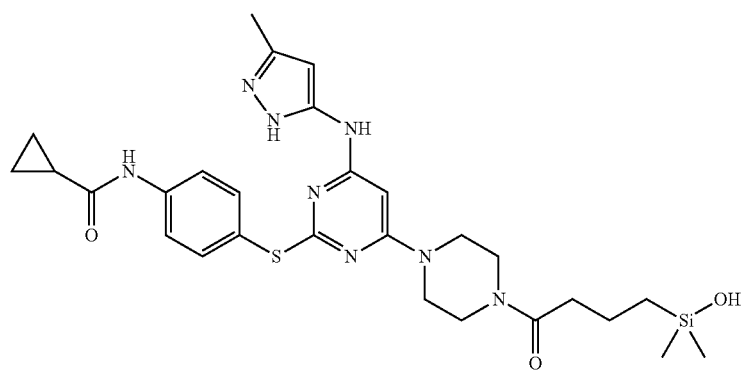
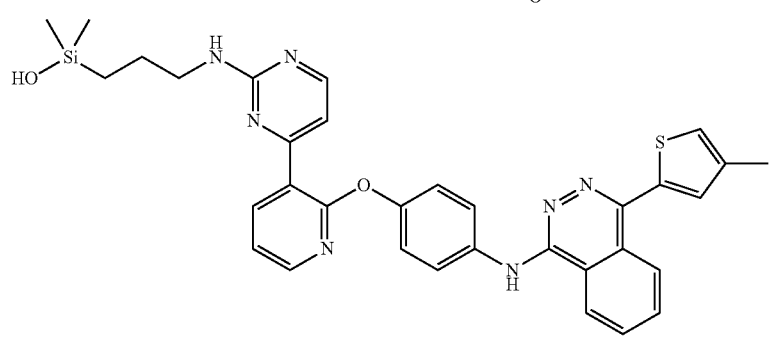

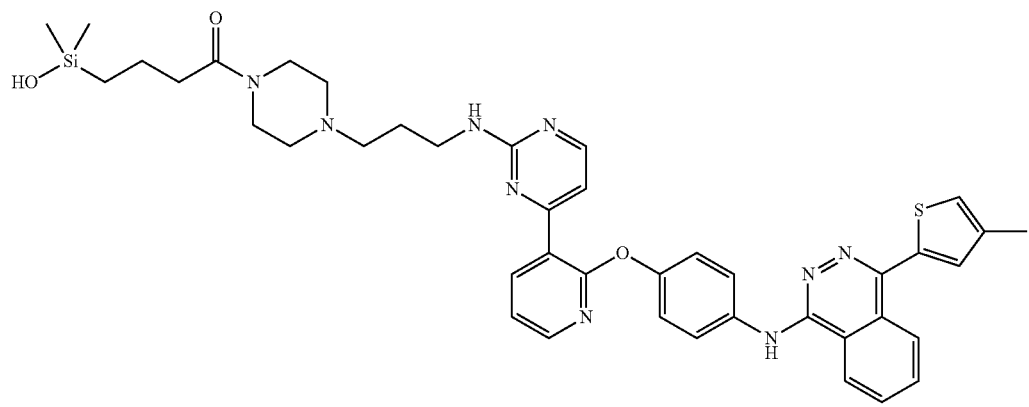
cMET Inhibitor Silanols:
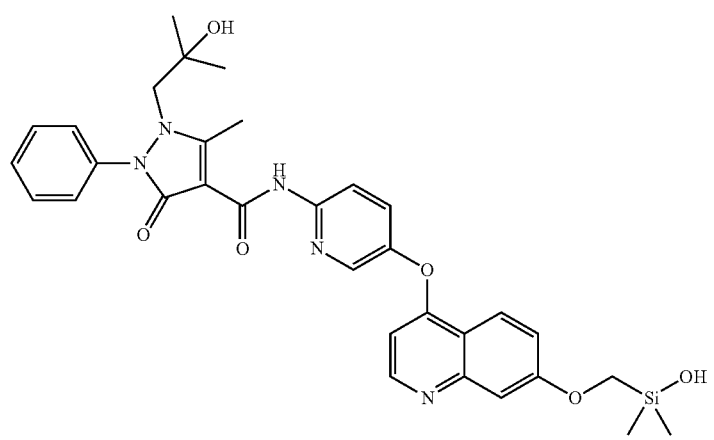
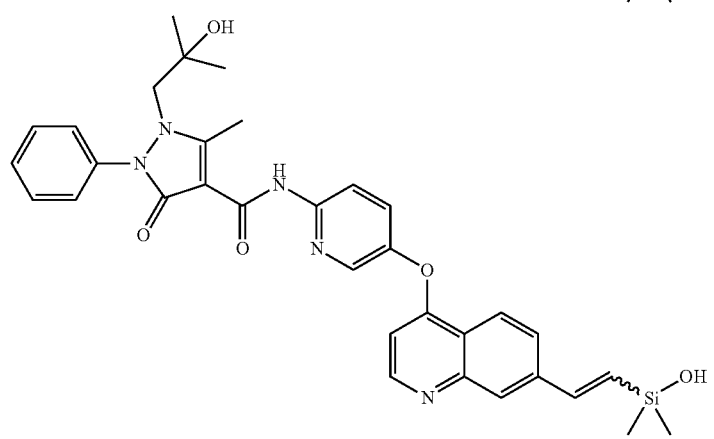
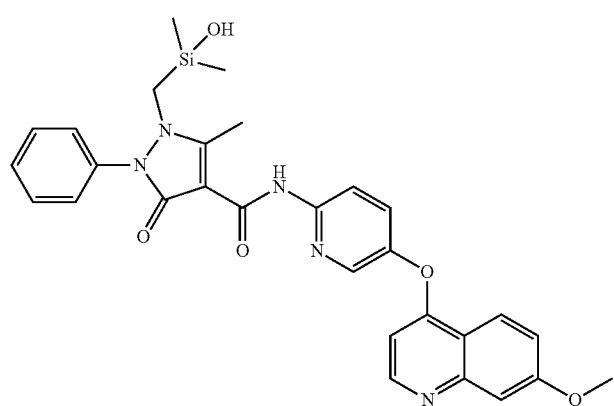

-continued
VEGF Inhibitor Silanols:
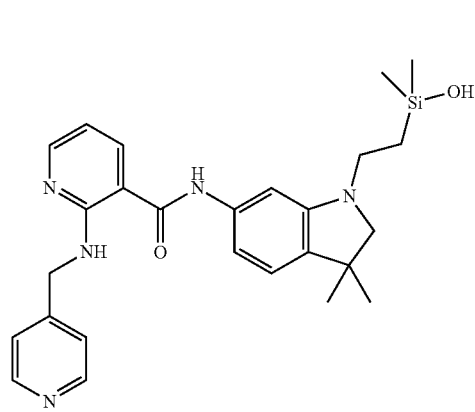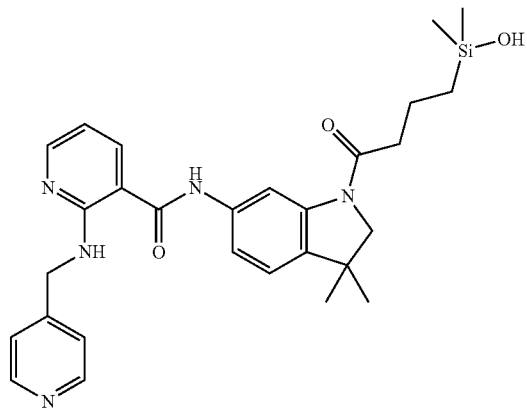
EGFR Inhibitor Silanols:
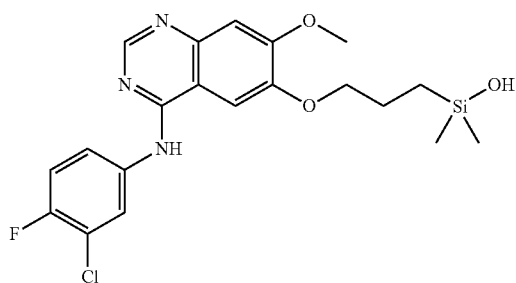
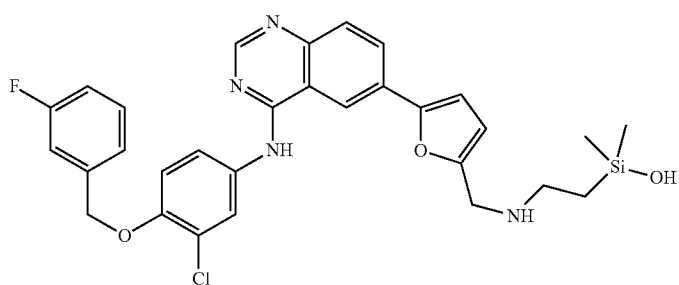
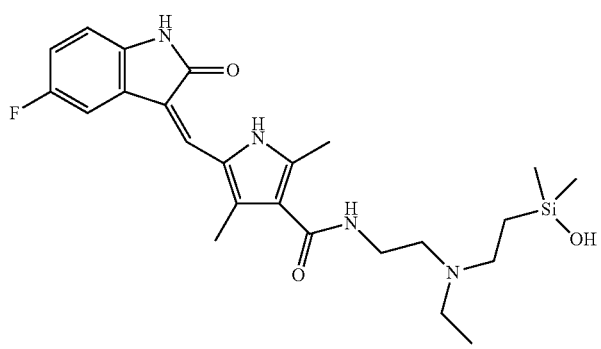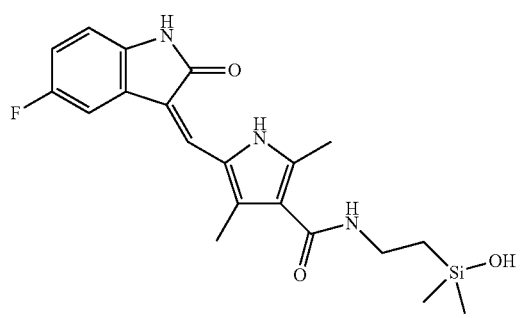

EGFR T790M Inhibitor Silanols:
111
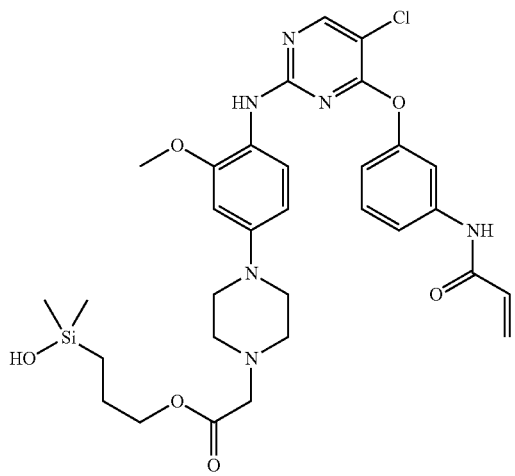
112
-continued
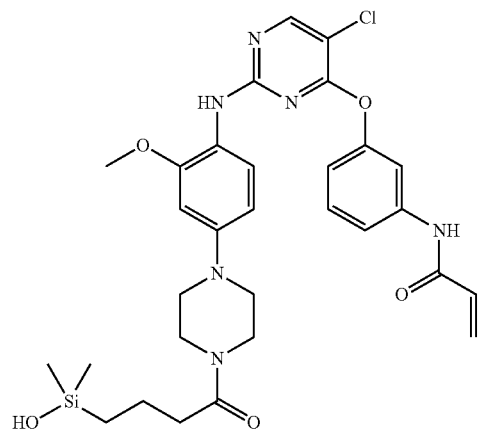
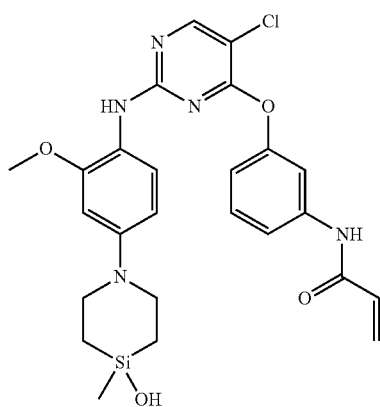
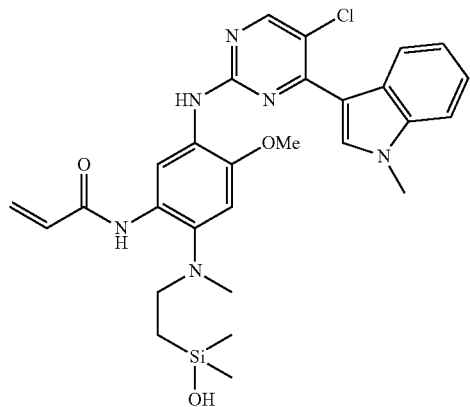
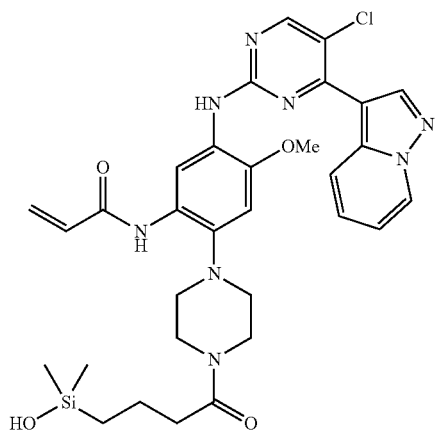
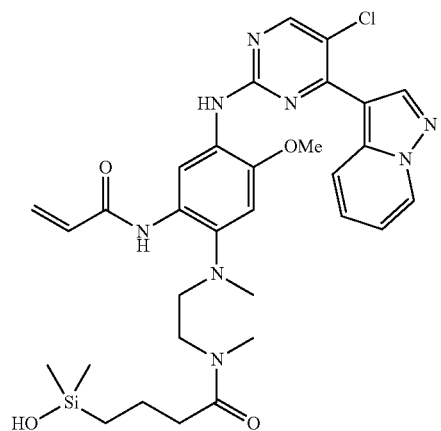

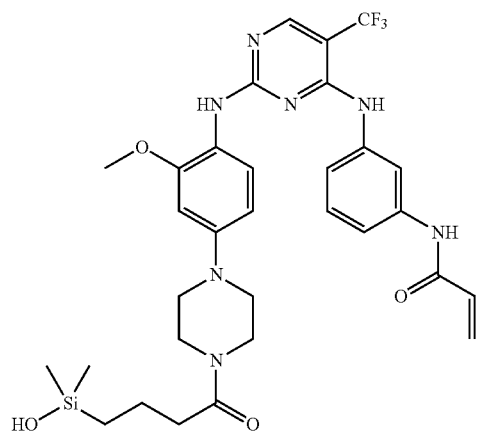
b-RAF Inhibitor Silanols:
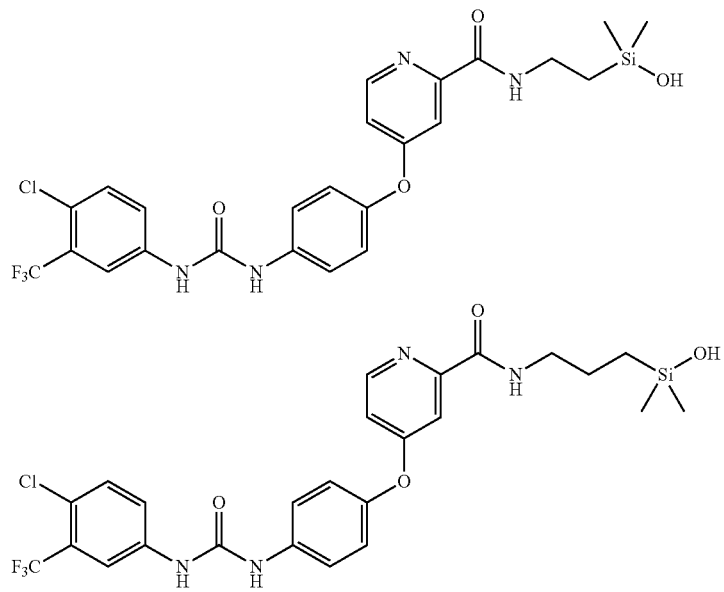
RHO/ROCK Inhibitor Silanols:
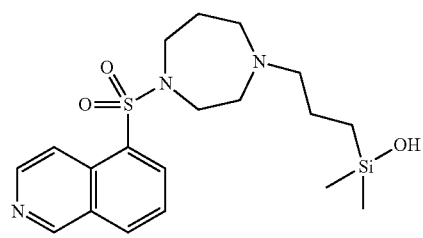
WEE1 Inhibitor Silanols:
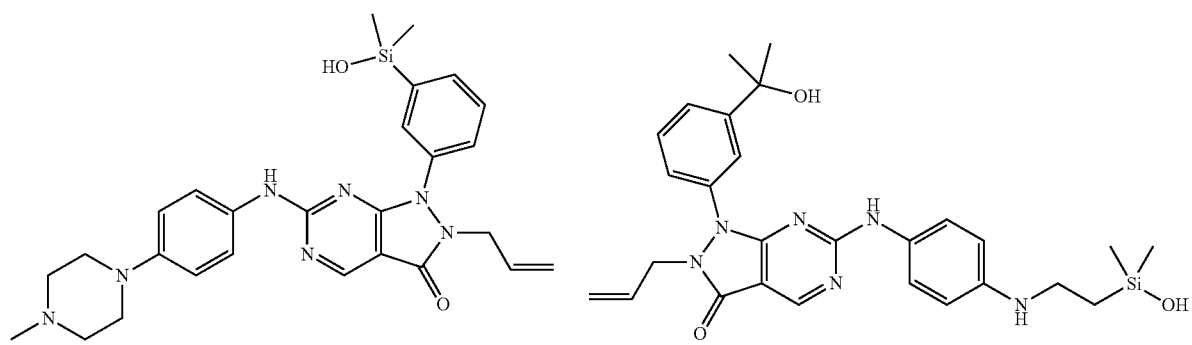

PARP Inhibitor Silanols:
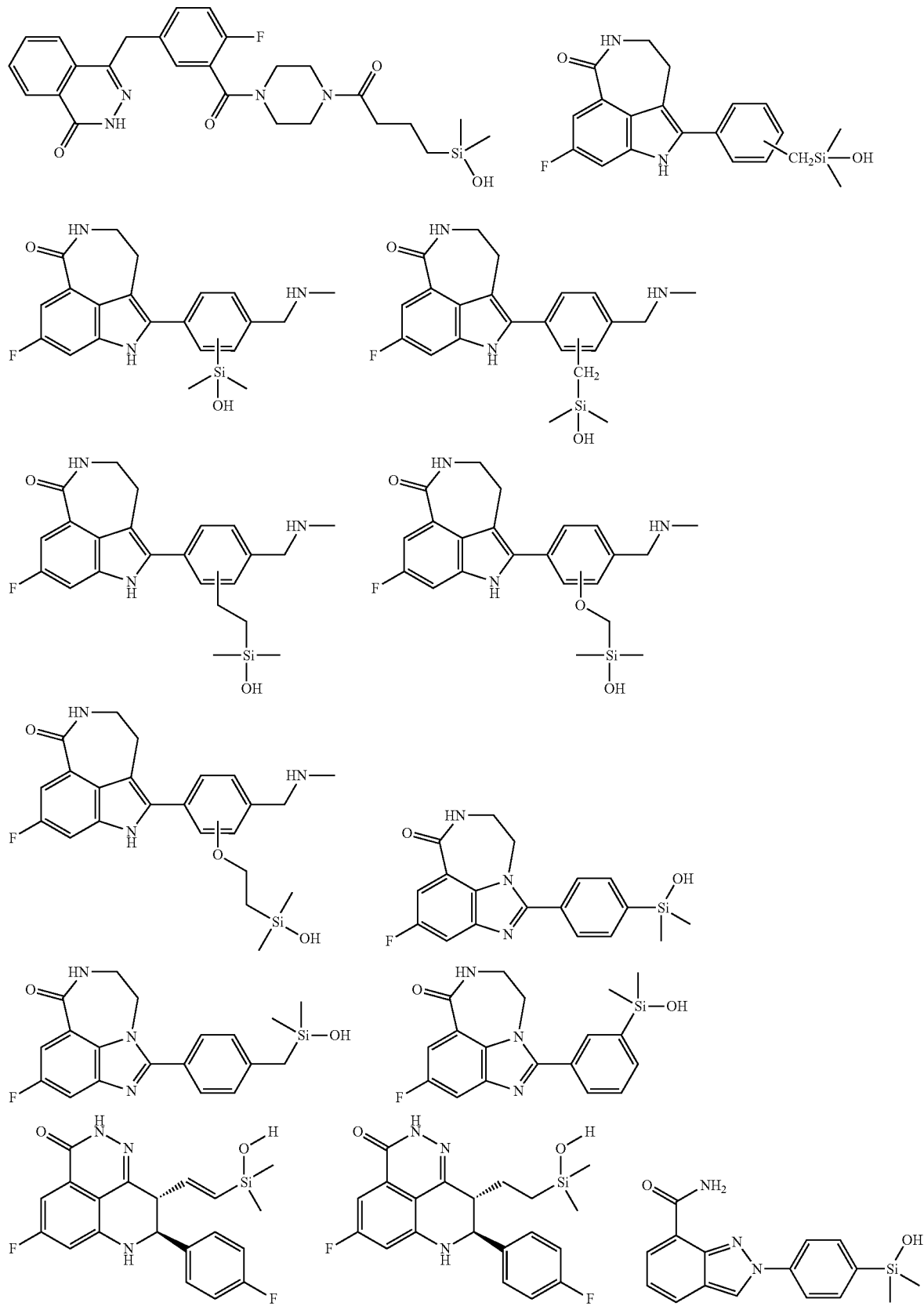

-continued
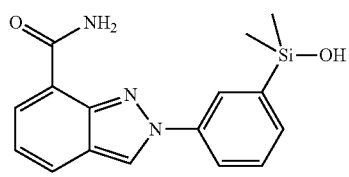
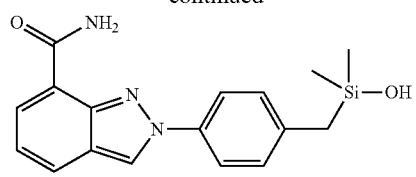
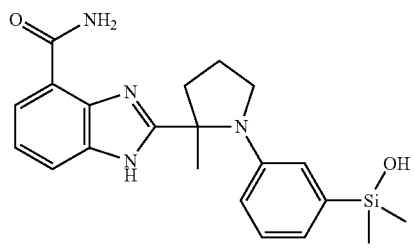
Bcl-2 Protein Inhibitor Silanols:
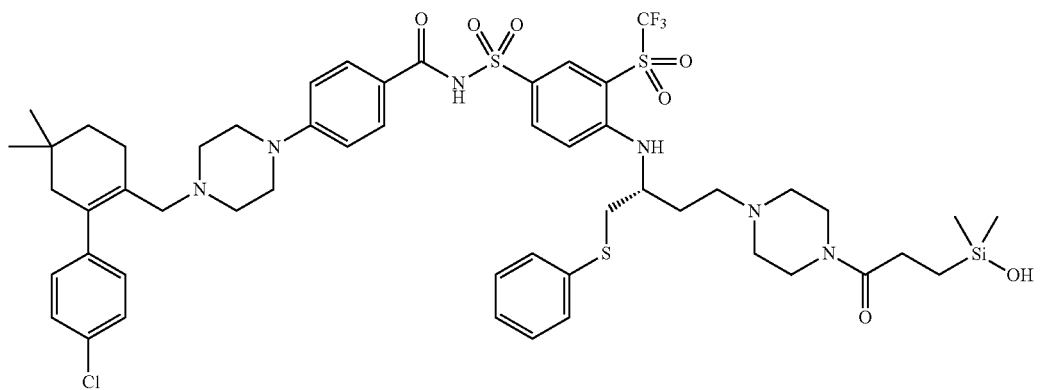
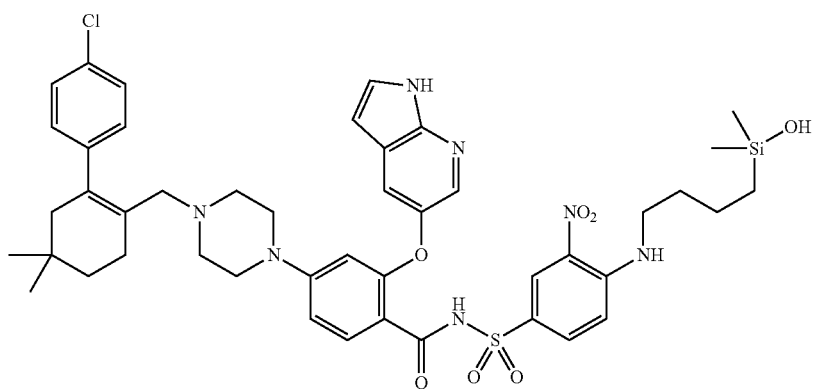
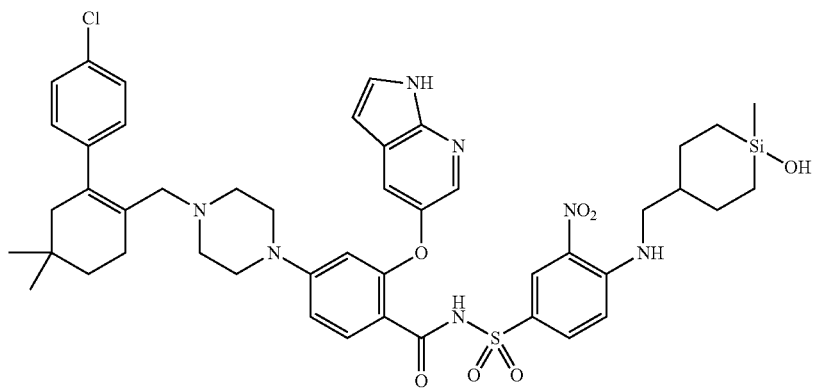

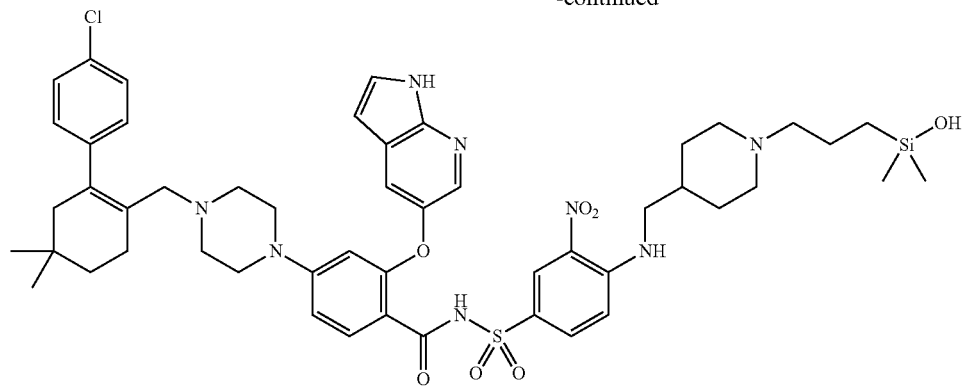
Taxol Silanols:
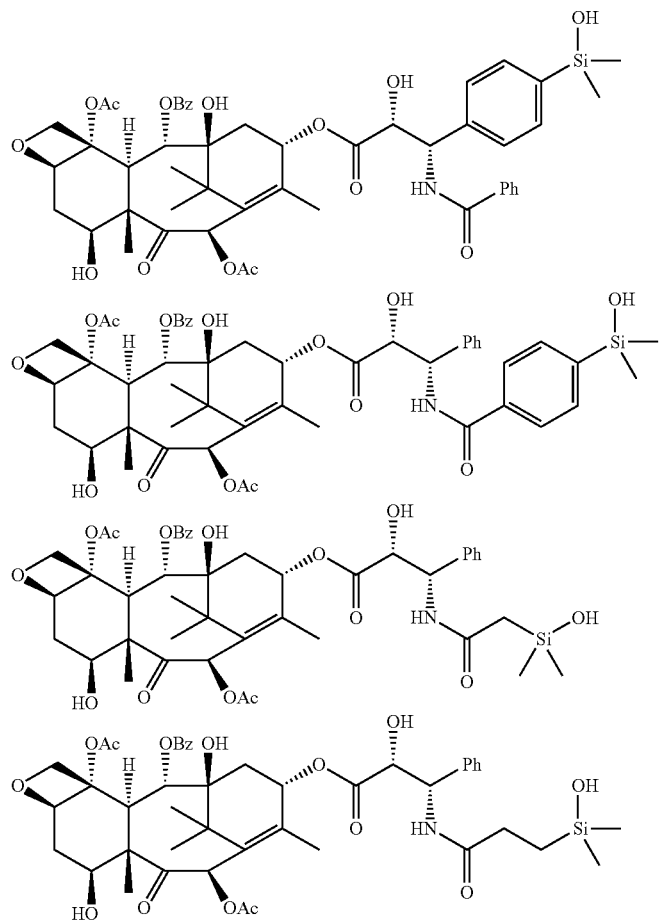
Vinblastine Silanols:
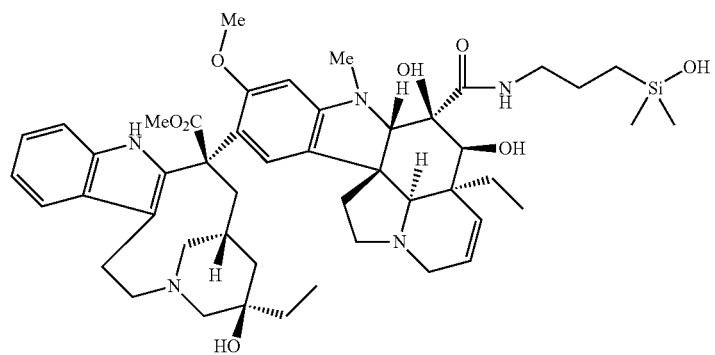

-continued
Tubulysin Silanols:
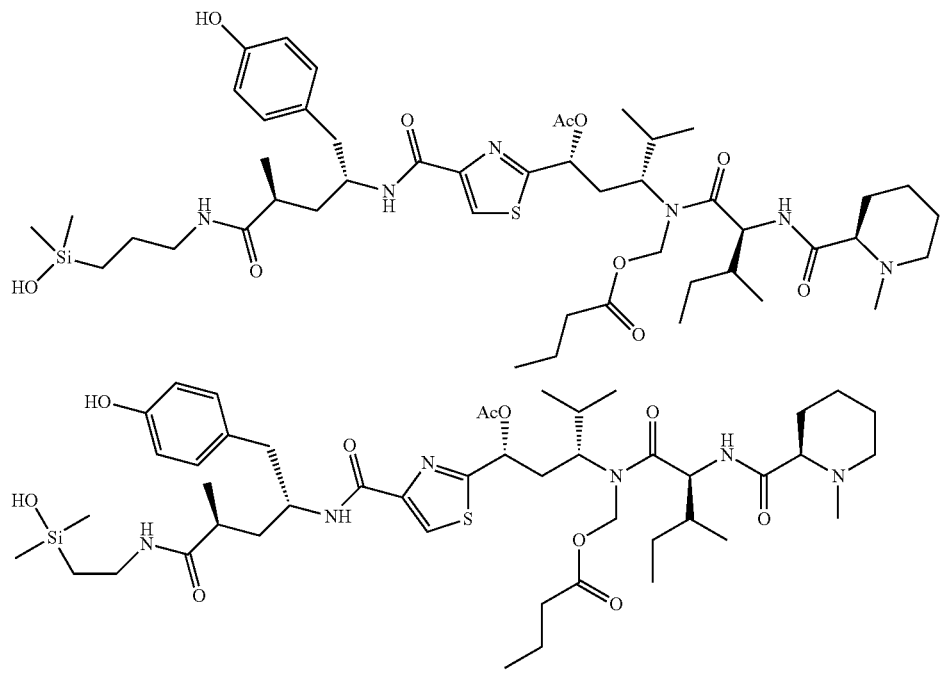
Auridtstin Silanols:
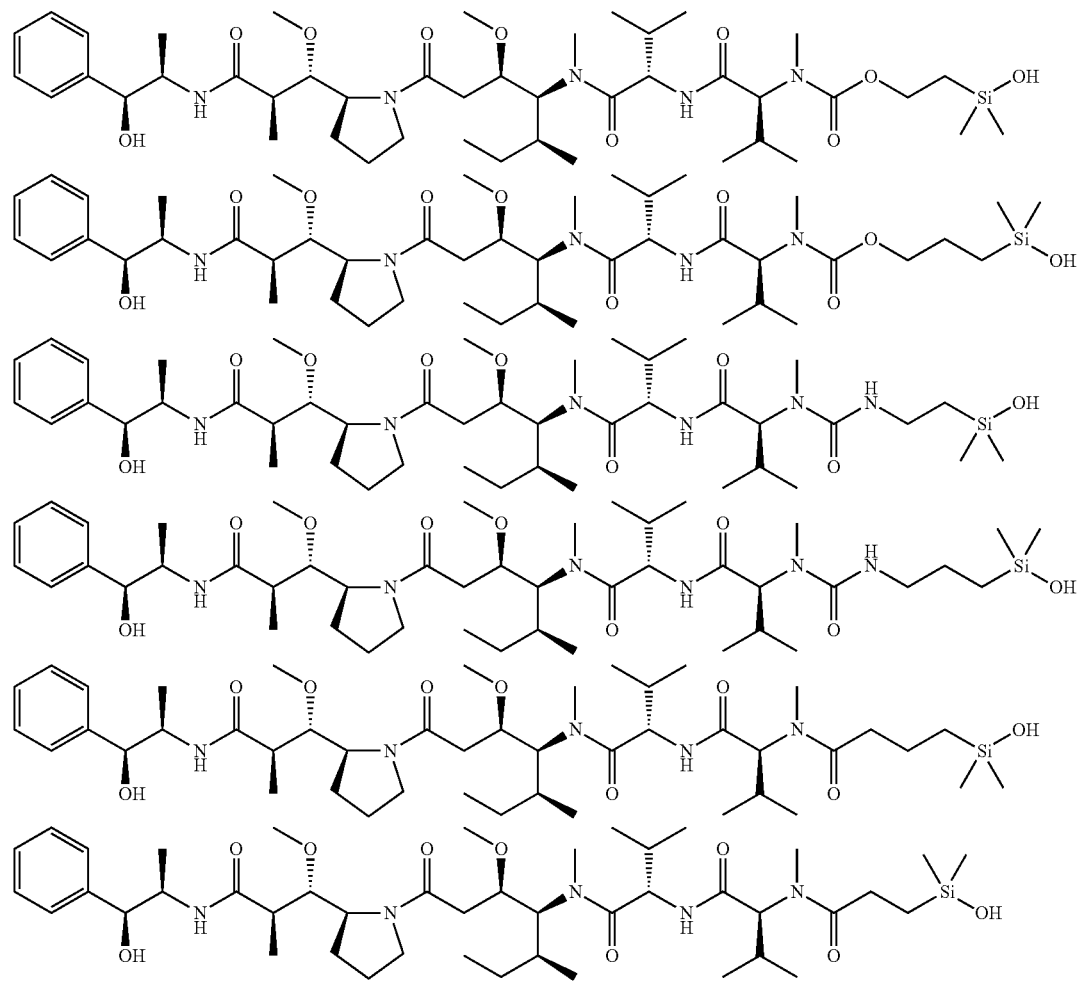

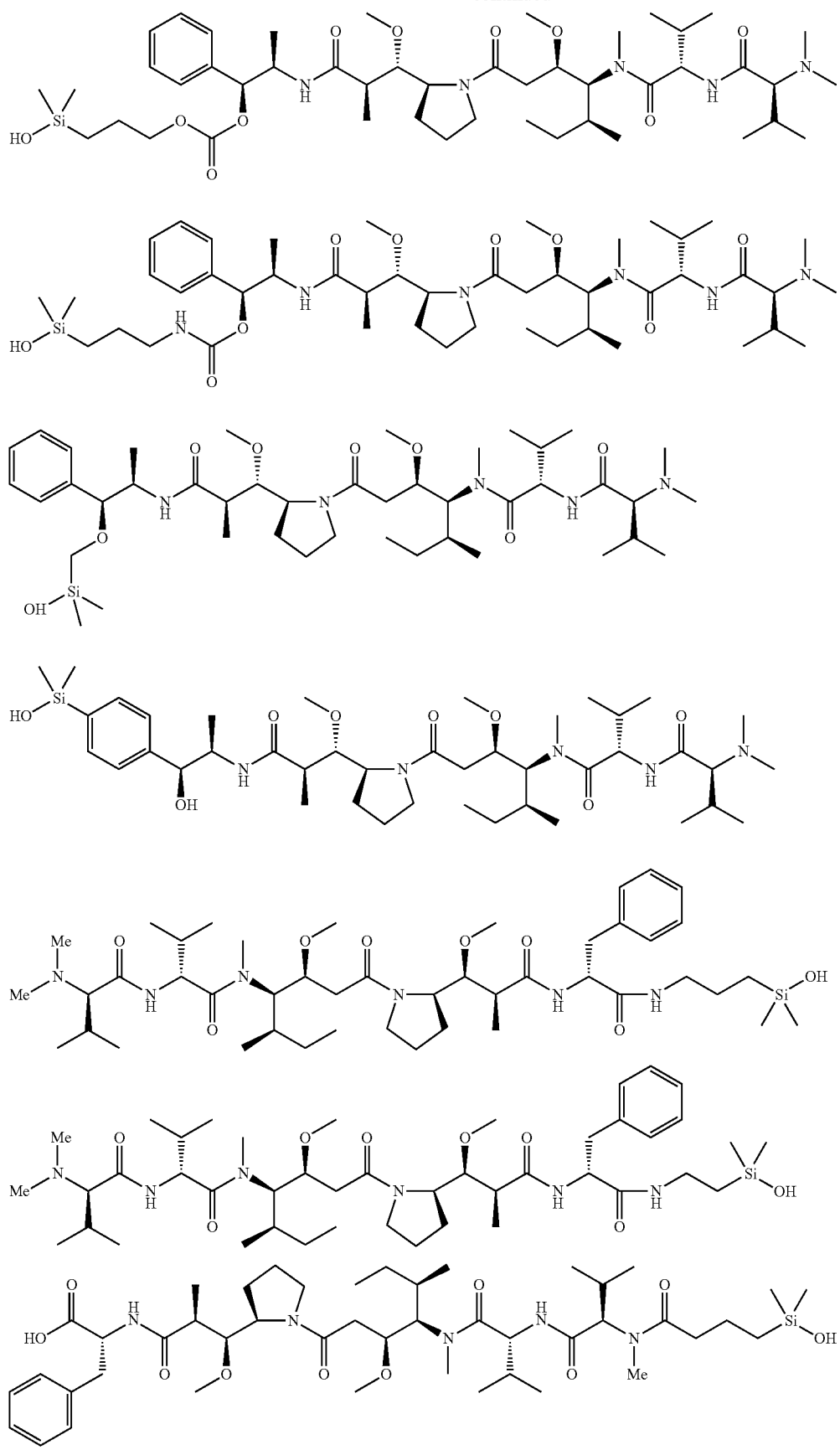

125
-continued
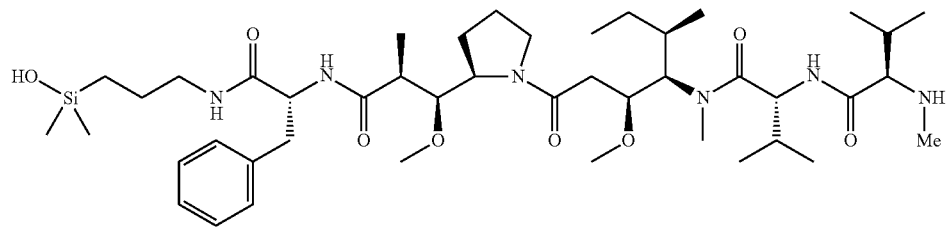
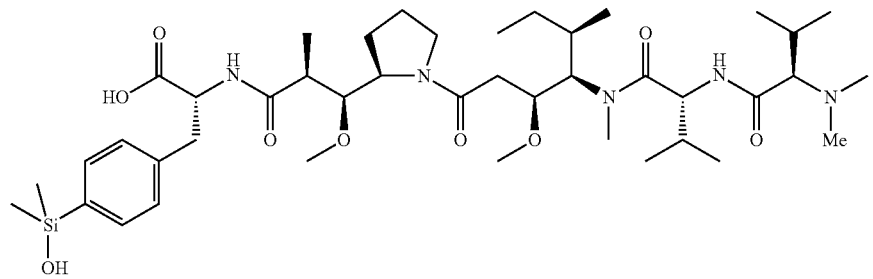
Maytansine Silanols:
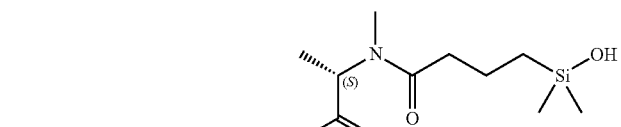
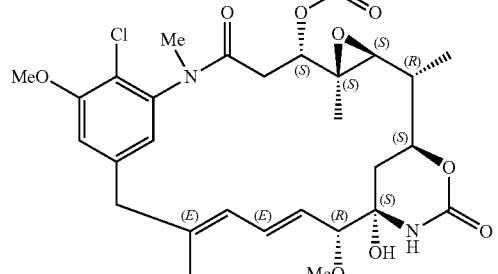
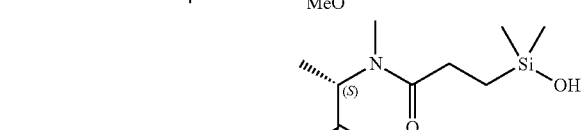
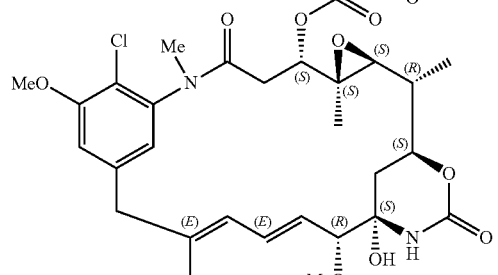
126
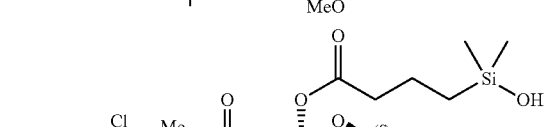
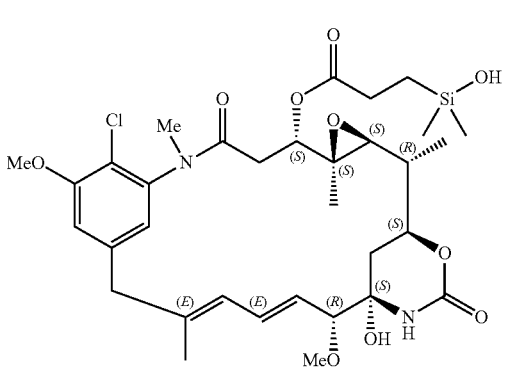

-continued
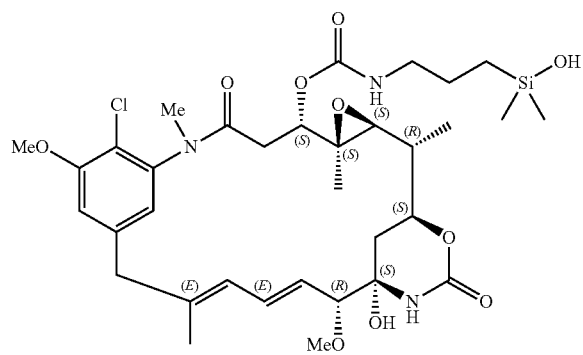
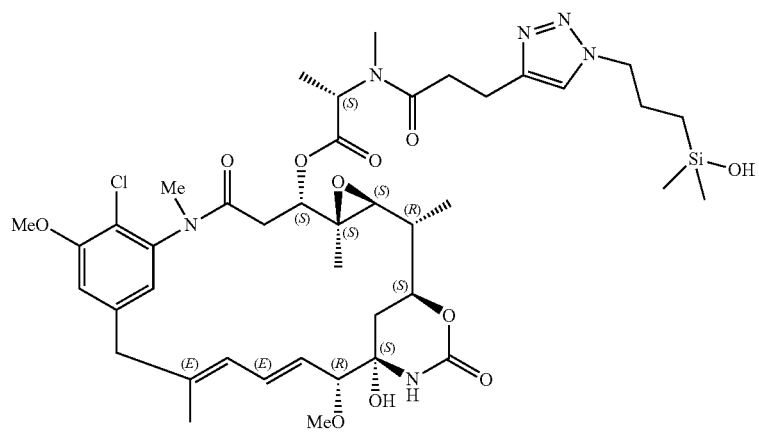
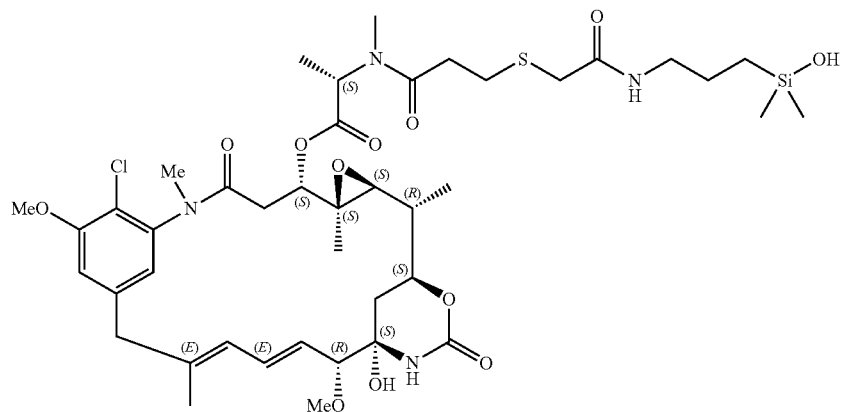
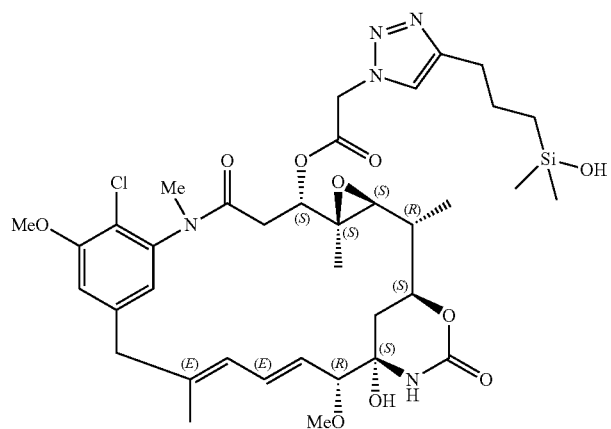

-continued
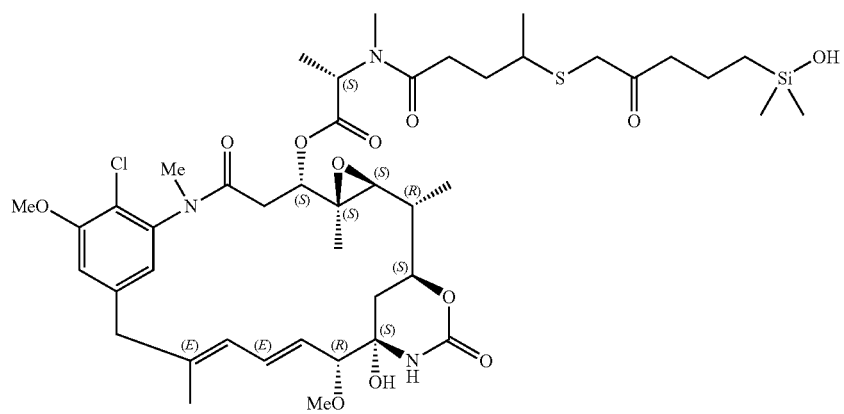
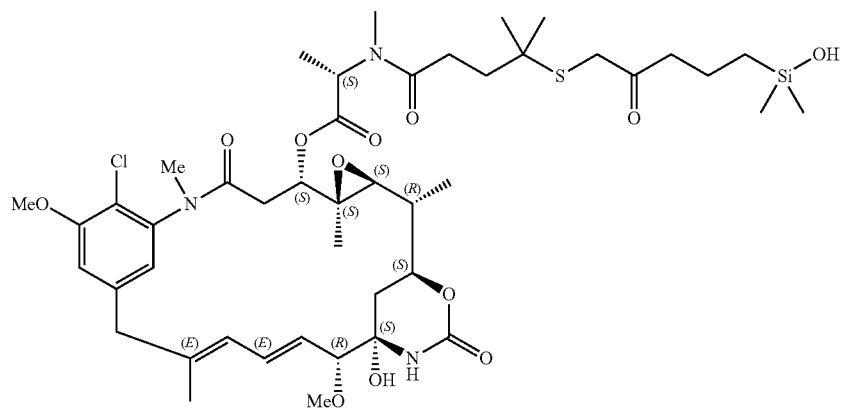
Colchicine Silanols:
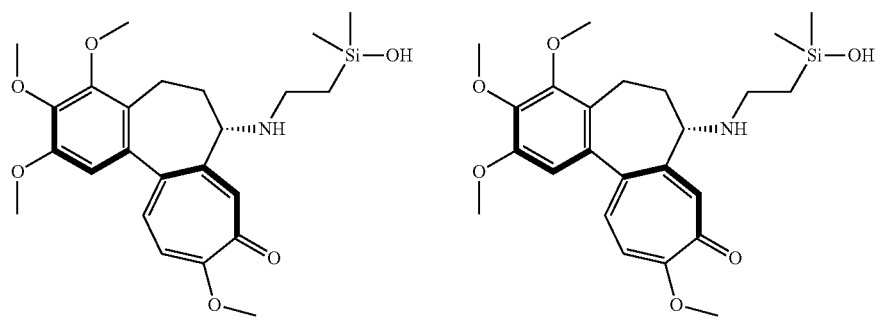
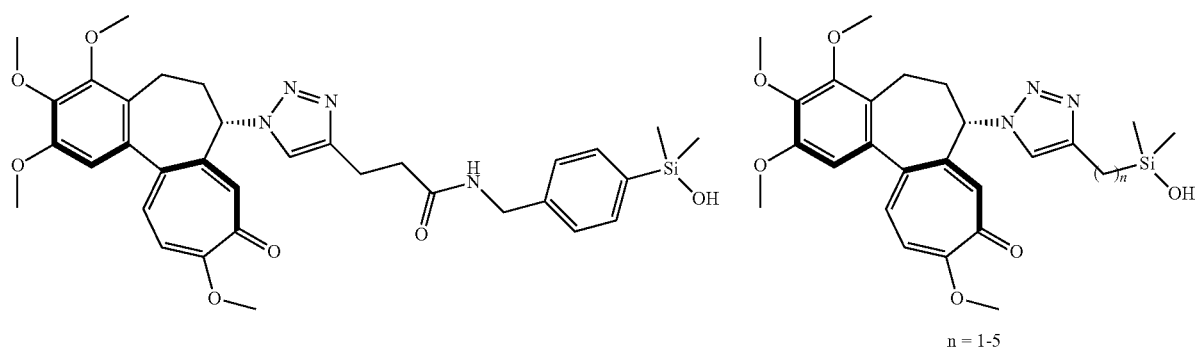
n = 1-5

-continued
Microtubule Depolymerizing Silanols:
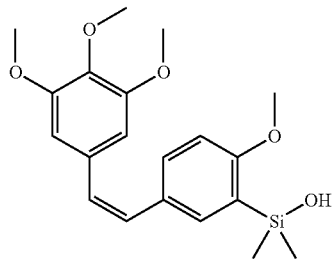 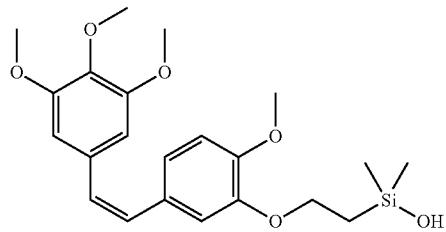
Tubulin-Based Antimitotic Silanols:
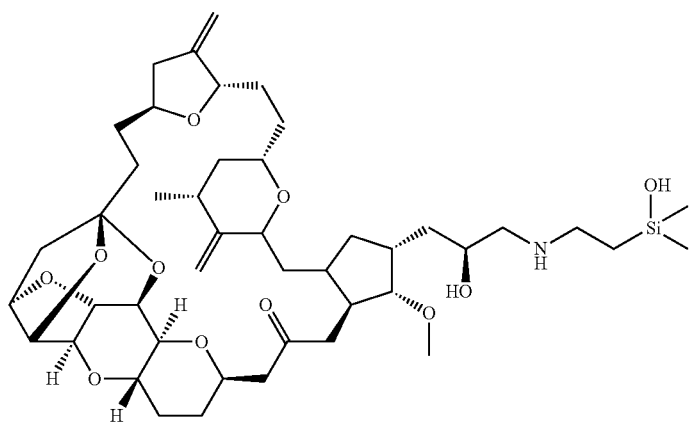
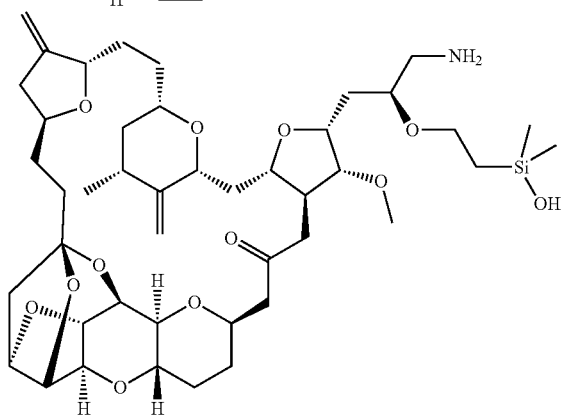
Mitomycin Silanols:
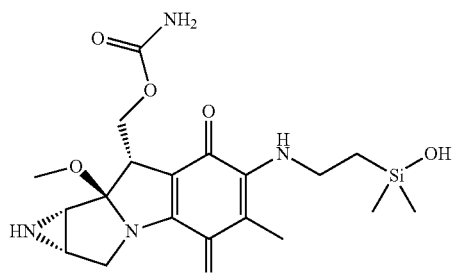
DNA-Crosslinking Silanols:
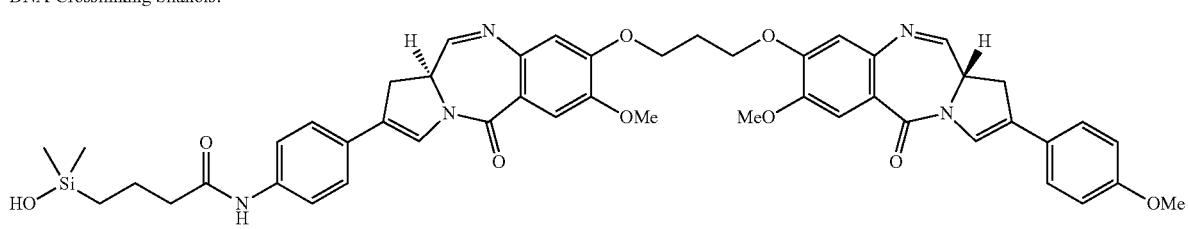

-continued
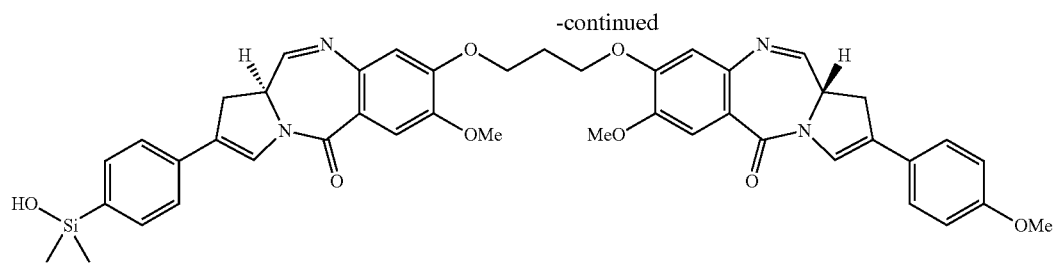
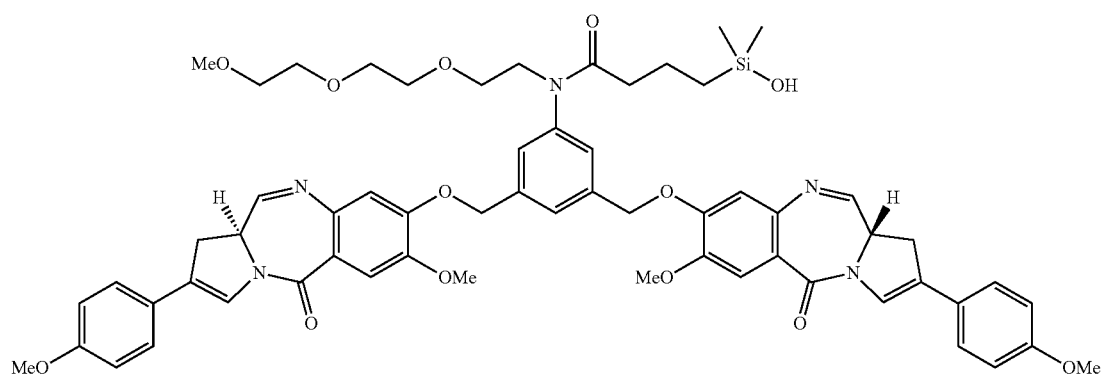
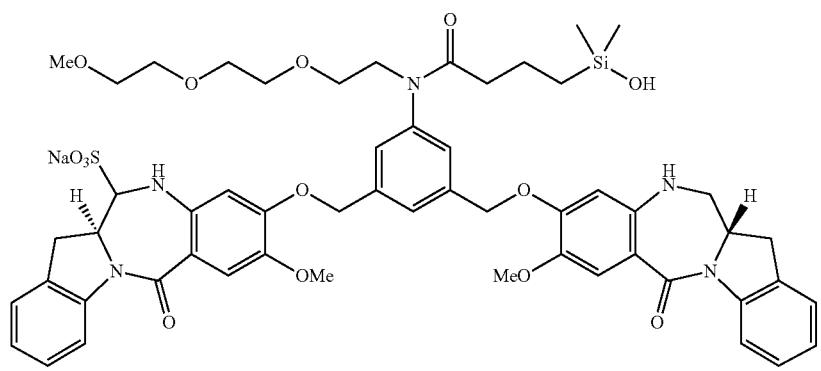
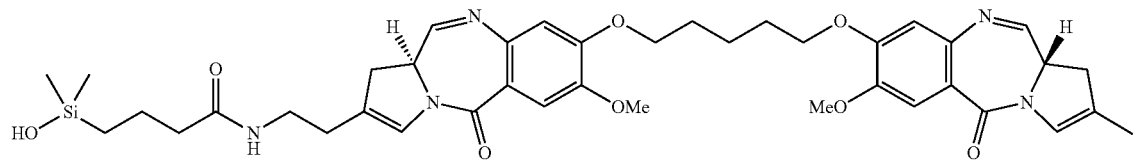
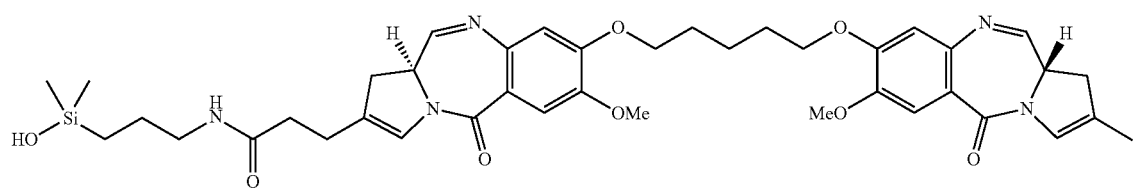

DNA-Strand Scission Silanols:
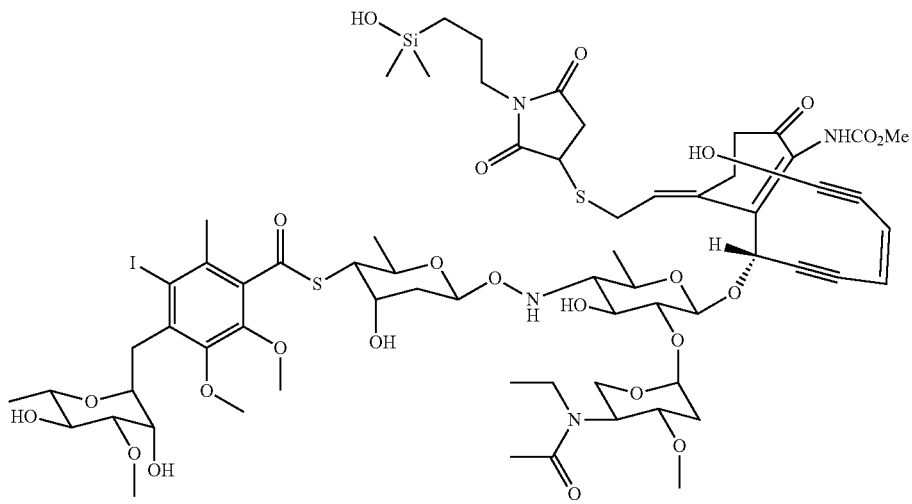
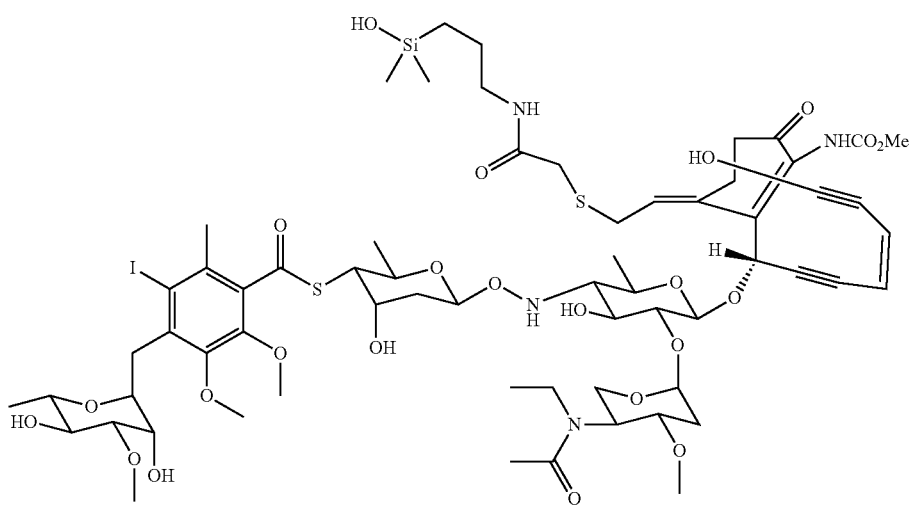
RNA-Strand Splicing Silanol
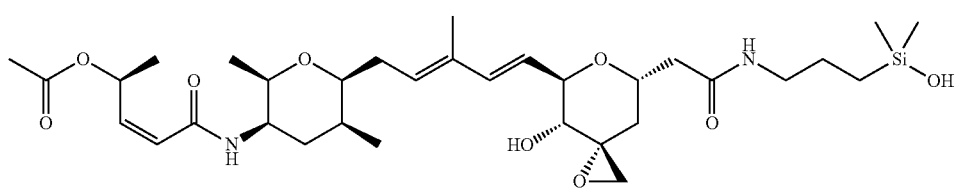
Platinum-Containing Silanols:
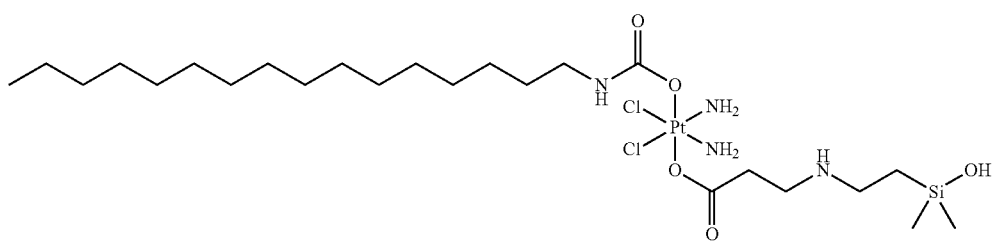

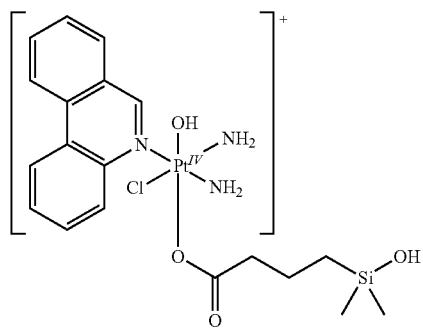
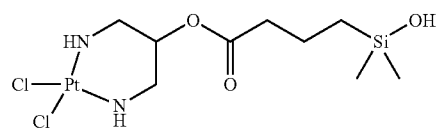
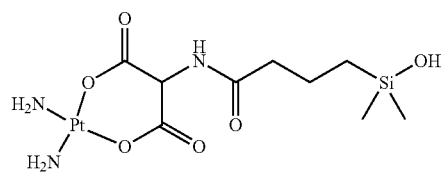
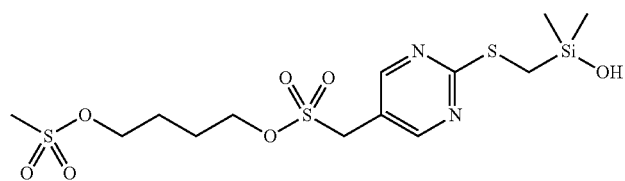
Doxorubicin Silanols:
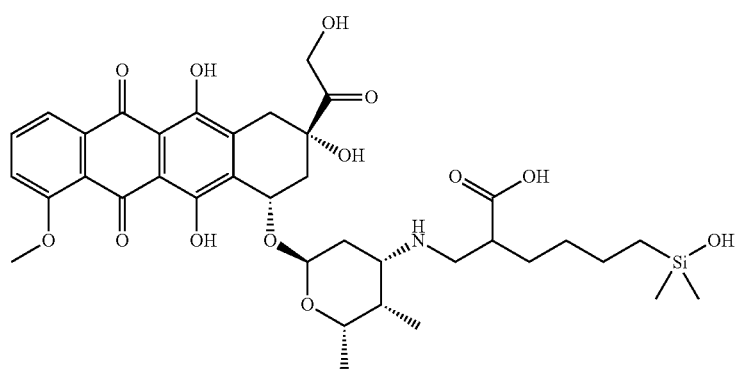
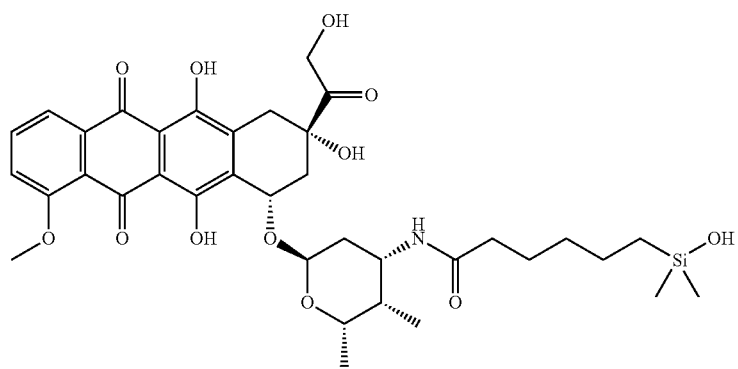

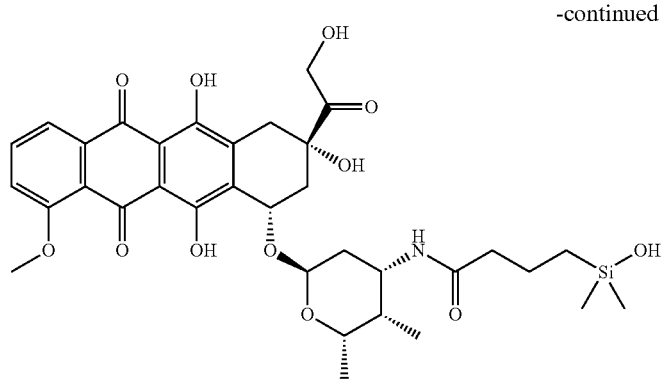
Camptothecin and SN38 Silanols:
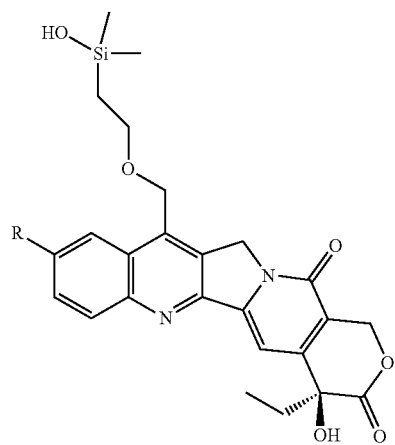
R = H, OH
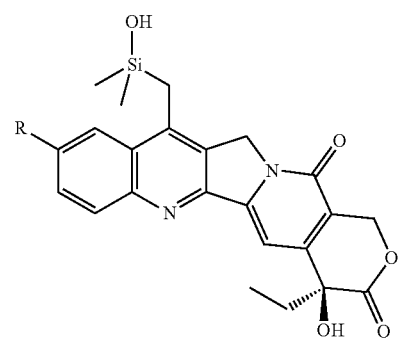
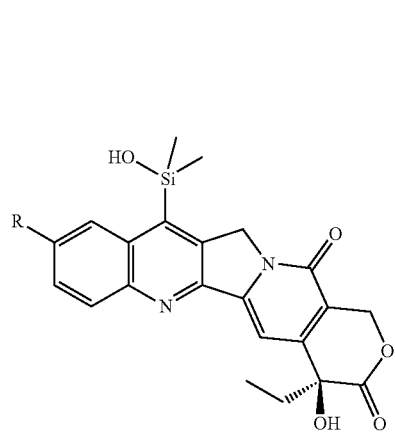
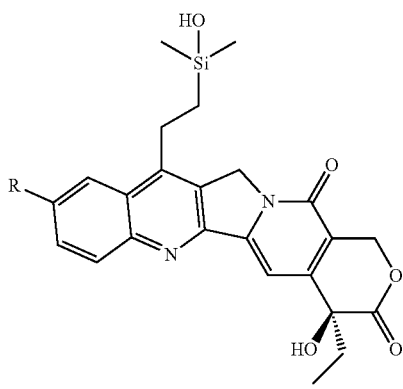
R = H, OH -continued
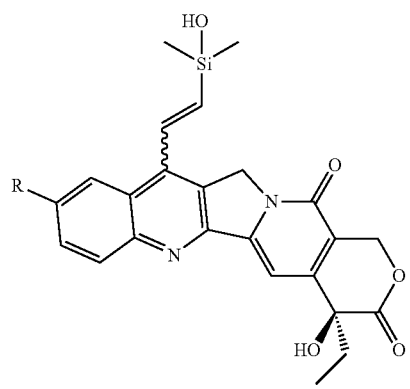
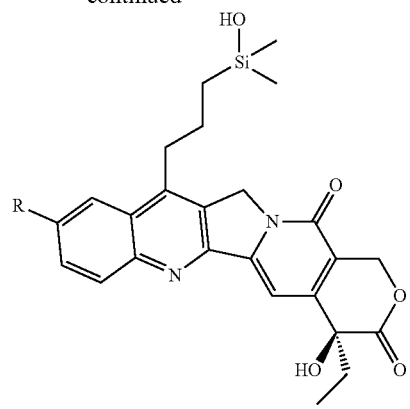
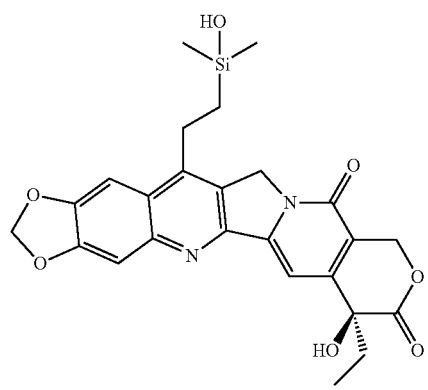
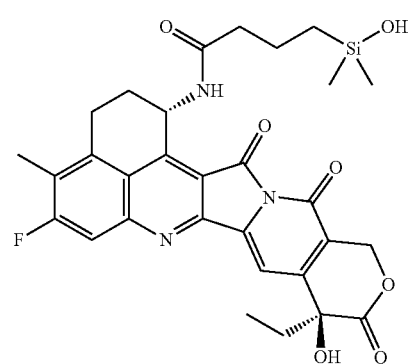
Estrogen Receptor Silanol Antagonists:
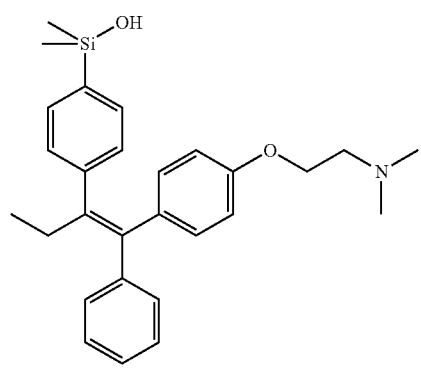
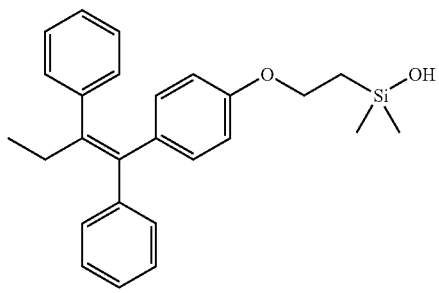
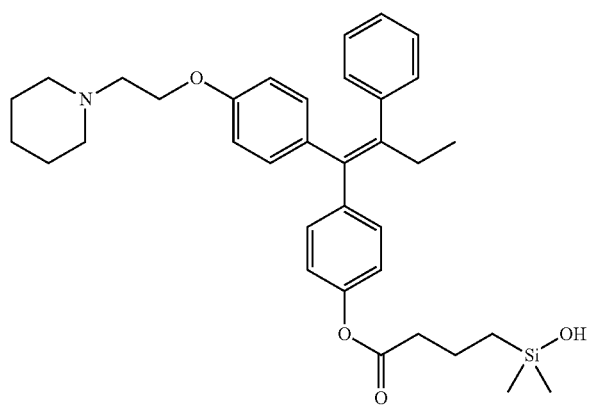

-continued
Triptolide Silanol:
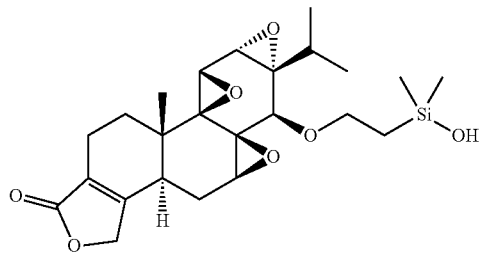
HSP70/HSP90 Silanol:
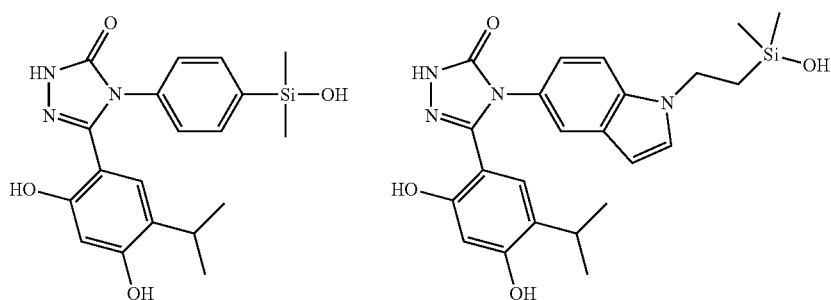
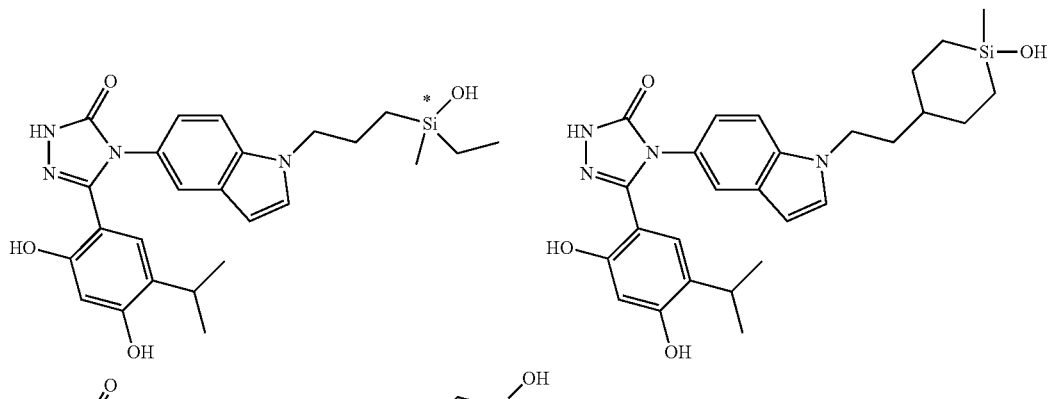
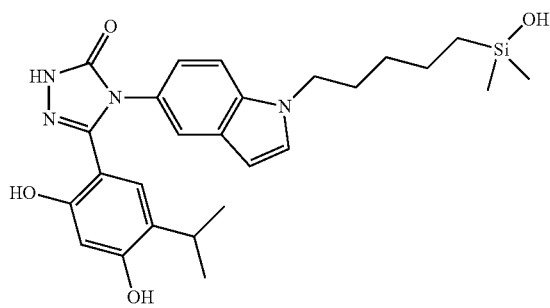
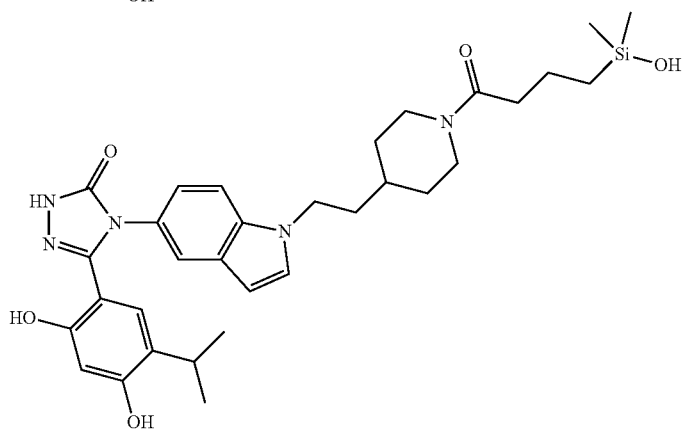

Cancer Stem Cell Inhibitor Silanol:
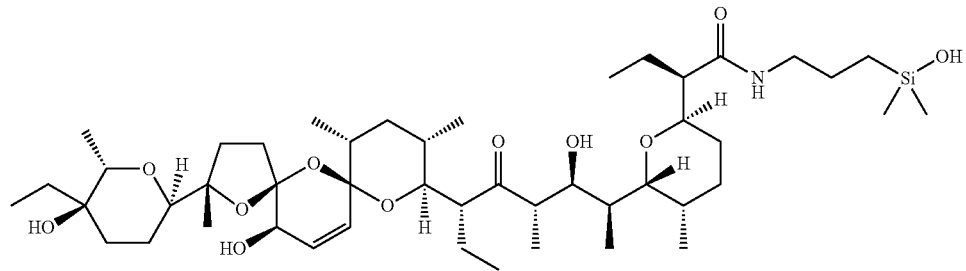
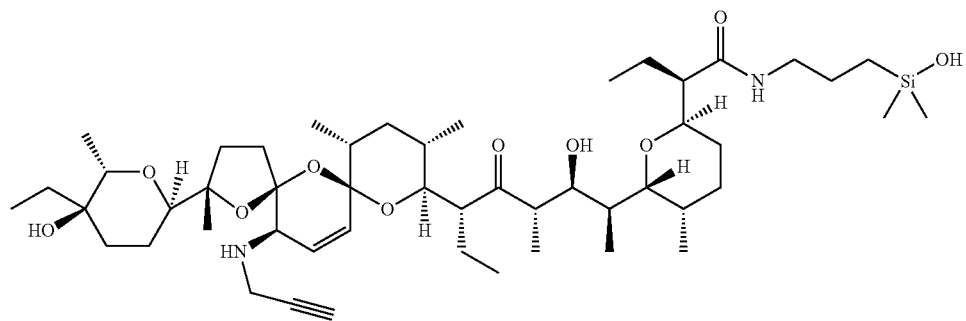
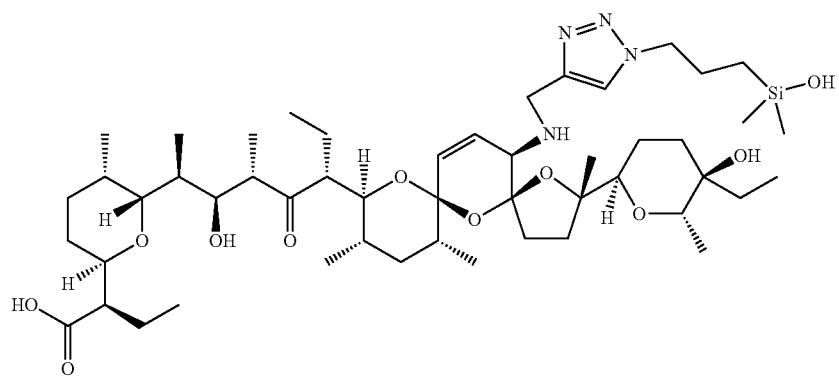
Proteosome Inhibitor Silanols:
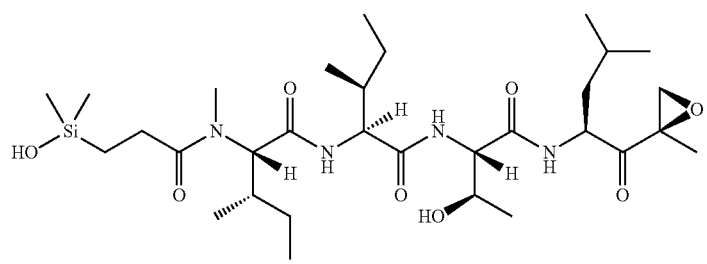
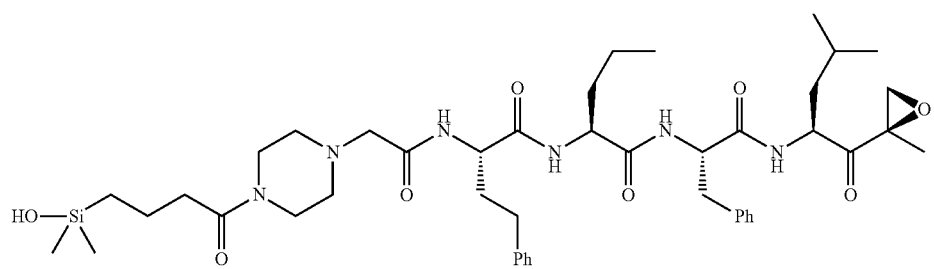

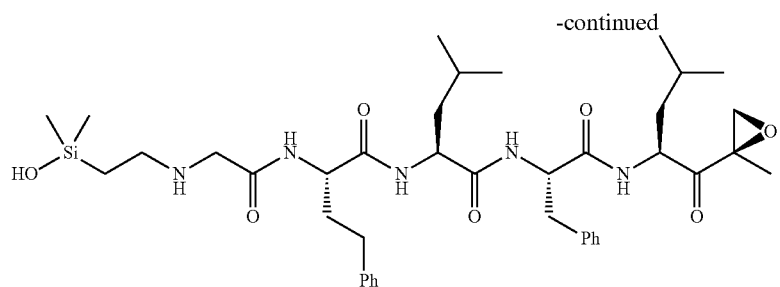
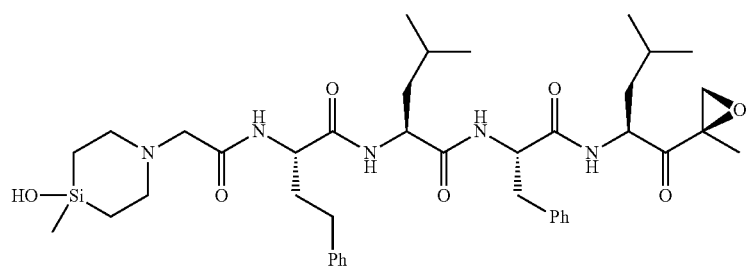
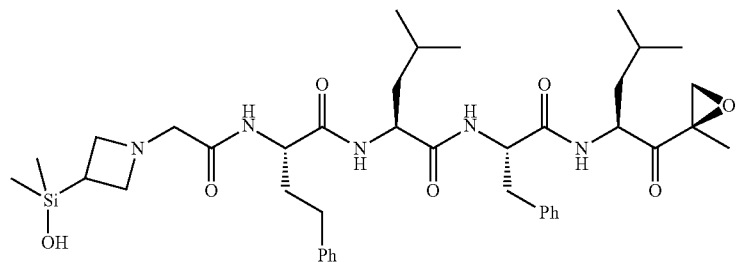
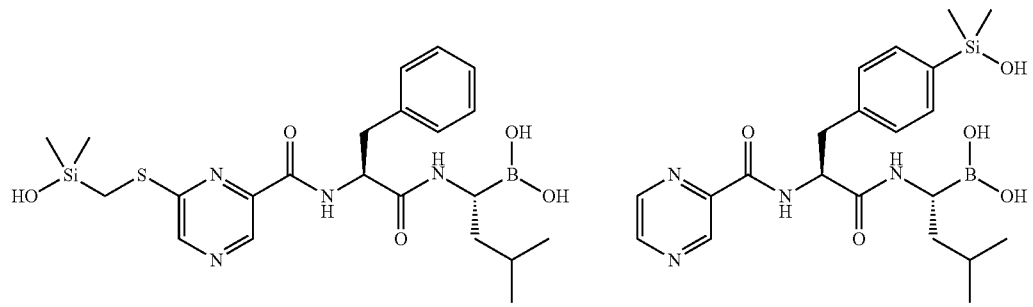
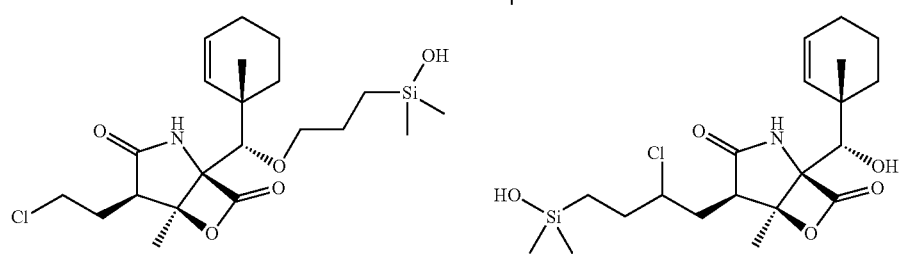
Antifolate Silanols
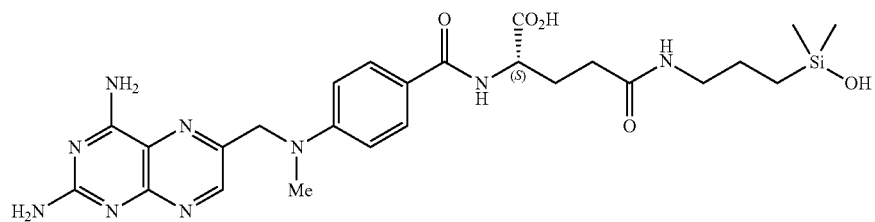

-continued
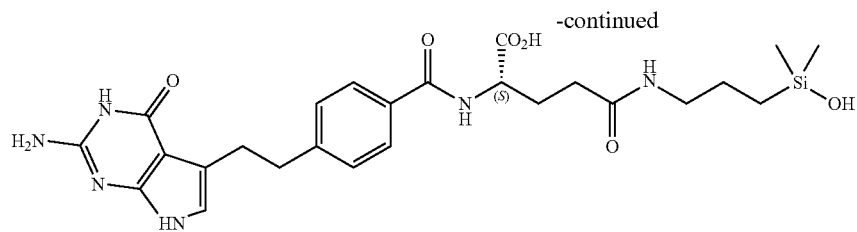
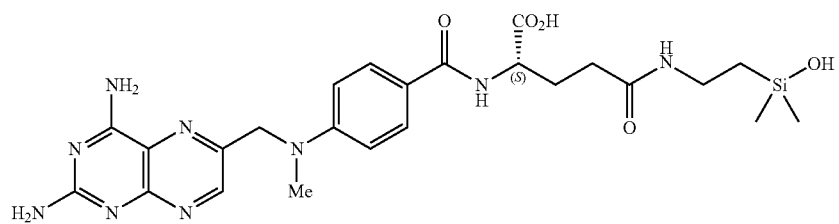
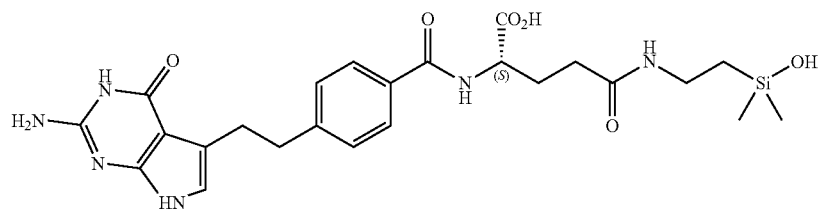
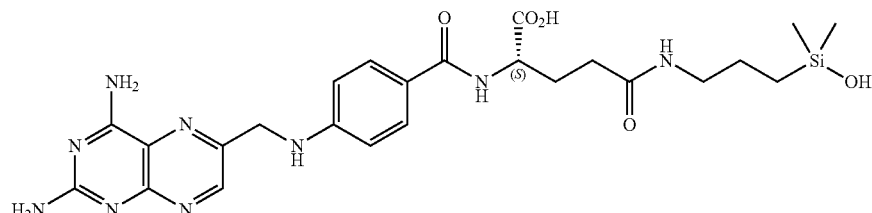
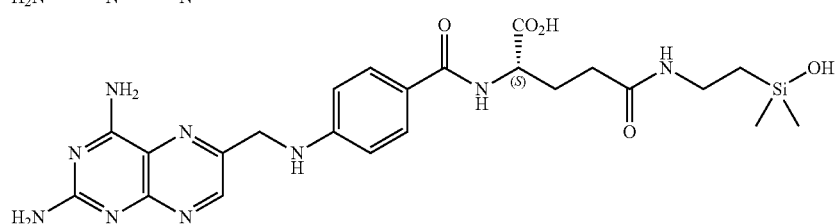
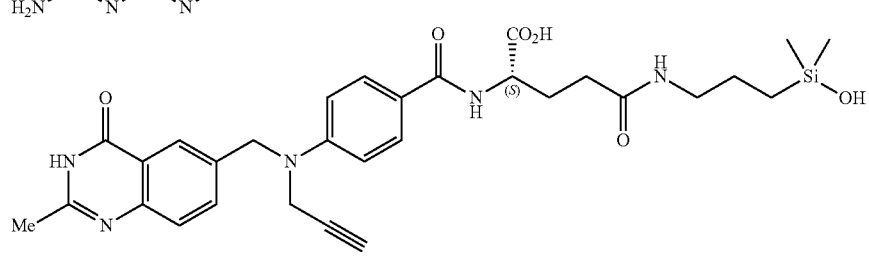
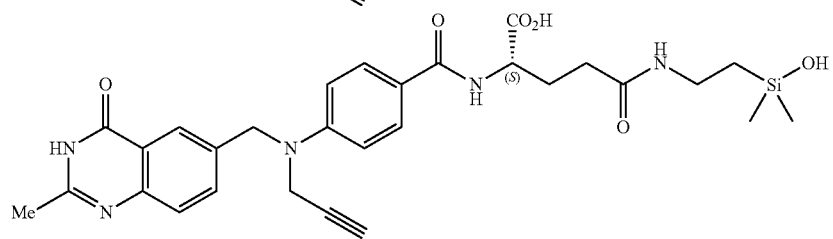

151 152
-continued
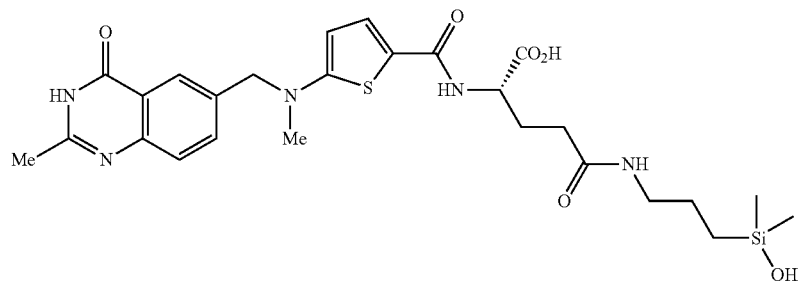
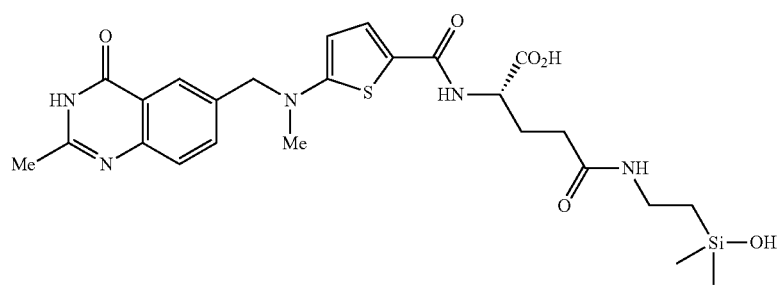
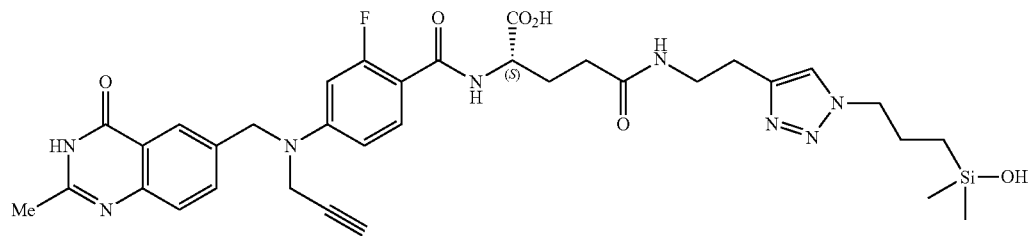
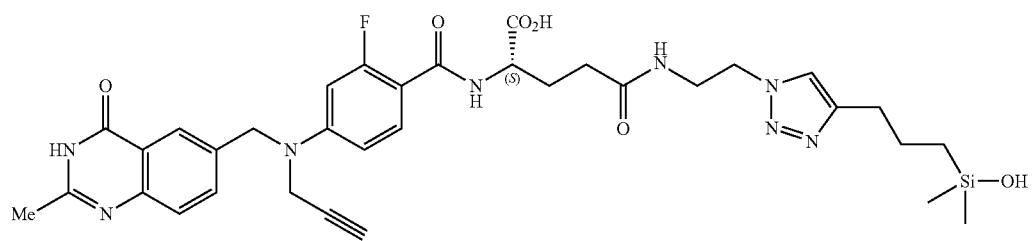
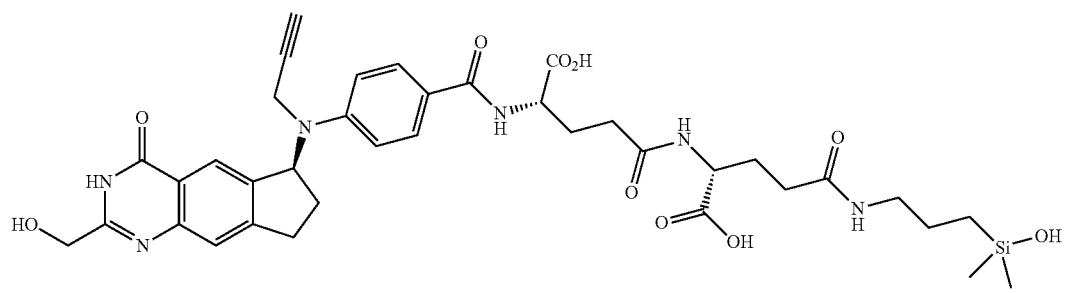
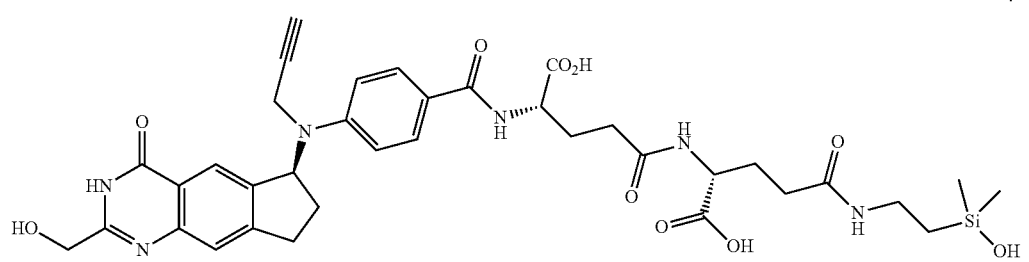

153
154
-continued
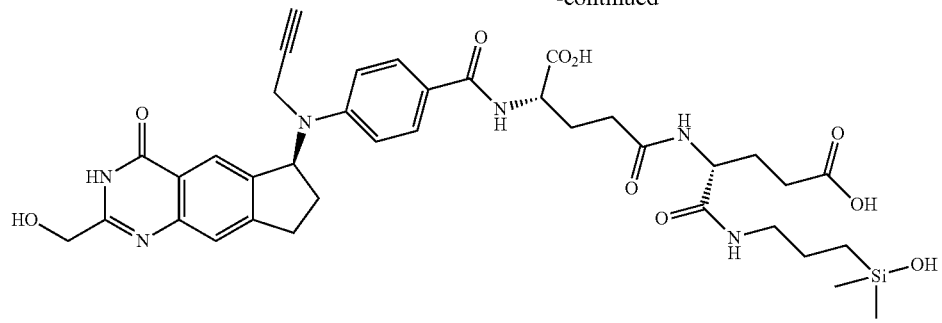
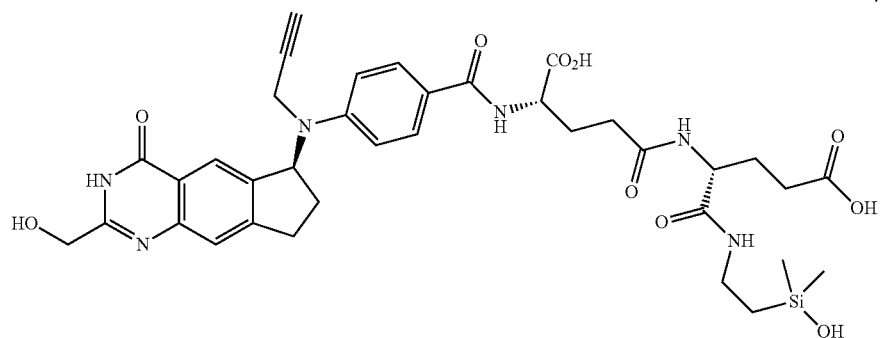
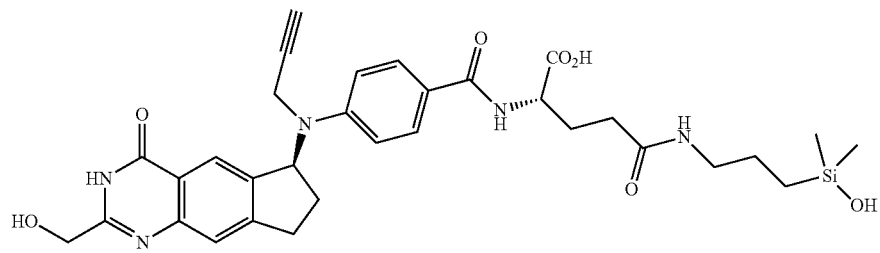
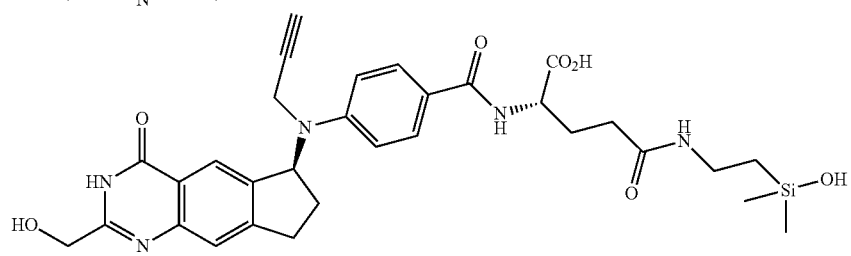
MDM2-P53 Silanols:
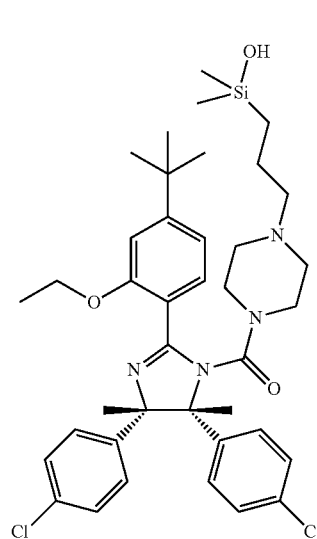
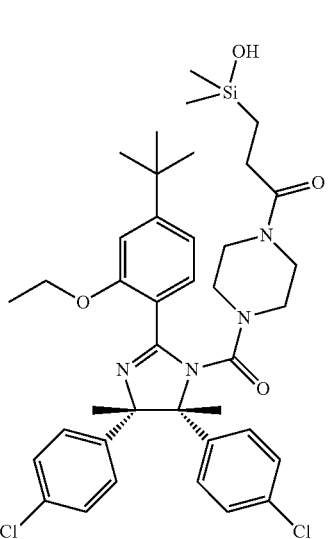
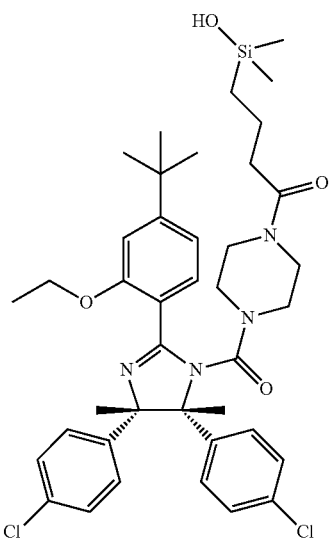

-continued
155
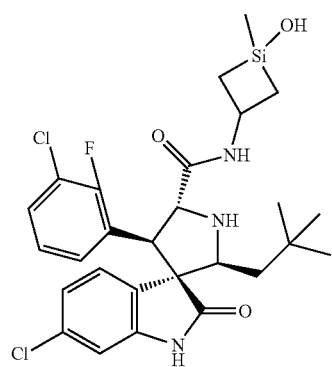
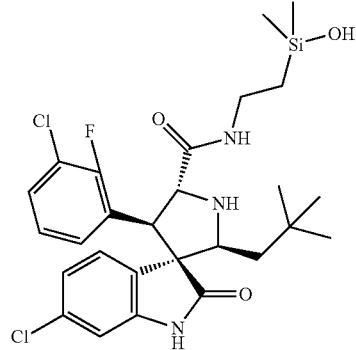
156
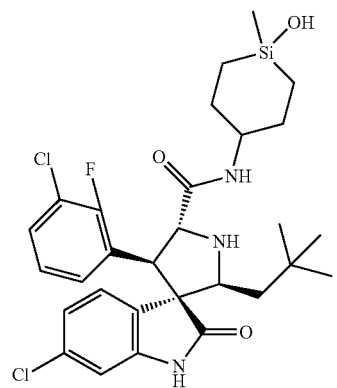
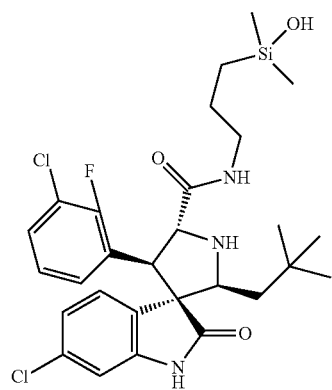
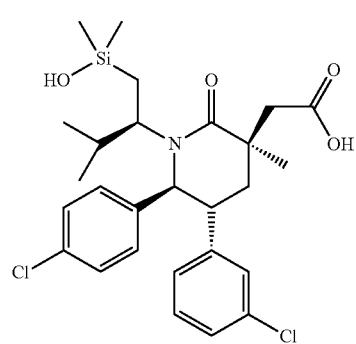
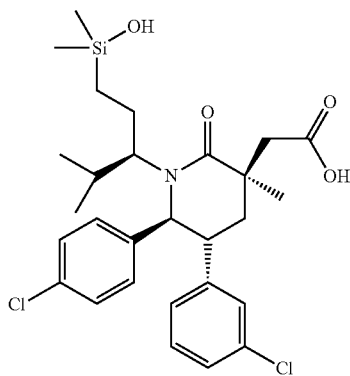
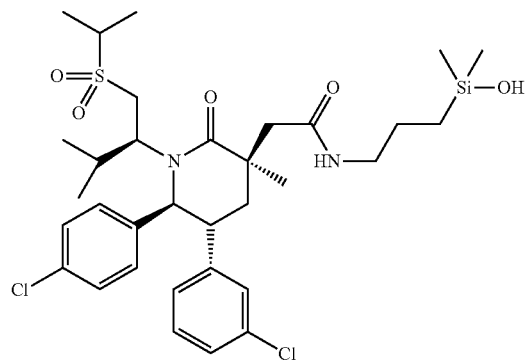
Epigenetic Silanols:
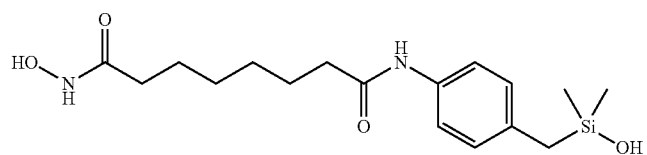
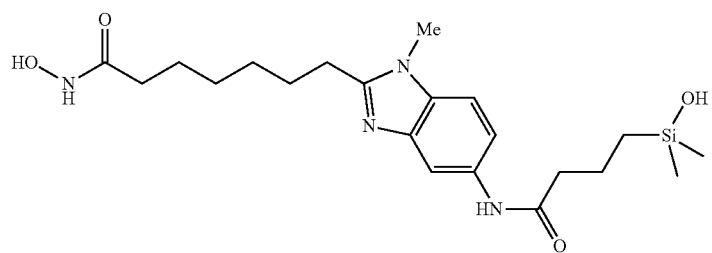

-continued
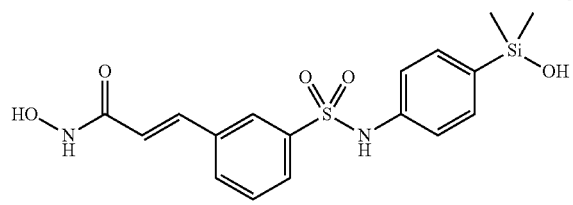
PPAR-γ Silanols:
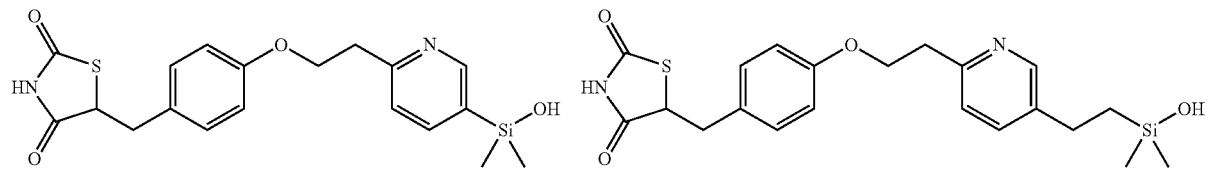
siRNA Silanols:
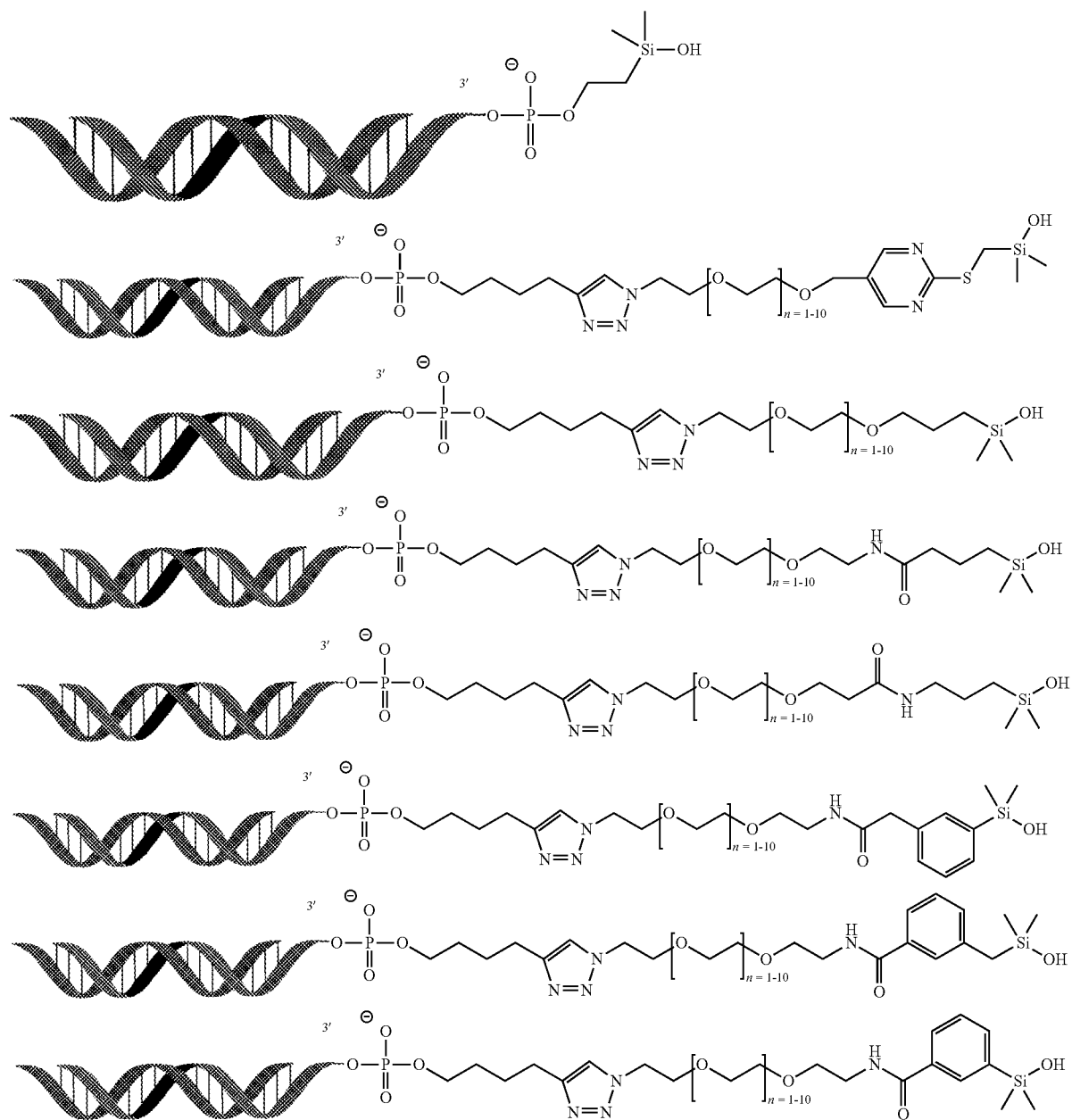

-continued
Lipid Lowering Silanols:
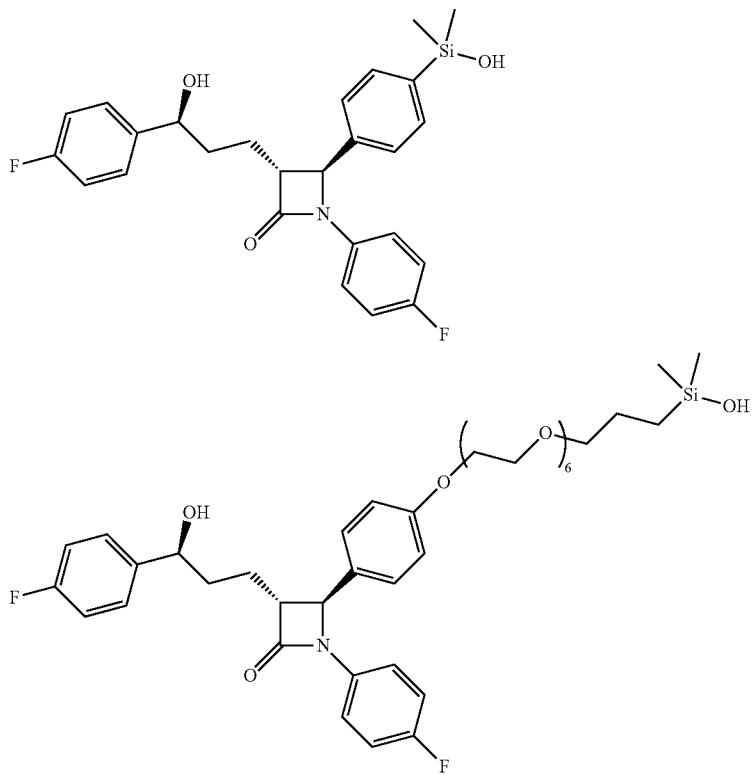
TGR5 (Non-Systemic Takeda G-protein Receptor 5) PEG Silanols:
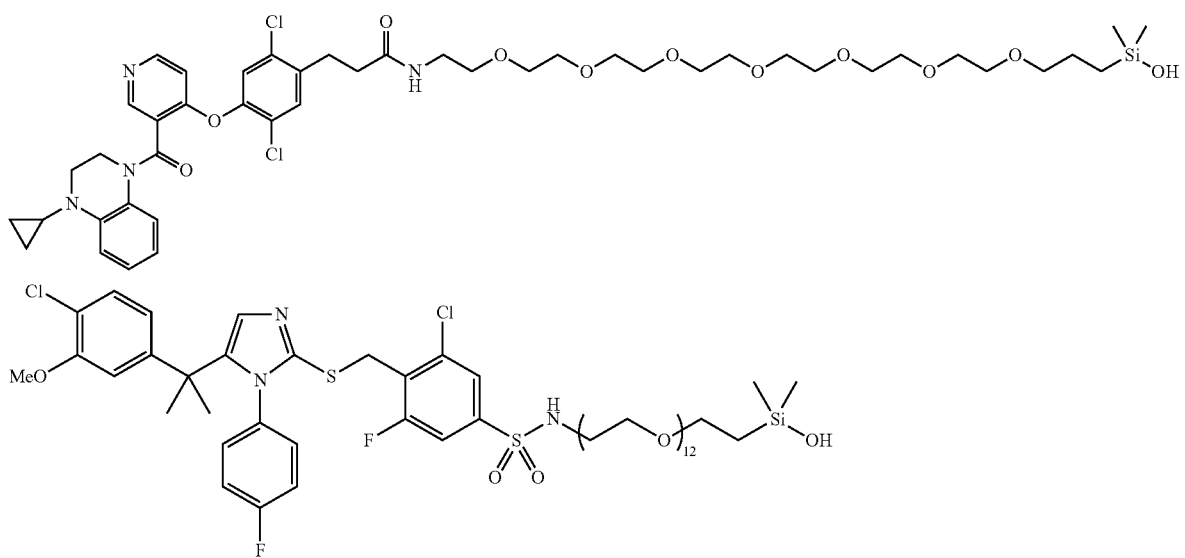
Non-Systemic µ-Opioid Silanols:
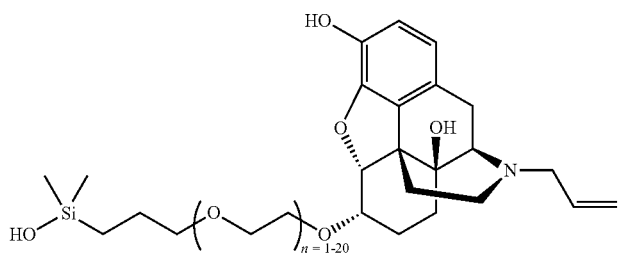

Bisphosphonate Silanols:

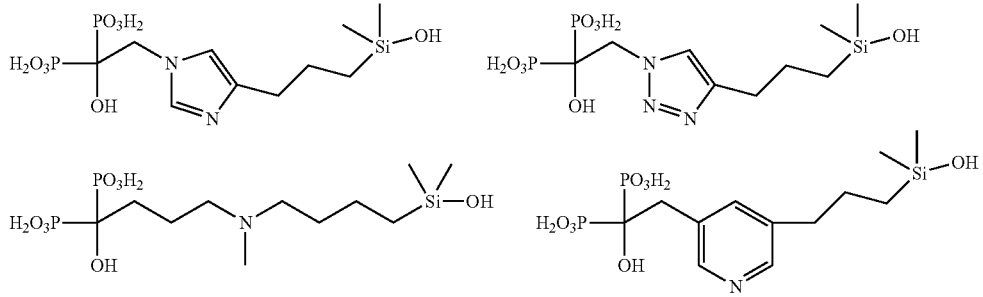

Example 21: N,N'-((1,1,3,3-Tetramethyldisiloxane-1,3-diyl)bis(propane-3,1-diyl))diacetamide

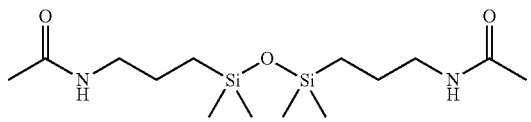 [SMILES: CC(=O)NCCC[Si](C)(C)O[Si](C)(C)CCCNC(C)=O]

A solution of 3,3'-(1,1,3,3-tetramethyldisiloxane-1,3-diyl) bis(propan-1-amine) (2 g, 8.04 mmol) in diethyl ether (100 mL) at 0° C. was charged with triethyl amine (2.8 mL, 20.1 mmol) and acetyl chloride (1.4 mL, 19.2 mmol) and stirred at room temperature for 1 h. The solid precipitated was filtered, washed with diethyl ether and the filtrate was concentrated in vacuo resulting in 2.67 g of the title compound as colorless oil. The crude compound was used in the next step without further purification. $^1$H NMR (400 MHz, DMSO-d$_6$) δ=7.77 (br. s, 2H), 2.94 (d, J=6.36 Hz, 4H), 1.69-1.83 (m, 6H), 1.35 (d, J=6.85 Hz, 4H), 0.36-0.50 (m, 4H), 0.00 (s, 12H), $^1$H NMR (400 MHz, CDCl$_3$) δ=6.04 (br. s, 1H), 3.21 (q, J=6.68 Hz, 4H), 1.93-2.07 (m, 6H), 1.53 (td, J=7.83, 15.65 Hz, 4H), 0.46-0.55 (m, 4H), 0.05 (s, 12H); MS (ESMS+): m/z=355.05 [M+Na]$^+$; ESMS: t$_R$=0.13 min, m/z=377.00 [M+2Na]$^+$; ESMS: t$_R$=0.15 min; MS (ES$^+$): m/z=333.00 [M+H]$^+$; LCMS: t$_R$=2.07 min.

Example 22: 2-(((1,1,3,3,3-Pentamethyldisiloxanyl) methyl)thio)pyrimidine

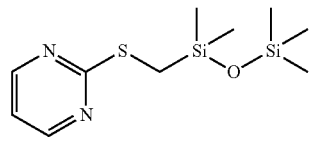 [SMILES: C[Si](C)(C)O[Si](C)(C)CSc1ncccn1]

A solution of pyrimidine-2-thiol (2 g, 17.8 mmol) in acetonitrile (60 mL) was charged with potassium carbonate (3.69 g, 26.7 mmol) and 1-(chloromethyl)-1,1,3,3,3-pentamethyldisiloxane 2 (3.86 g, 19.6 mmol) at room temperature and was further heated to 55° C. for 3 h. The reaction mixture was concentrated in vacuo, diluted with diethyl ether and stirred for 15 min. The solid precipitated was filtered and the filtrate was concentrated in vacuo resulting in the crude compound which was purified by column chromatography on silica gel eluting with 0-5% ethyl acetate in n-hexane to afford 3 g, 62% yield, of the title compound as a colorless oil. $^1$H NMR (400 MHz, DMSO-d$_6$) δ=8.55 (d, J=4.89 Hz, 2H), 7.12 (t, J=4.65 Hz, 1H), 2.31 (s, 2H), 0.09 (s, 6H), 0.00 (s, 9H); MS (ES$^+$): m/z=273.05 [M+H]$^+$; LCMS: t$_R$=3.46 min.

Example 23

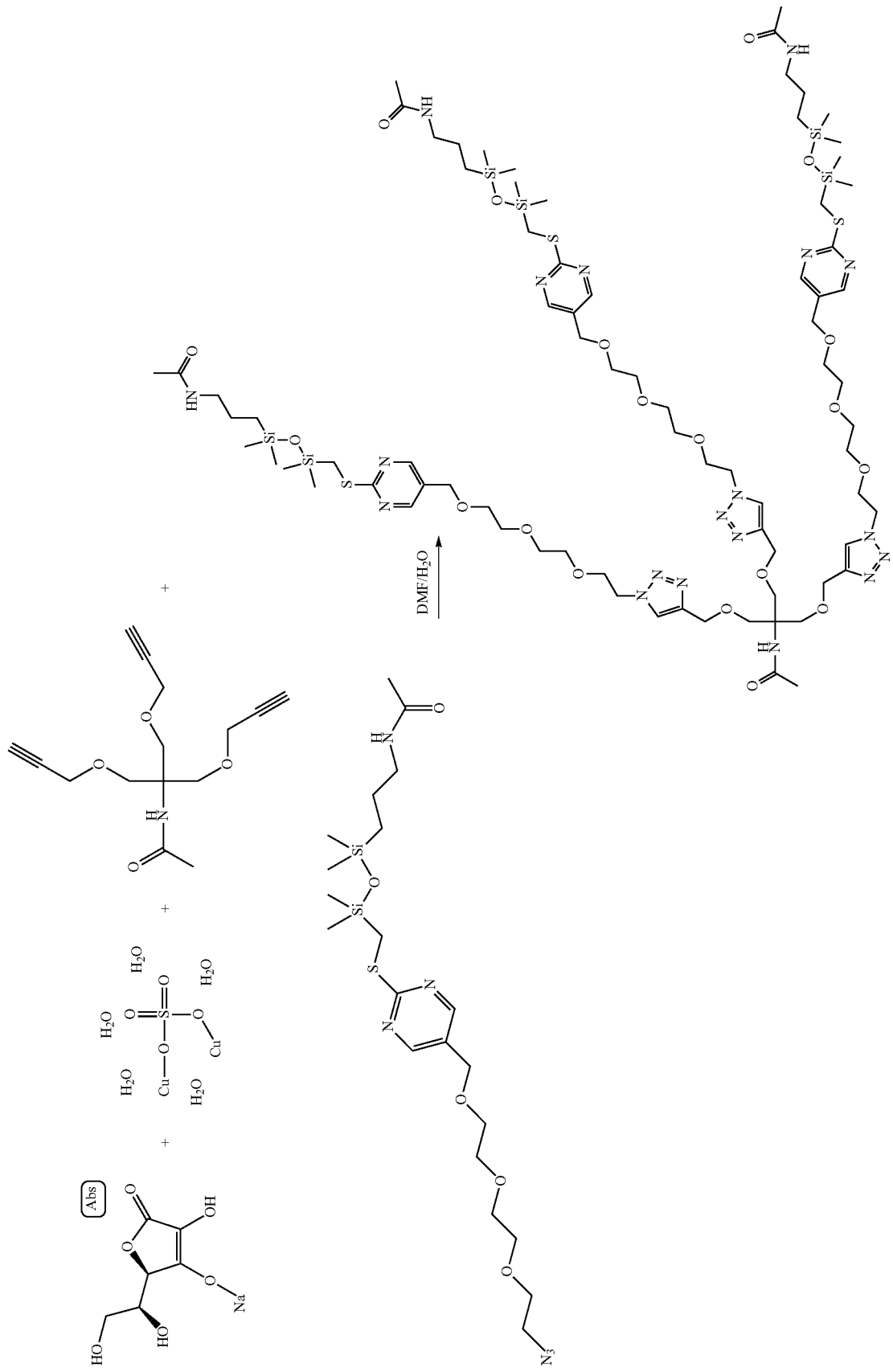

A solution of N-(1,3-bis(prop-2-yn-1-yloxy)-2-((prop-2-yn-1-yloxy)methyl)propan-2-yl)acetamide (10.00 mg, 0.036 mmol) and N-(3-(3-(((5-((2-(2-(2-azidoethoxy)ethoxy)ethoxy)methyl)pyrimidin-2-yl)thio)methyl)-1,1,3,3-tetramethyl disiloxanyl)propyl)acetamide (60.9 mg, 0.112 mmol) were dissolved in DMF (36.1 μl). The reaction mixture was charged with sodium ascorbate (7.14 mg, 0.036 mmol) in water (36.1 μl) followed by the addition of copper sulfate pentahydrate (8.47 mg, 0.027 mmol) in water (36.1 μl). After 15 min the reaction mixture was checked by LCMS and found to have a mass consistent with desired product. The reaction mixture was partitioned between DCM and water and separated. The aqueous was extracted with DCM (3×) and the combined fractions were dried over $Na_2SO_4$, filtered and concentrated in vacuo resulting in a crude which was purified by ISCO chromatography on silica gel [4 g cartridge, eluting with 0% of (10% $NH_4OH$ in MeOH) in DCM to 8% of (10% $NH_4OH$ in MeOH) in DCM] resulting in 11.000 mg, 15.96% yield of the title compound as a clear colorless oil $^1$H NMR (CHLOROFORM-d, 400 MHz): δ (ppm) 8.50 (s, 6H), 7.71 (s, 3H), 6.28 (s, 1H), 5.73-5.86 (m, 3H), 4.57 (s, 6H), 4.54 (t, J=5.2 Hz, 6H), 4.50 (s, 6H), 3.86-3.90 (m, 6H), 3.81 (s, 6H), 3.63 (d, J=10.9 Hz, 23H), 3.18-3.25 (m, 6H), 2.41 (s, 6H), 1.97 (s, 9H), 1.93 (s, 3H), 1.77 (s, 8H), 1.48-1.57 (m, 6H), 0.50-0.57 (m, 6H), 0.21 (s, 18H), 0.09 (s, 18H), MS (ES$^+$): m/z=1911.43, 1912.44. 1913.23 [M+H]$^+$; LCMS: $t_R$=2.31 min [polar_3 min_1500].

Example 24

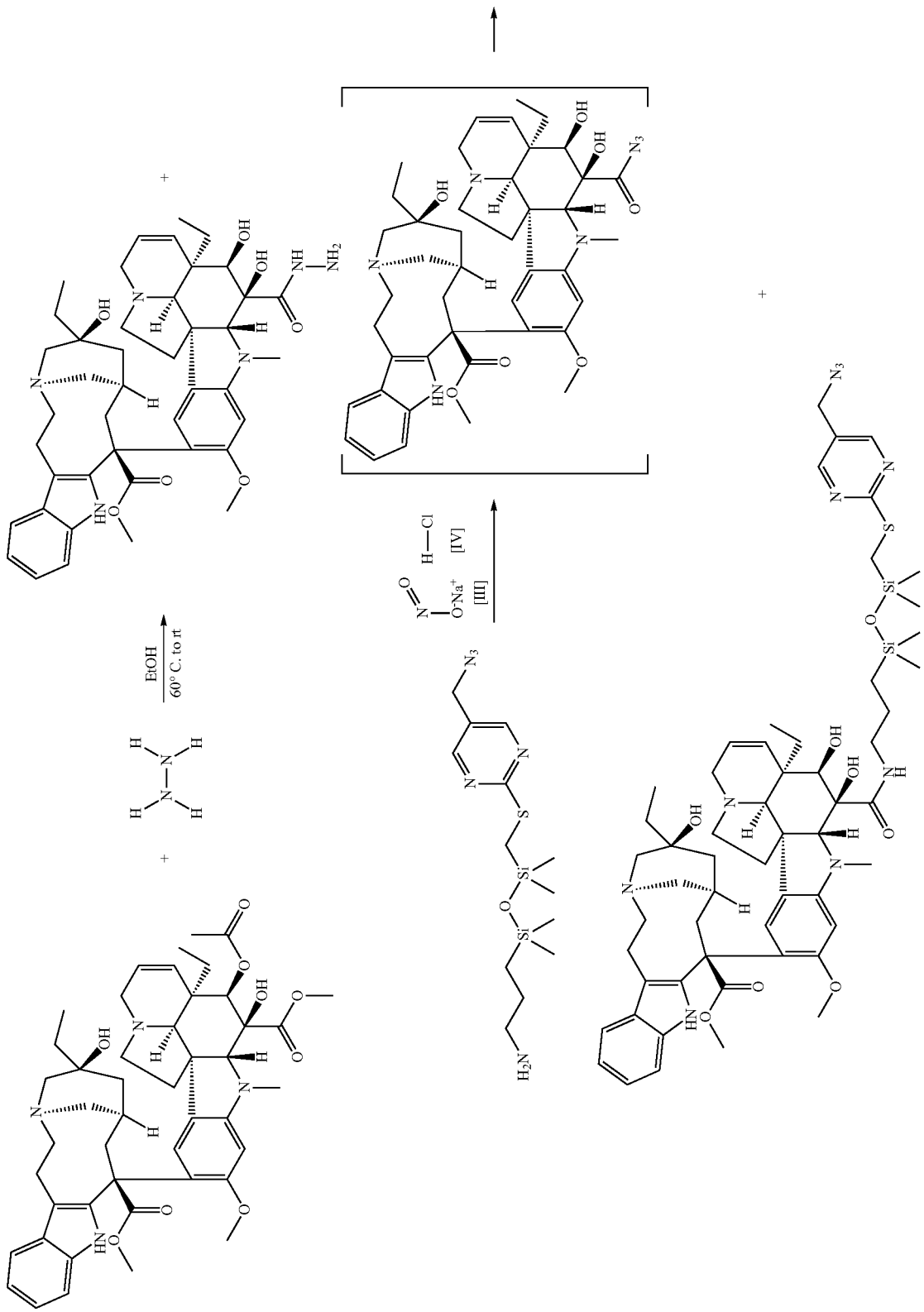

-continued
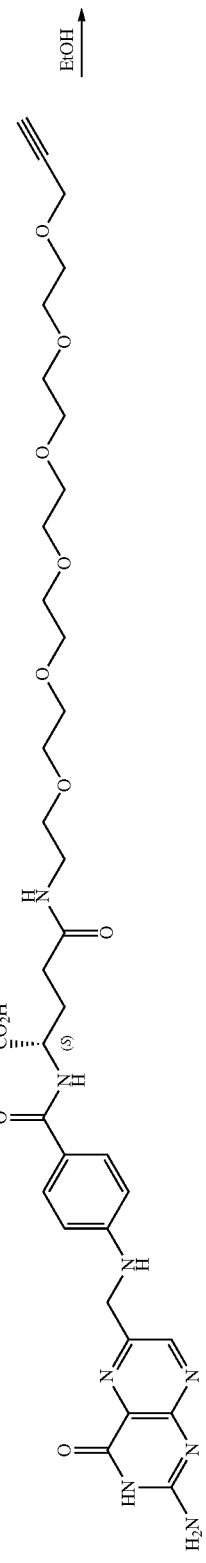
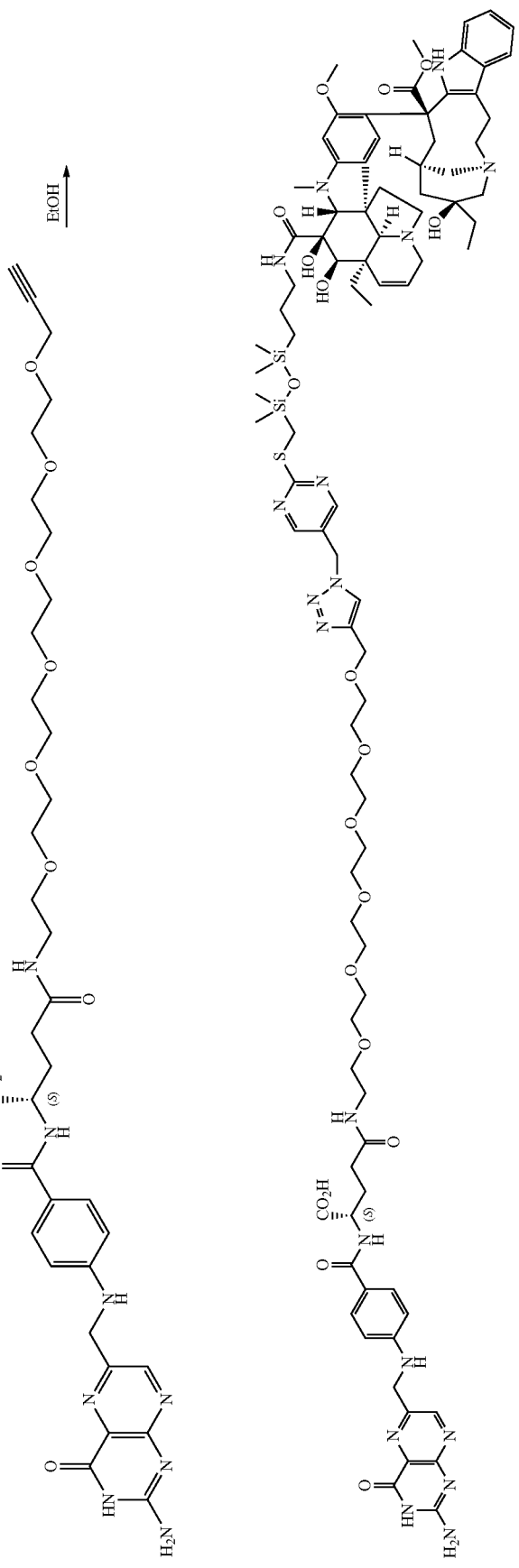
→ EtOH (S)-24-(4-(((2-amino-4-oxo-3,4-dihydropteridin-6-yl)methyl)amino)benzamido)-1-(1-((2-(((3-(3-((3aR,3a1R,4R,5S,5aR,10bR)-3a-ethyl-9-((3S,5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl) methyl)thio) pyrimidin-5-yl)methyl)-1H-1,2,3-triazol-4-yl)-21-oxo-2,5,8,11,14,17-hexaoxa-20-azapentacosan-25-oic acid in water (55 µL). The vial was purged with nitrogen gas, capped, sonicated for 5 min, and agitated on a shaker at rt. A yellow suspension was formed. As the reaction proceeded, more solids went into the solution. After 2.5 h, LCMS showed mainly product. The reaction was stopped. The whole was dissolved with 1.5 mL of DMSO, and passed through an ISCO solid loading filter plug with an aid of a vacuum. For the residue, dissolved with ~0.5 mL of DMSO and passed through the same filter plug. The combined filtrate (2 mL) was purified by a reversed phase preparative HPLC. Using the 10 mM ammonium bicarbonate in water and MeCN mobile phases with gradient 1 for reverse phase

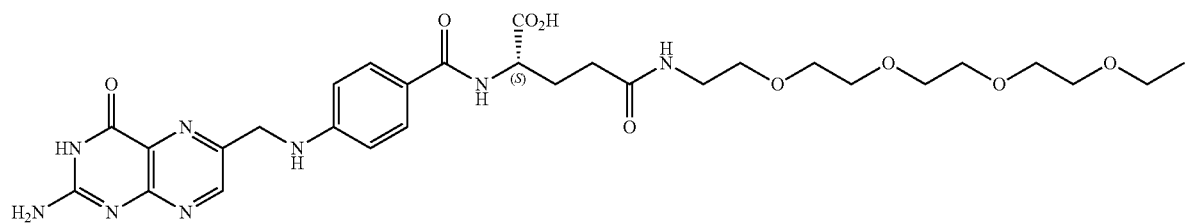

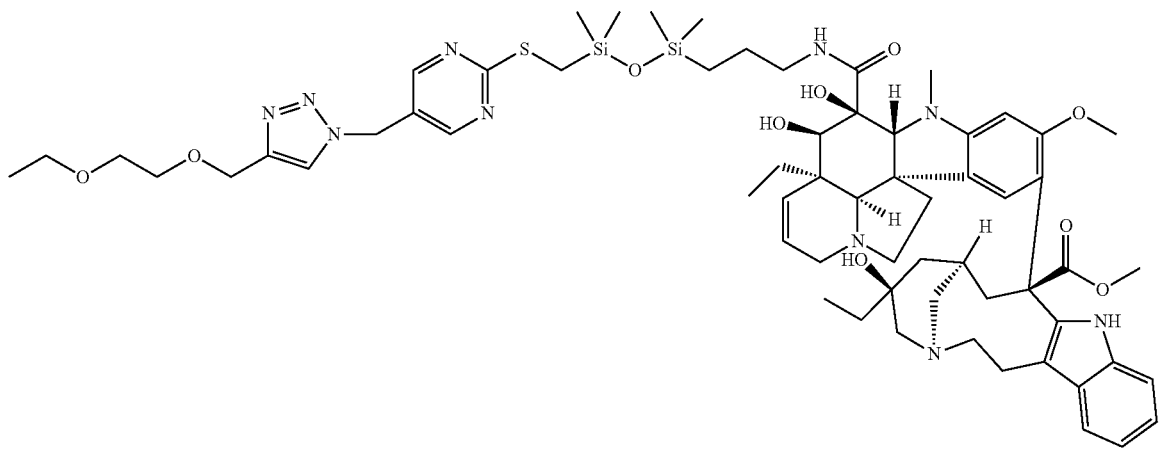

To an Eppendorf vial, DMF (219 µl) was added into a mixture of (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (15.87 mg, 0.021 mmol) and (3R,5S,7R,9S)-methyl 9-((3aR,3a1R,4R,5S,5aR,10bR)-5-((3-(3-(((5-(azidomethyl)pyrimidin-2-yl)thio) methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (18.2 mg, 0.016 mmol). More DMF (219 µL) was added to dissolve both reactants. The vial was purged with nitrogen gas, capped, and sonicated for 5 min. Then a freshly prepared solution of sodium ascorbate (100 mM in water, 32.9 µL, 3.29 µmol) in water (55 µL) was added, followed by the addition of a freshly prepared solution of copper sulfate pentahydrate (100 mM in water, 32.9 µL, 3.29 µmol)

preparative HPLC to obtain 6.15 mg, 20.2% yield of the title compound as a light yellow solid after lyophilizing. 1.51 min LCMS using acidic mobile phase and method [polar_3 min_0_1500] (M+2)=1851.2, (M+2)/2=926.0, (M+3)/3=617.7, (M+4)/4=463.6. $^1$H NMR (400 MHz, DMSO-$d_6$) δ ppm 0.01-0.09 (m, 7H) 0.16 (s, 7H) 0.43-0.55 (m, 2H) 0.63 (br s, 1H) 0.70-0.88 (m, 7H) 1.09-1.37 (m, 7H) 1.38-1.66 (m, 5H) 1.81-2.09 (m, 6H) 2.16 (br d, J=7.07 Hz, 2H) 2.27-2.43 (m, 6H) 2.60-2.77 (m, 8H) 2.89 (br d, J=9.85 Hz, 2H) 3.01-3.22 (m, 15H) 3.43-3.57 (m, 18H) 3.71 (s, 5H) 3.83 (br d, J=5.81 Hz, 1H) 3.91-4.11 (m, 3H) 4.23 (br s, 1H) 4.43-4.55 (m, 4H) 5.52-5.73 (m, 5H) 6.19 (s, 1H) 6.44 (s, 1H) 6.54-6.70 (m, 3H) 6.86-7.05 (m, 5H) 7.26 (d, J=8.08 Hz, 1H) 7.37 (d, J=7.83 Hz, 1H) 7.63 (br d, J=8.34 Hz, 2H) 7.77 (br t, J=5.68 Hz, 1H) 7.89 (br s, 1H) 8.09 (br s, 1H) 8.20 (s, 1H) 8.48-8.73 (m, 4H) 9.33 (s, 1H). MS (ES$^+$): m/z=(M+2)=1851.2, (M+2)/2=926.0, (M+3)/3=617.7, (M+4)/4=463.6. [M+H]$^+$; LCMS: $t_R$=1.51 min [polar_3 min_1500].

Methyl(3R,5S,7R,9S)-9-((3aR,3a1R,4R,5S,5aR,10bR)-5-((3-(3-(((5-(azidomethyl) pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate

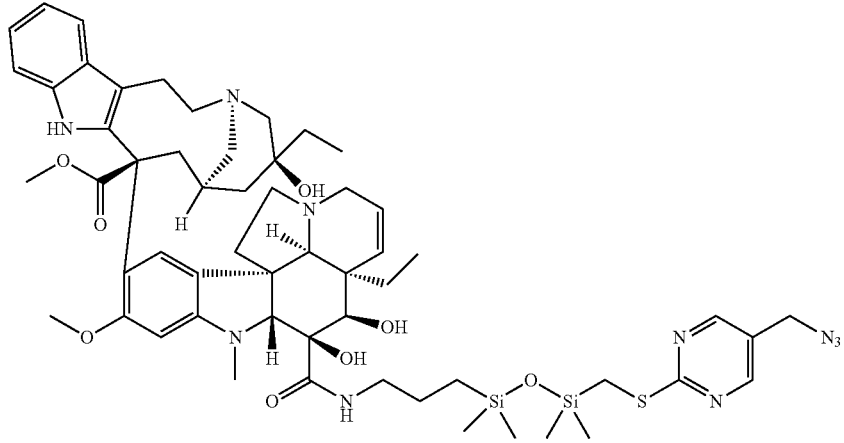

A solution of (3R,5S,7R,9S)-methyl 5-ethyl-9-((3aR,3a1R,4R,5S,5aR,10bR)-3a-ethyl-5-(hydrazinecarbonyl)-4,5-dihydroxy-8-methoxy-6-methyl-3a,3a1,4,5,5a,6,11,12-octahydro-1H-indolizino[8,1-cd]carbazol-9-yl)-5-hydroxy-2,4,5,6,7,8,9,10-octahydro-1H-3,7-methano[1]azacycloundecino[5,4-b]indole-9-carboxylate (200 mg, 0.260 mmol) in acetonitrile (3.34 ml) was cooled to −10° C. and charged with 1 M HCl in water (12.33 ml, 12.33 mmol) and maintained at −10° C. then charged with solid sodium nitrite (41.3 mg, 0.598 mmol) (Note: upon addition of NaNO₂ the color changed from pale yellow/colorless to a yellowish brown color) After 10 min the yellowish brown solution was adjusted to pH ~8.00 with dropwise addition of cold sat NaHCO₃ solution (~13.2 mL of NaHCO₃ added). The solution was extracted rapidly with DCM (5×10 mL) and the combined organic layers were washed with brine (1×20 mL) and dried over Na₂SO₄, filtered, and concentrated to ~8.00 mL-10 mL cooled to 0° C. and charged with a solution of 3-(3-(((5-(azidomethyl)pyrimidin-2-yl)thio)methyl)-1,1,3,3-tetramethyldisiloxanyl)propan-1-amine (96 mg, 0.260 mmol) in DCM (8.0 mL) and allowed to stir at 0° C. for 2 hr. The reaction mixture was concentrated in vacuo resulting in a light tan solid. The crude was further purified by chromatography on silica gel [ISCO CombiFlash, 12 g Gold cartridge, eluting with 0% of (10% 7N NH3 in MeOH) to 8% (10% 7N NH3 in MeOH) in DCM resulting in 127 mg, 44% yield of the title compound as a pale yellow foam solid. ¹H NMR (CHLOROFORM-d, 400 MHz): δ (ppm) 9.47-9.59 (m, 1H), 8.49 (s, 2H), 8.04 (s, 1H), 7.54 (d, J=8.1 Hz, 1H), 7.15-7.21 (m, 3H), 7.08-7.14 (m, 1H), 6.61 (s, 1H), 6.08 (s, 1H), 5.84 (s, 2H), 4.34 (s, 2H), 4.19 (d, J=4.8 Hz, 1H), 3.92-4.03 (m, 1H), 3.78 (s, 3H), 3.63-3.74 (m, 1H), 3.61 (s, 3H), 3.38-3.45 (m, 2H), 3.07-3.37 (m, 8H), 2.83-2.89 (m, 1H), 2.79-2.83 (m, 5H), 2.62 (s, 1H), 2.60 (d, J=4.8 Hz, 1H), 2.37-2.50 (m, 4H), 2.24-2.33 (m, 1H), 1.98-2.10 (m, 1H), 1.68-1.83 (m, 2H), 1.52-1.60 (m, 4H), 1.45-1.51 (m, 1H), 1.37-1.45 (m, 1H), 1.21-1.36 (m, 4H), 0.87-1.00 (m, 7H), 0.85 (br d, J=6.1 Hz, 1H), 0.54-0.62 (m, 2H), 0.19-0.25 (m, 6H), 0.10 (s, 6H), MS (ES⁺): m/z=1107.61, 1108.56 [M+H]⁺; LCMS: $t_R$=1.62 min [polar_3 min_1500].

Methyl(3R,5S,7R,9S)-9-((3aR,3a1R,4R,5S,5aR,10bR)-5-((3-(3-(((5-(azidomethyl)pyrimidin-2-yl)thio)methyl)-1,1,3,3-tetramethyldisiloxanyl) propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate

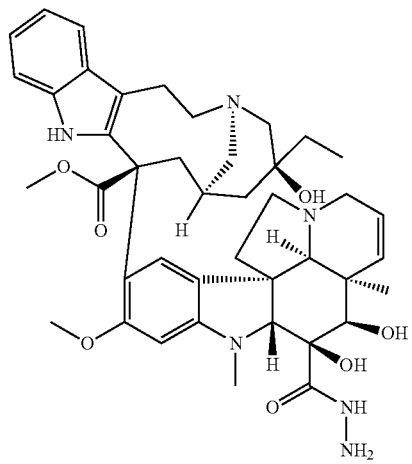

A solution of hydrazine (12.77 ml, 407 mmol) in Ethanol (15.03 ml) was charged with (3aR,3a1R,4R,5S,5aR,10bR)-methyl 4-acetoxy-3a-ethyl-9-((3R,5S,7R,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-5-hydroxy-8-methoxy-6-methyl-3a,3a1,4,5,5a,6,11,12-octahydro-1H-indolizino[8,1-cd]carbazole-5-carboxylate, sulfuric acid salt (2.5 g, 2.75 mmol) and heated to 60° C. under a N₂ atmosphere. The reaction mixture was heated to 60° C. for 16 h then stirred at rt for an additional 6 hrs. The reaction mixture was poured into 90 mL of HPLC grade water and the aqueous was extracted with 5×90 mL of DCM and the combined organic fractions were washed with water 1×90 mL and brine 1×120 mL and dried over anhydrous $Na_2SO_4$, filtered and concentrated in vacuo resulting in crude product that was further purified by column chromatography on silica gel [ISCO Combiflash, 12 g gold cartridge] eluting with a gradient of 100% DCM to 8% 7N NH3 in MeOH in DCM] resulting in 1.42 g, 67.1% yield of the title compound as an off-white solid. $^1$H NMR (DMSO-$d_6$, 400 MHz): δ (ppm) 9.31 (s, 1H), 8.87-9.03 (m, 1H), 8.81 (br s, 1H), 8.33 (s, 1H), 7.37 (d, J=7.8 Hz, 1H), 7.26 (d, J=8.1 Hz, 1H), 6.96-7.04 (m, 1H), 6.88-6.95 (m, 1H), 6.45 (s, 1H), 6.20 (s, 1H), 5.76 (s, 2H), 5.66-5.72 (m, 1H), 5.54-5.62 (m, 1H), 4.23 (br d, J=3.8 Hz, 2H), 4.12 (br d, J=3.5 Hz, 1H), 4.05 (br dd, J=15.2, 13.6 Hz, 1H), 3.90-3.97 (m, 2H), 3.82 (d, J=6.1 Hz, 1H), 3.65-3.78 (m, 4H), 3.54 (s, 3H), 3.36 (s, 1H), 3.26 (br d, J=14.1 Hz, 1H), 3.03-3.22 (m, 4H), 2.89 (br dd, J=14.4, 4.5 Hz, 1H), 2.61-2.77 (m, 6H), 2.28-2.42 (m, 2H), 1.97-2.05 (m, 1H), 1.88-1.97 (m, 1H), 1.74 (s, 2H), 1.51-1.66 (m, 2H), 1.25-1.38 (m, 2H), 1.12-1.21 (m, 3H), 0.71-0.85 (m, 6H), 0.56-0.67 (m, 1H), MS (ES$^+$): m/z=769.40, 770.41 [M+H]$^+$; LCMS: $t_R$=132 min [polar_3 min_1500].

Example 25

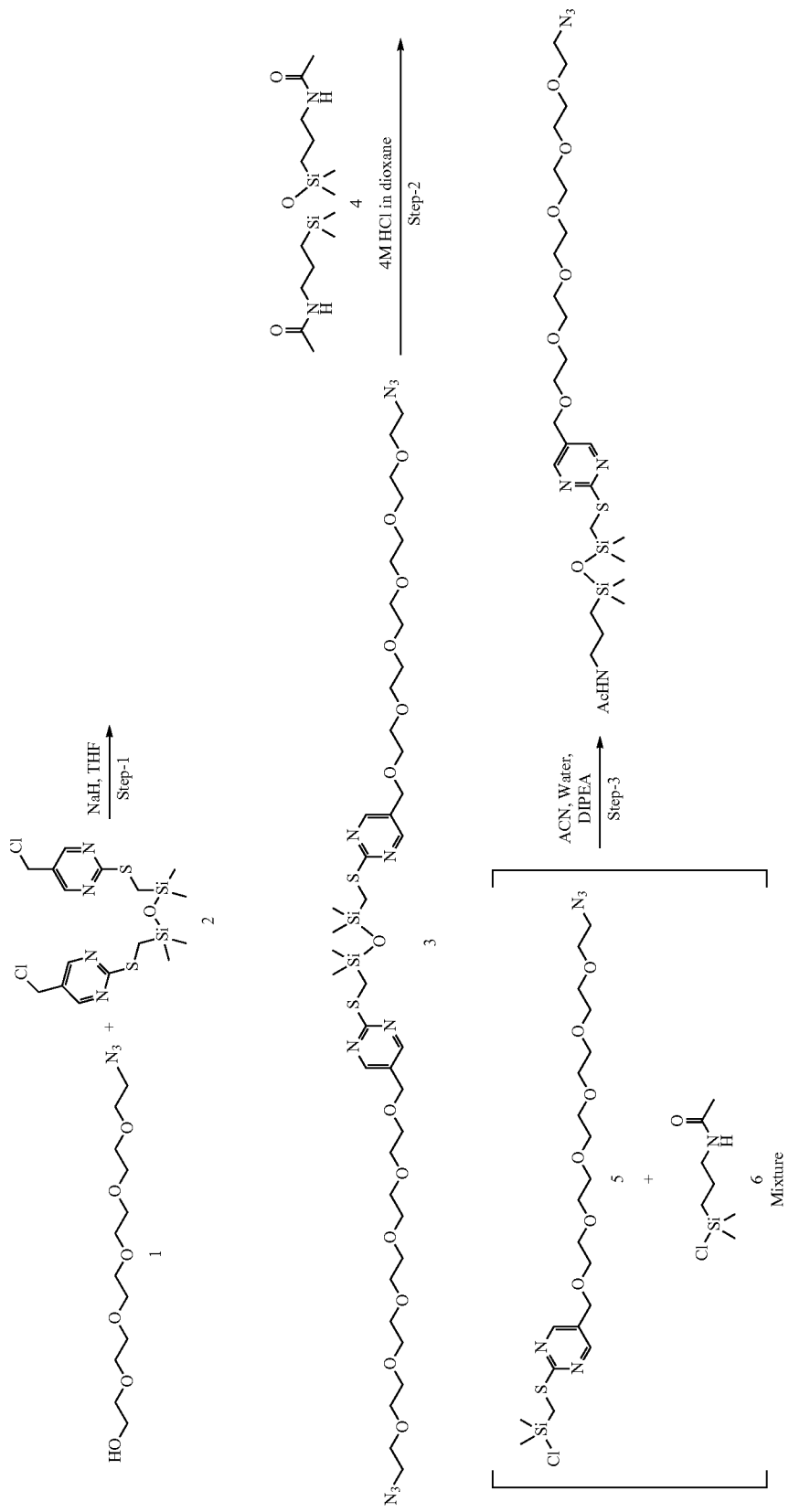

N-(3-(3-(((5-(19-azido-2,5,8,11,14,17-hexaoxanonadecyl)pyrimidin-2-yl)thio)methyl)-1,1,3,3-tetramethyldisiloxanyl)propyl)acetamide

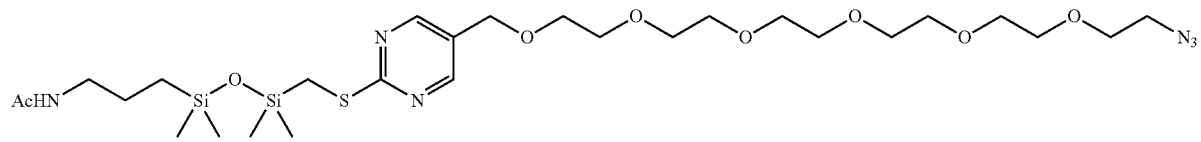 [SMILES: CC(=O)NCCC[Si](C)(C)O[Si](C)(C)CSc1ncc(COCCOCCOCCOCCOCCOCCN=[N+]=[N-])cn1]

A solution of 1,3-bis(((5-(19-azido-2,5,8,11,14,17-hexaoxanonadecyl)pyrimidin-2-yl)thio)methyl)-1,1,3,3-tetramethyldisiloxane (4.90 g, 4.799 mmol) and N,N-((1,1,3,3-tetramethyldisiloxane-1,3-diyl)bis(propane-3,1-diyl))diacetamide (3.30 g, 4.799 mmol) in 4M HCl in dioxane (100 mL) was stirred at room temperature for 1 h. The reaction mixture was concentrated in vacuo resulting in the crude intermediate 5 and 6. The intermediate 5 and 6 was dissolved in acetonitrile (250 mL) and followed by addition of water (250 mL) and DIPEA (4.90 mL, 28.79 mmol) and stirred at room temperature for another 1 h. The reaction mixture was concentrated in vacuo resulting in the crude compound which was purified by combiflash chromatography on silica gel eluting with 50-80% ethyl acetate in n-hexane to afford 3.56 g, 55% yield, of the title compound as a colorless oil. $^1$H NMR (400 MHz, DMSO-$d_6$) δ=8.60 (s, 2H), 7.76-7.82 (m, 1H), 4.47-4.51 (m, 2H), 3.49-3.64 (m, 22H), 3.37-3.42 (m, 2H), 2.94-3.02 (m, 2H), 2.36-2.42 (m, 2H), 1.78 (s, 3H), 1.34-1.45 (m, 2H), 0.44-0.53 (m, 2H), 0.18 (s, 6H), 0.07 (s, 6H); MS (ES$^+$): =676.70 [M+H]$^+$; LCMS: $t_R$=3.27 min.

1,3-Bis(((5-(19-azido-2,5,8,11,14,17-hexaoxanonadecyl)pyrimidin-2-yl)thio)methyl)-1,1,3,3-tetramethyldisiloxane (3)

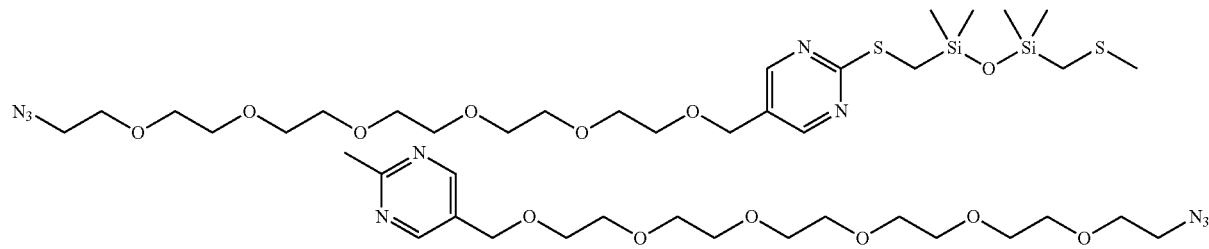

A solution of 17-azido-3,6,9,12,15-pentaoxaheptadecan-1-ol (3 g, 9.771 mmol) in THF (250 mL) at 0° C. was charged with sodium hydride (502 mg, 14.65 mmol) and stirred at same temperature for 30 min. Followed by addition of 1,3-bis(((5-(chloromethyl)pyrimidin-2-yl)thio)methyl)-1,1,3,3-tetramethyldisiloxane (7 g, 14.65 mmol) to the resulting solution and was stirred at the same temperature for another 1 h. The reaction mixture was concentrated in vacuo resulting in the crude compound which was purified by combiflash column chromatography eluting with 0-5% methanol in DCM to afford 5.90 g, 60% yield, of the title compound as colorless oil. $^1$H NMR (400 MHz, DMSO-$d_6$) δ=8.60 (s, 1H), 8.57 (s, 3H), 4.46-4.49 (m, 4H), 3.49-3.63 (m, 45H), 3.36-3.43 (m, 6H), 2.39-2.42 (m, 4H), 0.18 (s, 9H); MS (ES$^+$): =511.40 [M/2+H]$^+$; LCMS: $t_R$=3.53 min.

Examples 26 and 27

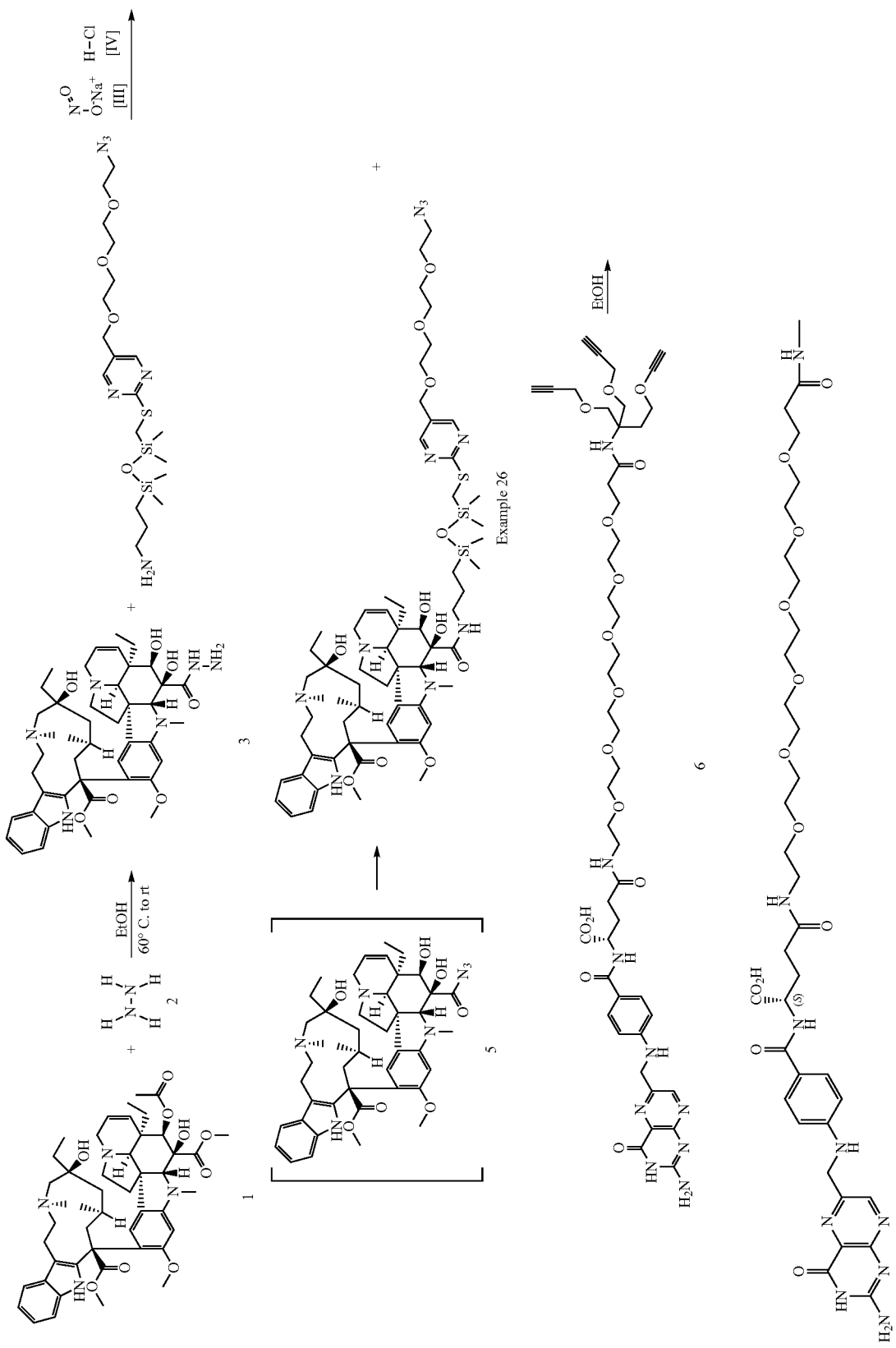

-continued
183 184
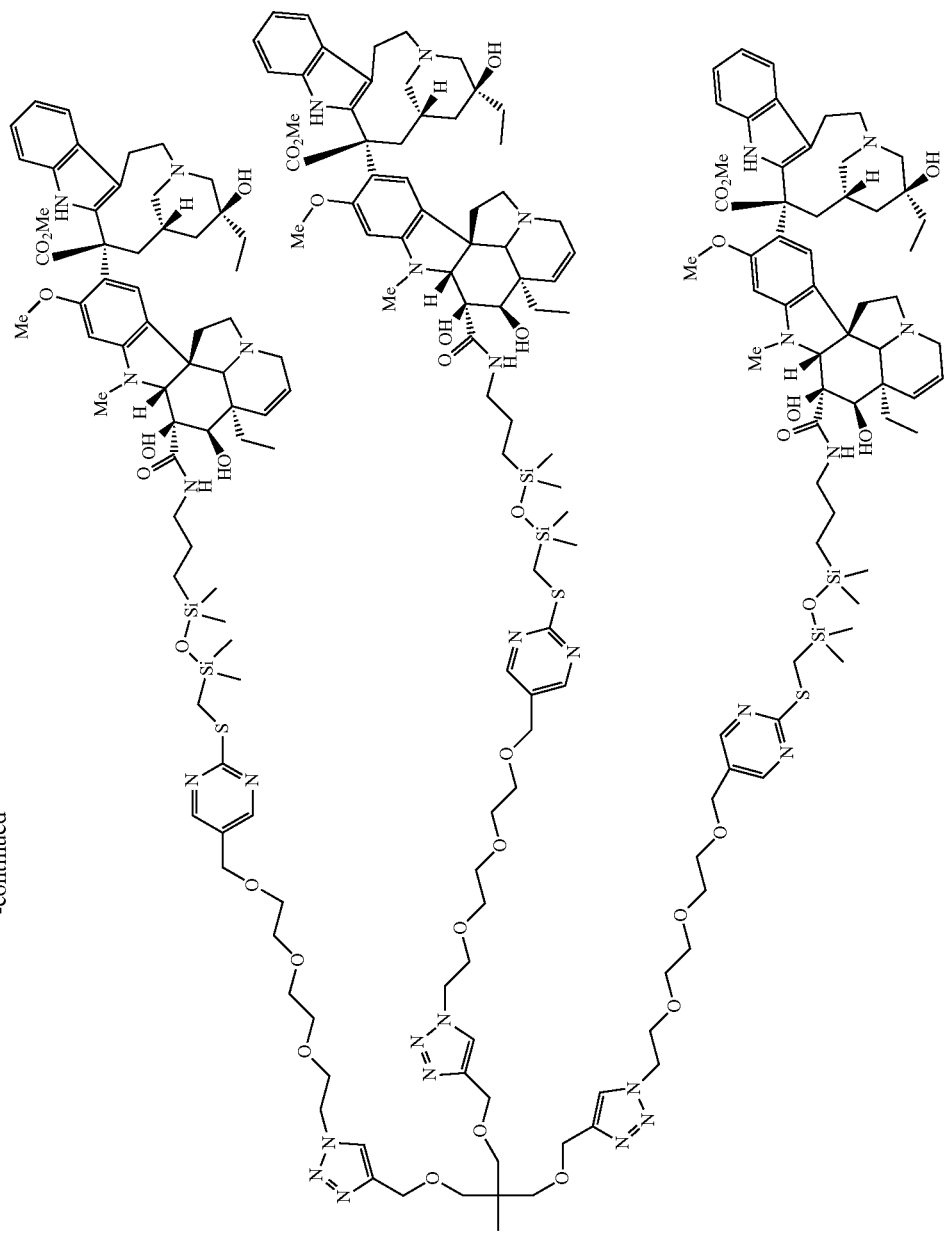
Example 27

Methyl (3R,5S,7R,9S)-9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate [Example 26]

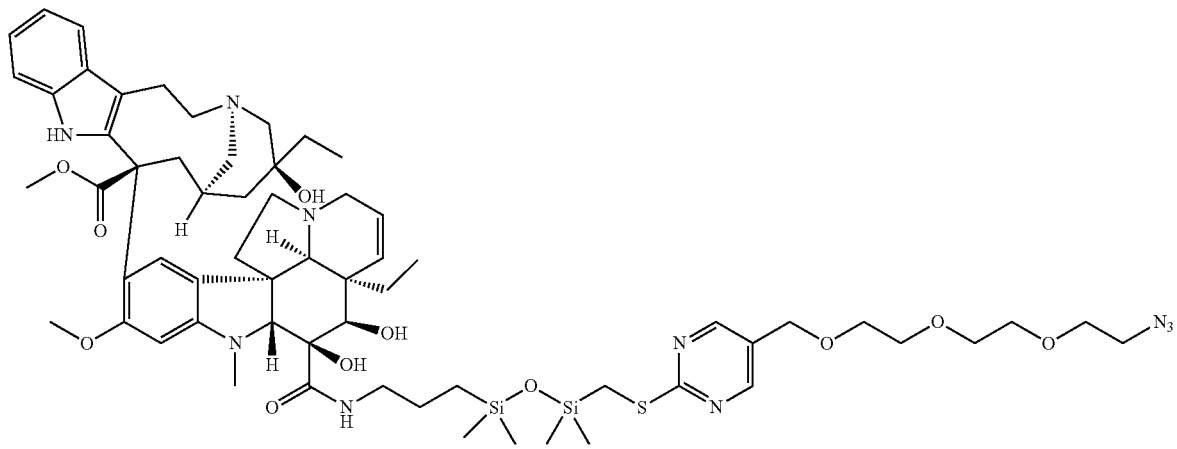

A solution of (3R,5S,7R,9S)-methyl 5-ethyl-9-((3aR,3a1R,4R,5S,5aR,10bR)-3a-ethyl-5-(hydrazinecarbonyl)-4,5-dihydroxy-8-methoxy-6-methyl-3a,3a1,4,5,5a,6,11,12-octahydro-1H-indolizino[8,1-cd]carbazol-9-yl)-5-hydroxy-2,4,5,6,7,8,9,10-octahydro-1H-3,7-methano[1]azacycloundecino[5,4-b]indole-9-carboxylate (100 mg, 0.130 mmol) in acetonitrile (1.67 ml) and 1 M HCl in water (6.16 ml, 6.16 mmol) cooled to −10° C. then charged with sodium nitrite (20.64 mg, 0.299 mmol). After 10 min the yellowish brown solution was adjusted to pH ~8.00 dropwise adding cold sat NaHCO$_3$ solution (~6.6 mL of NaHCO$_3$ added). The solution was extracted rapidly with DCM (5×5.0 mL) and the combined organic layers were washed with brine (1×10 mL) and dried over Na$_2$SO$_4$, filtered and concentrated to ~4.00 mL cooled to 0° C. in and charged with a solution of 3-(3-(((5-((2-(2-(2-azidoethoxy)ethoxy)ethoxy)methyl)pyrimidin-2-yl)thio)methyl)-1,1,3,3-tetramethyldisiloxanyl)propan-1-amine (65.4 mg, 0.130 mmol) in 4.0 mL of DCM and allowed to stir at 0° C. for 2 hr. The reaction mixture was concentrated in vacuo resulting in a light tan solid which was purified by chromatography on silica gel [ISCO CombiFlash, 12 g Gold cartridge, eluting with 0% of (10% 7N NH3 in MeOH) to 8% (10% 7N NH3 in MeOH) in DCM resulting in 65.5 mg, 41% yield of the title compound as a light yellow solid. $^1$H NMR (DMSO-d$_6$, 400 MHz): δ (ppm) 9.33 (s, 1H), 8.58 (s, 2H), 8.51 (s, 1H), 7.77 (br t, J=5.8 Hz, 1H), 7.37 (d, J=8.1 Hz, 1H), 7.26 (d, J=8.1 Hz, 1H), 7.00 (t, J=7.6 Hz, 1H), 6.88-6.95 (m, 1H), 6.44 (s, 1H), 6.19 (s, 1H), 5.69 (br dd, J=10.7, 5.4 Hz, 1H), 5.54-5.61 (m, 1H), 4.47 (s, 2H), 4.00-4.10 (m, 1H), 3.96 (s, 1H), 3.92 (s, 1H), 3.83 (d, J=5.8 Hz, 1H), 3.68-3.76 (m, 4H), 3.49-3.62 (m, 13H), 3.36-3.40 (m, 2H), 3.30-3.34 (m, 6H), 2.98-3.28 (m, 7H), 2.84-2.93 (m, 1H), 2.59-2.77 (m, 6H), 2.52-2.55 (m, 1H), 2.48-2.52 (m, 7H), 2.30-2.42 (m, 4H), 1.89-2.05 (m, 2H), 1.42-1.65 (m, 4H), 1.12-1.36 (m, 5H), 0.69-0.85 (m, 6H), 0.57-0.68 (m, 1H), 0.46-0.55 (m, 2H), 0.17 (s, 6H), 0.07 (s, 6H), MS (ES$^+$): m/z=1240.00, 1240.90 [M+H]$^+$; LCMS: t$_R$=1.65 min [polar_3 min_1500].

(31S)-31-(4-(((2-Amino-4-oxo-3,4-dihydropteridin-6-yl)methyl)amino)benzamido)-1-(1-(2-(2-(2-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methoxy)ethoxy)ethoxy)ethyl)-1H-1,2,3-triazol-4-yl)-4,4-bis(((1-(2-(2-(2-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl) methoxy)ethoxy)ethoxy)ethyl)-1H-1,2,3-triazol-4-yl)methoxy)methyl)-6,28-dioxo-2,9,12,15,18,21,24-heptaoxa-5,27-diazadotriacontan-32-oic acid [Example 27]

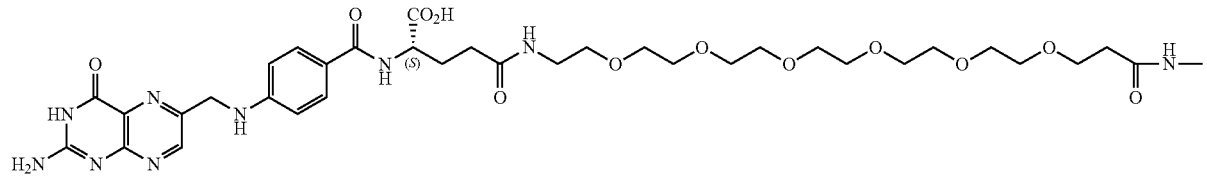

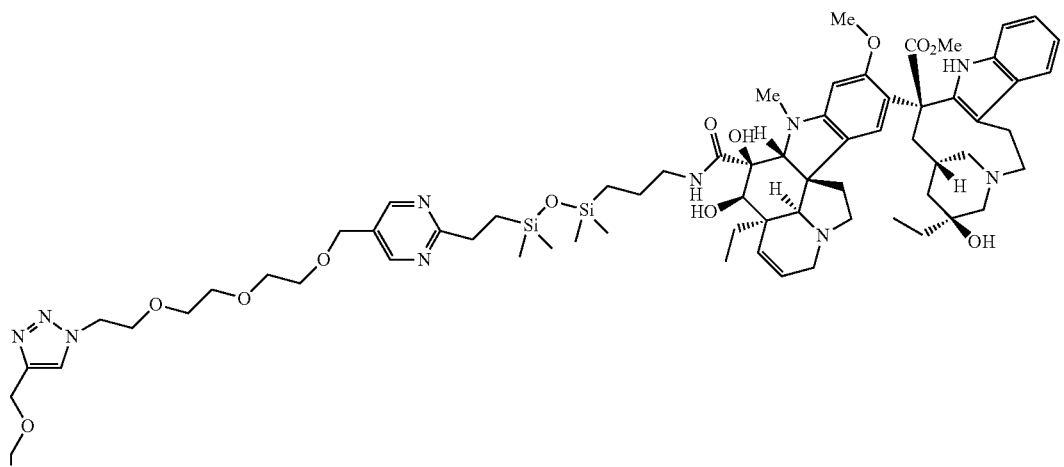

-continued

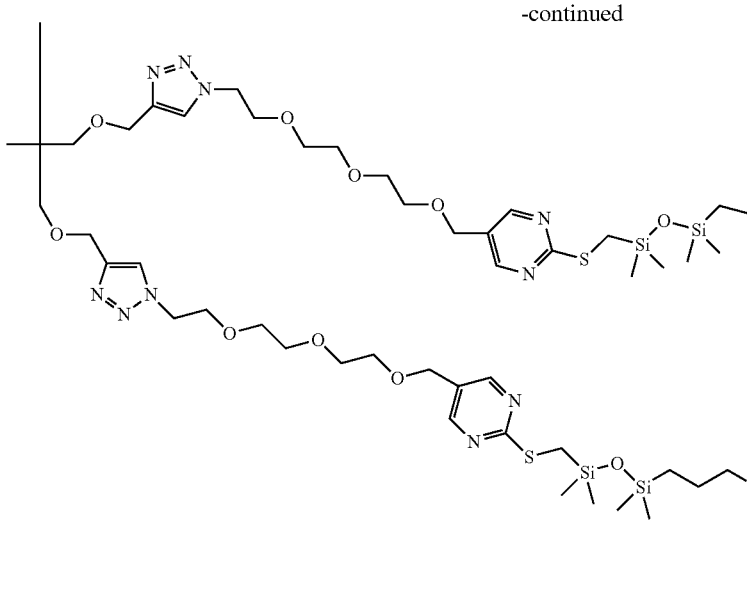
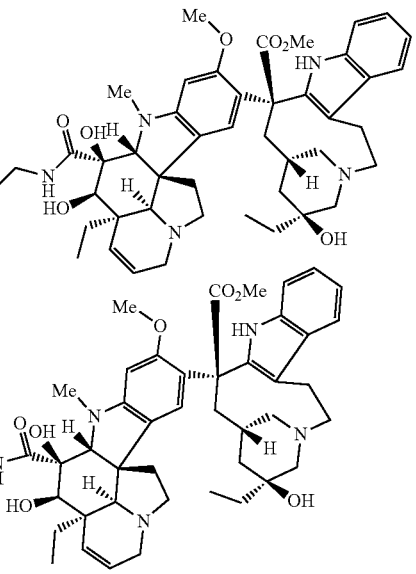

To an Eppendorf vial, DMF (134 µL) was added to a mixture of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (10 mg, 10.06 µmol) and (5S,7S,9S)-methyl 9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyl disiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (43.6 mg, 0.035 mmol). More DMF (134 µL) was added to dissolve both reactants. The whole was purged with nitrogen gas, capped, and sonicated for 5 min. Then a freshly prepared solution of sodium ascorbate (100 mM in water, 40.2 µL, 4.02 µmol) followed by the addition of a freshly prepared solution of copper sulfate pentahydrate (100 mM in water, 20.12 µL, 2.01 µmol). The whole was purged with nitrogen gas, capped, sonicated for 5 mM, and agitated on a shaker at rt. After 1.5 h LCMS showed mainly both SMs but a lot of gummy solid adhered to the Eppendorf vial. More sodium ascorbate (100 mM in water, 80 µL, 8 µmol) and copper sulfate pentahydrate (100 mM in water, 40 µL, 4 µmol) were added. After 15 min, the reaction was stopped. The whole was passed through an ISCO solid loading filter plug with an aid of a vacuum. For the residue, dissolved with ~0.5 mL of DMSO and passed through the same filter plug. The combined filtrate (1.7 mL) was purified by a reversed phase preparative HPLC [Gradient 2] resulting in 2.12 mg, 4.47% yield of the title compound as a light yellow solid. $^1$H NMR (400 MHz, DMSO-$d_6$) δ ppm 9.32 (s, 1H) 8.63 (s, 1H) 8.56 (s, 2H) 7.98 (s, 2H) 7.69-7.85 (m, 1H) 7.61 (br d, J=8.08 Hz, 1H) 7.32-7.49 (m, 1H) 7.16-7.32 (m, 1H) 6.85-7.13 (m, 3H) 6.63 (br d, J=8.84 Hz, 1H) 6.44 (s, 1H) 6.19 (s, 1H) 5.76 (br s, 1H) 5.63-5.73 (m, 1H) 5.49-5.63 (m, 1H) 5.39 (br d, J=7.58 Hz, 1H) 4.37-4.67 (m, 9H) 3.87-4.15 (m, 7H) 3.74-3.87 (m, 6H) 3.71 (s, 5H) 3.63 (br s, 5H) 3.41-3.57 (m, 26H) 3.21-3.27 (m, 1H) 3.00-3.21 (m, 4H) 2.89 (br d, J=10.36 Hz, 1H) 2.70 (s, 4H) 2.63 (br d, J=14.15 Hz, 2H) 2.53-2.58 (m, 1H) 2.29-2.40 (m, 3H) 1.86-2.03 (m, 1H) 1.59 (br dd, J=13.39, 7.33 Hz, 1H) 1.47 (dt, J=15.85, 7.61 Hz, 2H) 1.20-1.36 (m, 3H) 1.16 (br d, J=7.83 Hz, 3H) 0.67-0.86 (m, 5H) 0.63 (br s, 1H) 0.45-0.58 (m, 2H) 0.16 (s, 5H) 0.00-0.11 (m, 7H). MS (ES$^+$): m/z=(M+3)/3=1571.9, (M+4)/4=1179.4, (M+5)/5=943.7, (M+6)/6=786.6; LCMS: $t_R$=1.58 min [polar_3 min_1500].

Compound 6:
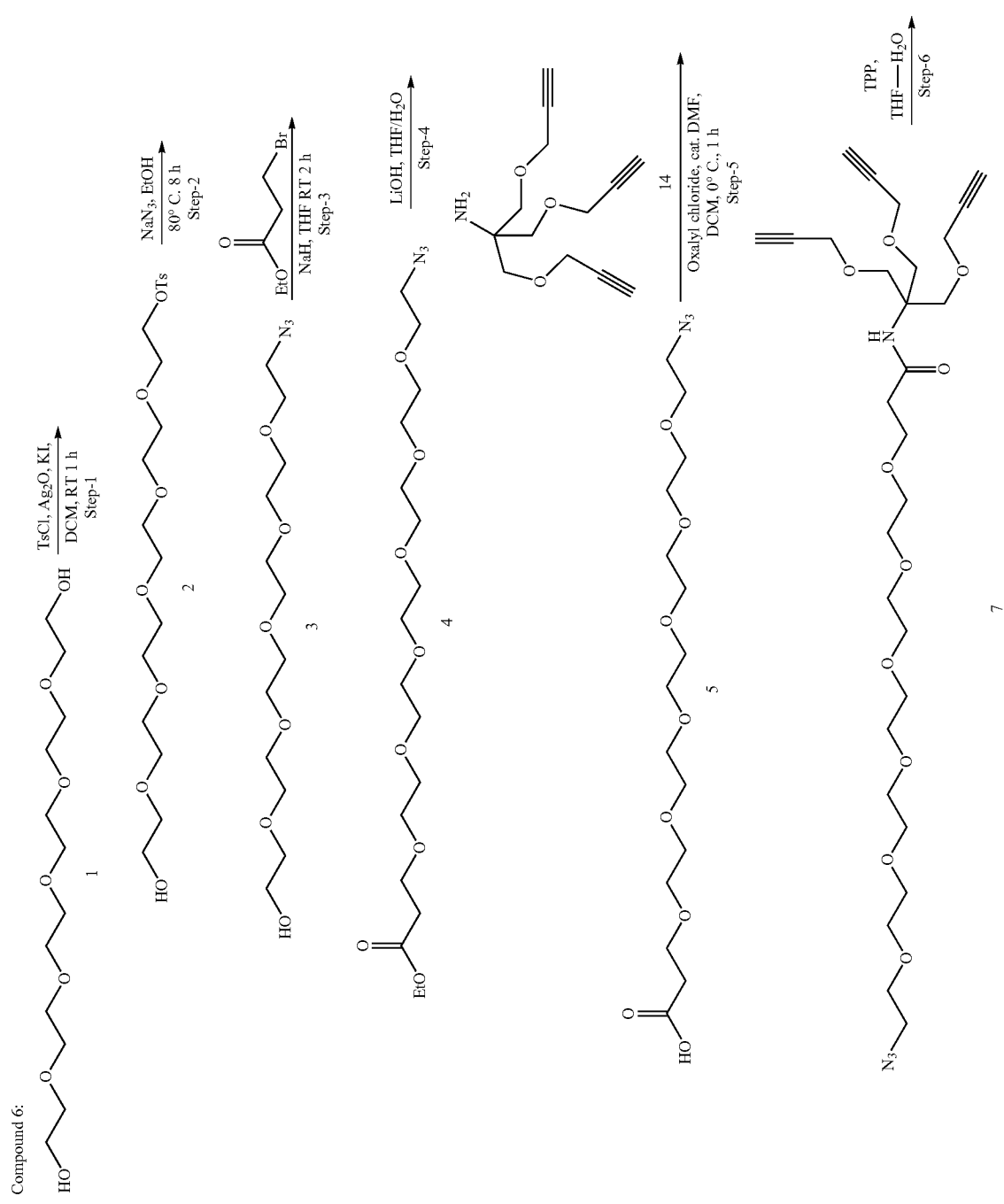

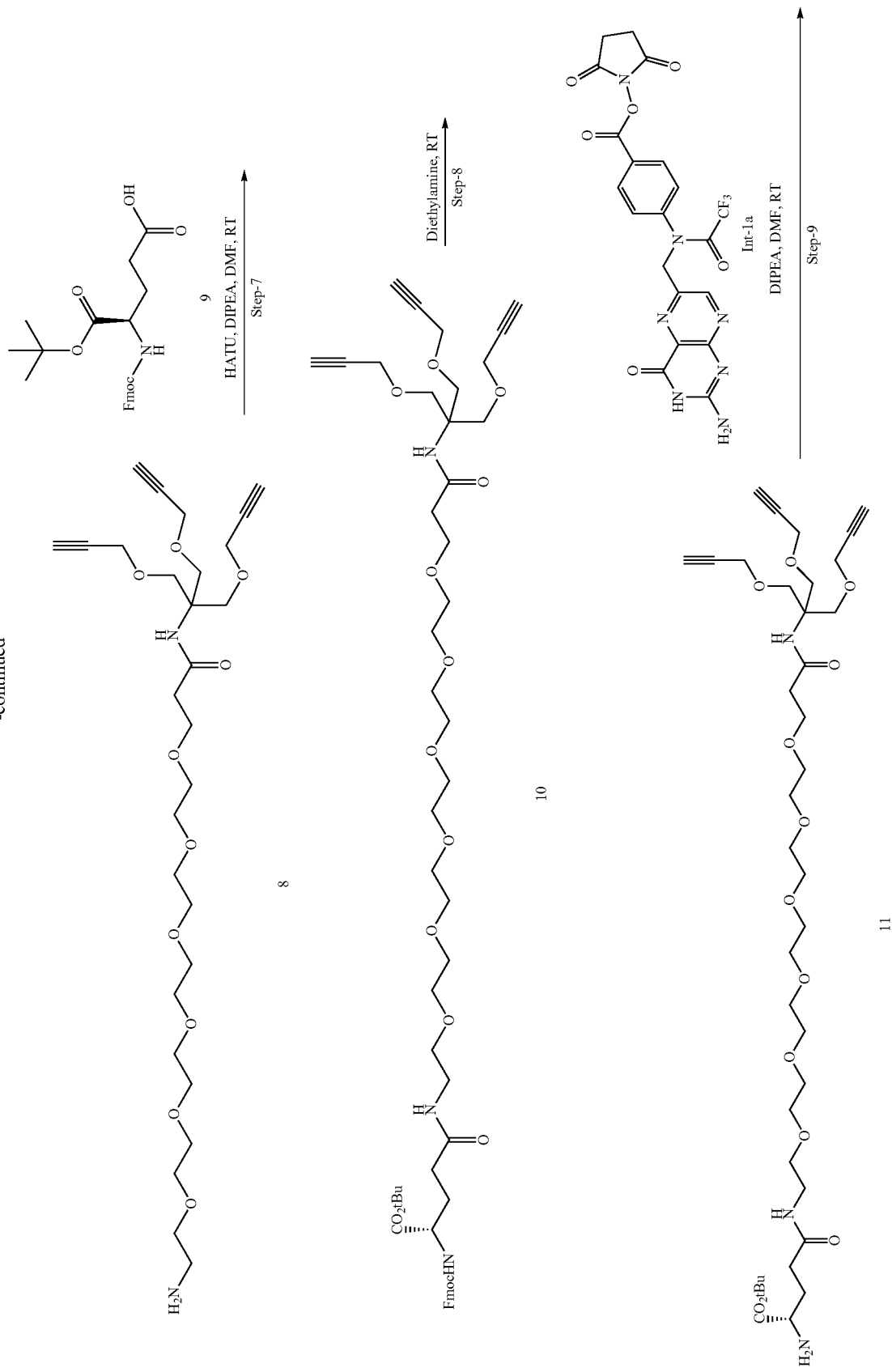

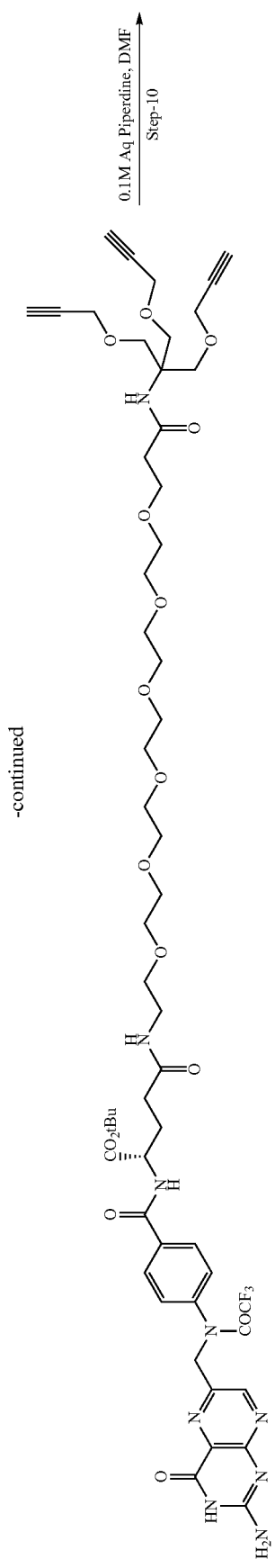

(S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (6)

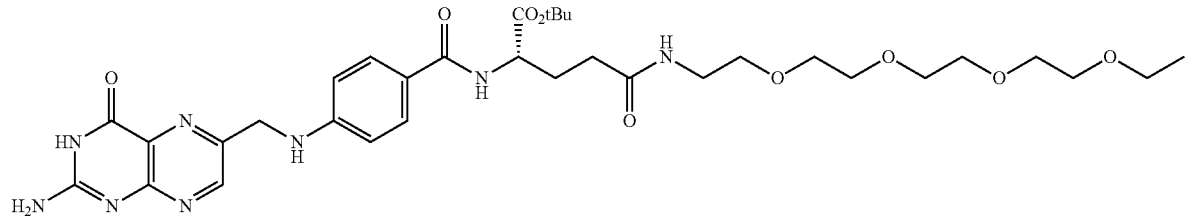

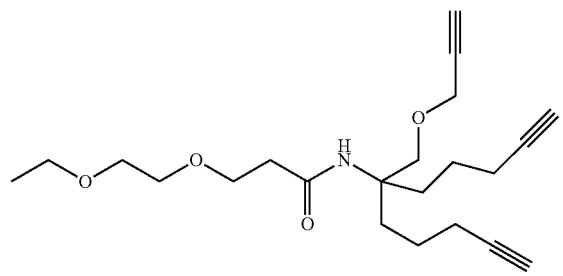

A solution of tert-butyl (S)-33-(4-(((2-amino-4-oxo-3,4-dihydropteridin-6-yl)methyl) amino)benzamido)-8,30-dioxo-6,6-bis((prop-2-yn-1-yloxy)methyl)-4,11,14,17,20,23,26-heptaoxa-7,29-diazatetratriacont-1-yn-34-oate (2.2 g, 2.095 mmol) in DCM (25 mL) was charged with trifluoroacetic acid (25 mL) and stirred at room temperature for 12 h. The reaction mixture was concentrated in vacuo resulting in the crude compound. The crude compound was purified by reverse phase combiflash column chromatography (acetonitrile:water: 0.1% TFA) to afford 91 mg, 4% yield of the title compound as a yellow solid. $^1$H NMR (400 MHz, DMSO-$d_6$) δ=12.44 (br. s, 2H), 11.56 (br. s, 2H), 8.71 (s, 1H), 8.20 (br. s, 1H), 7.96 (br. s, 1H), 7.71 (d, J=8.31 Hz, 2H), 7.37 (br. s, 1H), 6.97-7.03 (m, 2H), 6.70 (d, J=8.31 Hz, 2H), 4.55 (d, J=5.38 Hz, 1H), 4.31 (br. s, 1H), 4.18 (br. s, 4H), 3.71 (s, 4H), 3.35-3.65 (m, 31H), 3.23 (d, J=5.38 Hz, 2H), 2.35-2.42 (m, 2H), 2.24 (d, J=6.36 Hz, 2H), 2.04-2.19 (m, 1H), 1.87-2.00 (m, 1H), MS (ES$^+$): =994.55 [M+H]$^+$; LCMS: $t_R$=2.23 min.

tert-Butyl(S)-33-(4-(((2-amino-4-oxo-3,4-dihydropteridin-6-yl)methyl)amino) benzamido)-8,30-dioxo-6,6-bis((prop-2-yn-1-yloxy)methyl)-4,11,14,17,20,23,26-heptaoxa-7,29-diazatetratriacont-1-yn-34-oate (13)

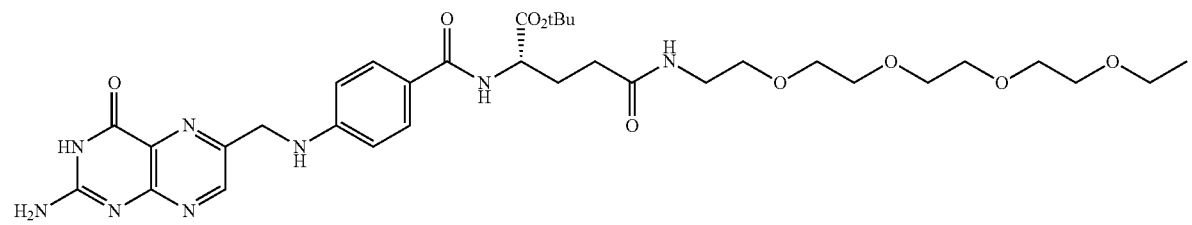

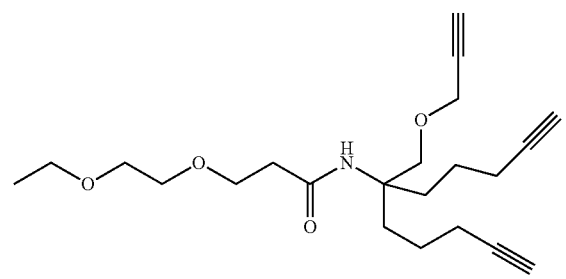

A solution of tert-butyl (S)-33-(4-(N-((2-amino-4-oxo-3,4-dihydropteridin-6-yl)methyl)-2,2,2-trifluoroacetamido)

benzamido)-8,30-dioxo-6,6-bis((prop-2-yn-1-yloxy)
methyl)-4,11,14,17,20,23,26-heptaoxa-7,29-
diazatetratriacont-1-yn-34-oate (2.9 g, 2.530 mmol) in DMF
(25 mL) was charged with 0.1M solution of piperdine (50
mL) and stirred at room temperature for 3 h. The reaction
mixture was concentrated in vacuo resulting in the crude
compound. The crude compound was stirred in diethyl ether
(40 mL) for 10 min and the solid was filtered and washed
with diethyl ether (20 mL) and dried to afford 2.2 g, 83%
yield of the title compound as a yellow solid. $^1$H NMR (400
MHz, DMSO-$d_6$) δ=8.64 (s, 1H), 8.17 (d, J=7.34 Hz, 1H),
7.95 (s, 2H), 7.89 (t, J=5.38 Hz, 1H), 7.64 (d, J=8.80 Hz,
2H), 7.30 (s, 1H), 6.89-6.94 (m, 2H), 6.64 (d, J=8.80 Hz,
2H), 4.48 (d, J=5.87 Hz, 2H), 4.17-4.23 (m, 1H), 4.11 (d,
J=1.47 Hz, 4H), 3.65 (s, 4H), 3.55 (t, J=6.36 Hz, 2H),
3.35-3.51 (m, 27H), 3.14-3.21 (m, 2H), 2.32 (t, J=6.11 Hz,
2H), 2.19 (dd, J=7.09, 11.49 Hz, 2H), 1.81-2.03 (m, 2H),
1.44-1.61 (m, 2H), 1.39 (s, 9H); MS (ES$^+$): m/z=1050.00
[M]$^+$; LCMS: $t_R$=1.90 min.

tert-Butyl(S)-33-(4-(N-((2-amino-4-oxo-3,4-dihy-
dropteridin-6-yl)methyl)-2,2,2-trifluoroacetamido)
benzamido)-8,30-dioxo-6,6-bis((prop-2-yn-1-yloxy)
methyl)-4,11,14,17,20,23,26-heptaoxa-7,29-
diazatetratriacont-1-yn-34-oate (12)

A solution of 2,5-dioxopyrrolidin-1-yl 4-(N-((2-amino-4-
oxo-3,4-dihydropteridin-6-yl)methyl)-2,2,2-trifluoroacet-
amido)benzoate (1.5 g, 2.913 mmol) and tert-butyl (S)-33-
amino-8,30-dioxo-6,6-bis((prop-2-yn-1-yloxy)methyl)-4,
11,14,17,20,23,26-heptaoxa-7,29-diazatetratriacont-1-yn-
34-oate (2.2 g, 2.913 mmol) in DMF (25 mL) was added
DIPEA (1.01 mL, 5.826 mmol) under nitrogen atmosphere
for 4 h. The reaction mixture was concentrated in vacuo
resulting in the crude compound. The crude compound was
stirred in diethyl ether (125 mL) for 15 min and the solid
precipitated was filtered and washed with diethyl ether (50
mL) and dried to afford 3 g, 90% yield, of the title compound
as a yellow semisolid. $^1$H NMR (400 MHz, DMSO-$d_6$)
δ=11.42 (s, 2H), 8.76 (d, J=6.85 Hz, 1H), 8.62 (br. s, 1H),
7.89 (d, J=7.34 Hz, 2H), 7.63 (d, J=7.82 Hz, 2H), 7.25-7.32
(m, 1H), 6.79-7.08 (m, 2H), 4.20-4.30 (m, 1H), 4.04-4.14
(m, 6H), 3.65 (s, 4H), 3.55 (t, J=6.11 Hz, 3H), 3.38-3.51 (m,
20H), 3.09-3.22 (m, 8H), 2.32 (t, J=5.87 Hz, 2H), 2.21 (d,
J=6.36 Hz, 2H), 1.99-2.11 (m, 2H), 1.91 (dd, J=6.60, 14.43
Hz, 2H), 1.40 (s, 9H); MS (ES$^+$): m/z=1146.63 [M+H]$^+$;
LCMS: $t_R$=2.64 min.

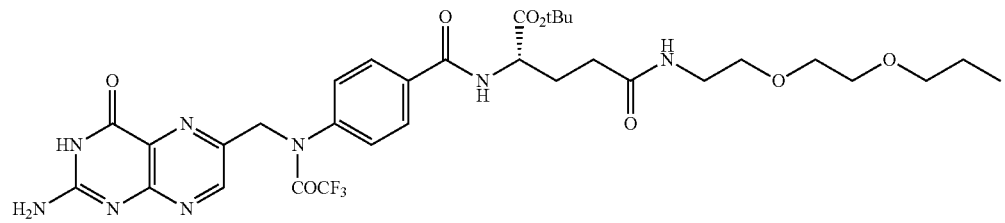

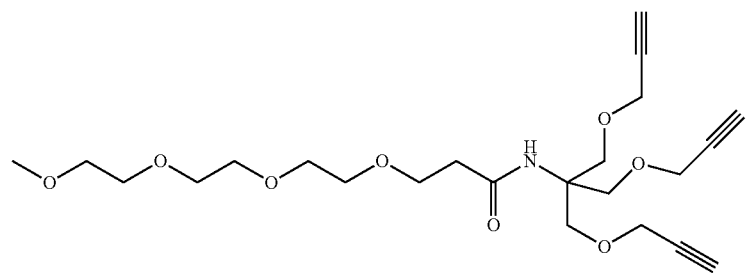

tert-Butyl (S)-33-amino-8,30-dioxo-6,6-bis((prop-2-yn-1-yloxy)methyl)-4,11,14,17,20,23,26-heptaoxa-7,29-diazatetratriacont-1-yn-34-oate (11)

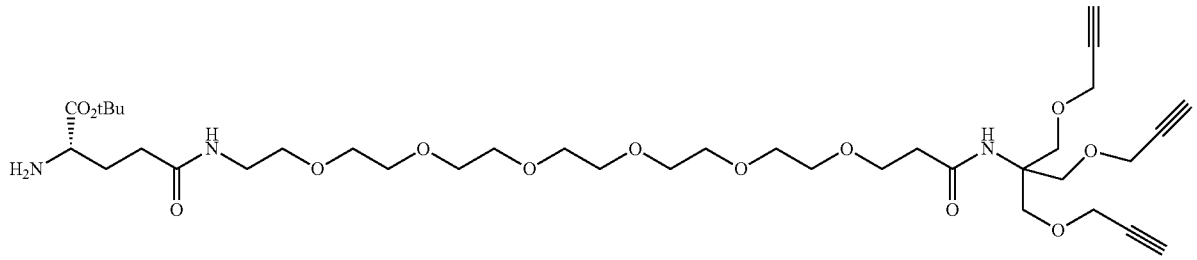 [SMILES: C#CCOCC(COCC#C)(COCC#C)NC(=O)CCOCCOCCOCCOCCOCCOCCNC(=O)CC[C@H](N)C(=O)OC(C)(C)C]

A solution of tert-butyl (S)-33-((((9H-fluoren-9-yl)methoxy)carbonyl)amino)-8,30-dioxo-6,6-bis((prop-2-yn-1-yloxy)methyl)-4,11,14,17,20,23,26-heptaoxa-7,29-diazatetratriacont-1-yn-34-oate (3.8 g, 3.885 mmol) in diethyl amine (50 mL) was stirred at room temperature under nitrogen atmosphere for 12 h. The reaction mixture was concentrated in vacuo resulting in the crude compound which was purified by flash column chromatography eluting with 0-15% methanol saturated with ammonia in DCM to afford 2.2 g, 75% yield, of the title compound as a colorless oil. $^1$H NMR (400 MHz, CDCl$_3$) δ=4.15 (d, J=2.45 Hz, 6H), 3.83 (s, 6H), 3.70-3.75 (m, 3H), 3.62-3.69 (m, 19H), 3.59 (t, J=5.14 Hz, 2H), 3.48-3.50 (m, 2H), 3.42-3.47 (m, 2H), 2.80 (s, 6H), 2.42-2.49 (m, 6H), 1.49 (s, 9H).

tert-Butyl (S)-33-((((9H-fluoren-9-yl)methoxy)carbonyl)amino)-8,30-dioxo-6,6-bis((prop-2-yn-1-yloxy)methyl)-4,11,14,17,20,23,26-heptaoxa-7,29-diazatetratriacont-1-yn-34-oate (10)

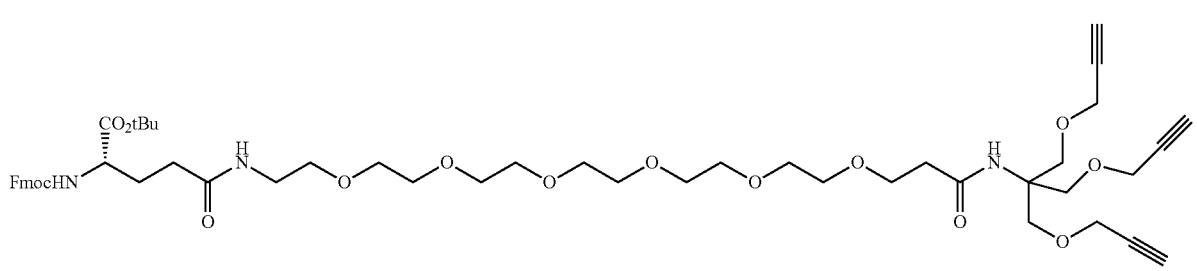

A solution of 1-amino-N-(1,3-bis(prop-2-yn-1-yloxy)-2-((prop-2-yn-1-yloxy)methyl)propan-2-yl)-3,6,9,12,15,18-hexaoxahenicosan-21-amide (1.71 g, 4.035 mmol) in DCM (50 mL) was charged with (R)-4-((((9H-fluoren-9-yl)methoxy)carbonyl)amino)-5-(tert-butoxy)-5-oxopentanoic acid (2.3 g, 4.035 mmol), HATU (2.3 g, 6.052 mmol) and DIPEA (1.4 mL, 8.070 mmol) and was stirred at room temperature for 16 h. The reaction mixture was diluted with water and extracted with ethyl acetate. The combined organic layers were dried over anhydrous Na$_2$SO$_4$, filtered and concentrated in vacuo resulting in a crude compound which was purified by column chromatography on combiflash eluting with 0-5% methanol in DCM to afford 3.51 g, 89% yield, of the title compound as a yellow oil. $^1$H NMR (400 MHz, CDCl$_3$) δ=7.76 (d, J=7.82 Hz, 2H), 7.59-7.64 (m, 2H), 7.37-7.43 (m, 2H), 7.29-7.34 (m, 2H), 6.44 (br. s, 1H), 6.26 (br. s, 1H), 5.74 (d, J=7.82 Hz, 1H), 4.39 (t, J=7.09 Hz, 2H), 4.23 (t, J=6.85 Hz, 2H), 4.14 (d, J=1.96 Hz, 5H), 3.83 (s, 4H), 3.60-3.73 (m, 16H), 3.56 (t, J=4.89 Hz, 2H), 3.39-3.48 (m, 2H), 3.17 (q, J=7.34 Hz, 1H), 2.80 (s, 4H), 2.41-2.46 (m, 4H), 2.15-2.32 (m, 2H), 1.90-2.04 (m, 1H), 1.54-1.60 (m, 6H), 1.47 (s, 9H); MS (ES$^+$): m/z=978.58 [M+H]$^+$; LCMS: t$_R$=3.24 min.

1-Amino-N-(1,3-bis(prop-2-yn-1-yloxy)-2-((prop-2-yn-1-yloxy)methyl)propan-2-yl)-3,6,9,12,15,18-hexaoxahenicosan-21-amide (8)

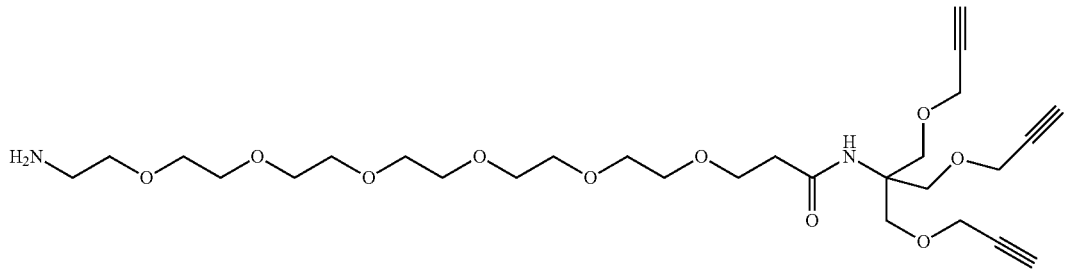 [SMILES: C#CCOCC(COCC#C)(COCC#C)NC(=O)CCOCCOCCOCCOCCOCCOCCN]

A solution of 1-azido-N-(1,3-bis(prop-2-yn-1-yloxy)-2-((prop-2-yn-1-yloxy)methyl)propan-2-yl)-3,6,9,12,15,18-hexaoxahenicosan-21-amide (3.2 g, 5.369 mmol) in THF:H$_2$O (4:1, 62.5 mL) was charged with TPP (4.22 g, 16.11 mmol) and was stirred at room temperature for 14 h. The reaction mixture was concentrated in vacuo resulting in the crude compound which was purified by column chromatography on silica gel eluting with 0-10% methanol in DCM to afford 2.35 g, 77% yield, of the title compound as light yellow oil. $^1$H NMR (400 MHz, CDCl$_3$) δ=6.37 (s, 1H), 4.13-4.17 (m, 6H), 3.84 (s, 6H), 3.71 (t, J=5.87 Hz, 2H), 3.61-3.68 (m, 23H), 3.48-3.53 (m, 2H), 2.86 (t, J=5.38 Hz, 2H), 2.43-2.46 (m, 4H).

1-Azido-N-(1,3-bis(prop-2-yn-1-yloxy)-2-((prop-2-yn-1-yloxy)methyl)propan-2-yl)-3,6,9,12,15,18-hexaoxahenicosan-21-amide (7)

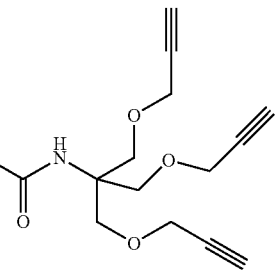

A solution of 1-azido-3,6,9,12,15,18-hexaoxahenicosan-21-oic acid (2.6 g, 6.860 mmol) in DCM (50 mL) was charged with oxalyl chloride (0.87 mL, 10.29 mmol) and catalytic DMF (3 drops) and stirred at room temperature for 1 h. The reaction mixture was concentrated in vacuo resulting in the crude intermediate acid chloride which was used directly without isolation for further reaction. To the resulting solution at 0° C. was added DIPEA (4.7 mL, 27.44 mmol) and 1,3-bis(prop-2-yn-1-yloxy)-2-((prop-2-yn-1-yloxy)methyl)propan-2-amine (2.28 g, 6.860 mmol) and was stirred at room temperature for 2 h. The reaction mixture was diluted with water and extracted with ethyl acetate. The combined organic layers were dried over anhydrous Na$_2$SO$_4$, filtered and concentrated in vacuo to afford 3.6 g, 88% yield, of the title compound as a light yellow solid. $^1$H NMR (400 MHz, CDCl$_3$) δ=6.59 (s, 1H), 4.13-4.19 (m, 6H), 3.82-3.89 (m, 6H), 3.61-3.71 (m, 25H), 3.39 (t, J=4.89 Hz, 2H), 2.43-2.48 (m, 2H), 1.47-1.52 (m, 2H).

1-Azido-3,6,9,12,15,18-hexaoxahenicosan-21-oic acid (5)

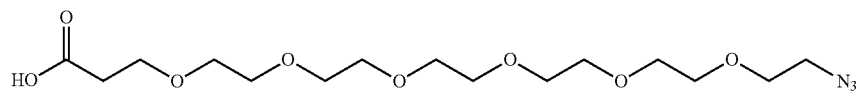 [SMILES: [N-]=[N+]=NCCOCCOCCOCCOCCOCCOCCC(=O)O]

A solution of ethyl 1-azido-3,6,9,12,15,18-hexaoxahenicosan-21-oate (5 g, 12.27 mmol) in THF:H$_2$O (4:1, 40 mL) at 0° C. was charged with lithium hydroxide (1.47 g, 61.35 mmol) and stirred at room temperature for 2 h. The reaction mixture solvent was evaporated and the aqueous layer was washed with DCM. The separated aqueous layer was acidified with 2N HCl solution and extracted with 10% methanol in DCM. The combined organic layers were dried over anhydrous Na$_2$SO$_4$, filtered and concentrated in vacuo resulting in the crude compound which was purified by column chromatography on silica gel eluting with 1-10% methanol in DCM to afford 3.8 g, 80% yield, of the title compound as a colorless oil. $^1$H NMR (400 MHz, CDCl$_3$) δ=3.79 (t, J=5.87 Hz, 2H), 3.63-3.71 (m, 23H), 3.40 (t, J=4.89 Hz, 2H), 2.61 (t, J=5.87 Hz, 2H).

Ethyl 1-azido-3,6,9,12,15,18-hexaoxahenicosan-21-oate (4)

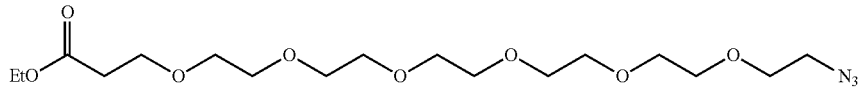

A solution of 17-azido-3,6,9,12,15-pentaoxaheptadecan-1-ol (10 g, 32.57 mmol) in THF (100 mL) at 0° C. was charged with sodium hydride (1.94 g, 48.85 mmol) over a period of 30 min Followed by addition of ethyl 3-bromopropanoate (5 mL, 39.08 mmol) at the same temperature and stirred for 2 h. The reaction mixture was quenched with ammonium chloride solution and extracted with ethyl acetate. The combined organic layers were dried over anhydrous $Na_2SO_4$, filtered and concentrated in vacuo resulting in the crude compound which was purified by silica gel column chromatography eluting with 1-3% methanol in DCM to afford 5.2 g, 40% yield, of the title compound as a colorless oil. $^1H$ NMR (400 MHz, $CDCl_3$) δ=4.11-4.19 (m, 2H), 3.73-3.79 (m, 2H), 3.60-3.70 (m, 21H), 3.36-3.43 (m, 2H), 2.56-2.62 (m, 2H), 1.26 (t, J=7.09 Hz, 3H).

17-Azido-3,6,9,12,15-pentaoxaheptadecan-1-ol (3)

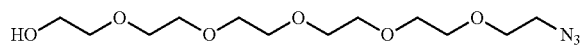

A solution of 17-hydroxy-3,6,9,12,15-pentaoxaheptadecyl 4-methylbenzenesulfonate (16 g, 36.69 mmol) in ethanol (200 mL) was charged with sodium azide (7.15 g, 110.1 mmol) and heated at 80° C. for 8 h. The reaction mixture was cooled to room temperature and the solvent was evaporated up to dryness. The residue obtained was stirred in ethyl acetate, filtered and the filtrate was concentrated in vacuo resulting in 11.6 g of the crude compound as yellow oil. The crude compound was used in the next step without further purification. $^1H$ NMR (400 MHz, $CDCl_3$) δ=3.59-3.77 (m, 23H), 3.37-3.41 (m, 2H).

17-Hydroxy-3,6,9,12,15-pentaoxaheptadecyl 4-methylbenzenesulfonate (2)

A solution of 3,6,9,12,15-pentaoxaheptadecane-1,17-diol (25 g, 88.59 mmol) in DCM (900 mL) at 0° C. was charged with silver oxide (30.5 g, 132.88 mmol), potassium iodide (2.94 g, 17.71 mmol) and tosyl chloride (18.51 g, 97.44 mmol) and stirred at 0° C. for 1 h. The reaction mixture was filtered, washed with DCM and the filtrate was concentrated in vacuo resulting in the crude compound which was purified by column chromatography on silica gel eluting with 1-3% methanol in DCM to afford 16 g, 41% yield of the title compound as a pale yellow oil. $^1H$ NMR (400 MHz, $CDCl_3$) δ=7.80 (d, J=7.83 Hz, 2H), 7.34 (d, J=7.83 Hz, 2H), 4.14-4.18 (m, 2H), 3.57-3.75 (m, 23H), 2.45 (s, 3H).

Example 28

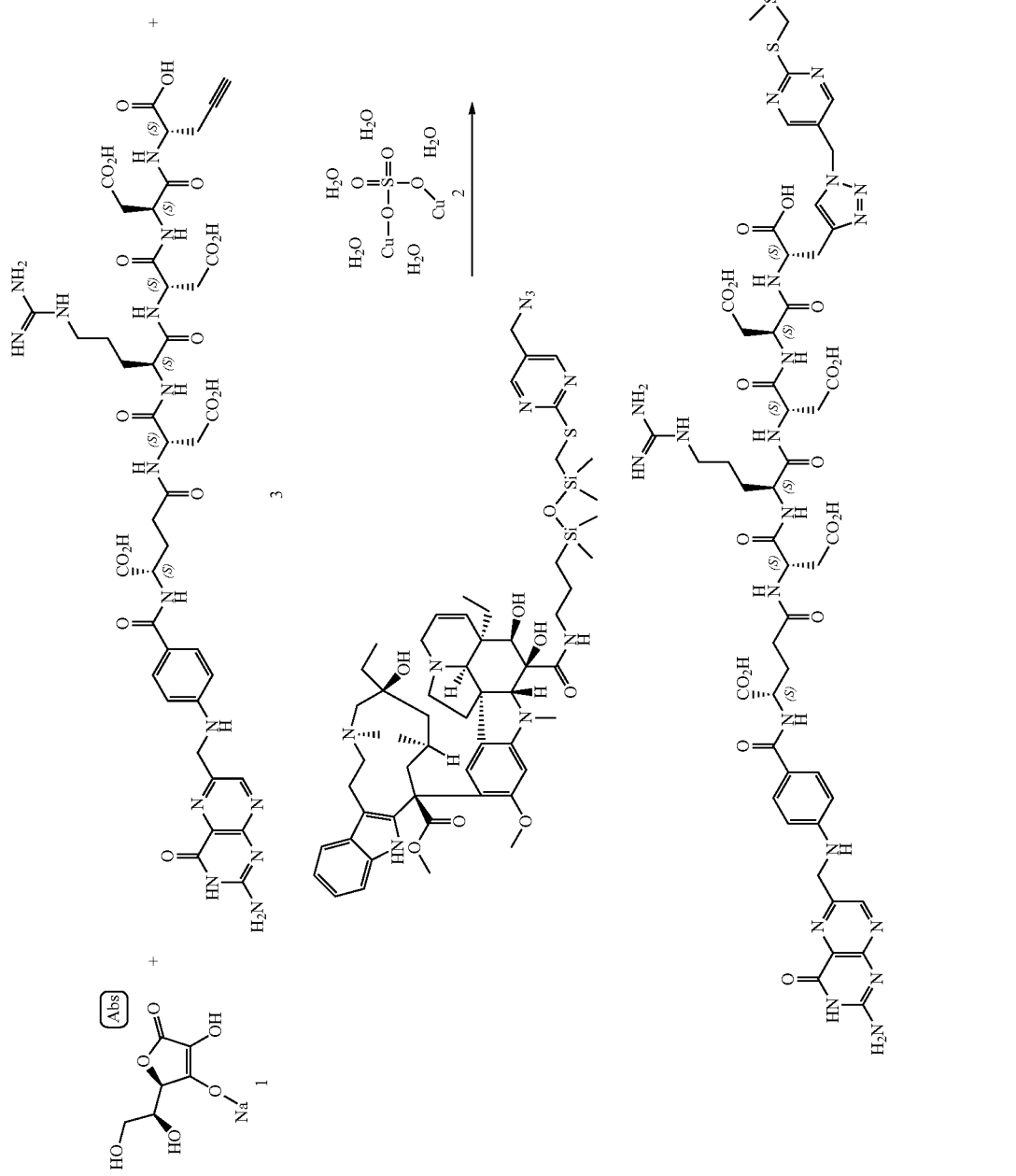

(2S,5S,8S,11S,14S,19S)-19-(4-(((2-amino-4-oxo-3,4-dihydropteridin-6-yl)methyl) amino)benzamido)-5,8,14-tris(carboxymethyl)-2-((1-((2-(((3-(3-((3aR,3a1R,4R,5S,5aR, 10bR)-3a-ethyl-9-((3S,5S,7S,9S)-5-ethyl-5-hydroxy-9-(methoxycarbonyl)-2,4,5,6,7,8,9,10-octahydro-1H-3,7-methano[1]azacycloundecino [5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio) pyrimidin-5-yl)methyl)-1H-1,2,3-triazol-4-yl) methyl)-11-(3-guanidinopropyl)-4,7,10,13,16-pentaoxo-3,6,9,12,15-pentaazaicosane-1,20-dioic acid solution of sodium ascorbate (100 mM in water 32.8 μL, 3.28 μmol) was added, followed by the addition of a freshly prepared solution of copper sulfate pentahydrate (100 mM in water, 32.8 μL, 3.28 μmol). The whole was purged with nitrogen gas, capped, sonicated for 5 min, and agitated on a shaker at rt. After 1 h, LCMS showed mainly product. The reaction was stopped. The whole was passed through an ISCO solid loading filter plug with an aid of a vacuum. For the residue, dissolved with ~0.5 mL of DMSO and passed through the same filter plug. The combined filtrate (2 mL) was purified by a reversed phase preparative HPLC [gradient 1] resulting in 10.3 mg, 29.3% yield of the title compound as a light yellow solid after lyophilizing. $^1$H NMR

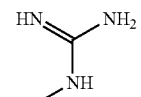
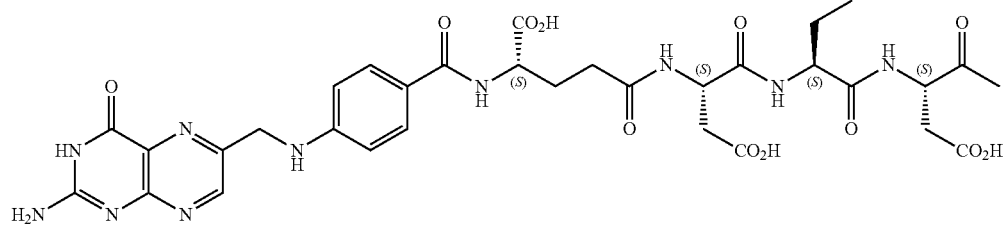
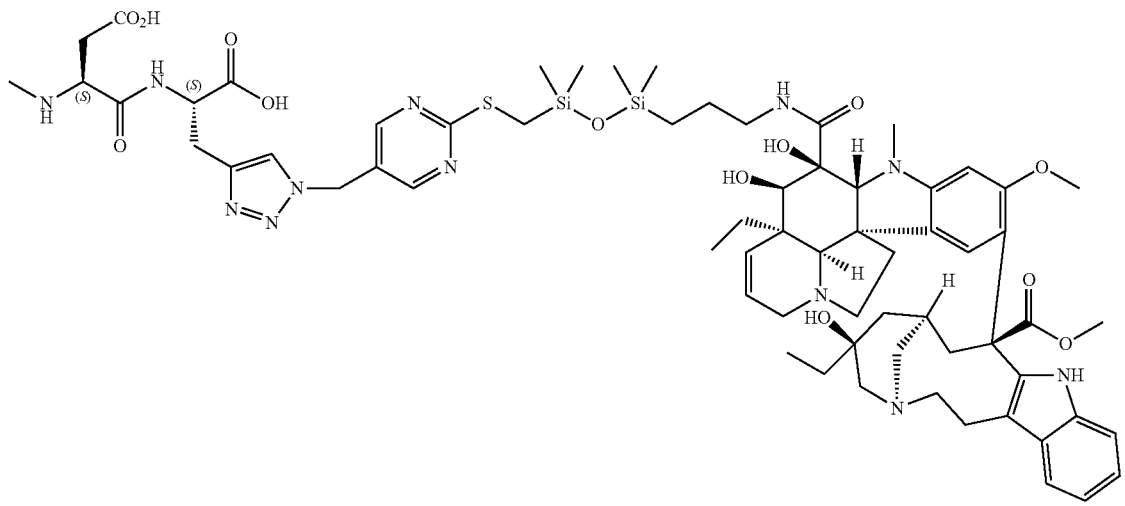

To an Eppendorf vial, DMSO (1 mL) was added to a mixture of (2S,5S,8S,11S,14S,19S)-19-(4-(((2-amino-4-oxo-3,4-dihydropteridin-6-yl)methyl)amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosane-1,20-dioic acid (17.0 mg, 0.016 mmol) and (3R,5S,7R,9S)-methyl-9-((3aR,3a1R,4R,5S,5aR,10bR)-5-((3-(3-(((5-(azidomethyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1] azacycloundecino[5,4-b]indole-9-carboxylate (18.14 mg, 0.016 mmol) at rt. The vial was purged with nitrogen gas, capped, and sonicated for 5 min. Then a freshly prepared (400 MHz, DMSO-d$_6$) δ ppm 8.52-8.70 (m, 4H) 8.45 (br s, 1H) 8.25 (br d, J=6.32 Hz, 1H) 8.17 (br s, 1H) 7.98 (s, 1H) 7.72-7.90 (m, 2H) 7.63 (m, J=8.84 Hz, 2H) 7.54 (br s, 1H) 7.35-7.43 (m, 1H) 7.12-7.33 (m, 2H) 6.85-7.11 (m, 6H) 6.62 (m, J=8.84 Hz, 2H) 6.43 (s, 1H) 6.20 (s, 1H) 5.68 (br dd, J=10.36, 5.56 Hz, 1H) 5.48-5.61 (m, 3H) 4.53-4.79 (m, 2H) 4.42-4.53 (m, 3H) 4.25-4.41 (m, 3H) 4.16 (br d, J=5.31 Hz, 2H) 3.94-4.10 (m, 3H) 3.89 (br s, 1H) 3.74-3.85 (m, 3H) 3.62-3.74 (m, 5H) 3.51-3.62 (m, 7H) 3.03-3.33 (m, 36H) 2.93 (br s, 4H) 2.64-2.78 (m, 7H) 2.53-2.64 (m, 2H) 2.21-2.47 (m, 10H) 1.80-2.05 (m, 5H) 1.39-1.65 (m, 7H) 1.13-1.39 (m, 6H) 0.64-0.86 (m, 7H) 0.44-0.61 (m, 2H) 0.16 (s, 6H) −0.03-0.14 (m, 8H), MS (ES$^+$): m/z=[M+2]=1073.3, [M+3]/3=716.1, [M+4]/4=537.4; LCMS: t$_R$=1.74 min [polar_3_min_0_1500].

(2S,5S,8S,11S,14S,19S)-19-(4-(((2-amino-4-oxo-3,4-dihydropteridin-6-yl)methyl) amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosanedioic acid (3)

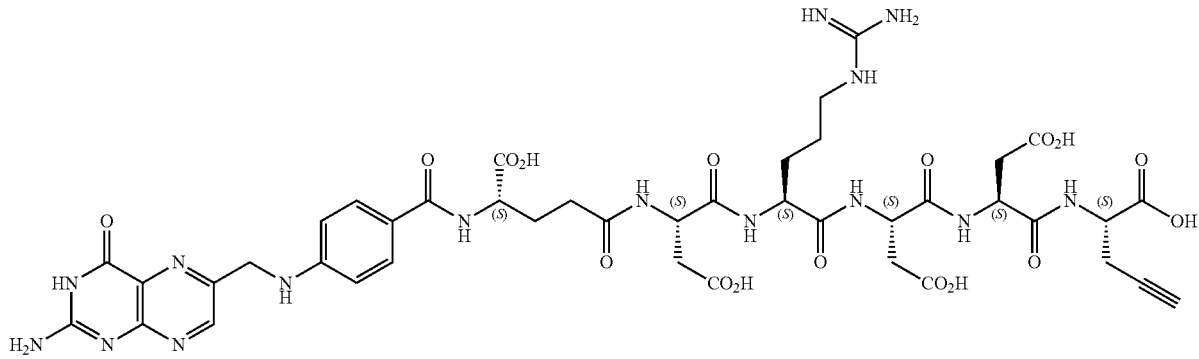

The title compound was prepared by a similar solid phase synthetic route using L-propargyl lysine as described in these publications: (1) Vlahov, Iontcho R., et al. "Design and regioselective synthesis of a new generation of targeted chemotherapeutics. Part 1: EC145, folic acid conjugate of desacetylvinblastine monohydrazide." *Bioorganic & medicinal chemistry letters* 16.19 (2006): 5093-5096. (2) Vlahov, Iontcho R., et al. "Design and regioselective synthesis of a new generation of targeted chemotherapeutics. Pan. II: Folic acid conjugates of tubulysins and their hydrazides." *Bioorganic & medicinal chemistry letters* 18.16 (2008): 4558-4561. $^1$HNMR (400 MHz, DMSO-$d_6$) δ ppm 8.65 (s, 1H) 8.25 (br d, J=7.33 Hz, 1H) 8.04-8.18 (m, 4H) 7.95 (d, J=7.58 Hz, 1H) 7.82 (br d, J=7.83 Hz, 1H) 7.67 (d, J=8.84 Hz, 2H) 7.35 (br s, 1H) 6.96 (br s, 3H) 6.65 (d, J=8.84 Hz, 3H) 4.45-4.66 (m, 6H) 4.15-4.36 (m, 4H) 3.04 (br d, J=6.57 Hz, 4H) 2.83-2.90 (m, 1H) 2.65-2.80 (m, 4H) 2.54-2.64 (m, 4H) 2.31 (br t, J=7.96 Hz, 3H) 1.80-2.08 (m, 3H) 1.63-1.78 (m, 2H) 1.38-1.59 (m, 4H). $^{19}$F NMR (400 MHz, DMSO-$d_6$) δ ppm −73.74. MS (ES$^+$): m/z=1038.3 [M+H]$^+$, 520.0 [M+2H]$^+$/2; LCMS: $t_R$=1.19 min [polar_3 min_1500].

Example 29

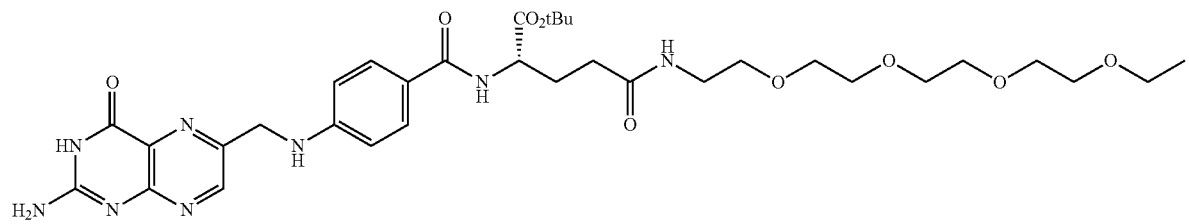

3

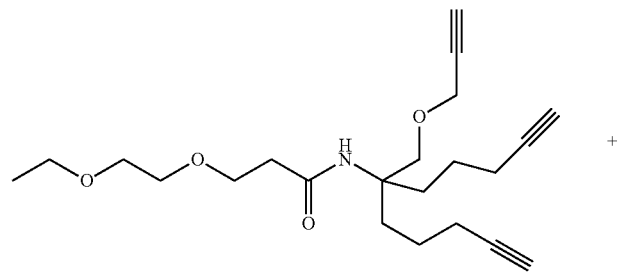

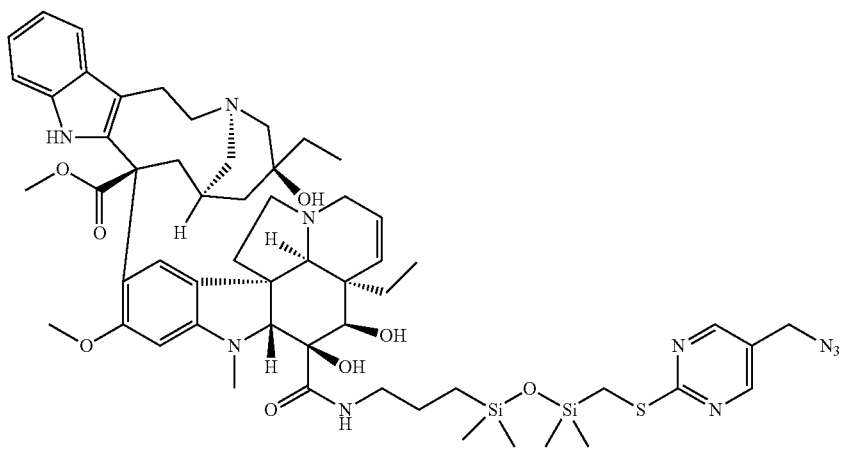
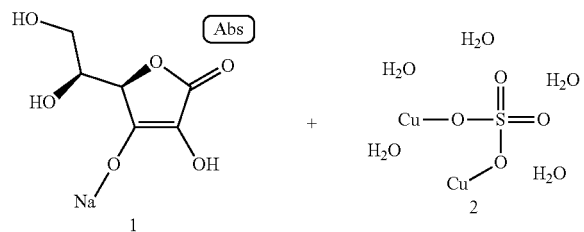
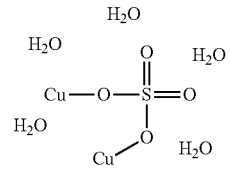
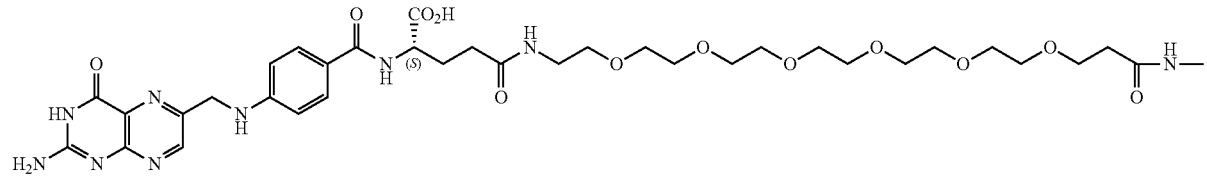
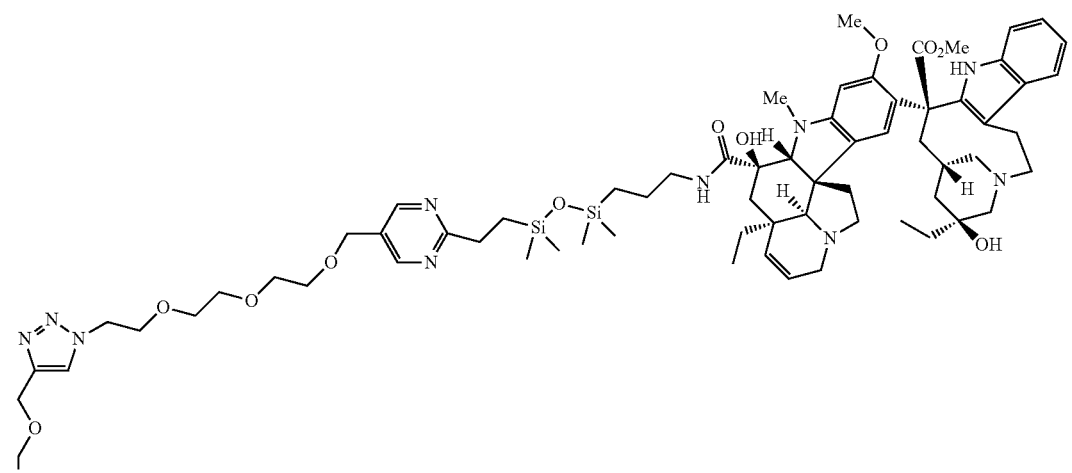

-continued

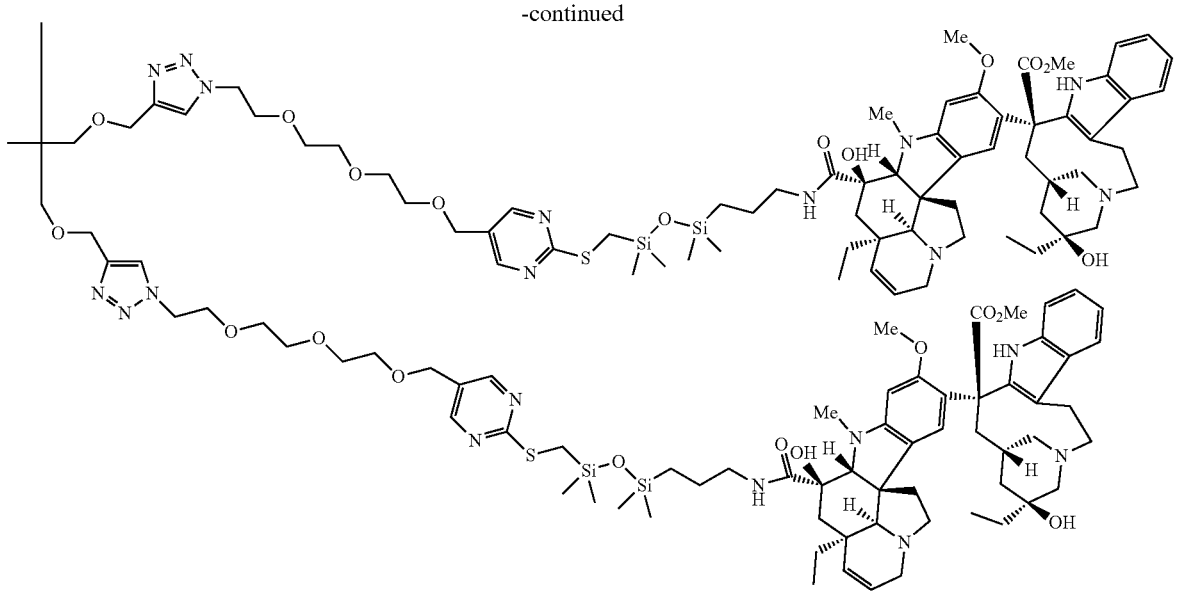

(31S)-31-(4-(((2-Amino-4-oxo-3,4-dihydropteridin-6-yl)methyl)amino)benzamido)-1-(1-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methyl)-1H-1,2,3-triazol-4-yl)-4,4-bis(((1-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methyl)-1H-1,2,3-triazol-4-yl)methoxy)methyl)-6,28-dioxo-2,9,12,15,18,21,24-heptaoxa-5,27-diazadotriacontan-32-oic acid

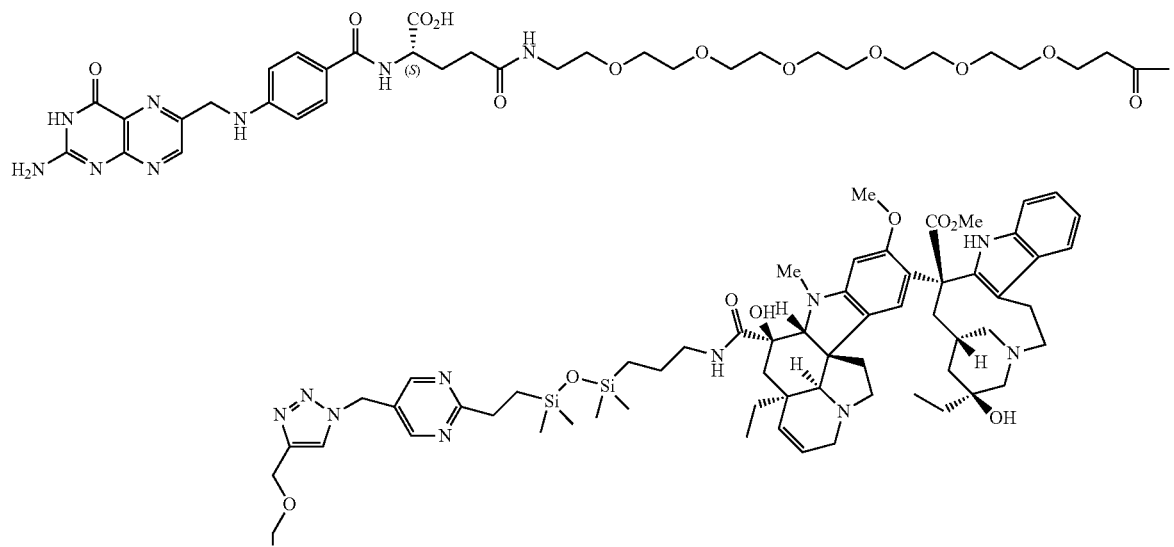

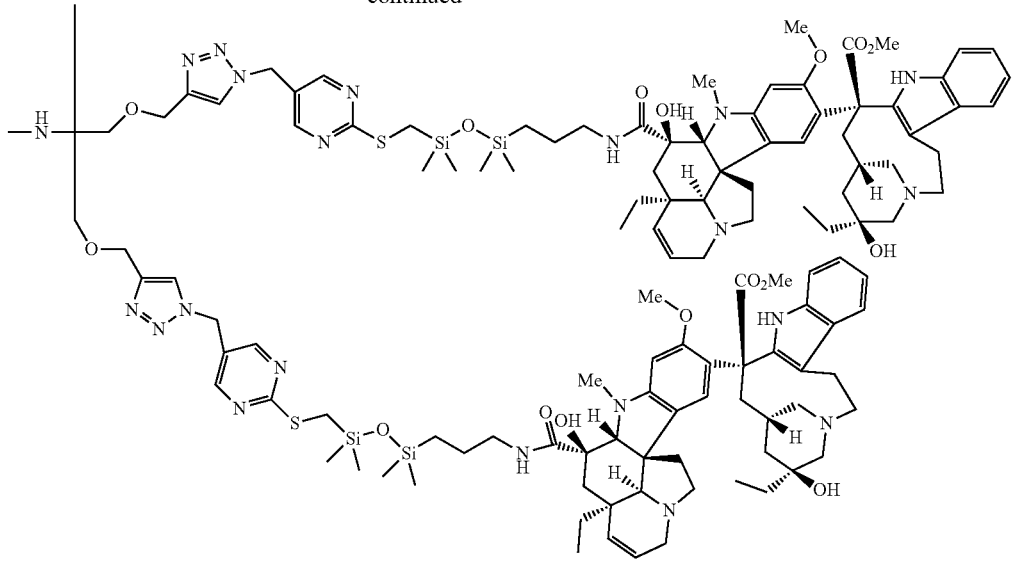

To an Eppendorf vial, DMF (87 μL) was added to a mixture of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (6.50 mg, 6.54 μmol) and (3R,5S,7R,9S)-methyl 9-((3aR,3a1R,4R,5S,5aR,10bR)-5-(((3-(3-(((5-(azidomethyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[,4-b]indole-9-carboxylate (25.3 mg, 0.023 mmol). More DMF (87 μL) to dissolve both reactants. The whole was purged with nitrogen gas, capped, and sonicated for 5 mM. Then a freshly prepared solution of sodium ascorbate (100 mM in water, 26.2 μL, 2.62 μmol) followed by the addition of a freshly prepared solution of copper sulfate pentahydrate (100 mM in water, 13.08 μL, 1.308 μmol). The whole was purged with nitrogen gas, capped, sonicated for 5 mM, and agitated on a shaker at rt for 1.5 h. The reaction was incomplete therefore additional sodium ascorbate (100 mM in water, 4.02 μL, 0.402 μmol) and copper sulfate pentahydrate (100 mM in water, 2.012 μL, 0.201 μmol) were added to the reaction mixture and agitated on a shaker for 1 h. The whole was diluted with 1 mL DMSO and passed through an ISCO solid loading filter plug with an aid of a vacuum. The residue was dissolved with ~0.3 mL of DMSO and passed through the same filter plug and the combined filtrate (1-2 mL) was purified by a reversed phase preparative HPLC [gradient 2] resulting in 1.94 mg, 6.87% yield of the title compound as a light yellow solid. $^1$H NMR (400 MHz, DMSO-$d_6$) δ ppm 9.33 (s, 2H) 8.61-8.71 (m, 7H) 8.52 (br s, 2H) 8.16 (s, 3H) 7.97 (br s, 1H) 7.77 (s, 3H) 7.57 (br s, 2H) 7.36 (br d, J=7.58 Hz, 3H) 7.26 (br d, J=7.83 Hz, 3H) 6.84-7.04 (m, 7H) 6.63 (d, J=8.59 Hz, 1H) 6.53-6.71 (m, 1H) 6.56 (s, 1H) 6.44 (s, 2H) 6.19 (s, 2H) 5.50-5.80 (m, 11H) 4.40-4.52 (m, 8H) 3.91-4.11 (m, 11H) 3.82 (br d, J=5.81 Hz, 2H) 3.71 (s, 15H) 3.38-3.62 (m, 61H) 2.96-3.22 (m, 21H) 2.88 (br d, J=10.61 Hz, 4H) 2.59-2.77 (m, 17H) 2.22-2.41 (m, 11H) 1.86-2.14 (m, 7H) 1.39-1.64 (m, 12H) 1.10-1.37 (m, 28H) 0.67-0.90 (m, 21H) 0.63 (br s, 3H) 0.42-0.54 (m, 6H) 0.15 (s, 18H) −0.02-0.08 (m, 21H), MS (ES$^+$): m/z=[M+3]/3=1439.3, [M+4]/4=1080.4, [M+5]/5=864.4, [M+6]/6=720.5; LCMS: $t_R$=1.52 min [polar_3 min_0_1500].

Example 30

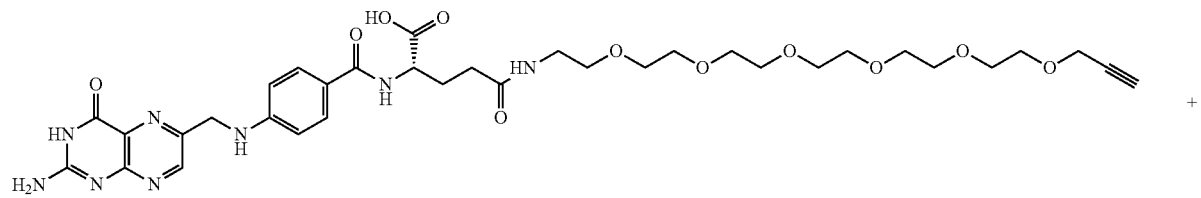

+

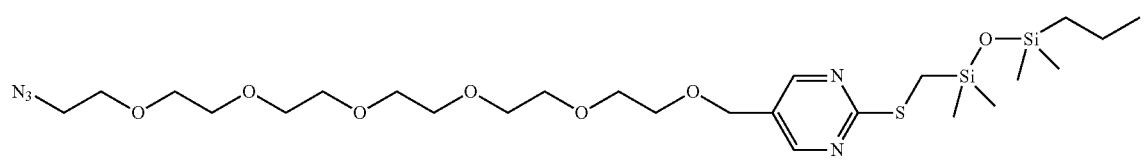

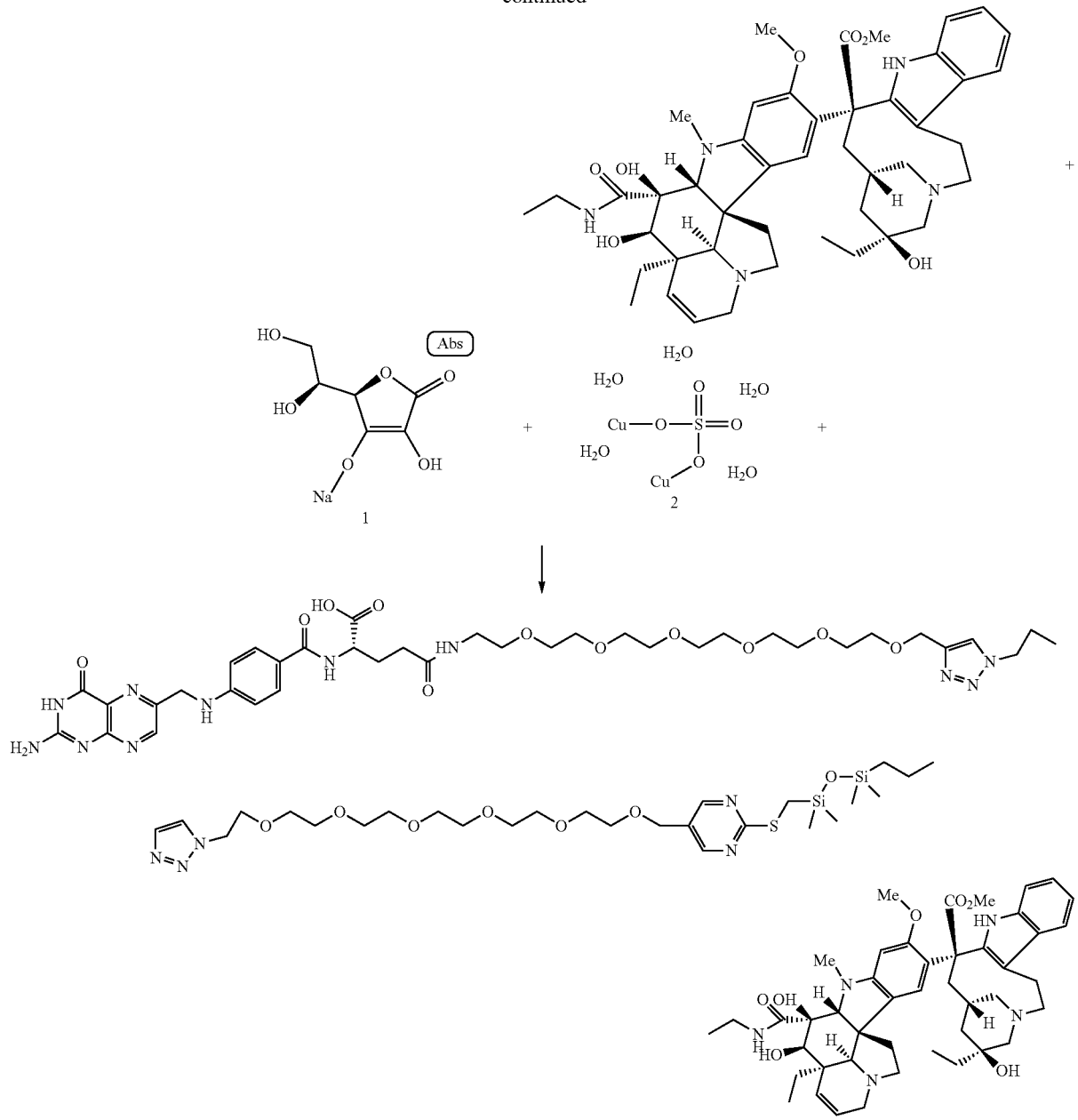

(24S)-24-(4-(((2-Amino-4-oxo-3,4-dihydropteridin-6-yl)methyl)amino)benzamido)-1-(1-(2-(2-(2-(((3-(3-(((3aR,3a1R,4R,5S,5aR,10bR)-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl) methyl)thio)pyrimidin-5-yl)methoxy)ethoxy)ethoxy)ethyl)-1H-1,2,3-triazol-4-yl)-21-oxo-2,5,8,11,14,17-hexaoxa-20-azapentacosan-25-oic acid Using similar procedure as above, the title compound was synthesized using, DMF (26 μL), (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (2 mg, 2.69 μmol), (5S,7S,9S)-methyl9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (5.01 mg, 4.04 μmol), sodium ascorbate (freshly prepared 100 mM in water, 5.39 μl, 0.539 μmol), water (13.46 μL), copper sulfate pentahydrate (freshly prepared 100 mM in water, 2.69 μl, 0.269 μmol), and water (13.46 μL). The sample was purified by reverse phase HPLC [gradient 1] resulting in 1.29 mg, 24.2% yield of the title compound as a light yellow solid after lyophilization. LCMS using acidic mobile phase and method polar_3 min_0_1500 (0.8 mL/min flow) showed 98.0% pure (retention time=1.56 min) and confirmed title compound. $^1$H NMR (400 MHz, DMSO-$d_6$) δ ppm 9.33 (s, 1H) 8.47-8.73 (m, 4H) 8.04 (s, 1H) 7.95 (br s, 1H) 7.78 (s, 1H) 7.59 (br d, J=8.08 Hz, 2H) 7.37 (d, J=7.83 Hz, 1H) 7.26 (d, J=8.34 Hz, 1H) 6.86-7.08 (m, 4H) 6.56-6.73 (m, 3H) 6.44 (s, 1H) 6.19 (s, 1H) 5.50-5.78 (m, 2H) 4.39-4.58 (m, 9H) 3.67-4.03 (m, 13H) 3.42-3.62 (m, 30H) 2.99-3.19 (m, 1H) 2.94-3.22 (m, 6H) 2.89 (br d, J=10.61 Hz, 1H) 2.58-2.79 (m, 6H) 2.28-2.42 (m, 4H) 1.77-2.20 (m, 5H) 1.07-1.66 (m, 10H) 0.58-0.89 (m, 7H) 0.52 (br d, J=7.58 Hz, 2H) 0.17 (s, 6H) 0.06 (s, 8H), MS (ES$^+$): m/z=. [M+2]/2=992.2, [M+3]/3=661.8; LCMS: $t_R$=1.52 min [polar_3 min_0_1500].
Example 31
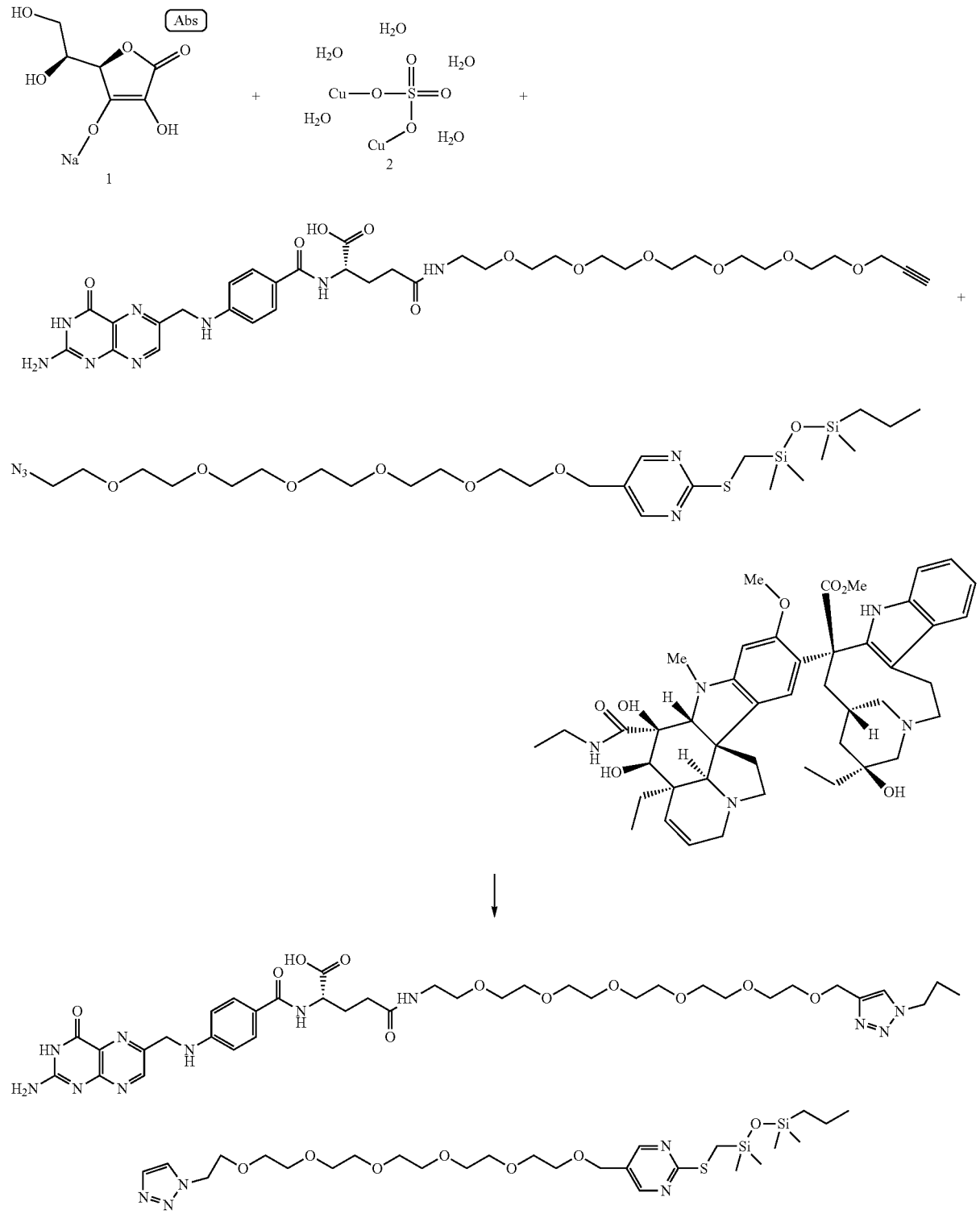

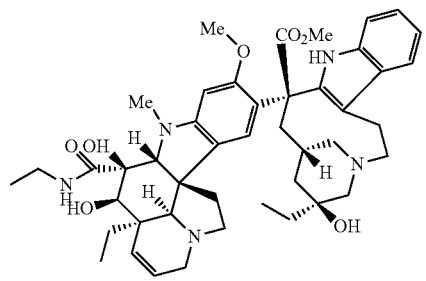

(24S)-24-(4-(((2-Amino-4-oxo-3,4-dihydropteridin-6-yl)methyl)amino)benzamido)-1-(1-(1-(2-(((3-(3-((3aR,3a1R,4R,5S,5aR,10bR)-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)-2,5,8,11,14,17-hexaoxanonadecan-19-yl)-1H-1,2,3-triazol-4-yl)-21-oxo-2,5,8,11,14,17-hexaoxa-20-azapentacosan-25-oic acid To an Eppendorf vial, DMSO (359 μL) was added into a mixture of (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (12.0 mg, 0.016 mmol) and (5S,7S,9S)-methyl 9-((3aR,3a1R,4R,5S,5aR,10bR)-5-((3-(3-(((5-(19-azido-2,5,8,11,14,17-hexaoxanonadecyl) pyrimidin-2-yl)thio)methyl)-1,1,3,3-tetramethyldisiloxanyl) propyl) carbamoyl)-3a-ethyl-4,5-dihydroxy-8-methoxy-6-methyl-3a,3a1,4,5,5a,6,11,12-octahydro-1H-indolizino[8,1-cd]carbaz-9-yl)-5-ethyl-5-hydroxy-2,4,5,6,7,8,9,10-octahydro-1H-3,7-methano[1]azacycloundecino[5,4-b]indole-9-carboxylate (22.2 mg, 0.016 mmol). The whole was purged with nitrogen gas, capped, and sonicated for 5 min. Then a freshly prepared solution of sodium ascorbate (100 mM in water, 32.3 μL, 3.23 μmol) followed by a freshly prepared solution of addition of copper sulfate pentahydrate (100 mM in water, 16.2 μL, 1.62 μmol). A dark brown homogenous solution was formed. The whole was purged with nitrogen gas, capped, sonicated for 5 min, and agitated on a shaker at rt. After 1 h, more sodium ascorbate (100 mM in water, 32.3 μL, 3.23 μmol) and copper sulfate pentahydrate (100 mM in water, 16.2 μL, 1.62 μmol) were added. After 1 h, the reaction was stopped. The whole was diluted with 2.5 mL DMSO and passed through an ISCO solid loading filter plug with an aid of a vacuum and the residue was dissolved with ~0.3 mL of DMSO and passed through the same filter plug. The combined filtrate (3 mL) was purified by a reversed phase preparative HPLC [gradient 1] resulting in 9.55 mg, 28.0% yield, of the title compound as a light yellow solid after lyophilization. $^1$H NMR (400 MHz, DMSO-$d_6$) δ ppm 8.64 (s, 1H) 8.58 (s, 2H) 8.04 (s, 1H) 7.64 (br d, J=8.34 Hz, 1H) 7.37 (d, J=8.08 Hz, 1H) 7.26 (d, J=7.83 Hz, 1H) 6.87-7.03 (m, 4H) 6.64 (br d, J=8.59 Hz, 2H) 5.66-5.71 (m, 1H) 4.44-4.52 (m, 8H) 3.89-4.09 (m, 3H) 3.69-3.84 (m, 8H) 3.65 (br d, J=9.09 Hz, 1H) 3.42-3.56 (m, 49H) 3.01-3.26 (m, 6H) 2.90 (br d, J=17.18 Hz, 2H) 2.61-2.78 (m, 6H) 2.30-2.46 (m, 4H) 2.17 (br s, 2H) 1.85-2.07 (m, 4H) 1.54-1.63 (m, 2H) 1.48 (br dd, J=15.66, 7.83 Hz, 2H) 1.21-1.35 (m, 2H) 1.13-1.21 (m, 3H) 0.70-0.84 (m, 6H) 0.64 (br s, 1H) 0.46-0.54 (m, 2H) 0.17 (s, 6H) 0.06 (s, 7H), MS (ES$^+$): m/z=[M+2]/2=1058.1, [M+3]/3=705.8; LCMS: $t_R$=1.57 min [polar_3 min_0_1500].

Example 32

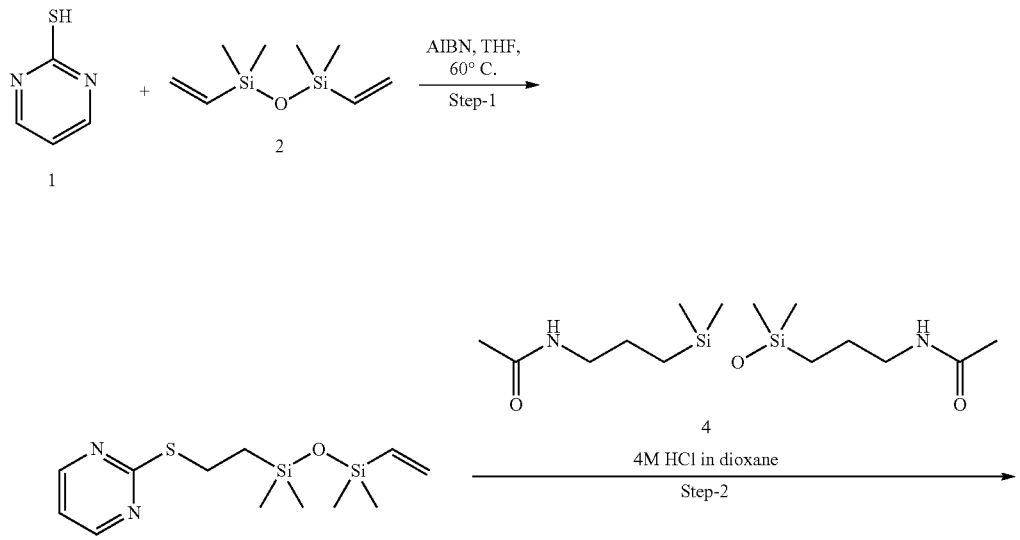

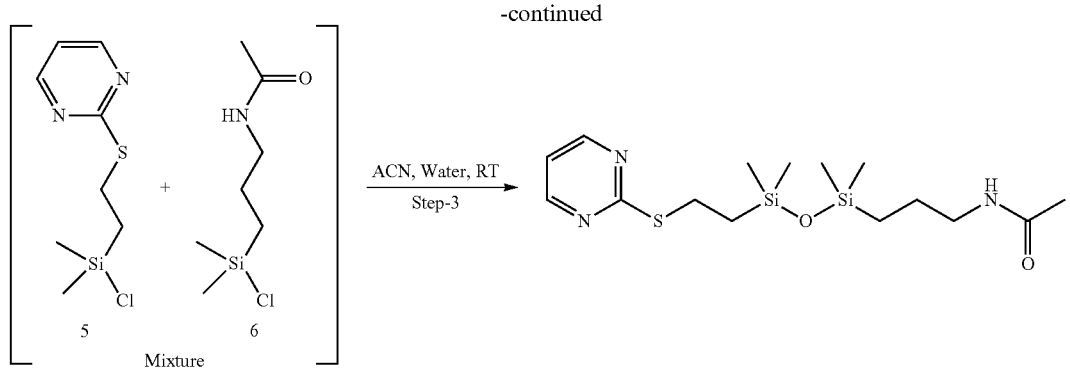

N-(3-(1,1,3,3-Tetramethyl-3-(2-(pyrimidin-2-ylthio)ethyl)disiloxanyl)propyl)acetamide [Example 33]

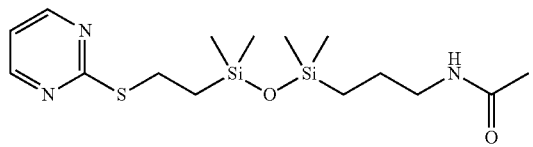 [SMILES: CC(=O)NCCC[Si](C)(C)O[Si](C)(C)CCSc1ncccn1]

A solution of mixture of 2-((2-(1,1,3,3-tetramethyl-3-vinyldisiloxanyl)ethyl)thio)pyrimidine (500 mg, 1.677 mmol) and N,N-((1,1,3,3-tetramethyldisiloxane-1,3-diyl)bis(propane-3,1-diyl))diacetamide (570 mg, 1.677 mmol) in 4M HCl in dioxane (25 mL) was stirred at room temperature for 1 h. The reaction mixture was concentrated in vacuo resulting in the crude intermediate 5 and 6. The mixture of intermediate 5 and 6 was dissolved in acetonitrile (20 mL) and followed by addition of water (0.12 mL, 6.711 mmol) and DIPEA (1.85 mL, 10.06 mmol) and stirred at room temperature for 1 h. The reaction mixture was concentrated in vacuo resulting in the crude compound which was purified by Combi Flash chromatography on silica gel eluting with 0-10% methanol in DCM to afford 510 mg, 41% yield, of the title compound as a light yellow oil. $^1$H NMR (400 MHz, DMSO-$d_6$) δ=8.55 (d, J=4.89 Hz, 2H), 7.72 (br. s, 1H), 7.09-7.15 (m, 1H), 3.04-3.11 (m, 2H), 2.88-2.96 (m, 2H), 1.72 (s, 3H), 1.27-1.38 (m, 2H), 0.89-0.97 (m, 2H), 0.39-0.46 (m, 2H), 0.05 (s, 6H), 0.00 (s, 6H); MS (ES$^+$): m/z=372.10 [M+H]$^+$; LCMS: $t_R$=3.20 min.

2-((2-(1,1,3,3-Tetramethyl-3-vinyldisiloxanyl)ethyl)thio)pyrimidine (3)

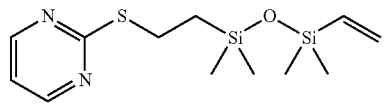 [SMILES: C=C[Si](C)(C)O[Si](C)(C)CCSc1ncccn1]

A solution of pyrimidine-2-thiol (1 g, 8.928 mmol) and 1,1,3,3-tetramethyl-1,3-divinyldisiloxane (3.32 g, 17.85 mmol) in THF (50 mL) was added AIBN (146 mg, 0.892 mmol) and silica (100 mg, 10% w/w) at room temperature. The resulting solution was heated to reflux at 60° C. for 4 h. The reaction mixture was concentrated in vacuo resulting in the crude compound which was purified by Combi Flash chromatography on silica gel eluting with 0-100% ethyl acetate in n-hexane to afford 1 g, 40% yield, of the title compound as a colorless oil. MS (ES$^+$): =299.05 [M+H]$^+$; LCMS: $t_R$=3.71, 3.87 and 3.97 min.

Example 34

227 228
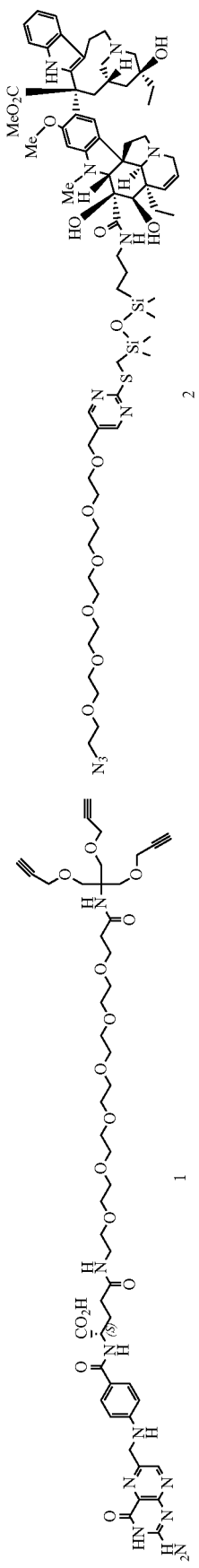
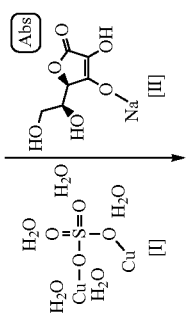
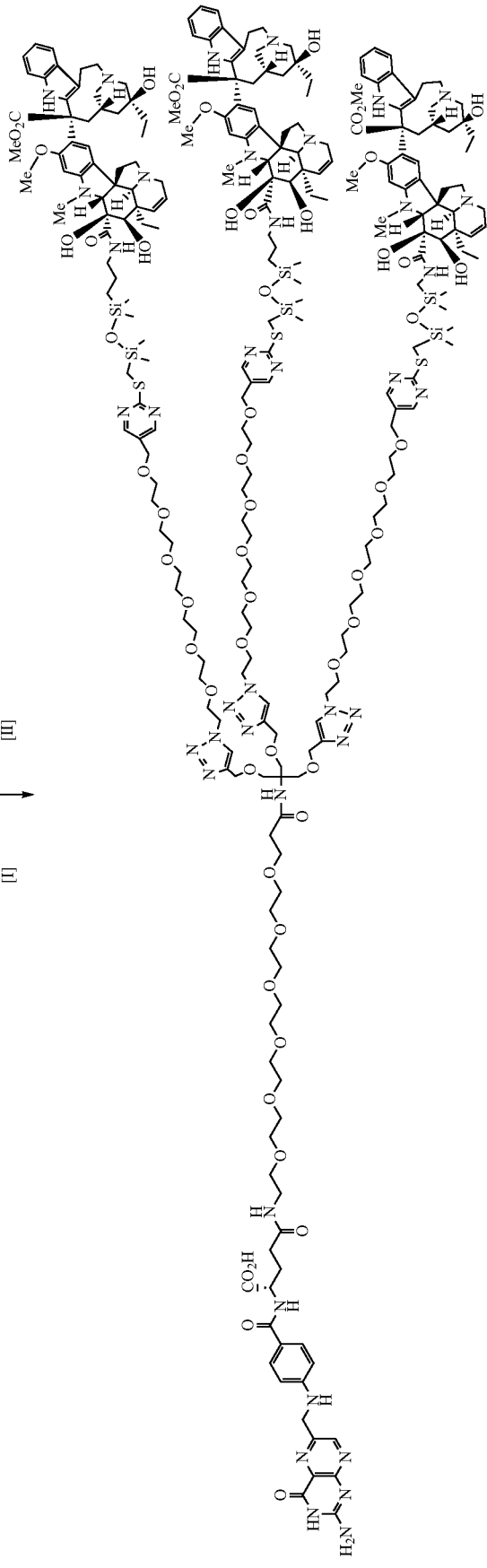

(31S)-31-(4-(((2-amino-4-oxo-3,4-dihydropteridin-6-yl)methyl)amino)benzamido)-1-(1-(1-(2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxaneyl)methyl)thio)pyrimidin-5-yl)-2,5,8,11,14,17-hexaoxanonadecan-19-yl)-1H-1,2,3-triazol-4-yl)-4,4-bis(01-(1-(2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxaneyl)methyl)thio)pyrimidin-5-yl)-2,5,8,11,14,17-hexaoxanonadecan-19-yl)-1H-1,2,3-triazol-4-yl)methoxy)methyl)-6,28-dioxo-2,9,12,15,18,21,24-heptaoxa-5,27-diazadotriacontan-32-oic acid [Example 34]

231
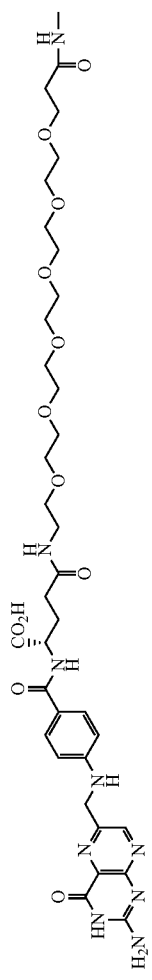
232
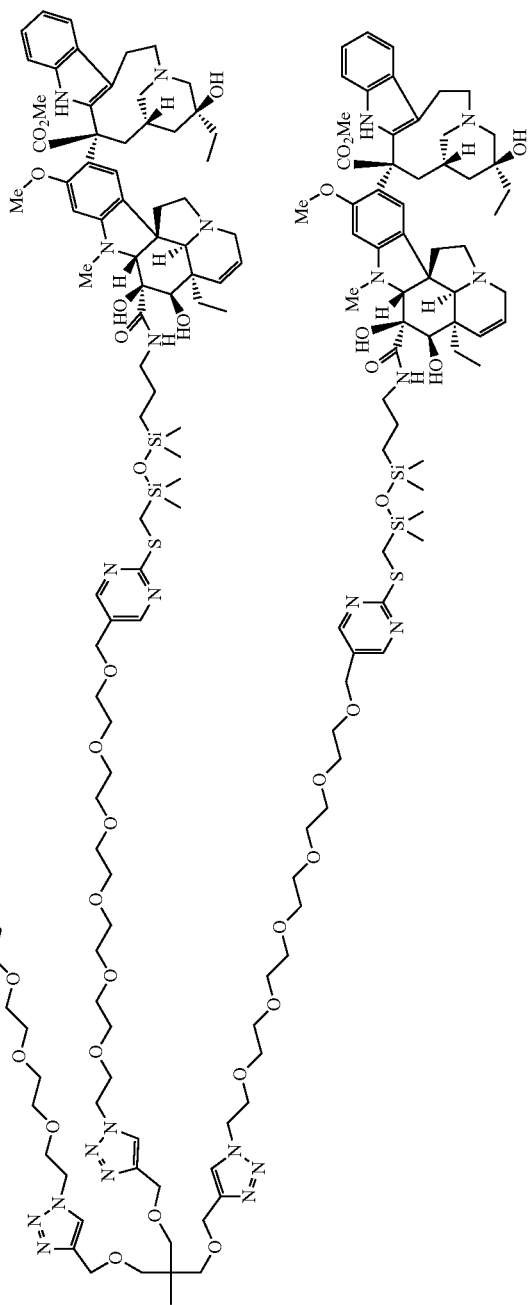

A solution of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (35 mg, 0.035 mmol) and (3S,5S,7S,9S)-methyl 9-((3aR,3a1R,4R,5S,5aR,10bR)-5-((3-(3-(((5-(19-azido-2,5,8,11,14,17-hexaoxanonadecyl) pyrimidin-2-yl)thio)methyl)-1,1,3,3-tetramethyldisiloxanyl) propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (147 mg, 0.109 mmol) in DMSO (5.00 mL) was degassed by evacuating under vacuum and charged with $N_2$ gas then charged with a solution of sodium (R)-2-((S)-1,2-dihydroxyethyl)-4-hydroxy-5-oxo-2,5-dihydrofuran-3-olate (6.93 mg, 0.035 mmol) in water (0.300 mL) followed by the addition of copper (II) sulfate pentahydrate (6.58 mg, 0.021 mmol) in water (0.300 mL) and stirred at rt for 3 h. The reaction was purified by reverse phase HPLC resulting in 78 mg, 43.5% yield of the title compound as a pale yellow solid. $^1$H NMR (DMSO-$d_6$, 400 MHz): δ (ppm) 9.33 (s, 2H), 8.63 (s, 1H), 8.57 (s, 5H), 8.51 (br s, 2H), 7.99 (s, 3H), 7.91-7.97 (m, 1H), 7.77 (br t, J=5.8 Hz, 3H), 7.59 (br d, J=8.1 Hz, 2H), 7.36 (br d, J=7.8 Hz, 3H), 7.26 (d, J=8.1 Hz, 2H), 6.87-7.04 (m, 8H), 6.64 (br d, J=8.6 Hz, 2H), 6.44 (s, 2H), 6.19 (s, 2H), 5.55-5.61 (m, 1H), 5.54-5.71 (m, 4H), 4.41-4.54 (m, 20H), 4.00-4.10 (m, 4H), 3.96 (s, 3H), 3.93 (d, J=6.1 Hz, 3H), 3.77-3.85 (m, 10H), 3.71 (s, 12H), 3.63 (br s, 8H), 3.41-3.57 (m, 95H), 3.00-3.23 (m, 21H), 2.84-2.93 (m, 4H), 2.61-2.76 (m, 22H), 2.39 (s, 6H), 2.27-2.36 (m, 6H), 1.85-2.17 (m, 10H), 1.57 (td, J=13.5, 7.6 Hz, 6H), 1.41-1.51 (m, 6H), 1.11-1.36 (m, 15H), 0.69-0.85 (m, 17H), 0.63 (br s, 3H), 0.44-0.54 (m, 6H), 0.16 (s, 18H), 0.03-0.09 (m, 20H); MS (ES$^+$): m/z=1371.43, 1372.17, 1373.50 [M+H]$^+$; LCMS: $t_R$=1.95 min [polar_3 min_1500].

Example 35

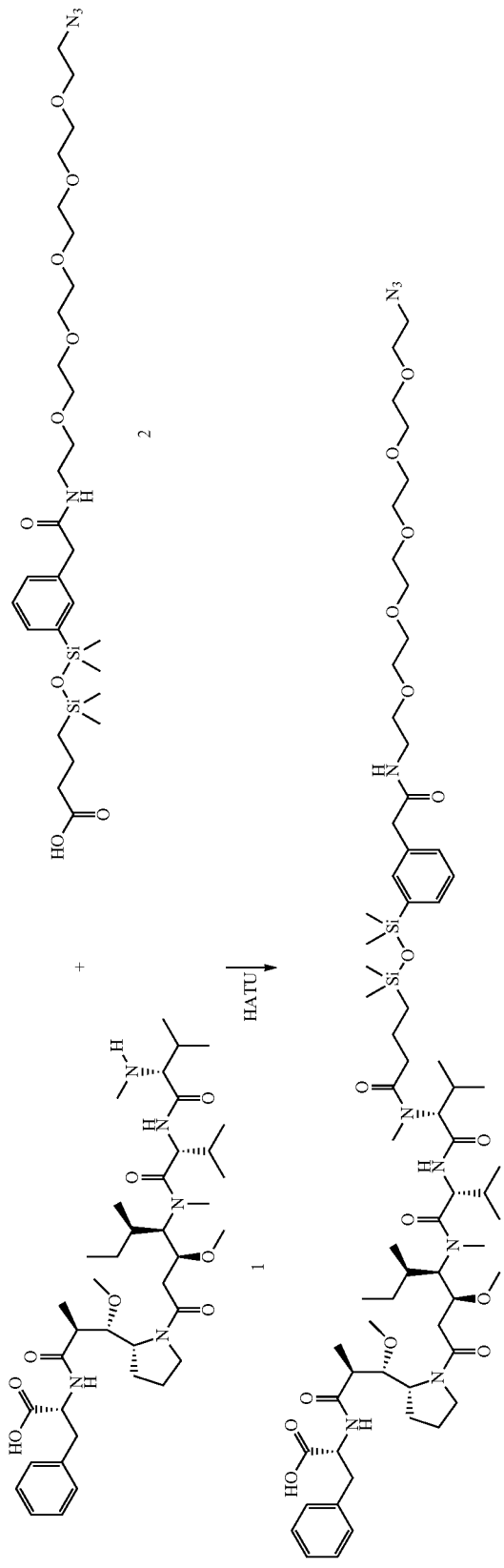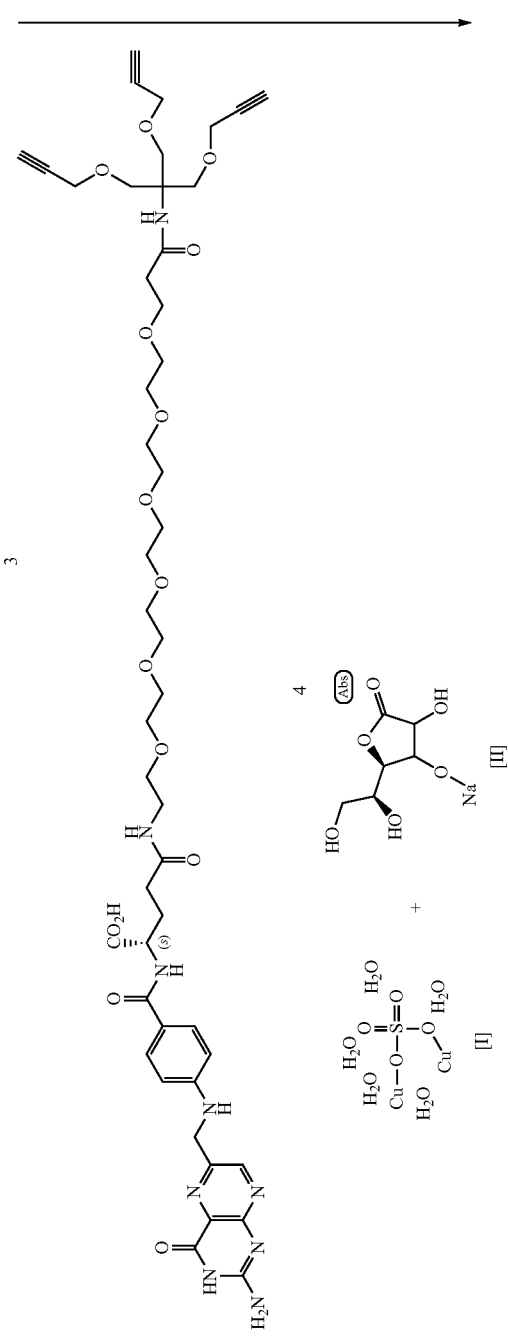

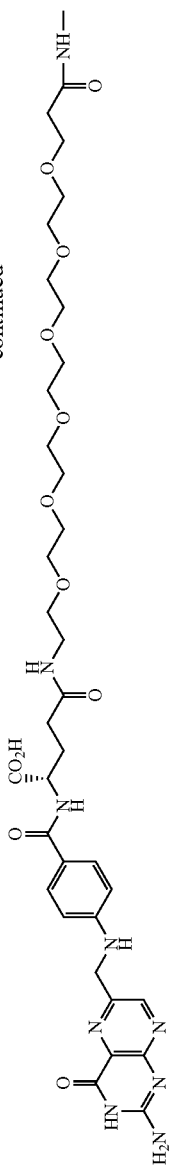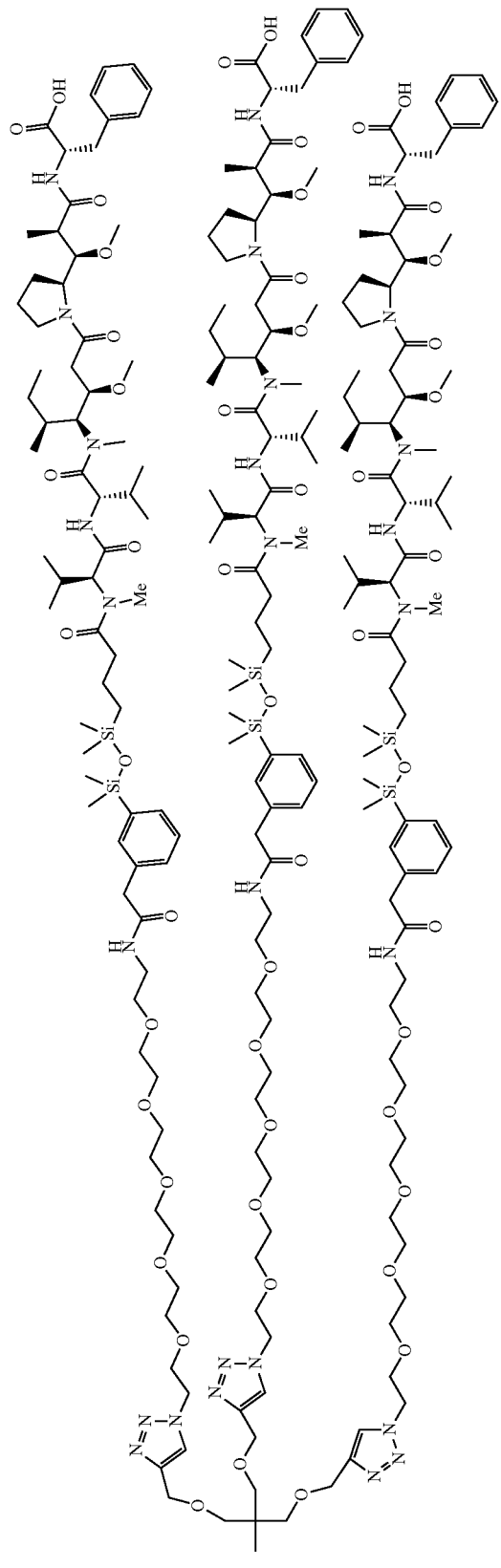
Example 35

Example 35:
Folate-PEG-Adaptor-PhenylSiLinker-TripleAuristatin

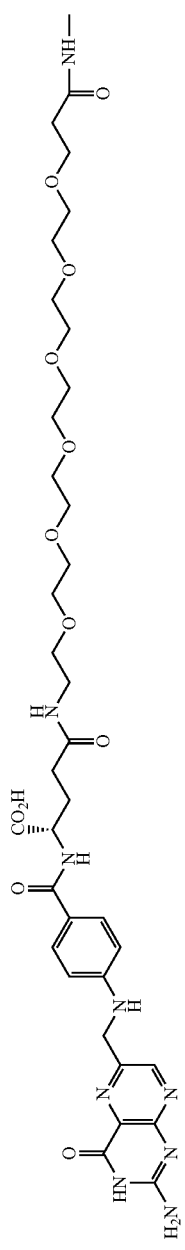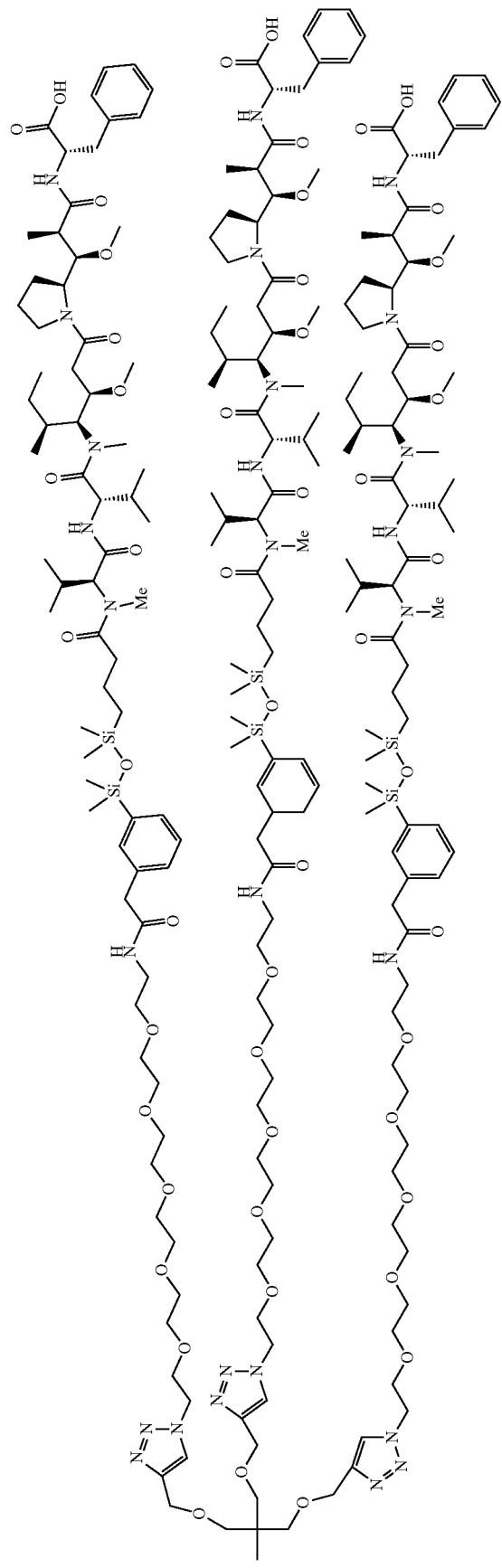

A solution of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (12 mg, 0.012 mmol) in DMSO (5.00 mL) was degassed by evacuating under vacuum and charged with $N_2$ gas then charged with a solution of sodium (R)-2-((S)-1,2-dihydroxyethyl)-4-hydroxy-5-oxo-2,5-dihydrofuran-3-olate (2.391 mg, 0.012 mmol) in Water (0.187 mL) followed by the addition of copper (II) sulfate pentahydrate (2.269 mg, 7.24 μmol) in Water (0.187 mL) and stirred at rt for 3 h. The reaction was purified by reverse phase HPLC resulting in the title compound as a pale yellow solid. $^1$H NMR (DMSO-$d_6$, 400 MHz): δ (ppm) 9.33 (s, 2H), 8.63 (s, 1H), 8.57 (s, 5H), 8.51 (br s, 2H), 7.99 (s, 3H), 7.91-7.97 (m, 1H), 7.77 (br t, J=5.8 Hz, 3H), 7.59 (br d, J=8.1 Hz, 2H), 7.36 (br d, J=7.8 Hz, 3H), 7.26 (d, J=8.1 Hz, 2H), 6.87-7.04 (m, 8H), 6.64 (br d, J=8.6 Hz, 2H), 6.44 (s, 2H), 6.19 (s, 2H), 5.55-5.61 (m, 1H), 5.54-5.71 (m, 4H), 4.41-4.54 (m, 20H), 4.00-4.10 (m, 4H), 3.96 (s, 3H), 3.93 (d, J=6.1 Hz, 3H), 3.77-3.85 (m, 10H), 3.71 (s, 12H), 3.63 (br s, 8H), 3.41-3.57 (m, 95H), 3.00-3.23 (m, 21H), 2.84-2.93 (m, 4H), 2.61-2.76 (m, 22H), 2.39 (s, 6H), 2.27-2.36 (m, 6H), 1.85-2.17 (m, 10H), 1.57 (td, J=13.5, 7.6 Hz, 6H), 1.41-1.51 (m, 6H), 1.11-1.36 (m, 15H), 0.69-0.85 (m, 17H), 0.63 (br s, 3H), 0.44-0.54 (m, 6H), 0.16 (s, 18H), 0.03-0.09 (m, 20H); MS (ES$^+$): m/z=1689.32 [M+H/3]$^+$; LCMS: $t_R$=2.62 min [nonpolar_3 min]; HPLC: Waters BEH, C18, column, 1.7 uM, 2.1 mm×100 mm: $t_R$=9.00 min, [PREP2_AmmBicarb_pH7.4_Method2]

((2S,3S)-3-((R)-1-((3S,4R,5R)-4-((R)-2-((R)-2-(4-(3-(3-(20-azido-2-oxo-6,9,12,15,18-pentaoxa-3-azaicosyl)phenyl)-1,1,3,3-tetramethyldisiloxaneyl)-N-methylbutanamido)-3-methylbutanamido)-N,3-dimethylbutanamido)-3-methoxy-5-methylheptanoyl)pyrrolidin-2-yl)-3-methoxy-2-methylpropanoyl)-D-phenylalanine [3]

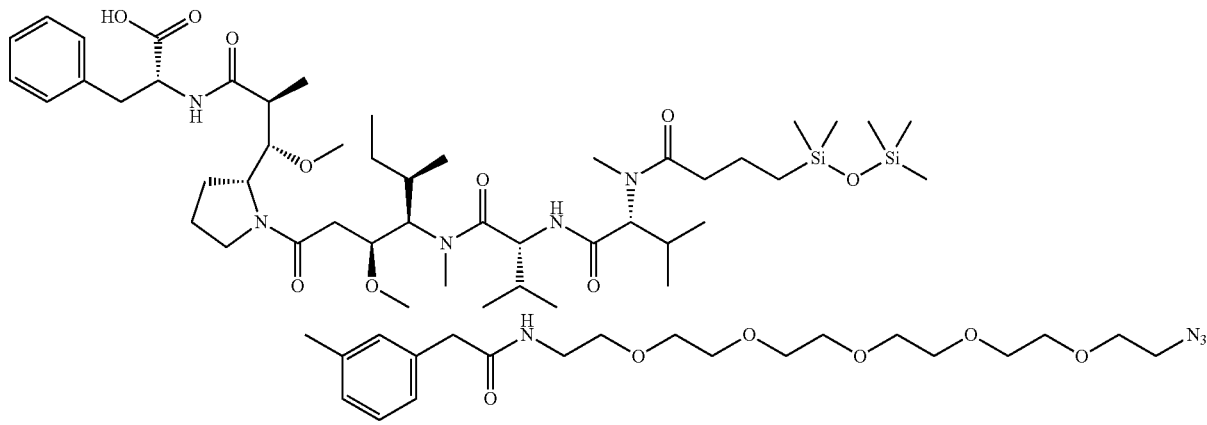

A solution of 4-(3-(4-(20-azido-2-oxo-6,9,12,15,18-pentaoxa-3-azaicosyl)phenyl)-1,1,3,3-tetramethyldisiloxanyl)butanoic acid (165 mg, 0.256 mmol), TEA (0.048 mL, 0.342 mmol) and HATU (97 mg, 0.256 mmol) in DMF (2.00 mL) was cooled to 0° C. and stirred for 30 min then charged with a solution of (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid (125 mg, 0.171 mmol) in DMF (2.50 mL) and stirred at rt for 16 h. From LCMS looked like a the product had formed therefore the reaction was purified by Prep HPLC using (Waters BEH, C18, column, 1.7 uM, 2.1 mm×100 mm, [PREP2_AmmBicarb_pH7.4_Method1B], resulting in 100 mg, 43.2% yield of the title compound as a foam solid. $^1$H NMR (DMSO-$d_6$, 400 MHz): δ (ppm) 8.49-8.58 (m, 1H), 8.10-8.23 (m, 1H), 7.85-7.94 (m, 1H), 7.83-8.09 (m, 1H), 7.54-7.75 (m, 1H), 7.38-7.42 (m, 1H), 7.32-7.37 (m, 1H), 7.24-7.32 (m, 2H), 7.07-7.23 (m, 5H), 4.23-4.76 (m, 3H), 3.93-4.03 (m, 1H), 3.63-3.87 (m, 1H), 3.46-3.62 (m, 20H), 3.38-3.43 (m, 8H), 3.14-3.24 (m, 10H), 3.03-3.10 (m, 3H), 2.96 (br d, J=9.9 Hz, 1H), 2.80-2.90 (m, 4H), 2.17-2.43 (m, 5H), 1.03 (dd, J=13.0, 6.7 Hz, 3H), 0.69-0.95 (m, 20H), 0.49-0.59 (m, 2H), 0.25-0.31 (m, 6H), 0.02-0.07 (m, 6H); MS (ES$^+$): m/z=1356.89 [M+H]$^+$; LCMS: $t_R$=2.57 min [polar_3 min_1500].

Synthetic Scheme for Compound 2

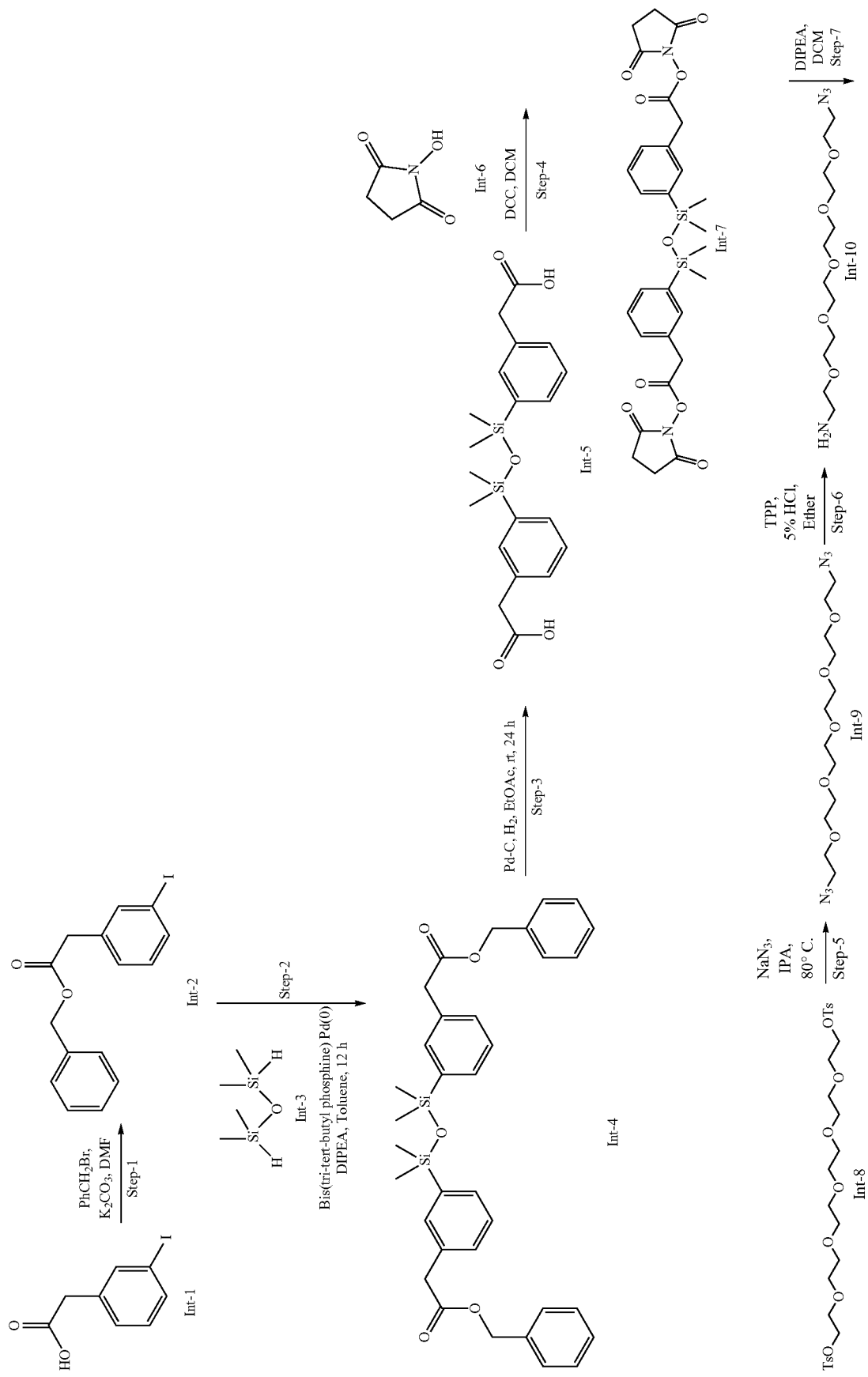

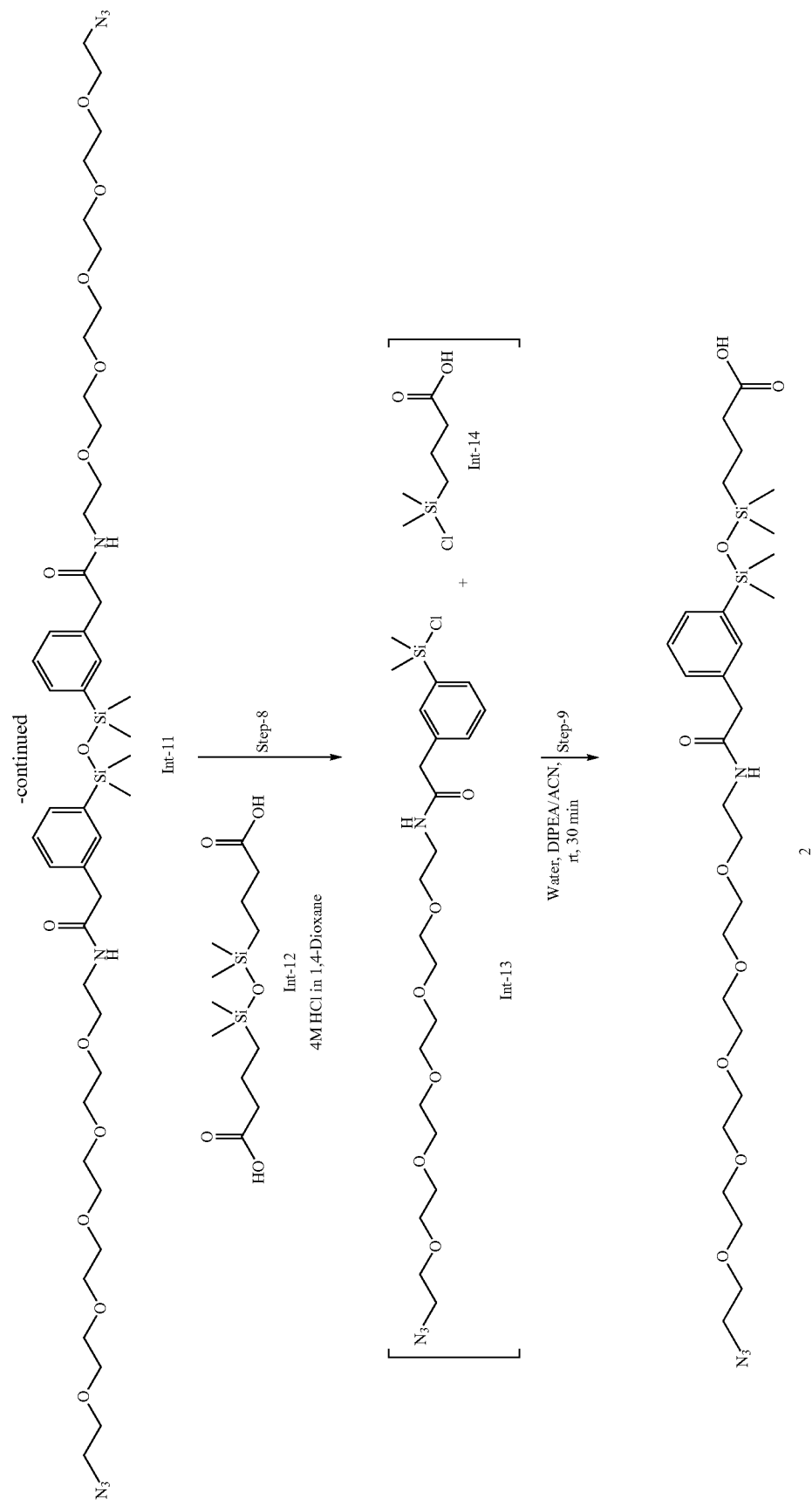

4-(3-(3-(20-azido-2-oxo-6,9,12,15,18-pentaoxa-3-azaicosyl)phenyl)-1,1,3,3-tetramethyl disiloxaneyl)butanoic acid [2]

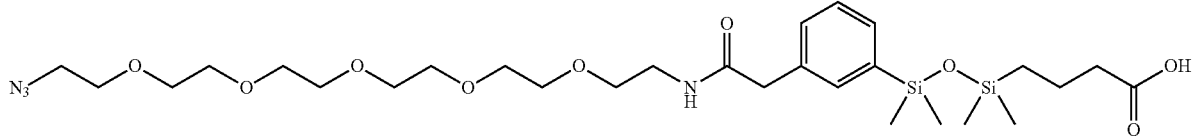 [SMILES: C[Si](C)(CCCC(=O)O)O[Si](C)(C)c1cccc(CC(=O)NCCOCCOCCOCCOCCOCCN=[N+]=[N-])c1]

A solution of 2,2'-((1,1,3,3-tetramethyldisiloxane-1,3-diyl)bis(3,1-phenylene))bis(N-(17-azido-3,6,9,12,15-pentaoxaheptadecyl)acetamide) (1 g, 1.021 mmol; Int-11) and 4,4'-(1,1,3,3-tetramethyldisiloxane-1,3-diyl)dibutyric acid (312 g, 1.021 mmol; Int-12) in 4M HCl in dioxane (30 mL) was stirred at room temperature for 30 min. The reaction mixture was concentrated under reduced pressure resulting in the crude Int-13 and Int-14. To Int-13 and Int-14 in acetonitrile (30 mL) was added water (0.073 mL, 4.084 mmol) and DIPEA (1.06 mL, 6.126 mmol) at room temperature and stirred for 30 min. After completion of the reaction, the reaction mixture was concentrated under reduced pressure resulting in the crude compound which was purified by CombiFlash column chromatography eluting with 0-10% methanol in DCM to afford 700 mg, 53% yield of the title compound 2 as a colorless oil. $^1$H NMR (400 MHz, DMSO-$d_6$) δ=11.95 (s, 1H), 8.12 (t, J=5.38 Hz, 1H), 7.41 (s, 1H), 7.37 (d, J=6.36 Hz, 1H), 7.28-7.32 (m, 2H), 3.58-3.62 (m, 2H), 3.49-3.57 (m, 16H), 3.37-3.44 (m, 6H), 3.21 (q, J=5.87 Hz, 2H), 2.21 (t, J=7.34 Hz, 2H), 1.49-1.58 (m, 2H), 0.51-0.56 (m, 2H), 0.30 (s, 6H), 0.06 (s, 6H); MS (ES$^+$): m/z=643.90 [M+H]$^+$; LCMS: $t_R$=2.01 min.

Example 36

Folate-PEG-Adaptor-AmideSiLinker-TripleAuristatin

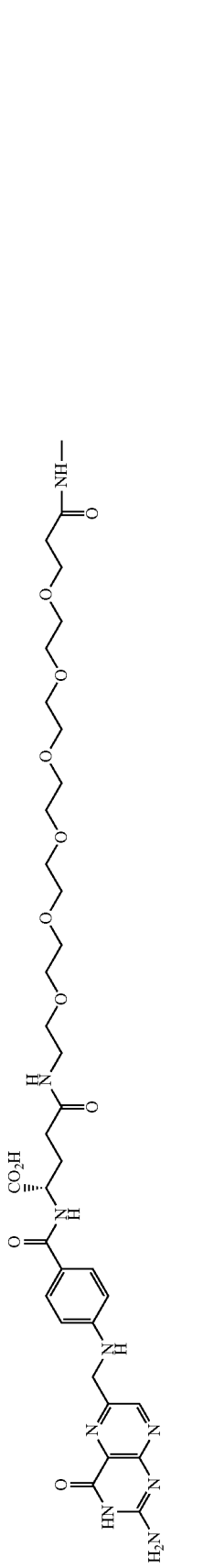
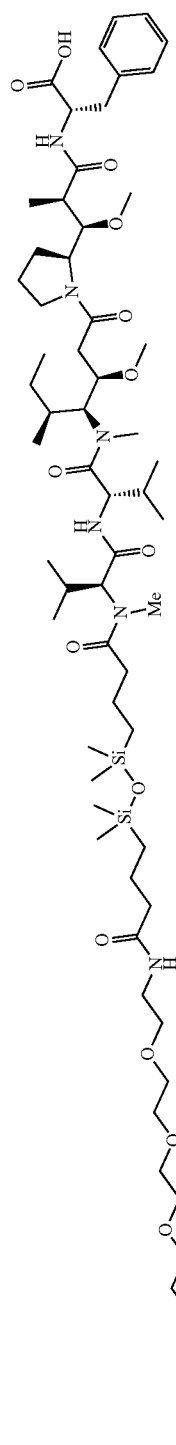
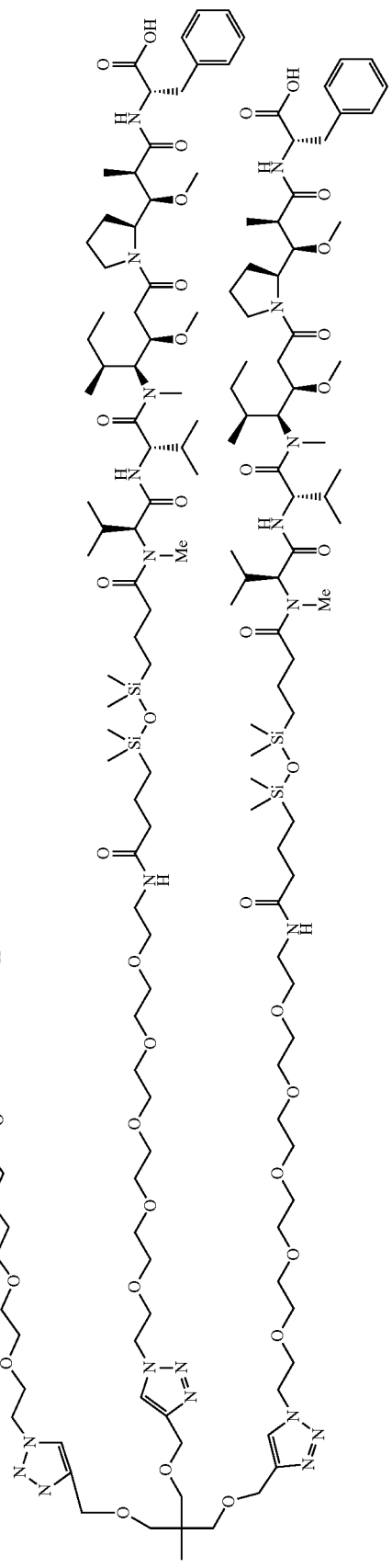

Example 36 was synthesized according to the procedure described for Example 35 employing the intermediates shown in the Scheme below:

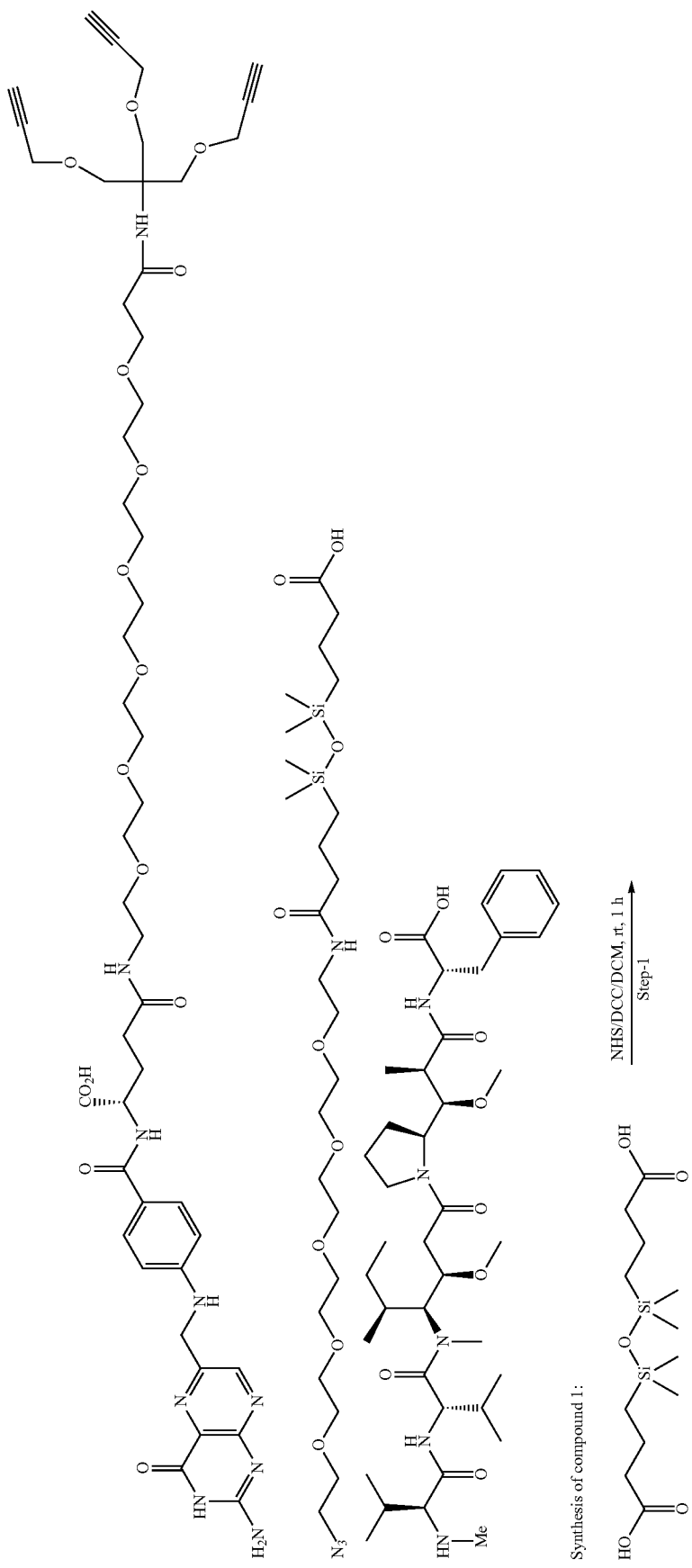
Synthesis of compound 1:

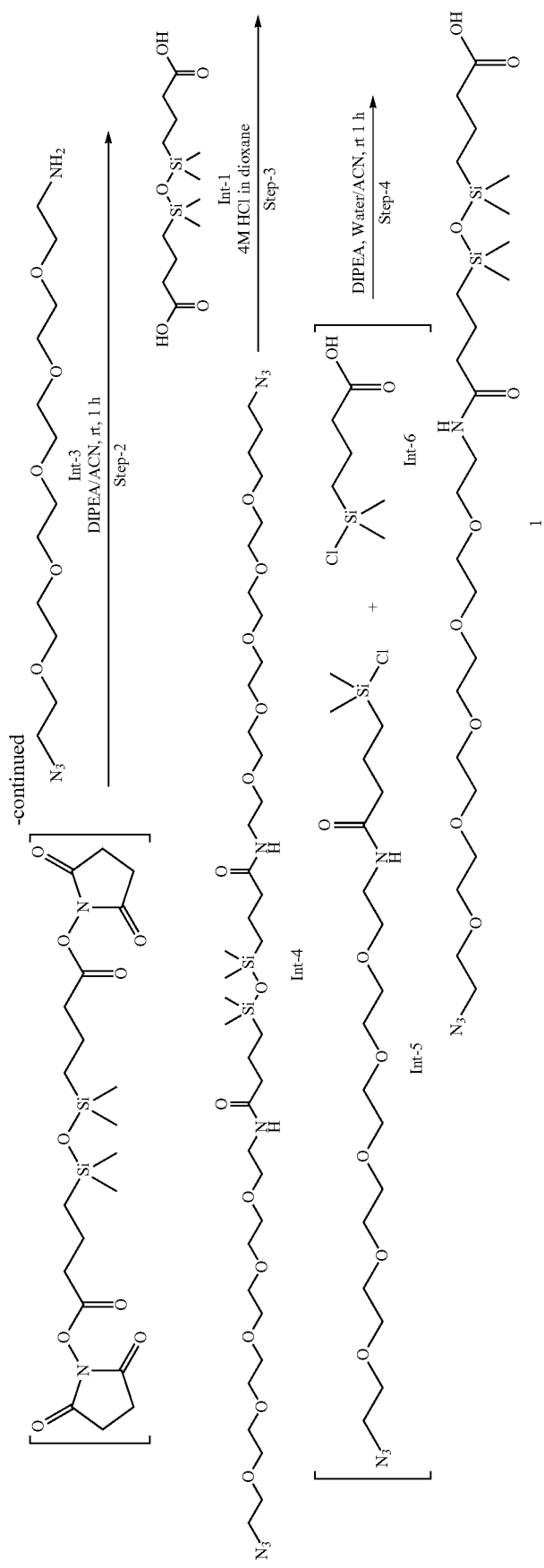

1-Azido-23,23,25,25-tetramethyl-19-oxo-3,6,9,12,15,24-hexaoxa-18-aza-23,25-disilanonacosan-29-oic acid (1)

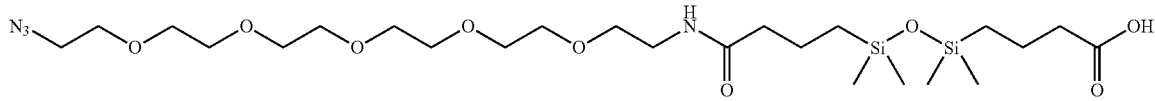 [SMILES: C[Si](C)(CCCC(=O)O)O[Si](C)(C)CCCC(=O)NCCOCCOCCOCCOCCOCCN=[N+]=[N-]]

A solution of mixture of 4,4'-(1,1,3,3-tetramethyldisiloxane-1,3-diyl)bis(N-(17-azido-3,6,9,12,15-pentaoxaheptadecyl)butanamide) Int-4 (1.43 g, 1.614 mmol) and bis(2,5-dioxopyrrolidin-1-yl) 4,4'-(1,1,3,3-tetramethyldisiloxane-1,3-diyl)dibutyrate Int-1 (495 mg, 1.614 mmol; commercially available) in 4M HCl in dioxane (40 mL) was stirred at room temperature for 1 h. The reaction mixture was concentrated in vacuo resulting in the crude intermediates Int-5 and Int-6. The mixture of intermediate Int-5 and Int-6 was dissolved in acetonitrile (50 mL) and followed by addition of water (0.12 mL, 6.459 mmol) and DIPEA (1.7 mL, 9.689 mmol) and stirred at room temperature for 1 h. The reaction mixture was concentrated in vacuo resulting in the crude compound which was purified by Combiflash chromatography eluting with 0-5% methanol in DCM to afford 57 mg (30% yield) of 1 as colorless oil. $^1$H NMR (400 MHz, DMSO-d$_6$) δ=11.91 (s, 1H), 7.75 (t, J=5.38 Hz, 1H), 3.54-3.58 (m, 2H), 3.51 (d, J=2.93 Hz, 3H), 3.43-3.48 (m, 10H), 3.32-3.37 (m, 4H), 3.14 (q, J=5.87 Hz, 2H), 2.17 (t, J=7.34 Hz, 3H), 2.03 (t, J=7.34 Hz, 2H), 1.47 (qd, J=8.05, 15.96 Hz, 5H), 0.39-0.50 (m, 5H), 0.01 (s, 12H); MS (ES$^+$): m/z=593.00 [M−H]$^+$; LCMS: $t_R$=2.29 min.

4,4'-(1,1,3,3-Tetramethyldisiloxane-1,3-diyl)bis(N-(17-azido-3,6,9,12,15-pentaoxaheptadecyl)butanamide) (Int-4)

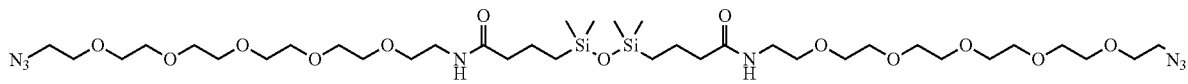 [SMILES: C[Si](C)(CCCC(=O)NCCOCCOCCOCCOCCOCCN=[N+]=[N-])O[Si](C)(C)CCCC(=O)NCCOCCOCCOCCOCCOCCN=[N+]=[N-]]

A solution of 4,4'-(1,1,3,3-tetramethyldisiloxane-1,3-diyl)dibutyric acid Int-1 (1 g, 3.267 mmol) in DCM (30 mL) was charged with DCC (1.4 g, 6.535 mmol) and NHS (789 mg, 6.862 mmol) and stirred at room temperature for 1 h. The reaction mixture was concentrated in vacuo, diluted with acetonitrile and re-concentrated. The slurry was cooled and the solid was filtered, washed and concentrated in vacuo resulting in the crude Int-2. A solution of bis(2,5-dioxopyrrolidin-1-yl) 4,4'-(1,1,3,3-tetramethyldisiloxane-1,3-diyl)dibutyrate Int-2 (1.63 g, 3.267 mmol) in acetonitrile (100 mL) and followed by addition of DIPEA (1.7 mL, 9.803 mmol) and azide amine hexa PEG Int-3 (2.21 g, 7.189 mmol) and stirred at room temperature for another 1 h. The reaction mixture was concentrated in vacuo resulting in the crude compound which was purified by purified by Combiflash chromatography eluting with 0-10% methanol in DCM to afford 1.43 g (50% yield) of the title compound Int-4 as colourless oil. $^1$H NMR (400 MHz, DMSO-d$_6$) δ=7.83 (t, J=5.38 Hz, 2H), 3.60-3.64 (m, 4H), 3.56 (d, J=2.93 Hz, 8H), 3.52 (t, J=3.18 Hz, 23H), 3.38-3.42 (m, 8H), 3.19 (q, J=5.71 Hz, 4H), 2.08 (t, J=7.34 Hz, 4H), 1.47-1.56 (m, 5H), 0.45-0.50 (m, 4H), 0.05 (s, 12H).

Example 37

Folate-PEG-Adaptor-PyrimidineSiLinker-TripleAuristatin

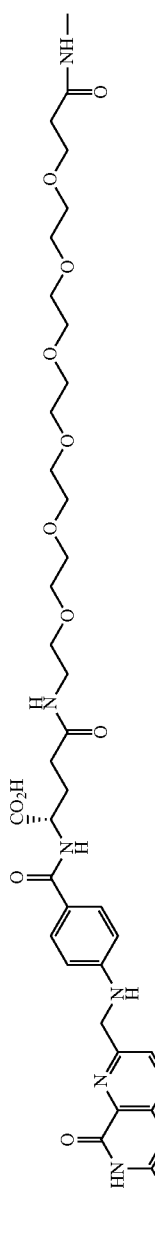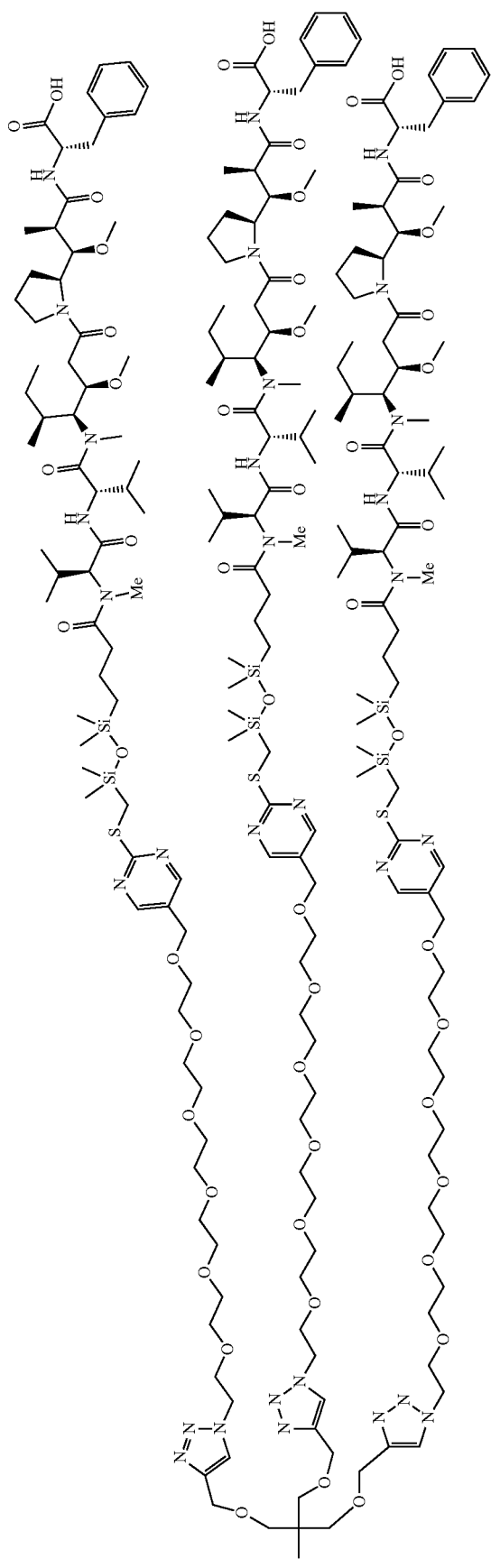

Example 37 was synthesized according to the procedure described for Example 35 employing the intermediates shown in the Scheme below:
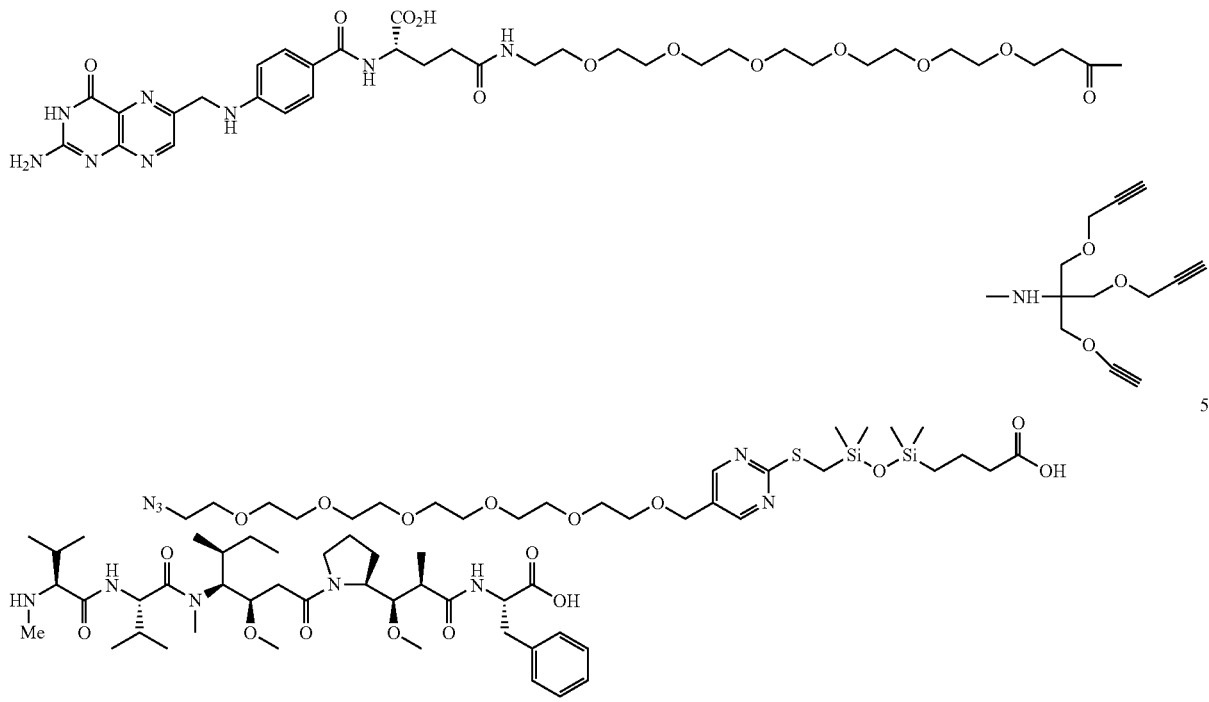
Synthesis of 5: 4-(3-(((5-(Azidomethyl)pyrimidin-2-yl)thio)methyl)-1,1,3,3-tetramethyldisiloxanyl)butanoic acid

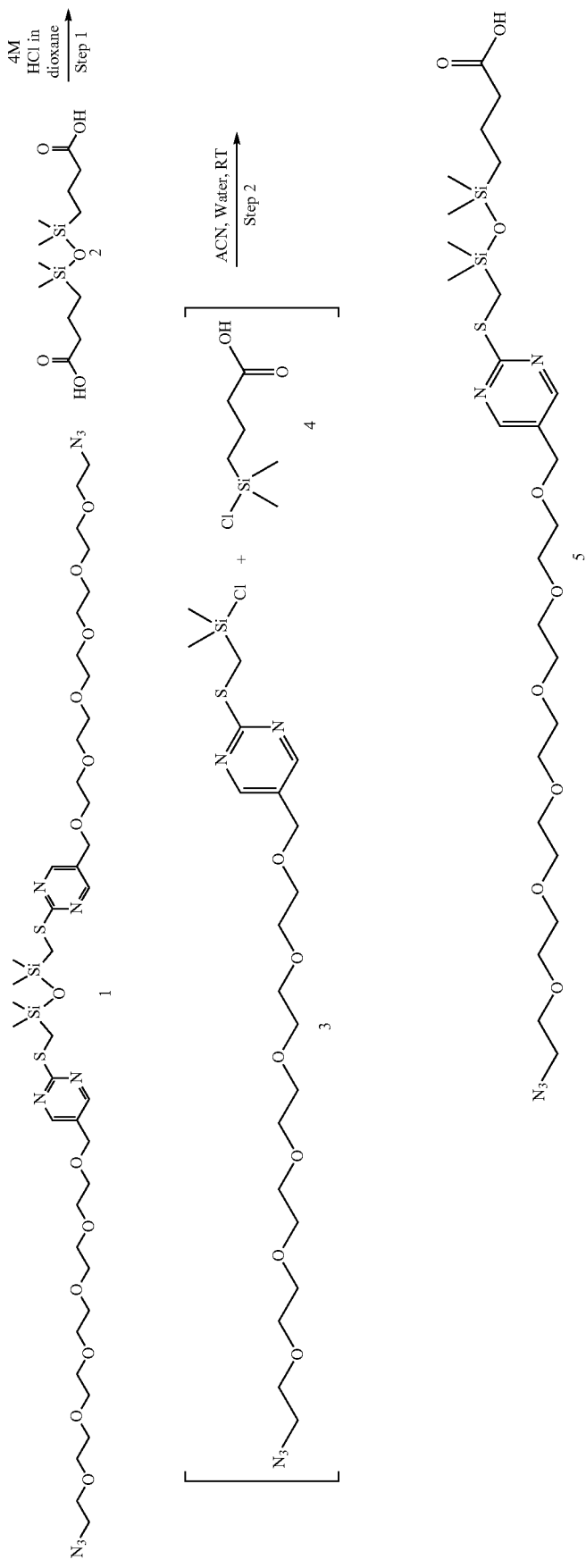

A solution of 1,3-bis(((5-(19-azido-2,5,8,11,14,17-hexaoxanonadecyl)pyrimidin-2-yl)thio)methyl)-1,1,3,3-tetramethyldisiloxane 1 (3.000 mmol) and 4,4'-(1,1,3,3-tetramethyldisiloxane-1,3-diyl)dibutyric acid 2 (932 mg, 3.000 mmol) in 4M HCl in dioxane (30 mL) was stirred at room temperature for 1 h. The reaction mixture was concentrated in vacuo resulting in the crude intermediate 3 and 4. The intermediate 3 and 4 was dissolved in acetonitrile (200 mL) and followed by addition of water (6.000 mmol) and DIPEA (18.00 mmol) and stirred at room temperature for another 1 h. The reaction mixture was concentrated in vacuo resulting in the crude compound which was purified by CombiFlash column chromatography eluting with 10-30% ethyl acetate in n-hexane to afford 4-(3-(((5-(19-azido-2,5,8,11,14,17-hexaoxanonadecyl)pyrimidin-2-yl)thio)methyl)-1,1,3,3-tetramethyldisiloxaneyl)butanoic acid.

Example 38

Folate-PEG-Adaptor-PhenylSiLinker-TripleAuristatin

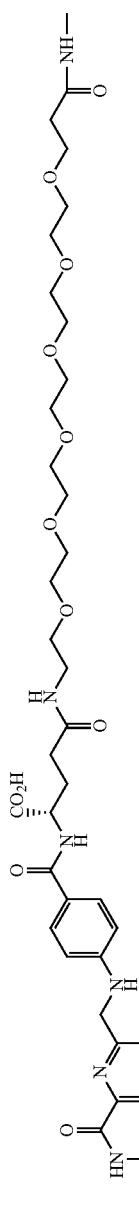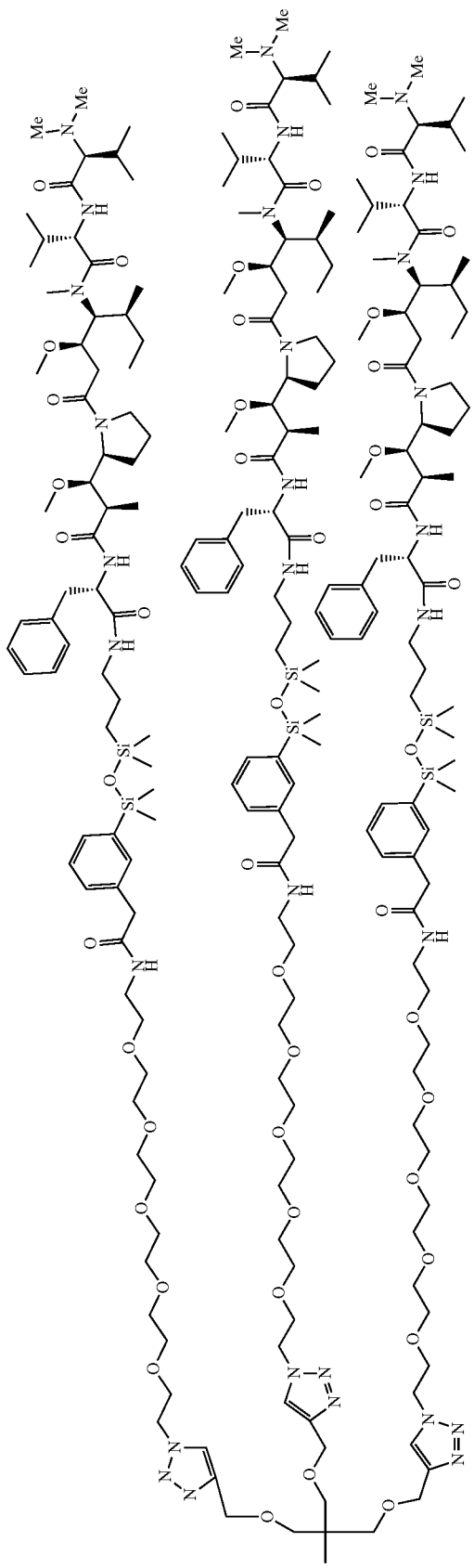

Example 38 was synthesized according to the procedure described for Example 35 employing the intermediates shown in the Scheme below:
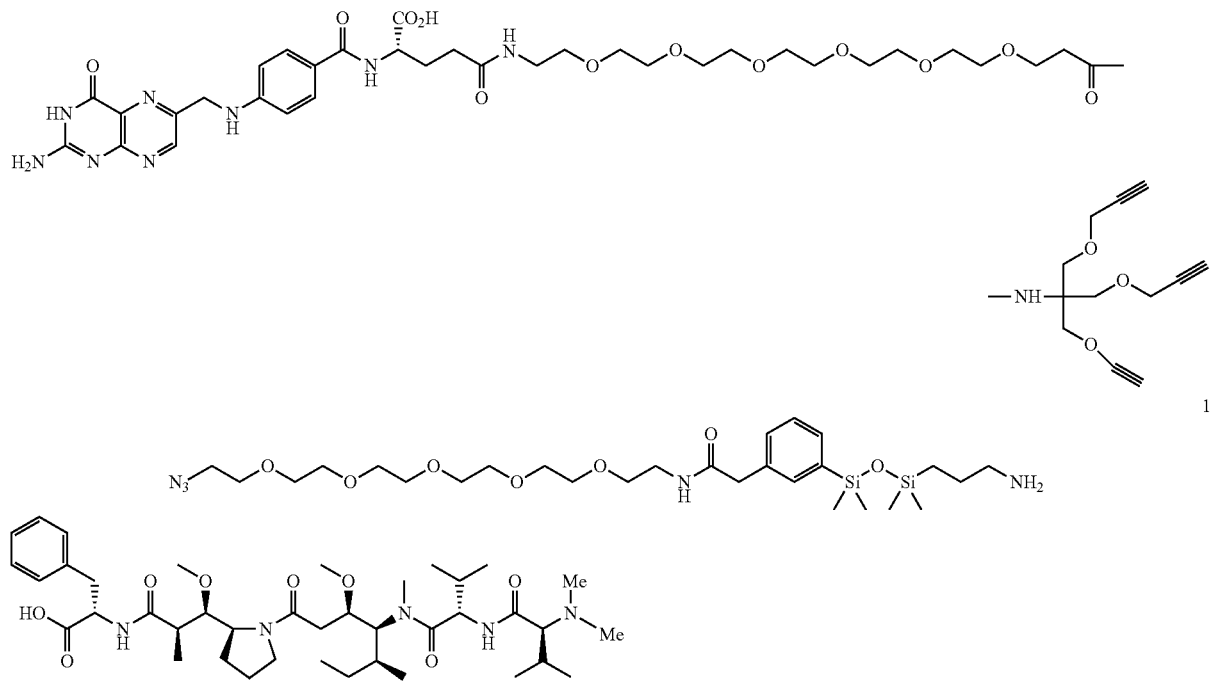
Synthetic Scheme for 1:

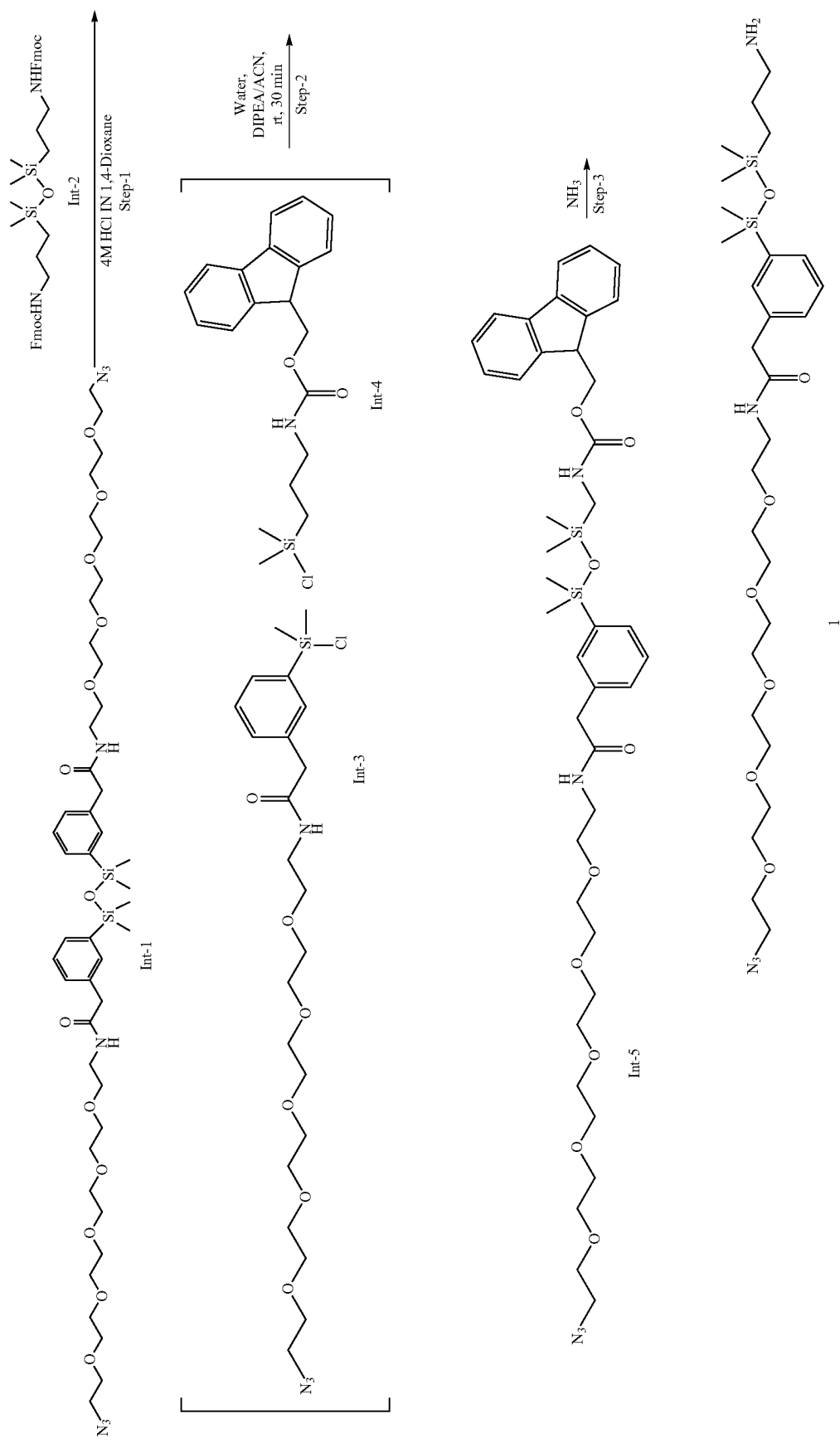

(9H-Fluoren-9-yl)methyl (3-(3-(3-(20-azido-2-oxo-6,9,12,15,18-pentaoxa-3-azaicosyl)phenyl)-1,1,3,3-tetramethyldisiloxanyl)propyl)carbamate (Int-5)

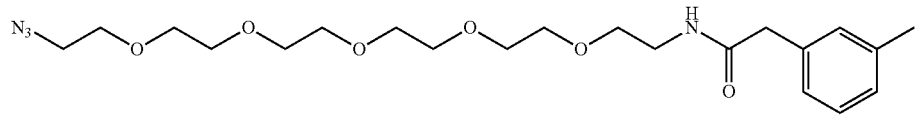

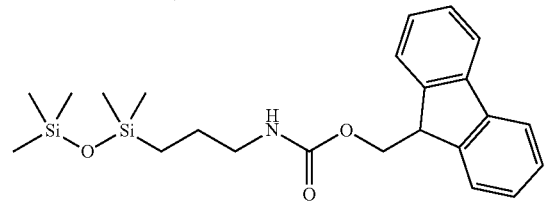

A solution of 2,2'-((1,1,3,3-tetramethyldisiloxane-1,3-diyl)bis(3,1-phenylene))bis(N-(17-azido-3,6,9,12,15-pentaoxaheptadecyl)acetamide) Int-1 (3 g, 3.063 mmol) and bis((9H-fluoren-9-yl)methyl) ((1,1,3,3-tetramethyldisiloxane-1,3-diyl)bis(propane-3,1-diyl))dicarbamate Int-2 (2.12 g, 3.063 mmol; Int-2 was prepared from 3,3'-(1,1,3,3-tetramethyldisiloxane-1,3-diyl)bis(propan-1-amine) and Fmoc-Cl) in 4M HCl in dioxane (30 mL) was stirred at room temperature for 30 min. The reaction mixture was concentrated under reduced pressure resulting in the crude Int-3 and Int-4. To Int-3 and Int-4 in acetonitrile (50 mL) was added water (0.22 mL, 12.25 mmol) and DIPEA (3.2 mL, 18.38 mmol) at room temperature and stirred for 30 min After completion of the reaction, the reaction mixture was concentrated under reduced pressure resulting in the crude compound which was purified by CombiFlash column chromatography eluting with 0-10% methanol in DCM to afford 1.8 g (35% yield) of Int-5 as colorless oil. $^1$H NMR (400 MHz, DMSO-$d_6$) δ=8.10 (br. s, 1H), 7.87 (d, J=7.83 Hz, 2H), 7.66 (d, J=7.34 Hz, 2H), 7.23-7.42 (m, 9H), 4.26 (d, J=6.85 Hz, 2H), 4.16-4.22 (m, 1H), 3.57 (t, J=4.40 Hz, 2H), 3.45-3.53 (m, 16H), 3.39 (s, 2H), 3.34-3.39 (m, 4H), 3.15-3.21 (m, 2H), 2.87-2.95 (m, 2H), 1.39 (td, J=7.58, 15.16 Hz, 2H), 0.42-0.49 (m, 2H), 0.26 (s, 6H), 0.03 (s, 6H); MS (ES$^+$): m/z=836.40 [M+H]$^+$; LCMS: $t_R$=2.03 min.

2-(3-(3-(3-Aminopropyl)-1,1,3,3-tetramethyldisiloxaneyl)phenyl)-N-(17-azido-3,6,9,12,15-pentaoxaheptadecyl)acetamide (1)

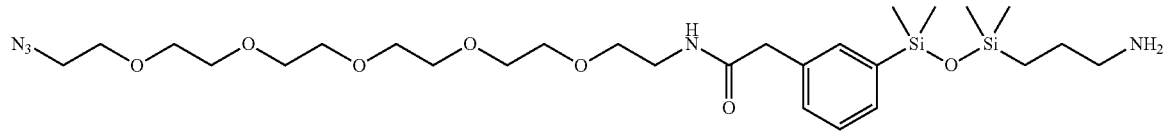 [SMILES: C[Si](C)(CCCN)O[Si](C)(C)c1cccc(CC(=O)NCCOCCOCCOCCOCCOCCN=[N+]=[N-])c1]

A solution of (9H-fluoren-9-yl)methyl (3-(3-(3-(20-azido-2-oxo-6,9,12,15,18-pentaoxa-3-azaicosyl)phenyl)-1,1,3,3-tetramethyldisiloxanyl)propyl)carbamate (1.00 g, 1.196 mmol) in 2 M Ammonia in Ethanol (21.29 ml, 42.6 mmol) was charged with ammonia gas bubbling for 3 min at −5° C. then stirred at rt in a sealed tube for 16 h (Note: over ~5 hr time frame the reaction mixture turned cloudy). From TLC and LCMS the reaction was complete therefore the reaction was purified. The crude reaction mixture was charged with silica gel and dry loaded onto the ISCO CombiFlash for purification [eluting with 0% (10% 7N NH$_3$ in MeOH) in DCM to 8% (10%-7N NH$_3$ in MeOH) in DCM resulting in 488 mg, 66.5% yield of the title compound as a clear/colorless oil. From HNMR and LCMS this material looked clean enough to use in the next reaction. $^1$H NMR (CHLOROFORM-d, 400 MHz): δ (ppm) 7.40-7.47 (m, 2H), 7.29-7.37 (m, 2H), 6.42 (br s, 1H), 3.60-3.69 (m, 16H), 3.55-3.58 (m, 6H), 3.50-3.55 (m, 3H), 3.40-3.45 (m, 2H), 3.36-3.40 (m, 2H), 2.64 (t, J=7.1 Hz, 2H), 1.40-1.50 (m, 2H), 0.50-0.56 (m, 2H), 0.32 (s, 6H), 0.08 (s, 6H)' MS (ES$^+$): m/z=614.28[M+H]$^+$; LCMS: $t_R$=1.93 min [polar_3 min_1500].

Example 39

Folate-PEG-Adaptor-AmideSiLinker-TripleAuristatin

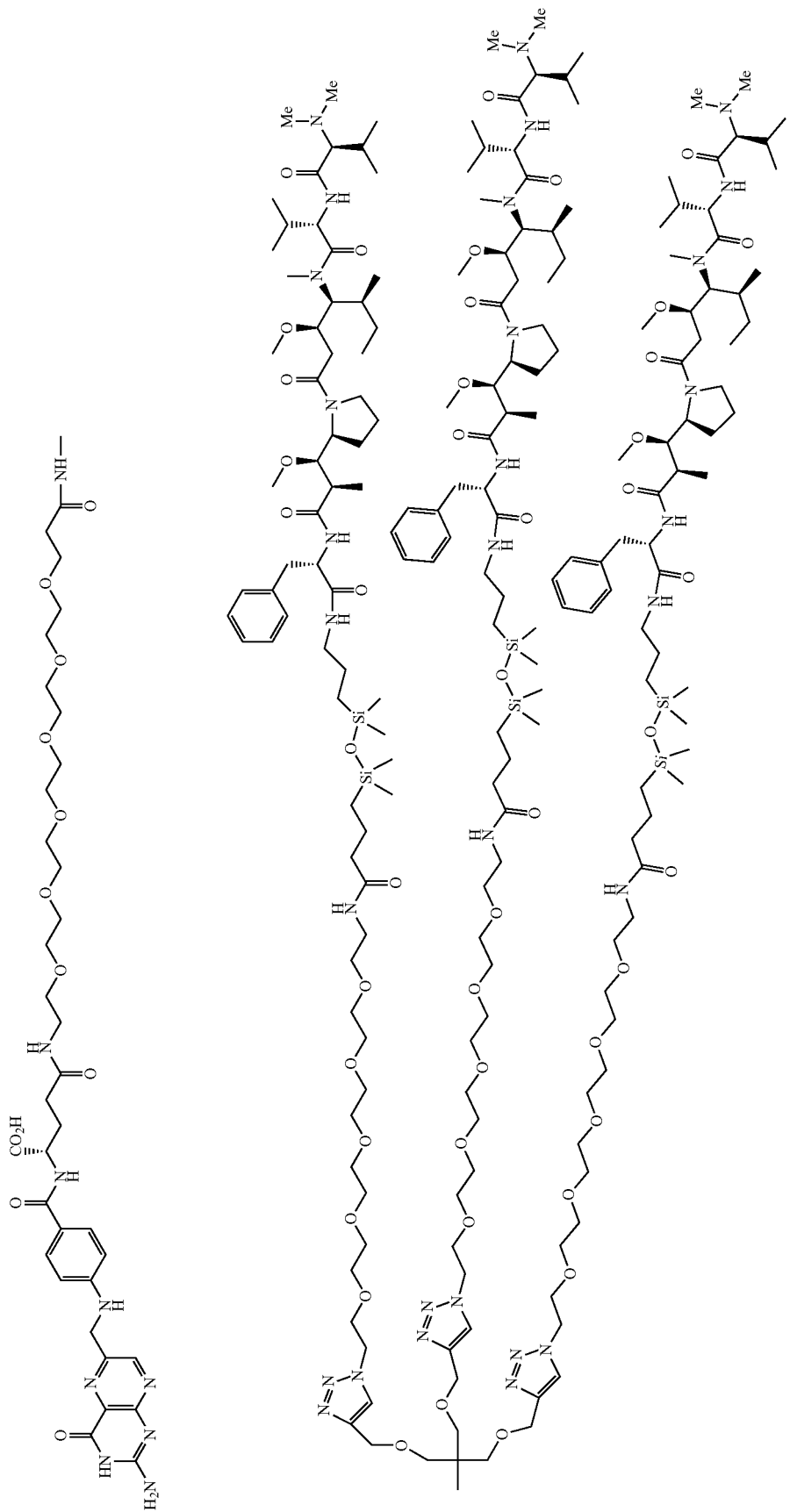

Example 39 was synthesized according to the procedure described for Example 35 employing the intermediates shown in the Scheme below:

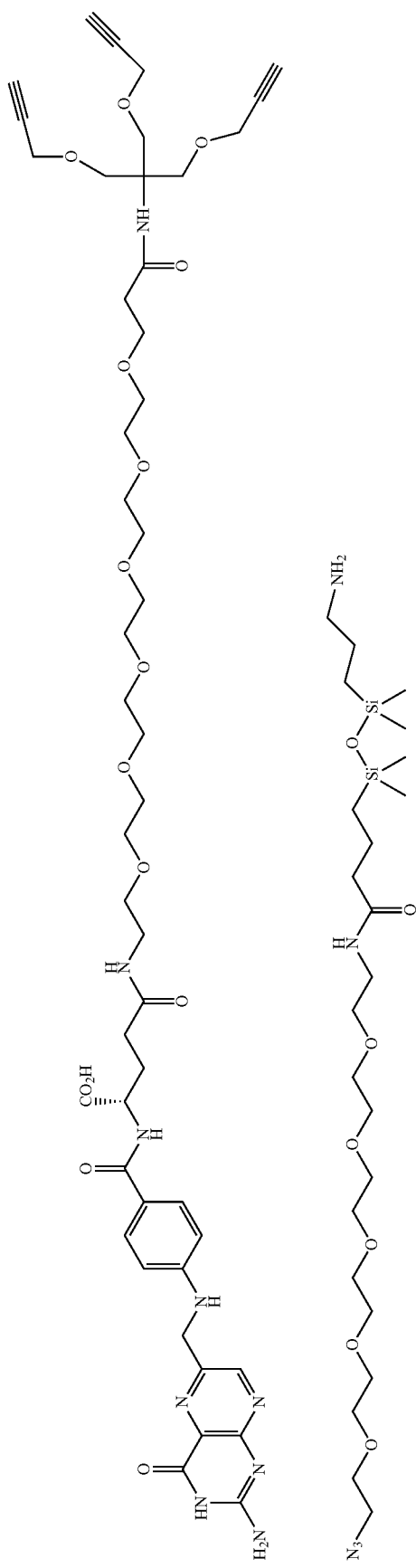
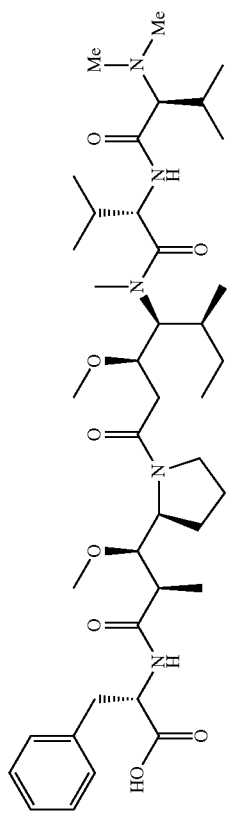

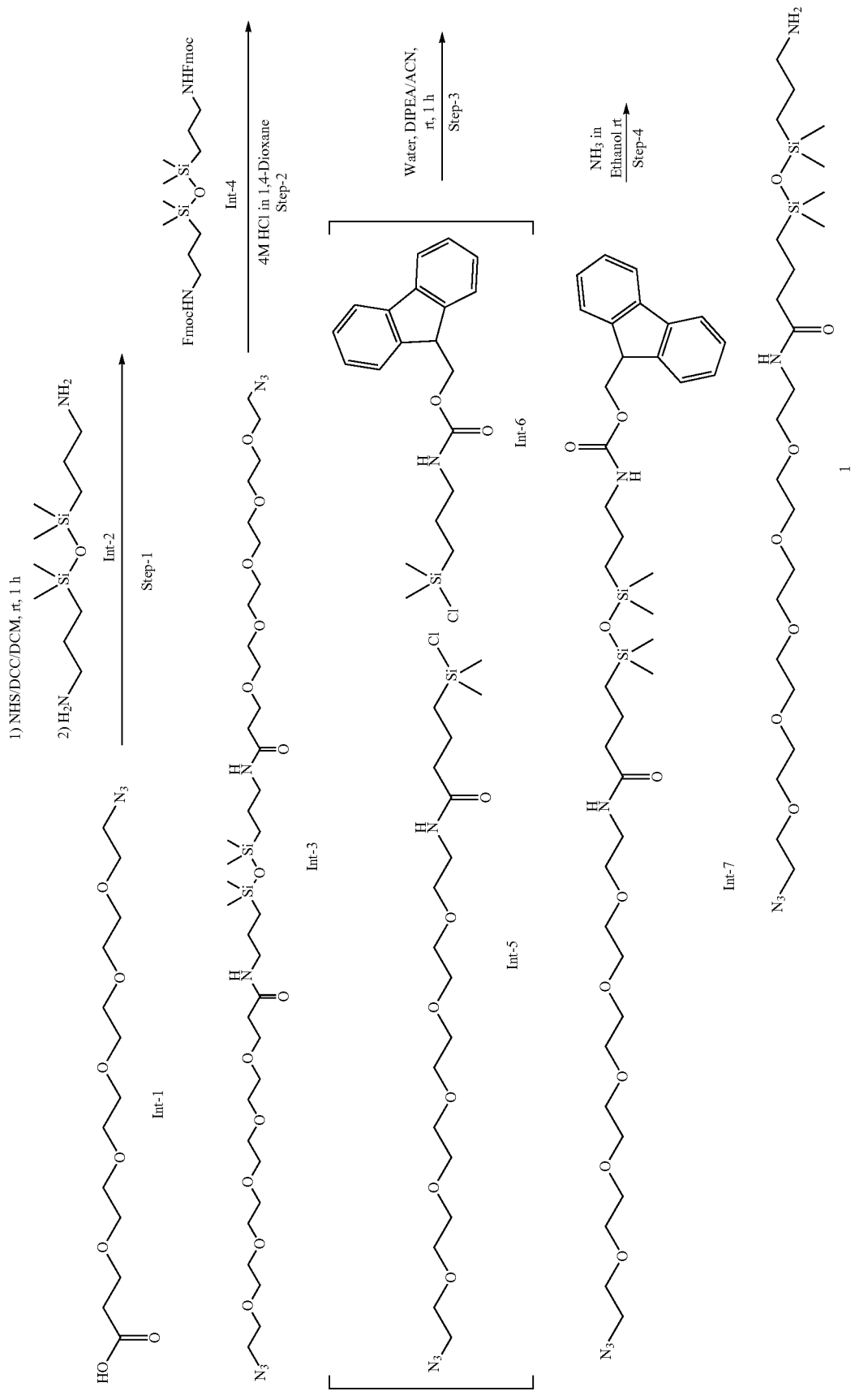

4-(3-(3-aminopropyl)-1,1,3,3-tetramethyldisiloxaneyl)-N-(17-azido-3,6,9,12,15-pentaoxaheptadecyl)butanamide (1)

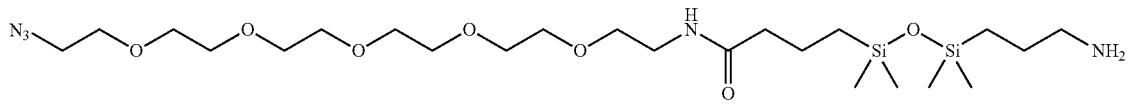 [SMILES: C[Si](C)(CCCN)O[Si](C)(C)CCCC(=O)NCCOCCOCCOCCOCCOCCN=[N+]=[N-]]

A solution of (9H-Fluoren-9-yl)methyl (1-azido-23,23,25,25-tetramethyl-19-oxo-3,6,9,12,15,24-hexaoxa-18-aza-23,25-disilaoctacosan-28-yl)carbamate (1.196 mmol) in 2 M Ammonia in Ethanol (42.6 mmol) was charged with ammonia gas bubbling for 3 min at −5° C. then stirred at rt in a sealed tube for 16 h (Note: over ~5 hr time frame the reaction mixture turned cloudy). From TLC and LCMS the reaction was complete therefore the reaction was purified. The crude reaction mixture was charged with silica gel and dry loaded onto the ISCO CombiFlash for purification [eluting with 0% (10% 7N $NH_3$ in MeOH) in DCM to 8% (10%-7N $NH_3$ in MeOH) in DCM resulting in the title compound as a clear/colorless oil. From HNMR and LCMS this material looked clean enough to use in the next reaction.

(9H-Fluoren-9-yl)methyl (1-azido-23,23,25,25-tetramethyl-19-oxo-3,6,9,12,15,24-hexaoxa-18-aza-23,25-disilaoctacosan-28-yl)carbamate (Int-8)

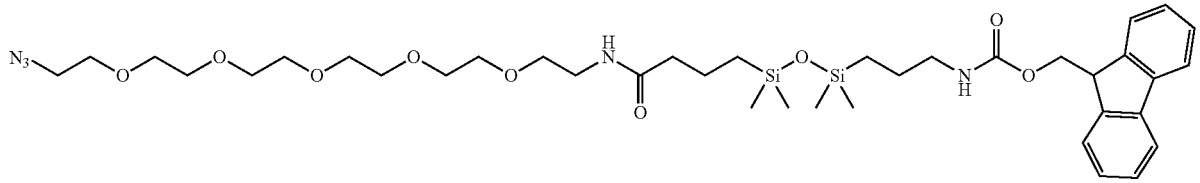 [SMILES: C[Si](C)(CCCNC(=O)OCC1c2ccccc2-c2ccccc21)O[Si](C)(C)CCCC(=O)NCCOCCOCCOCCOCCOCCN=[N+]=[N-]]

A solution of N,N'-((1,1,3,3-tetramethyldisiloxane-1,3-diyl)bis(propane-3,1-diyl))bis(1-azido-3,6,9,12,15-pentaoxaoctadecan-18-amide) Int-4 (2.16 g, 2.445 mmol) and bis((9H-fluoren-9-yl)methyl) ((1,1,3,3-tetramethyldisiloxane-1,3-diyl)bis(propane-3,1-diyl))dicarbamate Int-5 (1.694 g, 2.445 mmol) in 4M HCl in dioxane (40 mL) was stirred at room temperature for 30 min. The reaction mixture was concentrated under reduced pressure resulting in the crude Int-6 and Int-7. To Int-6 and Int-7 in acetonitrile (100 mL) was added water (0.17 mL, 9.782 mmol) and DIPEA (2.56 mL, 14.67 mmol) at room temperature and stirred for 30 min. After completion of the reaction, the reaction mixture was concentrated under reduced pressure. The crude compound was purified by CombiFlash column chromatography eluting with 0-10% methanol in DCM to afford 1 g (52% yield) of Int-8 as colorless oil. $^1$H NMR (400 MHz, DMSO-$d_6$) δ=7.86 (d, J=7.82 Hz, 2H), 7.77 (br. s, 1H), 7.66 (d, J=7.82 Hz, 2H), 7.38 (t, J=7.58 Hz, 2H), 7.24-7.32 (m, 3H), 4.26 (d, J=6.85 Hz, 2H), 4.15-4.20 (m, 1H), 3.54-3.58 (m, 2H), 3.51 (d, J=2.93 Hz, 2H), 3.47 (d, J=4.40 Hz, 12H), 3.35 (t, J=5.14 Hz, 4H), 3.15 (q, J=5.71 Hz, 2H), 2.88-2.95 (m, 2H), 2.04 (t, J=7.09 Hz, 2H), 1.30-1.53 (m, 6H), 0.40-0.47 (m, 4H), 0.00 (s, 6H), 0.00 (s, 6H); MS (ES$^+$): m/z=788.45 [M+H]$^+$; LCMS: $t_R$=2.32 min.

Example 40. Folate-PEG-Adaptor-Pyrimidine-SiLinker-TripleAuristatin

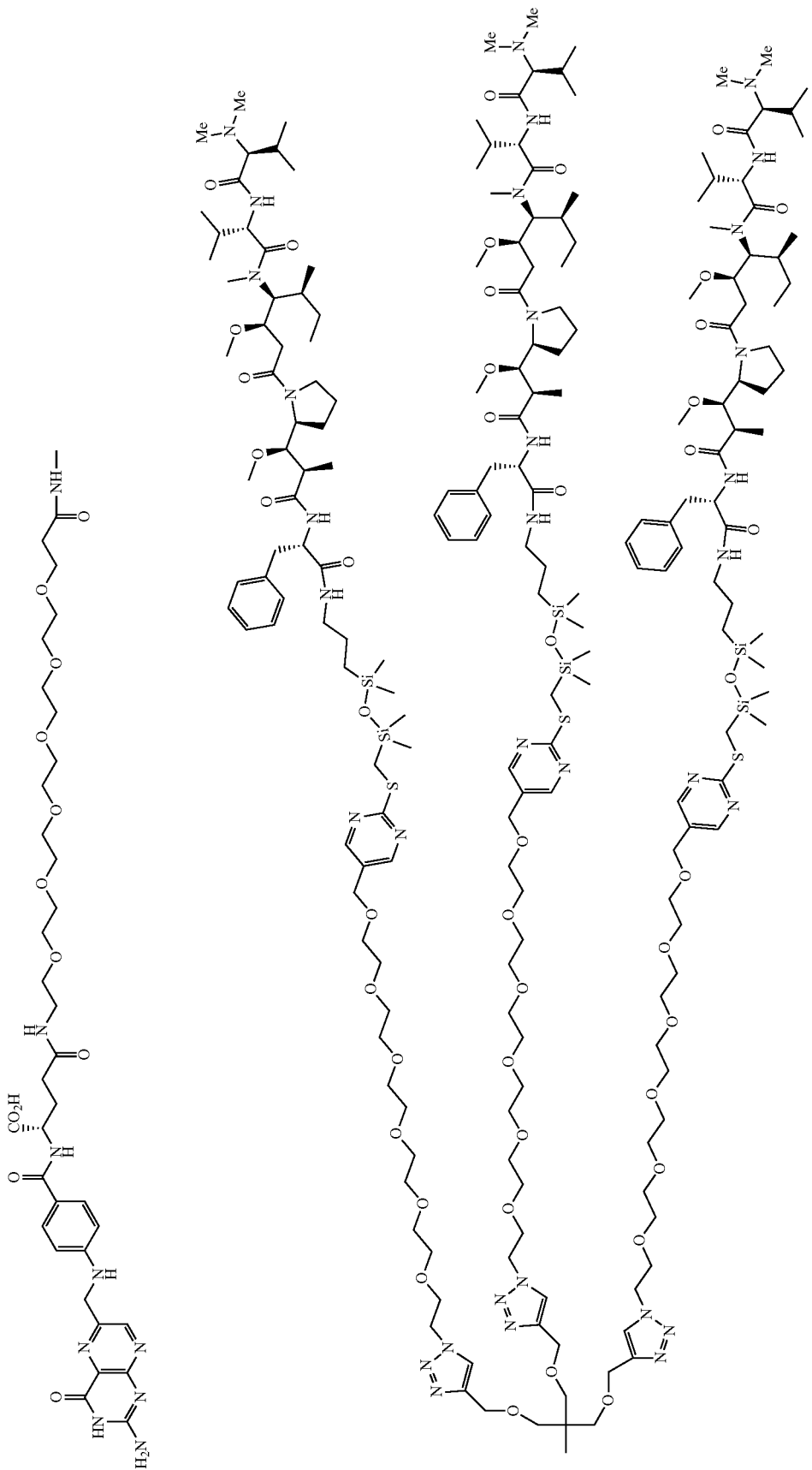

Example 40 was synthesized according to the procedure described for Example 35 employing the intermediates shown in the Scheme below:

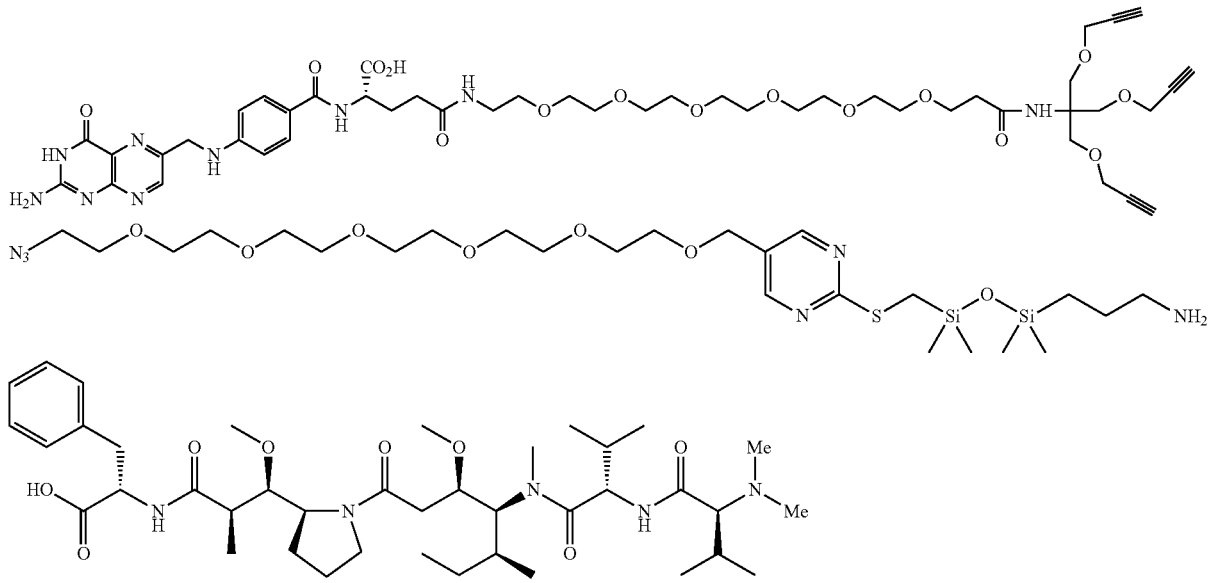

Example 41: Synthesis of Conjugates

Conjugates are synthesized as exemplified in Schemes 1 and 2, below. Scheme 1 depicts a route where first a targeting moiety, folic acid, is activated by reaction with DCC and N-hydroxysuccinimide and then reacted with a protected siloxane or silylether core to form a targeting moiety-core conjugate.

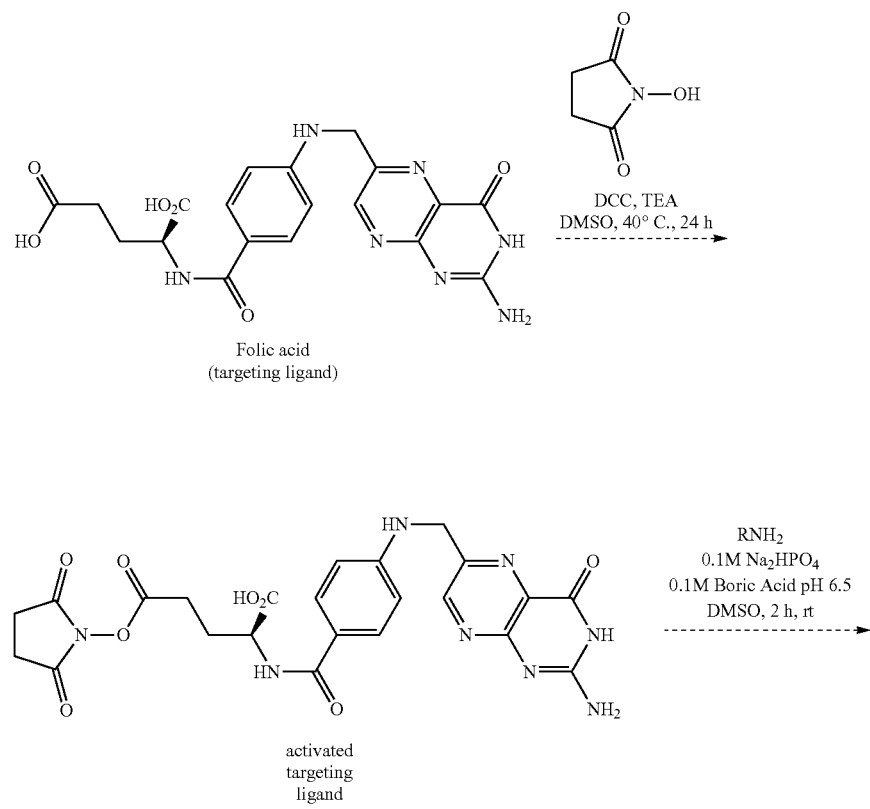

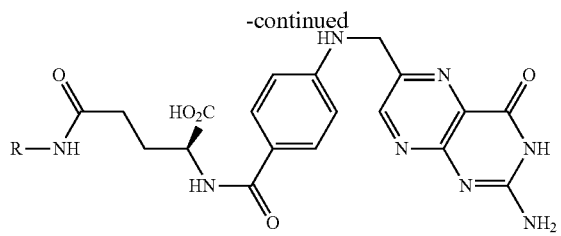
targeting ligand-core conjugate
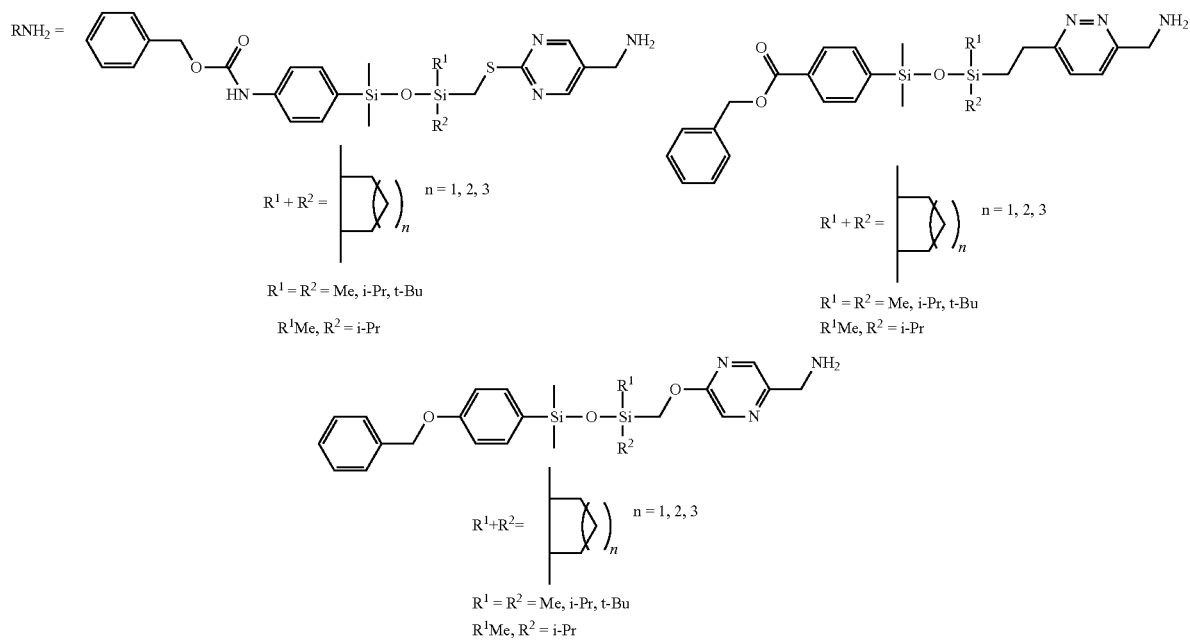
Scheme 2, below, shows an alternate route where a protected targeting moiety-core conjugate is reacted with an activated payload to form a targeting moiety-core-payload conjugate.
Scheme 2.
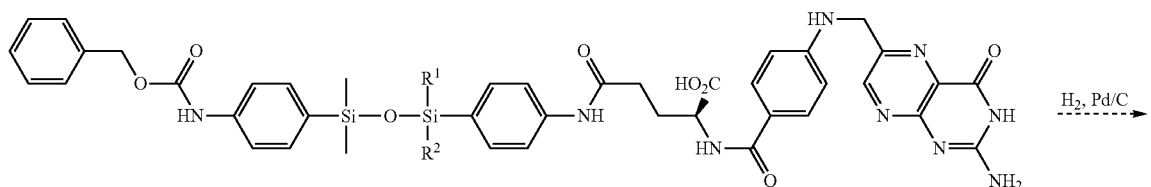
protected targeting ligand-core conjugate -continued
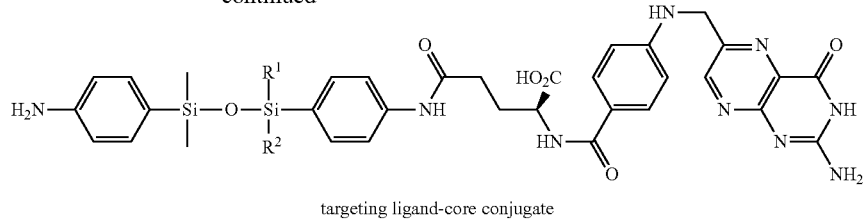
targeting ligand-core conjugate
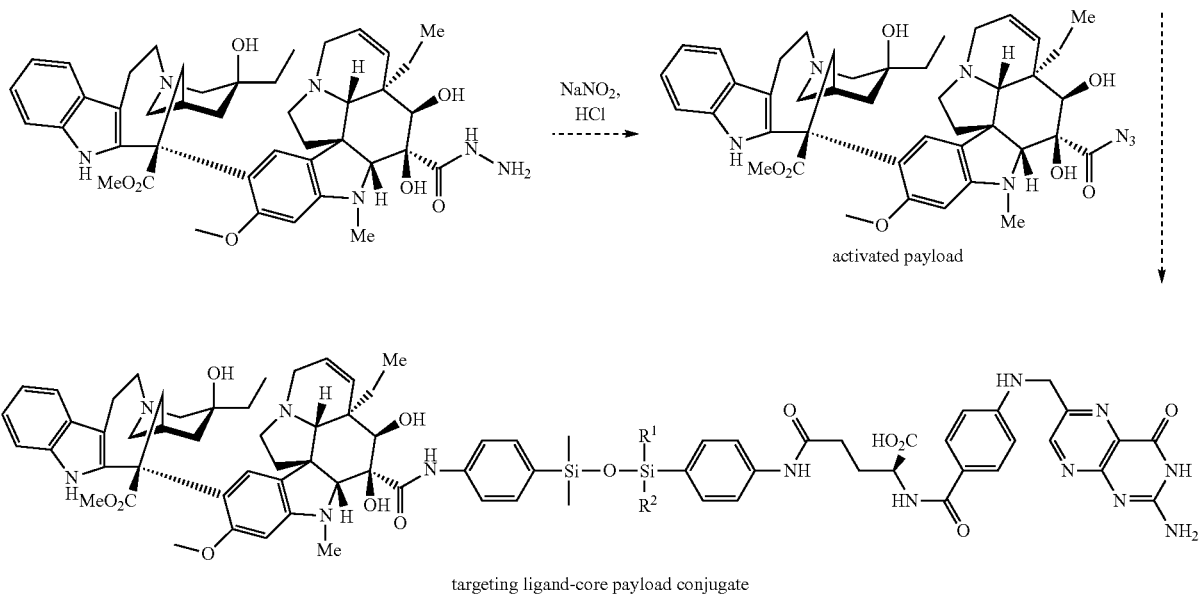
targeting ligand-core payload conjugate
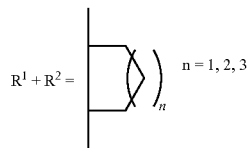
$R^1 = R^2 =$ Me, i-Pr, t-Bu
$R^1$Me, $R^2 =$ i-Pr
Example 42: Vinblastine-Folic Acid Conjugates
Siloxane conjugates with a vinblastine payload and a folic acid targeting moiety are synthesized following a route as described in Example 41.
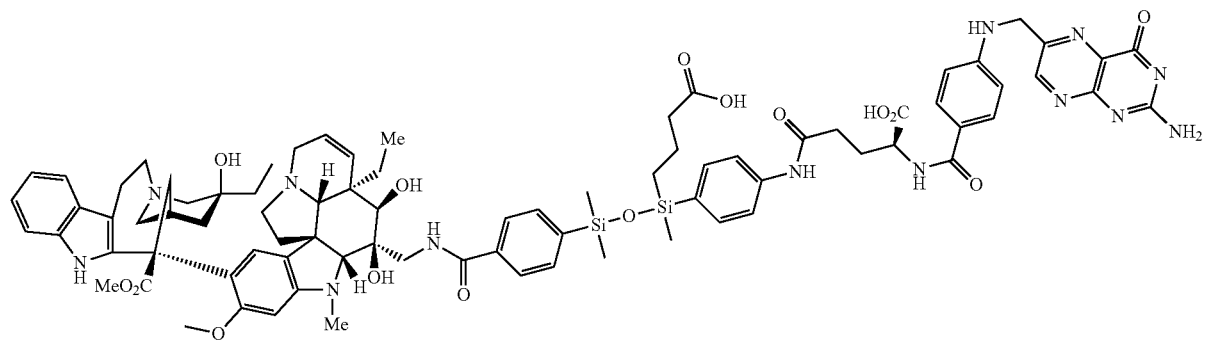

295 296
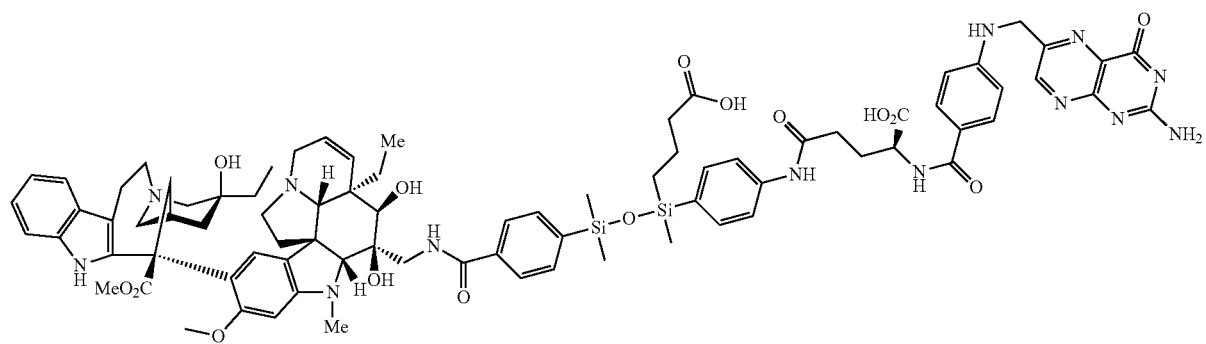
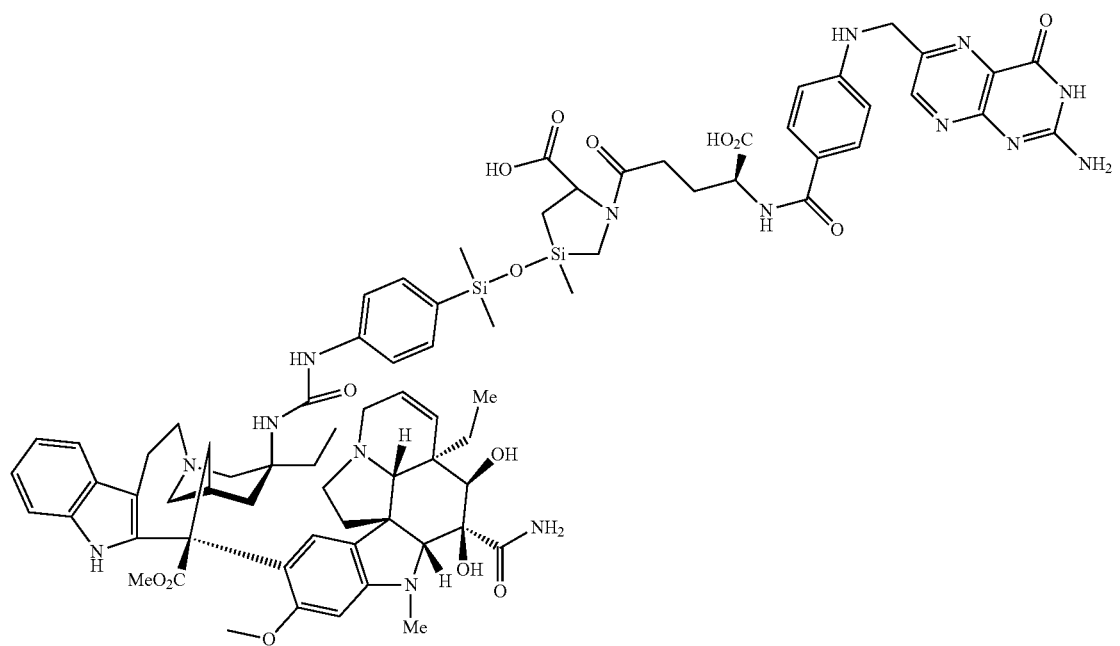
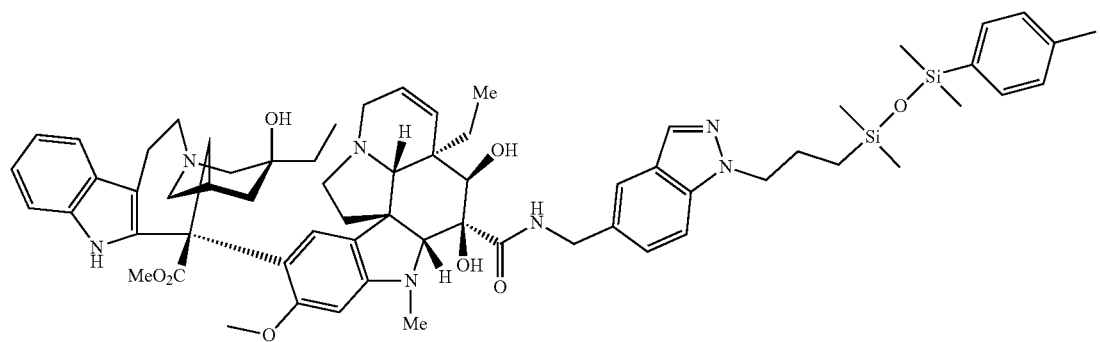

-continued

AA = amino acids (natural, unatural)

Example 43: Vinblastine-Arginylglycylaspartic Acid (Vinblastine-RGD) Conjugate Siloxane conjugates with vinblastine payload and a RGD targeting moiety are synthesized following a route as described in Example 41.

cyclo-diketopiperazine-RGD-disiloxane vinblastine construct

Example 44: Vinblastine-2-[3-(1,3-dicarboxypropyl) ureido] pentanedioic acid (Vinblastine-DUPA) Conjugates Siloxane conjugates with vinblastine payload and DUPA targeting moiety are synthesized following a route as described in Example 41.

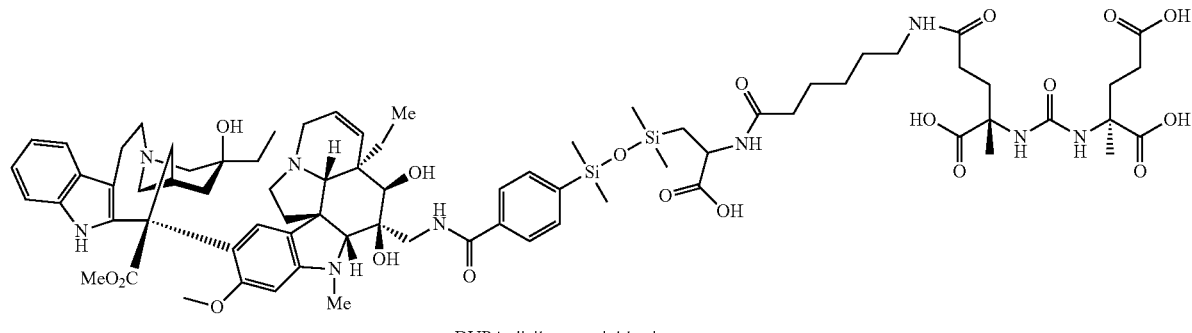

DUPA-disiloxane vinblastine construct

Example 45: Camptothecin-Folic Acid Conjugates

Siloxane conjugates with camptothecin/SN38 payload and folic acid-targeting moiety are synthesized following a route as described in Example 41.

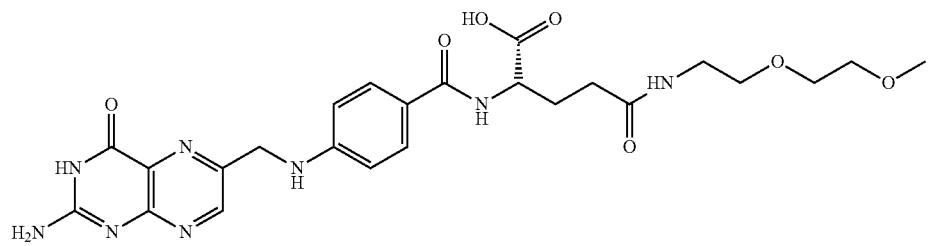

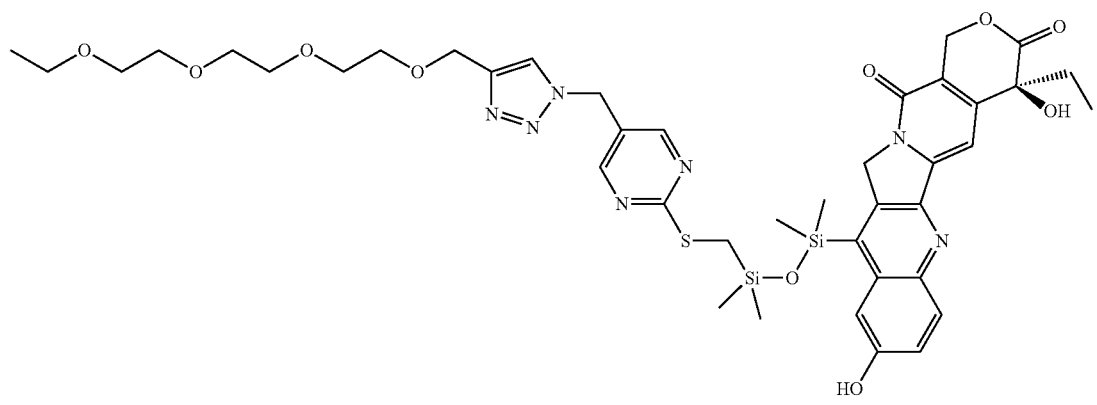

FA-PEG-SiLinker-SilaCamptothecin

-continued
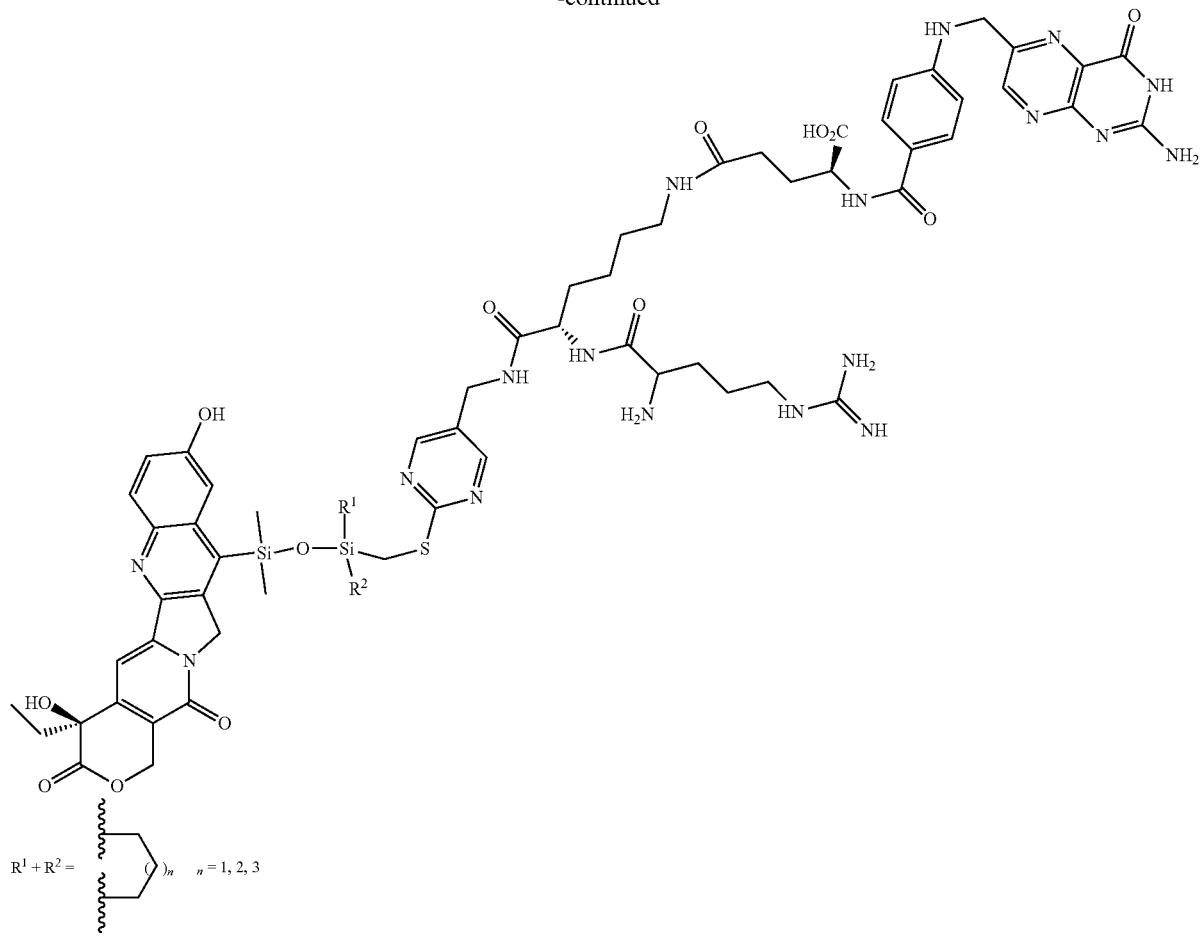
$R^1, R^{2'}$ = independently selected: Me, i-Pr, t-Bu, (CH2)n-carboxylic acid, (CH2)n-amino acid, (CH2)n-amine (optionally further substituted)
Example 46: Platinum(II)-Folic Acid and Platinum(IV)-DUPA Acid Conjugates
Siloxane conjugates with platinum (II) and platinum (IV) payload and DUPA targeting moieties are synthesized following a route as described in Example 41.

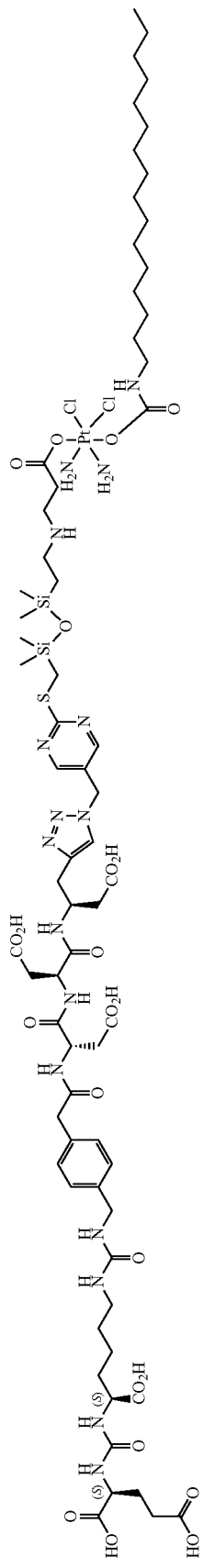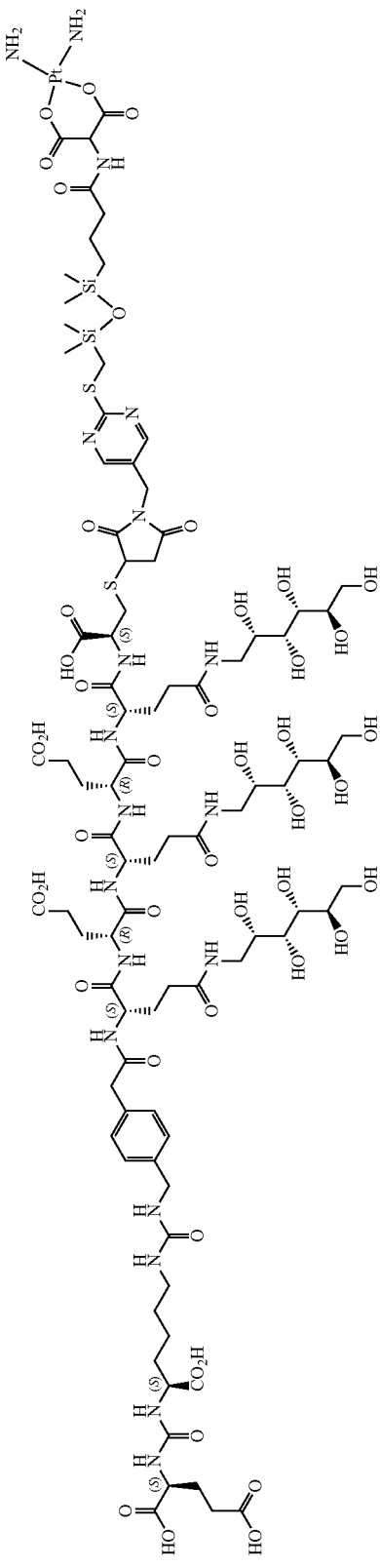

-continued
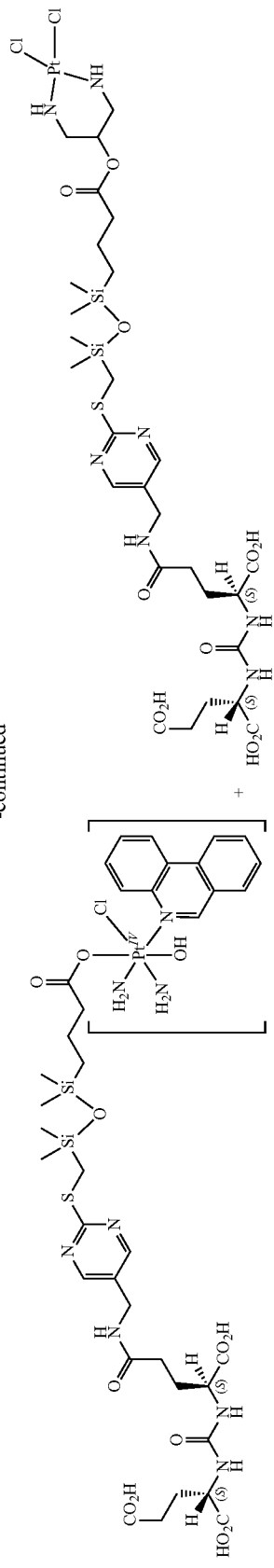
+
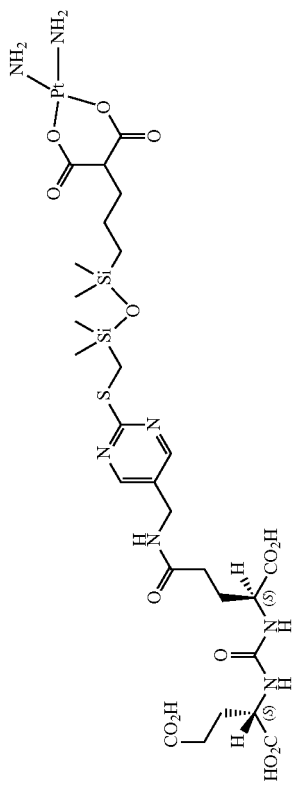

Example 47: Fluorophore/Quencher-Folic Acid Conjugates
Siloxane conjugates with a fluorophor/quencher payload and folic acid-targeting moieties are synthesized following a route as described in Example 41.
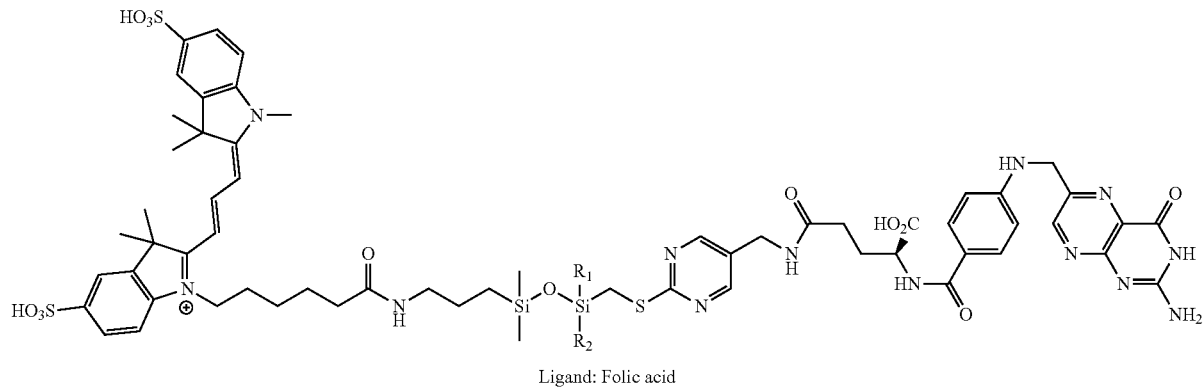
Ligand: Folic acid
$R^1, R^{2'}$ = independently selected: Me, i-Pr, t-Bu, (CH2)n-carboxylic acid, (CH2)n-amino acid, (CH2)n-amine (optionally further substituted)
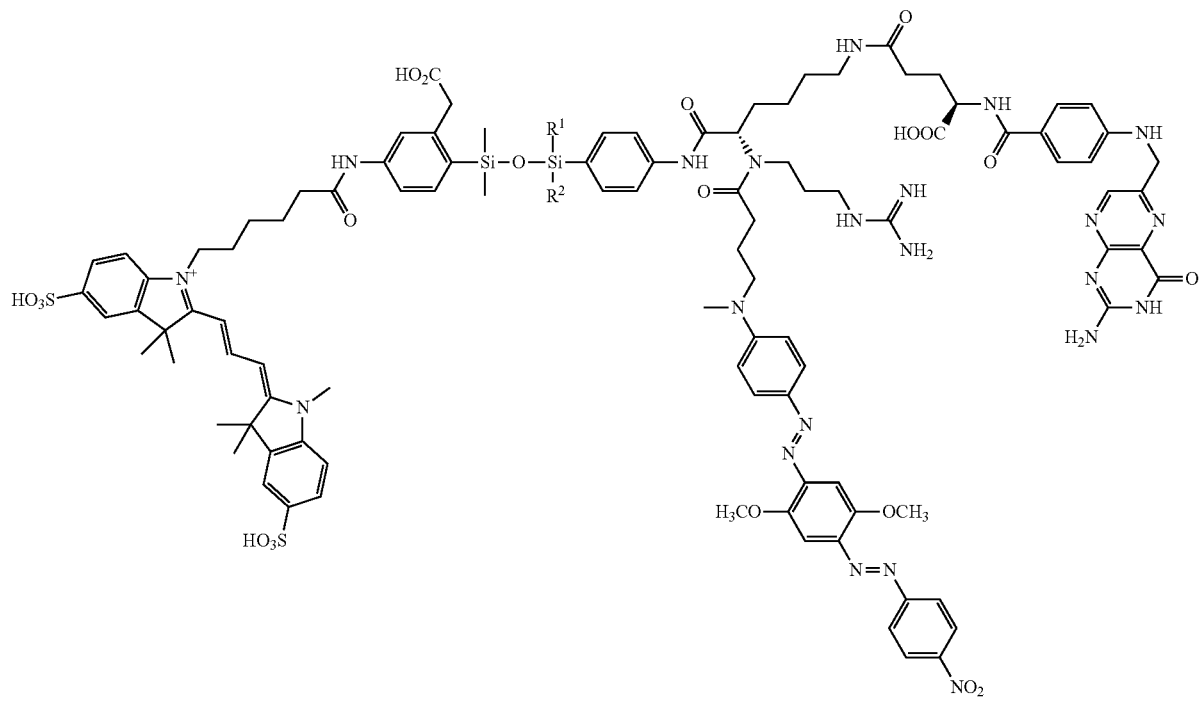

-continued
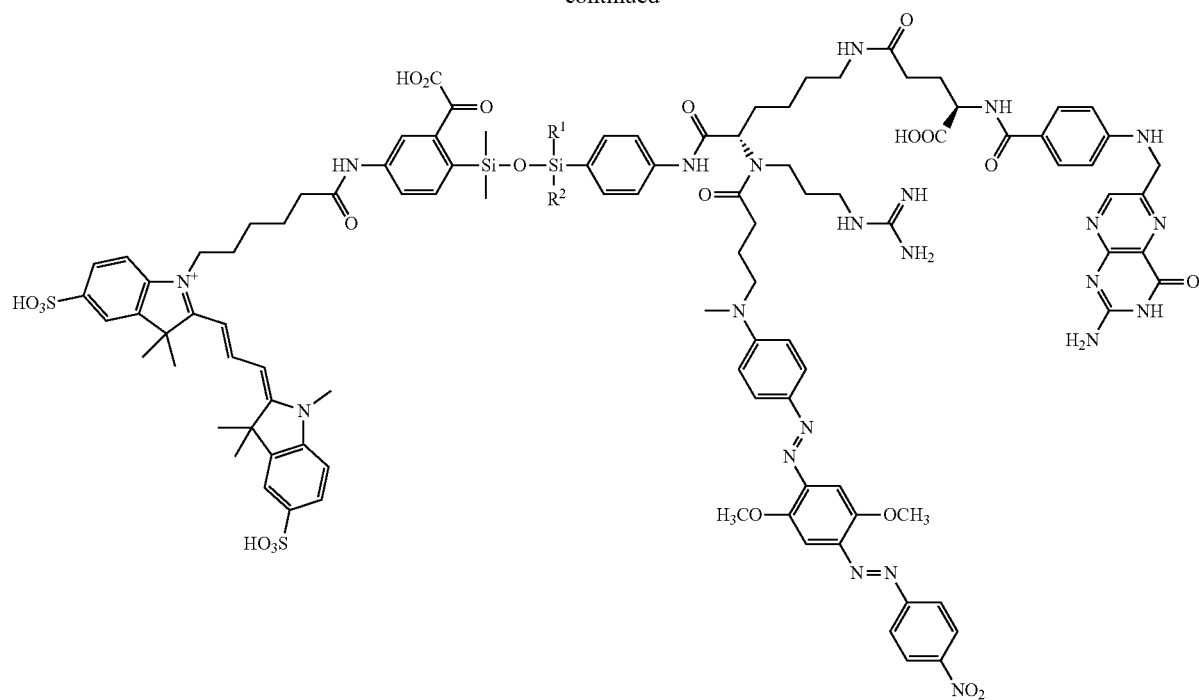
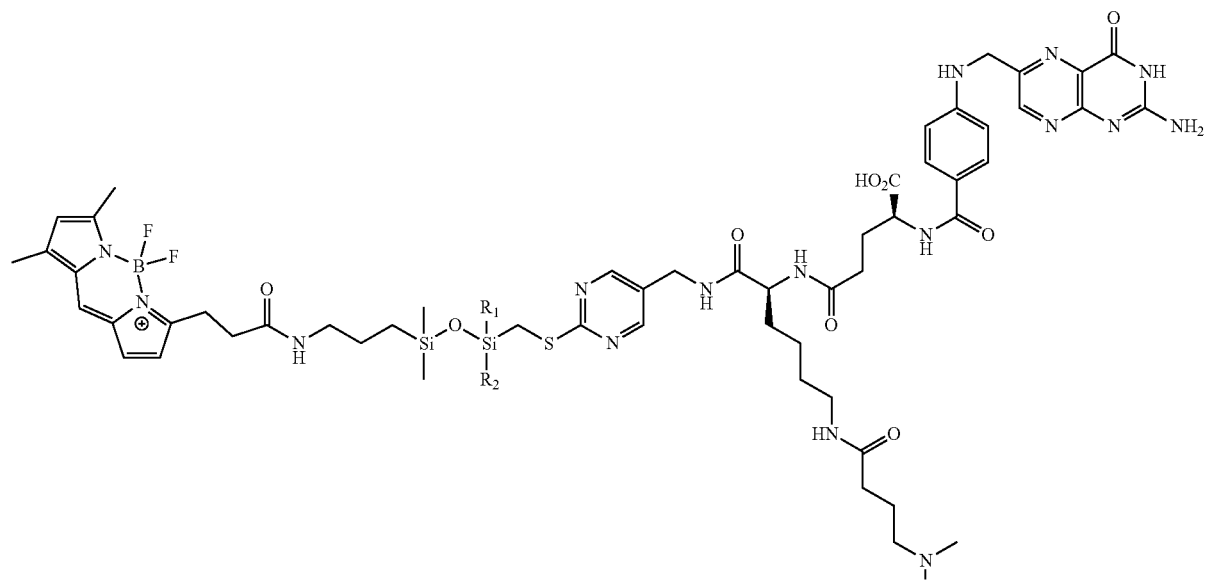

311
312
-continued
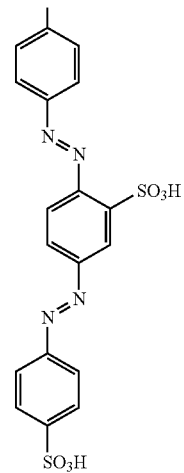
BODIPY/BHQ-10
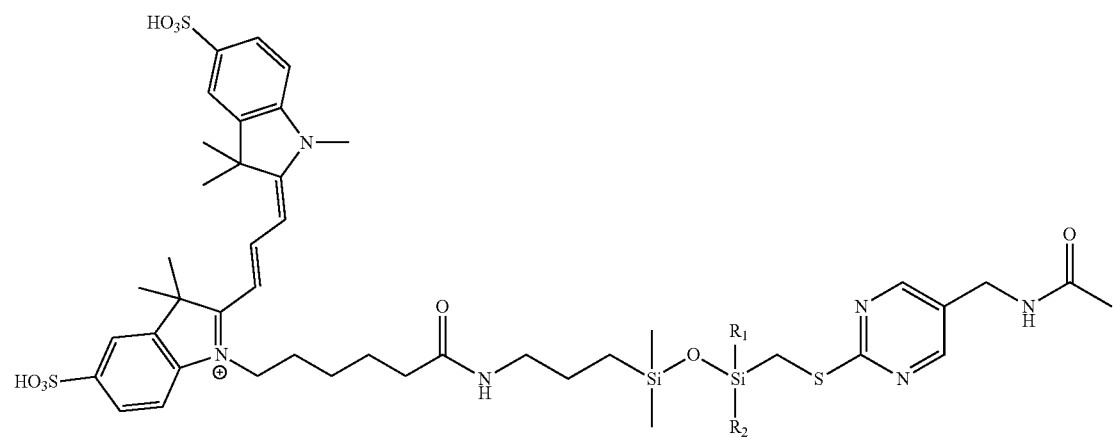

-continued
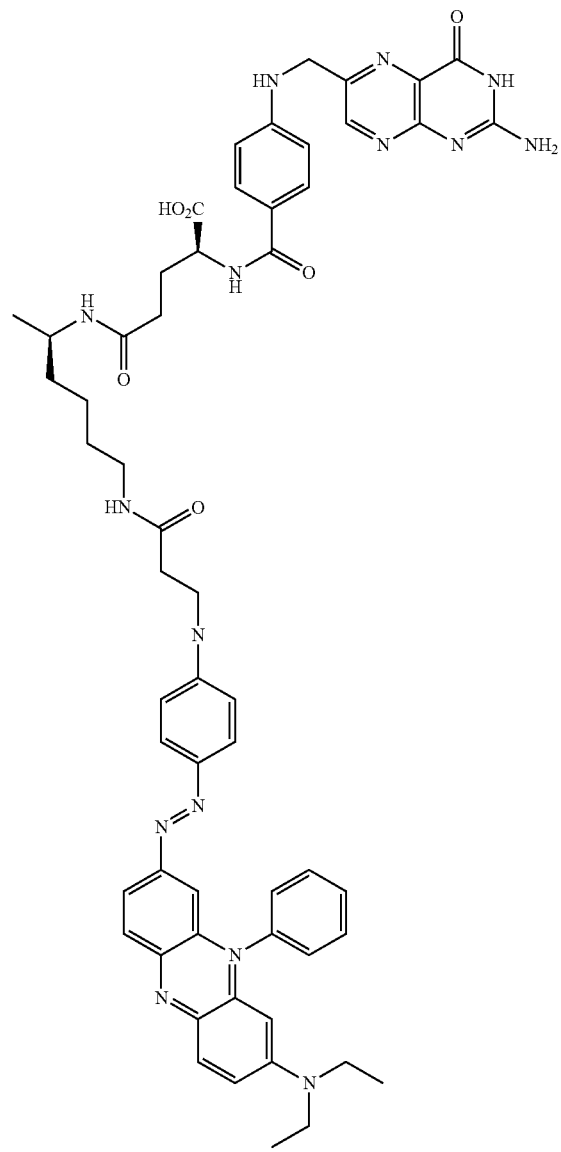
CY5/BHQ3
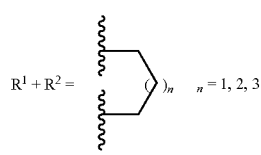 $n = 1, 2, 3$
$R^1, R^{2'}$ = independently selected: Me, i-Pr, t-Bu, (CH2)n-carboxylic acid, (CH2)n-amino acid, (CH2)n-amine (optionally further substituted)

Example 48: Fluorescein-Folic Acid Conjugates

Siloxane conjugates with a fluorescein payload and folic acid targeting moieties are synthesized following a route as described in Example 41.

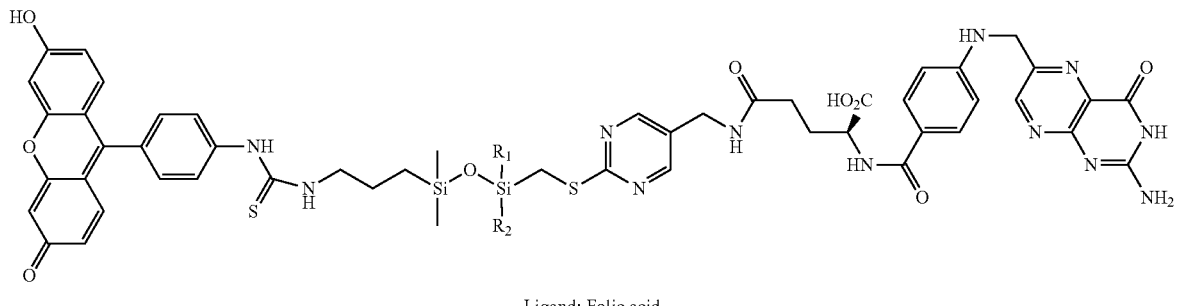

Ligand: Folic acid

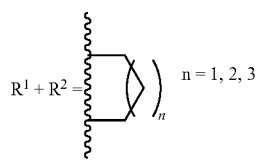  n = 1, 2, 3

$R^1$, $R^2$, = independently selected: Me, i-Pr, t-Bu, $(CH_2)$n-carboxylic acid, $(CH_2)$n-amino acid, $(CH_2)$n-amine (optionally further substituted)

Example 49: Silyldiether and Silylmonoether Conjugates

Silyldiether and silylmonoether conjugates with a payload and a targeting moiety are synthesized following a route as described in Example 41.

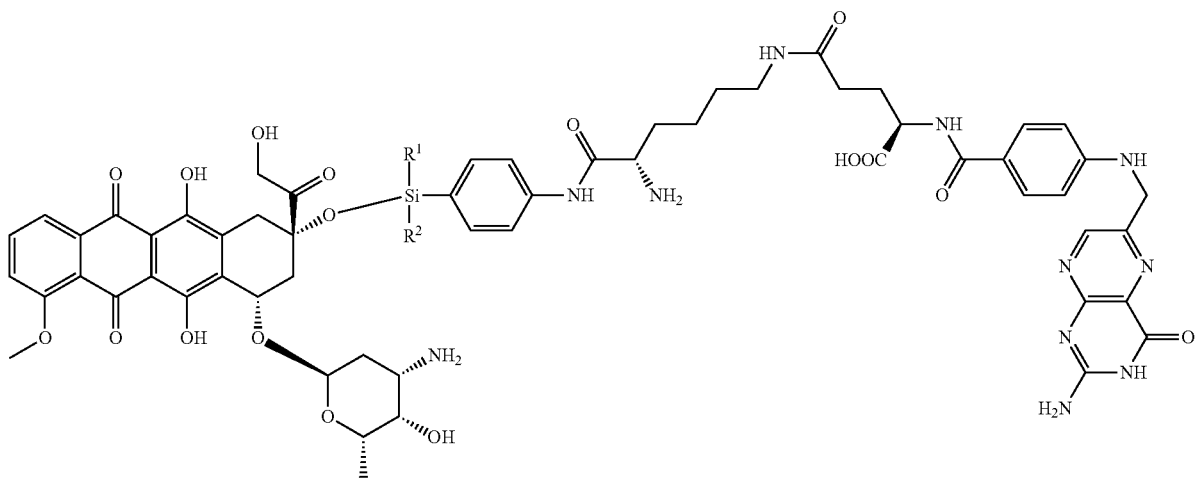

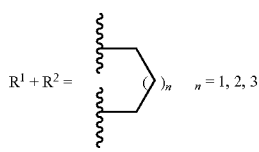  n = 1, 2, 3

$R^1$, $R^2$, = independently selected: Me, i-Pr, t-Bu, $(CH2)$n-carboxylic acid, $(CH2)$n-amino acid, $(CH2)$n-amine (optionally further substituted)

317
318
-continued
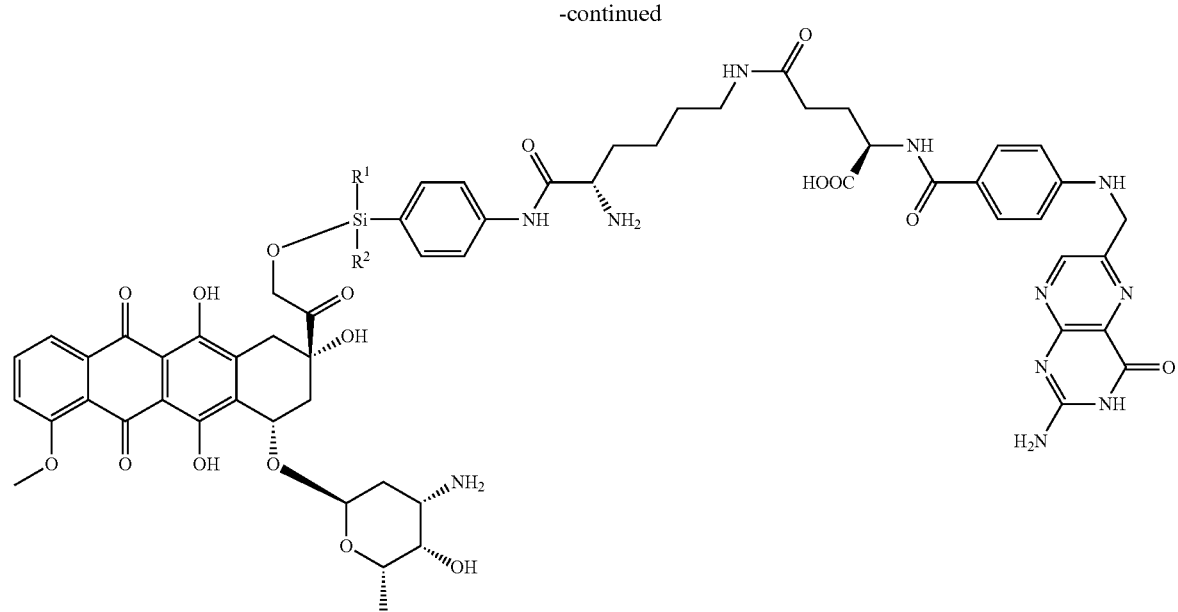
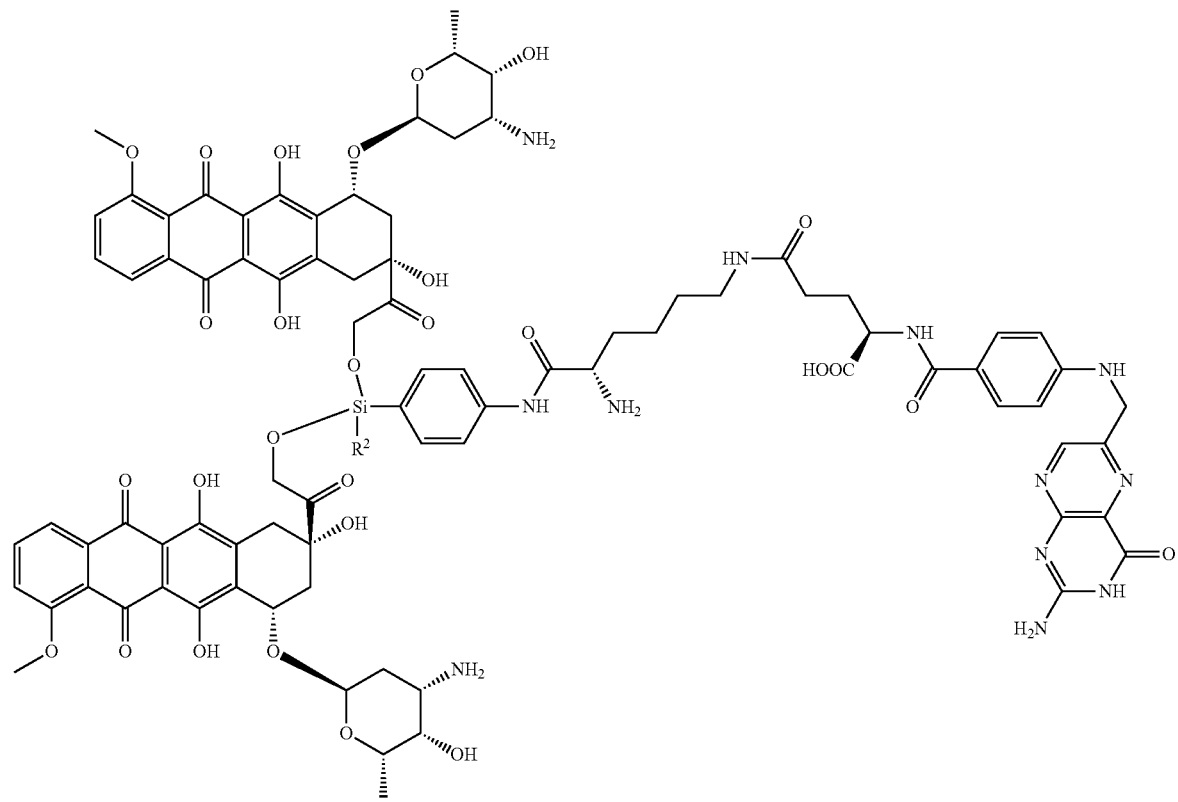

Example 50: Paclitaxel-Folic Acid Conjugates
Siloxane conjugates with a paclitaxel payload and folic acid targeting moiety are synthesized following a route as described in Example 41.
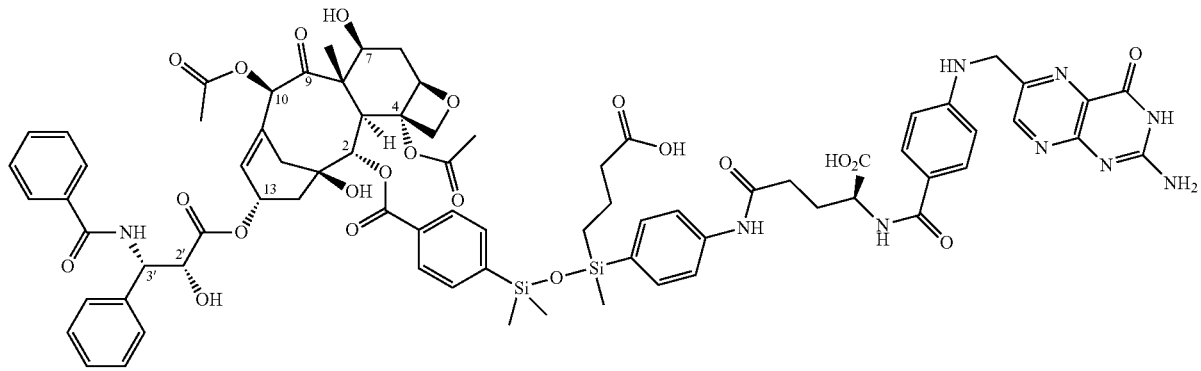
(attachment at paclitaxel C2 position)
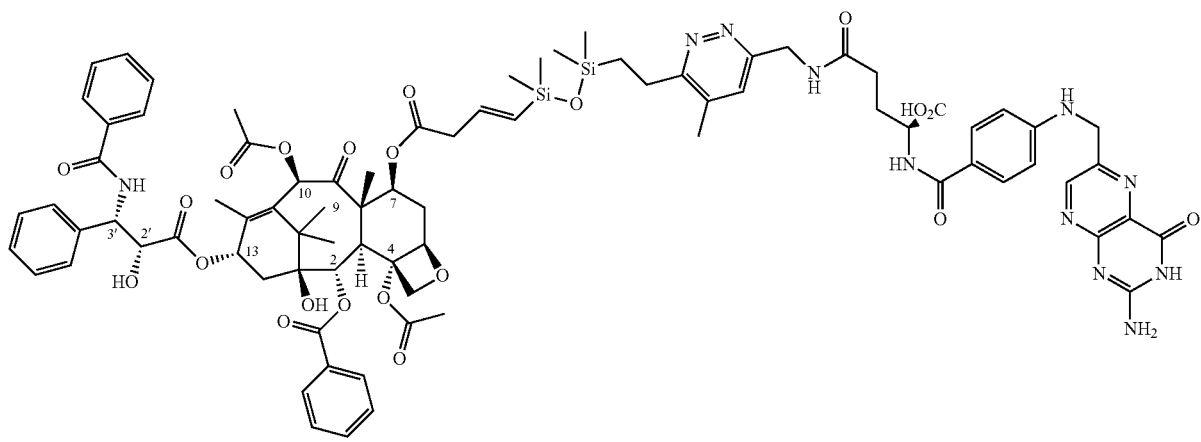
(attachment at paclitaxel C7 position)
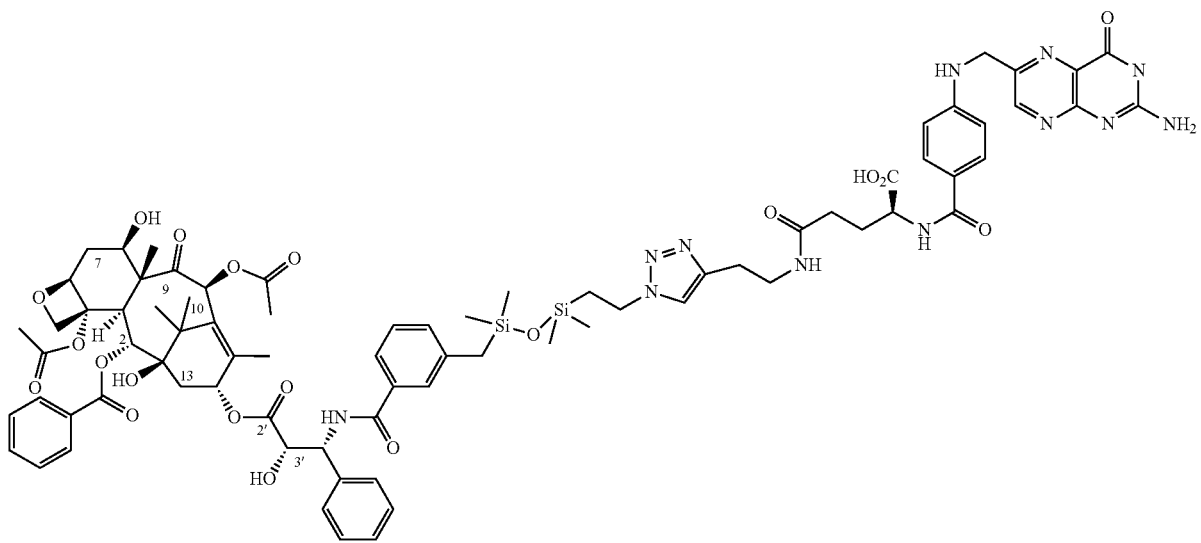
(attachment at paclitaxel C3' position)

-continued
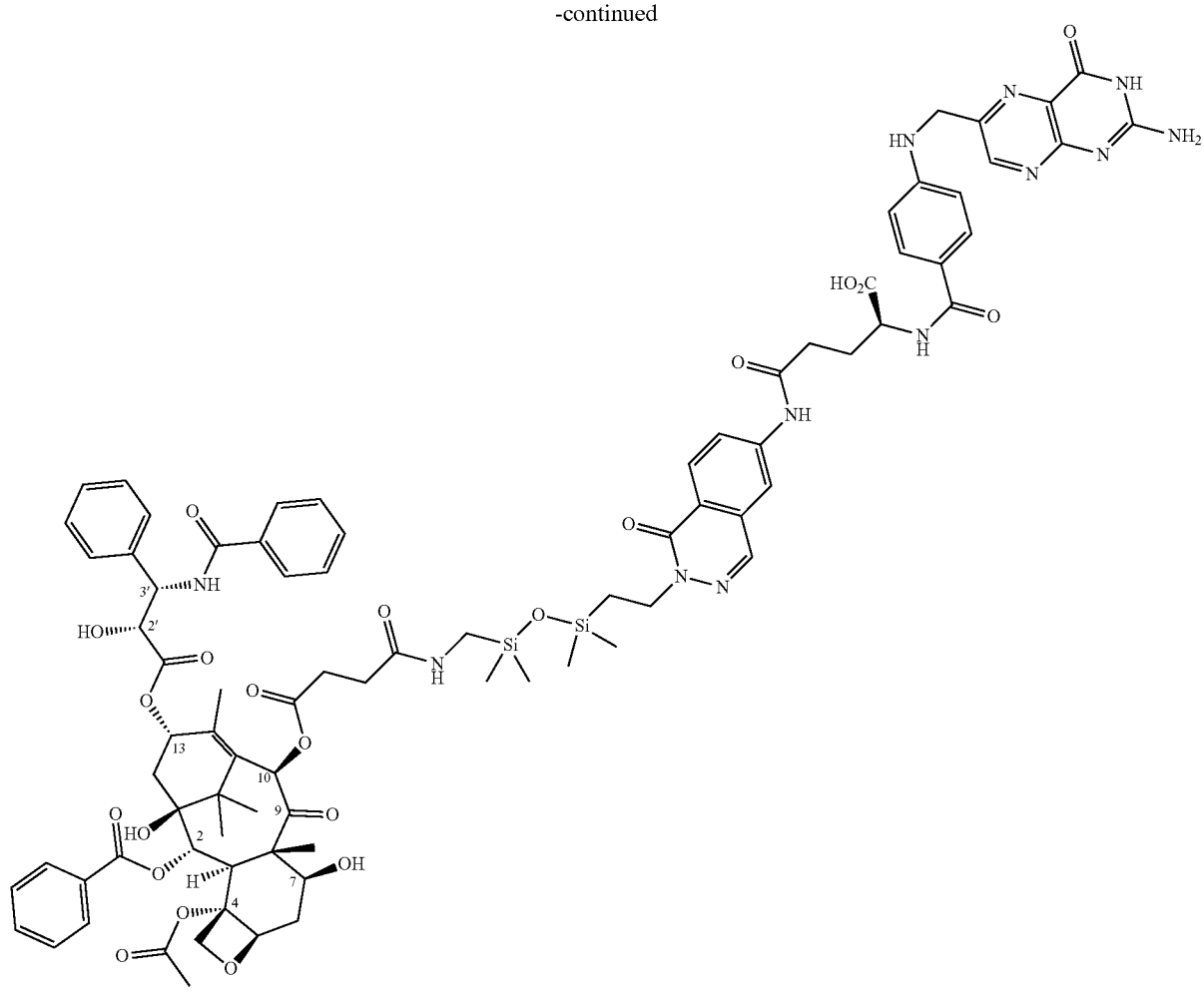
(attachment at paclitaxel C10 position)
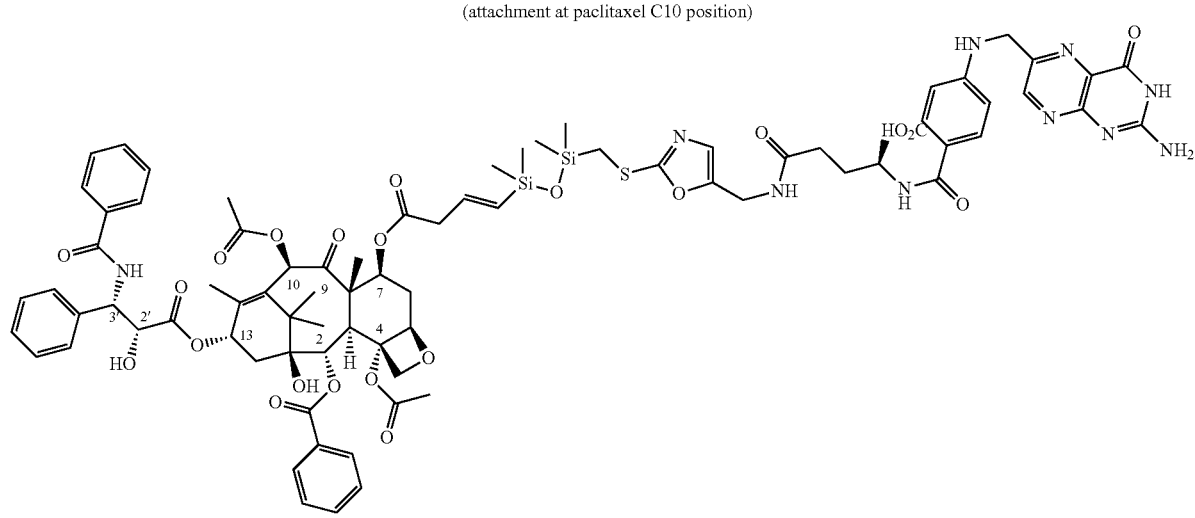
(C10/C7 hybrid with attachment at paclitaxel C7 position and modification at paclitaxel C10 position).
Example 51

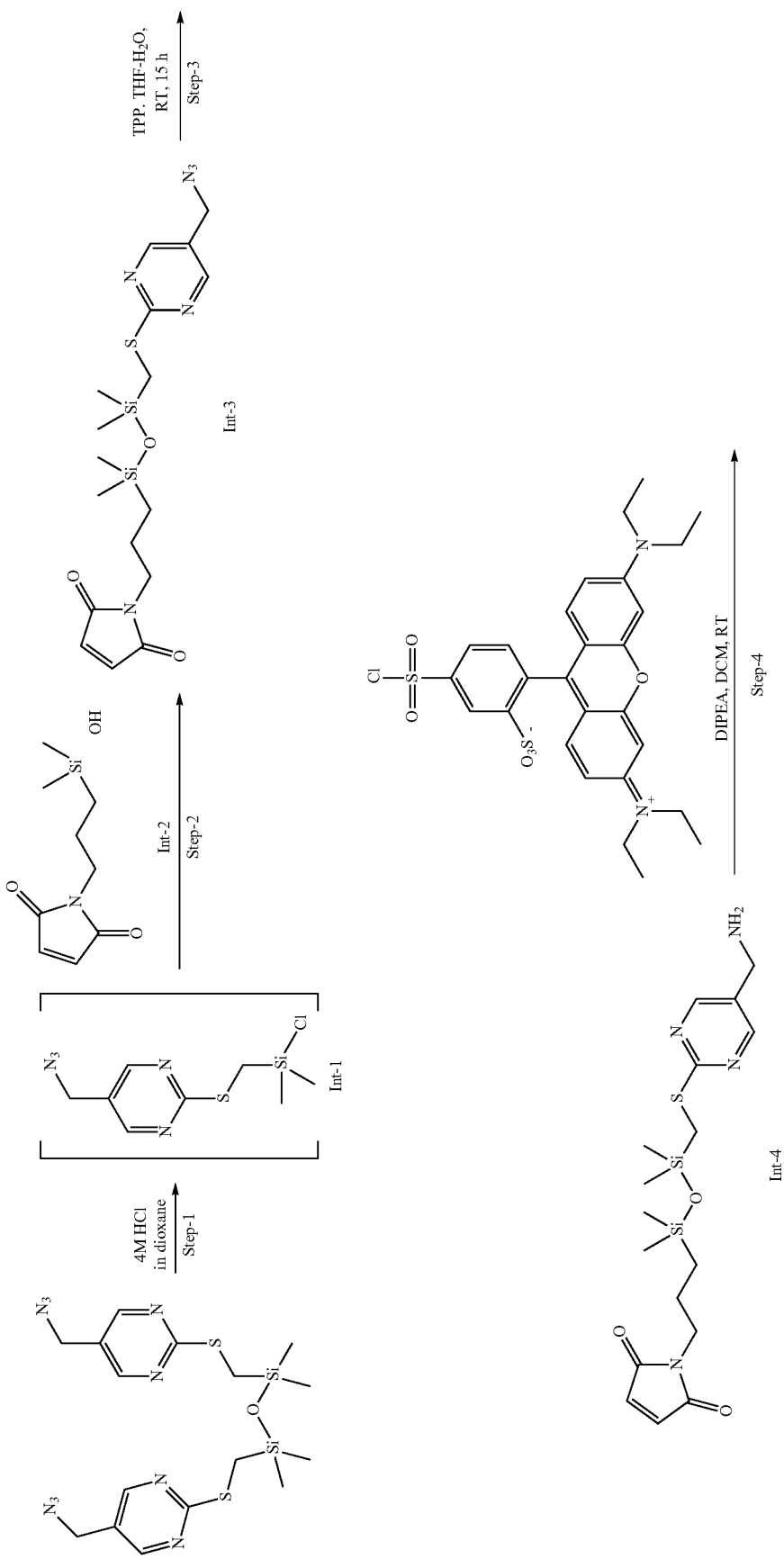

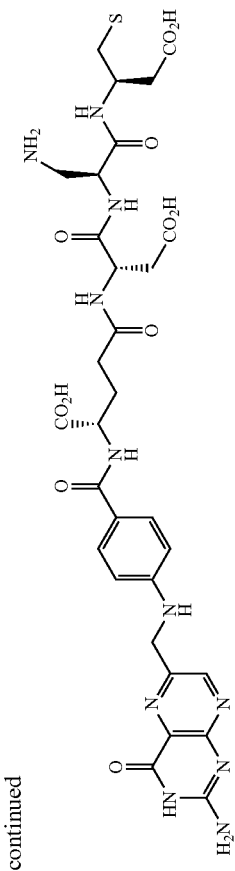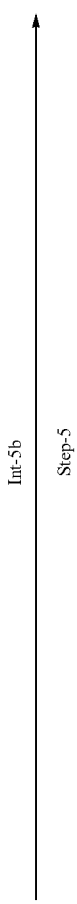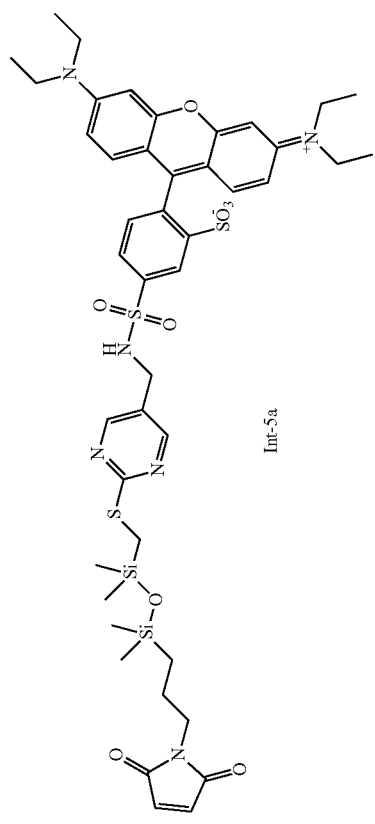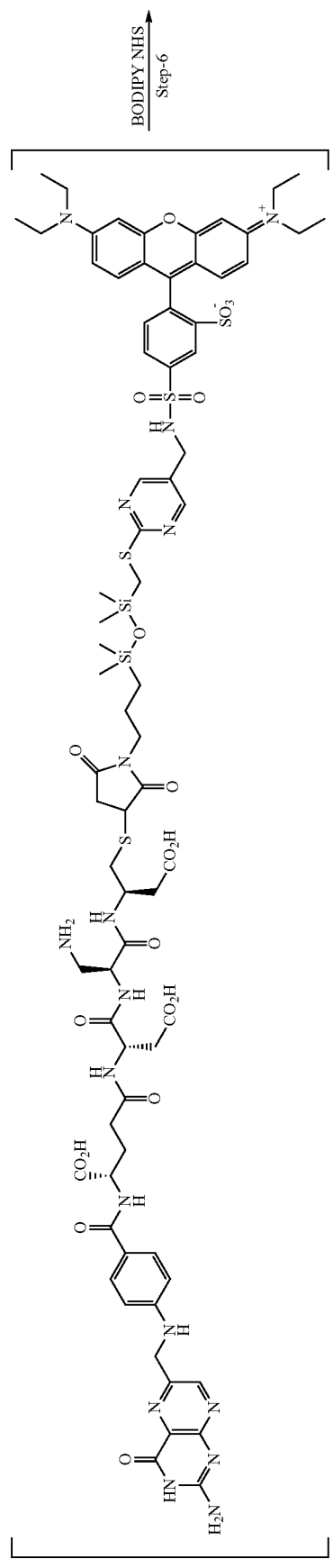

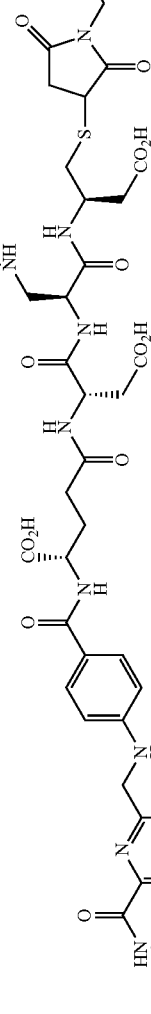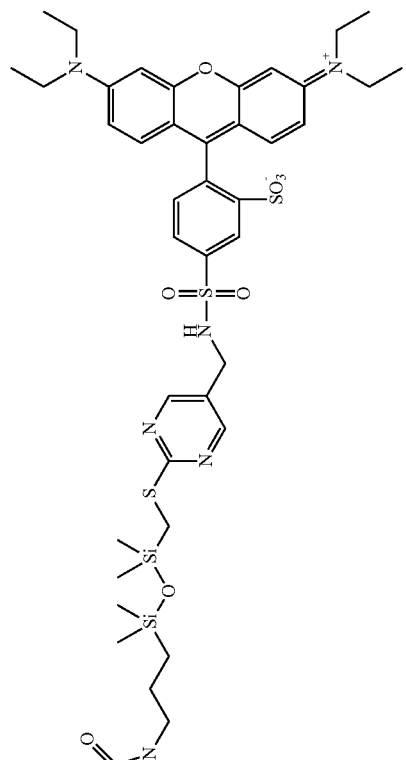

329

5-(N-((2-(3-(3-(3-(((3S,8S,11S,14R)-1-(4(((2-amino-4-oxo-3,4-dihydropteridin-6- yl)methyl)amino)phenyl)-(-3,14-dicarhoxy-8-(carboxymethyl)-11-((3-(5, 5-difluoro-7,9- dimethyl-5H-4l4,5l4-dipyrrolo[1,2-c: 2',1'-*f* ][1,3,2]diazaborinin-3- yl)propanamido) methyl)-1.6,9,12-tetraoxo-2,7,10,13-tetraazapentadecan-15-yl)thio)-2,5- dioxopyrrolidin-1-yl)propyl)-l,l,3,3-tetramethyldisiloxanyl)melhyl)(thio)pyrimidin-5- yl)methyl)sulfamoyl)-2-(6-(diethylamino)-3(diethyliminio)-3H-xanthen-9-yl)benzenesulfonate:

330

DMF was added Bodipy NHS ester stirred at room temperature for 1 h. The TLC showed consumption of starting material. The reaction mixture was concentrated in vacuo resulting in the crude intermediate and purified by triturating in acetonitrile to afford 35 mg (crude) of the title compound as violet solid. $^1$H NMR (400 MHz, DMSO-d$_6$) δ=12.98 (s, 1H), 12.45 (s, 1H), 12.28 (s, 1H), 11.38 (s, 1H), 8.62 (br. s, 1H), 8.55 (s, 1H), 8.44 (br. s, 2H), 8.26 (s, 2H), 8.20 (d, J=6.36 Hz, 1H), 8.16 (d, J=6.36 Hz, 1H), 8.01 (s, 2H), 7.85 (d, J=7.83 Hz, 2H), 7.60-7.68 (m, 4H), 7.40 (d, J=7.34 Hz, 1H), 6.85-7.06 (m, 8H), 6.61 (d, J=7.34 Hz, 2H), 6.28 (d,

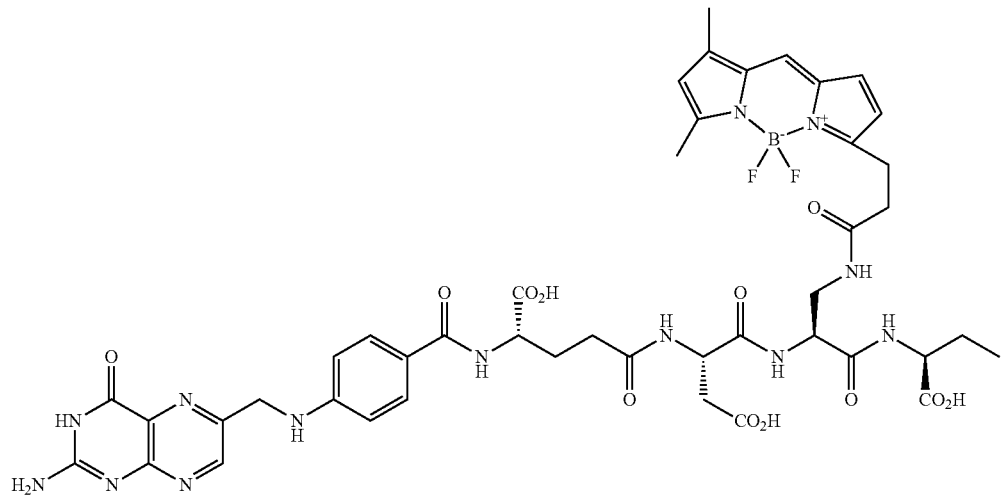

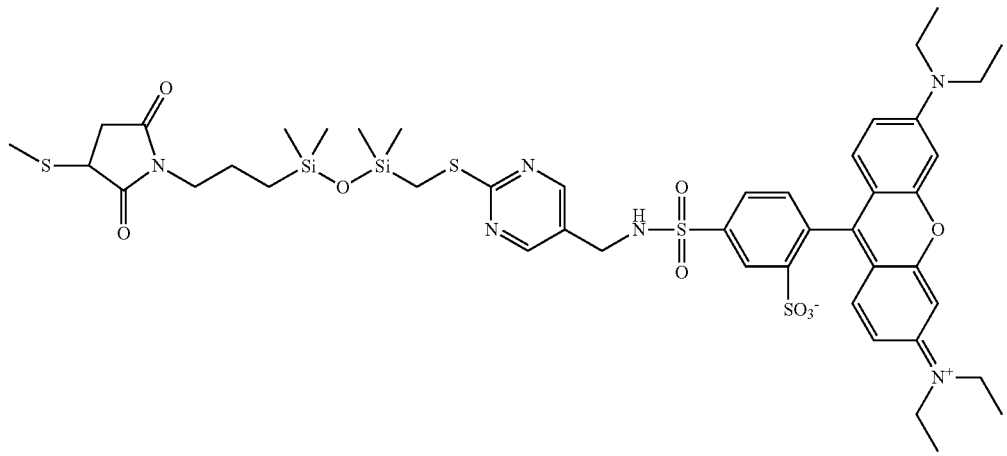

A solution of 5-(N-((2-(((3-(3-(3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)propyl)-1,1,3,3-tetramethyldisiloxanyl)methyl)thio)pyrimidin-5-yl)methyl)sulfamoyl)-2-(6-(diethylamino)-3-(diethyliminio)-3H-xanthen-9-yl)benzenesulfonate (17.62 mg, 10.30 mmol) in J=19.56 Hz, 2H), 4.45 (br. s, 4H), 4.25-4.38 (m, 4H), 4.13 (br. s, 2H), 3.98 (d, J=16.63 Hz, 2H), 3.55-3.70 (m, 8H), 3.02-3.07 (m, 2H), 2.84-2.89 (m, 2H), 2.65 (br. s, 3H), 2.32 (d, J=10.27 Hz, 4H), 2.22 (br. s, 6H), 1.82-2.11 (m, 8H), 1.42-1.46 (m, 2H), 1.12-1.27 (m, 12H), 0.10 (br. s, 6H), 0.03 (br. s, 6H); MS (ES$^+$): =993.40 [M+H]$^+$; LCMS: t$_R$=3.07 min.

5-(N-((2-(((3-(3-(3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)propyl)-1,1,3,3-tetramethyldisiloxanyl)methyl)thio)pyrimidin-5-yl)methyl)sulfamoyl)-2-(6-(diethylamino)-3-(diethyliminio)-3H-xanthen-9-yl)benzenesulfonate (6)

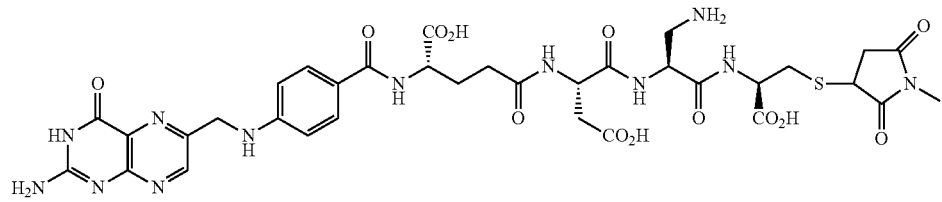

To a solution of 2-(6-(diethylamino)-3-(diethyliminio)-3H-xanthen-9-yl)-5-(N-((2-(((3-(3-(2,5-dioxo-2,5-dihydro-1H-pyrrol-1-yl)propyl)-1,1,3,3-tetramethyl disiloxanyl) methyl)thio) pyrimidin-5-yl)methyl)sulfamoyl)benzenesulfonate (10 mg, 0.01 mmol) and N5-((S)-1-(((S)-3-amino-1-(((R)-1-carboxy-2-(11-sulfanyl)ethyl)amino)-1-oxopropan-2-yl)amino)-3-carboxy-1-oxopropan-2-yl)-N2-(4-(((2-amino-4-oxo-3,4-dihydropteridin-6-yl)methyl)amino)benzoyl)-L-glutamine (7.7 mg, 0.01 mmol) in DMF (1 mL) was added DIPEA (0.01 mL, 0.04 mmol) at room temperature and stirred for 1 h. The reaction was monitored by LCMS (showed 80% desired product 6). The reaction mixture was used as such in the next step without workup. MS (ES$^+$): m/z=857.15 [M/2+H]$^+$; LCMS: t$_R$=2.47 min.

2-(6-(Diethylamino)-3-(diethyliminio)-3H-xanthen-9-yl)-5-(N-((2-(((3-(3-(2,5-dioxo-2,5-dihydro-1H-pyrrol-1-yl)propyl)-1,1,3,3-tetramethyldisiloxanyl)methyl)thio)pyrimidin-5-yl)methyl)sulfamoyl)benzenesulfonate (5a)

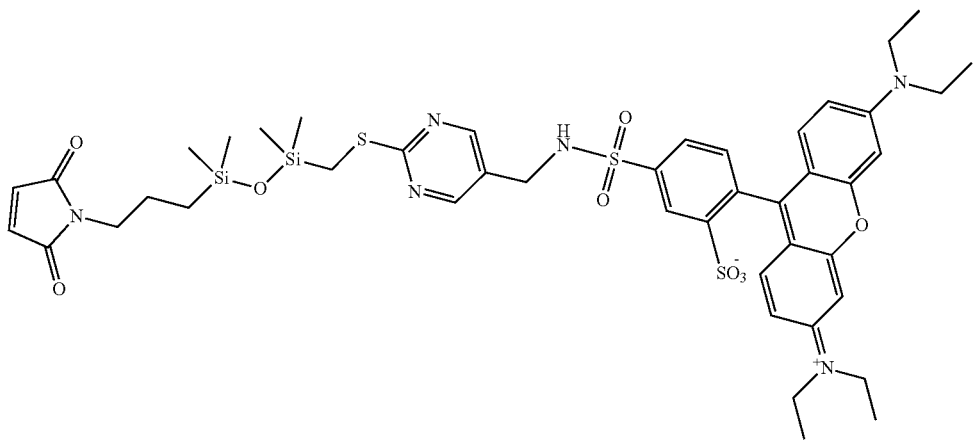

A solution of 1-(3-(3-(((5-(aminomethyl)pyrimidin-2-yl)thio)methyl)-1,1,3,3-tetramethyldisiloxanyl)propyl)-1H-pyrrole-2,5-dione (300 mg, 0.707 mmol) in THF (10 mL) was added DIPEA (0.24 mL, 1.41 mmol) and 5-(chlorosulfonyl)-2-(6-(diethylamino)-3-(diethyliminio)-3H-xanthen-9-yl)benzenesulfonate (408 mg, 0.707 mmol) at room temperature and stirred for 1 h. The completion of reaction was monitored by TLC. The reaction mixture was concentrated in vacuo resulting in the crude compound which was purified column chromatography on silica gel eluting with 0-10% methanol in DCM to afford 150 mg, 22% yield of the title compound as dark pink solid. MS (ES+): m/z=965.20 [M+H]+, 483.40 [M/2+H]+; LCMS: $t_R$=3.47 min.

1-(3-(3-(((5-(aminomethyl)pyrimidin-2-yl)thio)methyl)-1,1,3,3-tetramethyl disiloxanyl) propyl)-1H-pyrrole-2,5-dione (4)

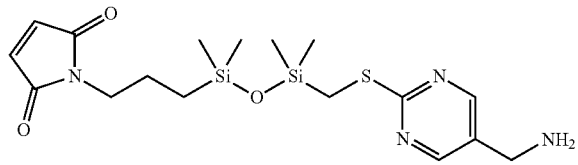 [SMILES: C[Si](C)(CCCN1C(=O)C=CC1=O)O[Si](C)(C)CSc1ncc(CN)cn1]

A solution of 1-(3-(3-(((5-(azidomethyl)pyrimidin-2-yl)thio)methyl)-1,1,3,3-tetramethyldisiloxanyl)propyl)-1H-pyrrole-2,5-dione (750 mg, 1.66 mmol) in THF: H$_2$O (2.25: 0.75 mL) was added TPP (1.3 g, 4.99 mmol) and stirred at room temperature for 10 h. The completion of reaction was monitored by TLC. The reaction mixture was concentrated in vacuo resulting in the crude compound which was purified by column chromatography on silica gel eluting with 0-10% methanol in DCM to afford 300 mg, 42% yield of the title compound as colorless oil. MS (ES+): =424.67 [M+H]+

1-(3-(3-(((5-(azidomethyl)pyrimidin-2-yl)thio)methyl)-1,1,3,3-tetramethyldisiloxanyl) propyl)-1H-pyrrole-2,5-dione (3)

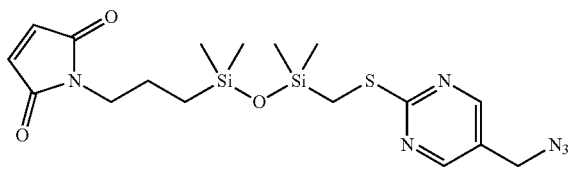 [SMILES: C[Si](C)(CCCN1C(=O)C=CC1=O)O[Si](C)(C)CSc1ncc(CN=[N+]=[N-])cn1]

A solution of 1,3-bis(((5-(azidomethyl)pyrimidin-2-yl)thio)methyl)-1,1,3,3-tetramethyldisiloxane (1 g, 2.03 mmol) in 4M HCl in dioxane (20 mL) was stirred at room temperature for 1 h. The reaction mixture was concentrated in vacuo resulting in the crude intermediate Int-1. The crude intermediate Int-1 (1.1 g, 4.02 mmol) was dissolved in acetonitrile (20 mL) and was added 1-(3-(hydroxydimethylsilyl)propyl)-1H-pyrrole-2,5-dione 2 (865 mg, 4.06 mmol) was added triethyl amine (1.09 mL, 8.05 mmol) and stirred at room temperature for 1 h. The reaction mixture was concentrated in vacuo resulting in the crude compound which was purified by column chromatography on silica gel eluting with 0-40% ethyl acetate in n-hexane to afford 750 mg, 82% yield of the title compound as a colorless oil. MS (ES+): m/z=450.66 [M+H]+.

Example 52: Imaging Study Demonstrating Endocytosis and Si—O Cleavage

Example 51 as shown above contains a folate receptor targeting ligand, a spacer moiety, a siloxane core and two different fluorescent dyes (BODIPY and rhodamine) positioned on either side of the siloxane core. Folate receptor alpha expressing KB cells were grown in folic acid free media. The cells were incubated for 30 minutes on ice with 50 nM of Example 51, washed with fresh culture medium and then incubated in media at 37° C. for the desired length of time. The fate of both dyes was simultaneously monitored using confocal microscopy using Zeiss LSM 780 laser scanning microscope. Imaging studies revealed that at t=0 the intact Example 51 was bound to the folate receptor on the cell surface as visualized by colocalization of red and green signals and overlap of fluorescent dyes on the cell surface, thereby showing Folate Receptors-specific binding of the silicon based conjugate. At t=30 min, endocytosis of intact Example 51 into the cell was observed as visualized by BODIPY and rhodamine fluorescent signals and overlap of dyes inside the cells (i.e., inside the endosomes). At t=30 min, cleavage of the siloxane core was observed as visualized by color separation of the two fluorescent dyes.

Example 53: Cellular Data

Washout protocol: KB cells in culture were seeded in white clear bottom 96-well tissue culture plate at a density of 5,000 cells per well in a folate free RPMI media with 10% FBS a day prior to compound addition. Cells were counted visually with a hemocytometer and diluted accordingly to obtain the desired density. Cells were allowed to incubate for 24 hours in a humidified CO2 atmosphere in an incubator at 37° C. The spent media was aspirated and replenished with 100 μL of fresh media containing a 3-fold serial dilution of compound with concentrations ranging from 0.3 to 2000 nM and with a final DMSO concentration of 0.1%. Blank wells without compound were also treated with media containing 0.1% DMSO. Cells were incubated for 2 h and washed 4 times with fresh media. The plates were incubated for an additional 70 h in an incubator at 37° C. in 100 uL fresh folate free RPMI. At the end of 70 h, the spent media was removed and cells were washed once with fresh media and then suspended 100 μL of PBS. 100 μL of constituted Cell titer-glo reagent was added to each well and luminescence was recorded with a VICTOR plate reader according to manufacturers' protocol.

72 hour incubation protocol: The CellTiter-Glo (CTG) assay (Promega) was used to measure cell viability in various different cell lines included KB cells obtained from American Type Culture Collection (ATCC). Only cells that showed greater than 95% viability were used. For this assay, 5,000 cells per well were plated in a 96-well tissue culture treated plate in RPMI 1640 medium (ThermoFisher Scientific) containing 5% FBS. Cells were allowed to settle at 37° C. in a humidified CO2 incubator for 24 hours. Cells were dosed with compound or vehicle control in duplicate for 72 hours at 37° C. in a humidified CO2 incubator. After the 72 hour dosing period, the CTG assay was performed according to the manufacturer's specifications Luminescence was read using a Victor X5 (PerkinElmer) plate reader. Data was analyzed using Prism software and was normalized to the vehicle control.

Table 3 shows EC50 values (72 h incubation protocol) for silanol based payloads.

TABLE 3

| Compound | EC50 |
| --- | --- |
| Example 1 | ~6 nM |
| Example 5 | ~0.5 nM |
| Example 6 | ~500 nM (CAP example) |
| Example 7 | ~56 nM |
| Example 13 | <0.1 nM |

Table 4 shows EC50 values (washout protocol) of siloxane based conjugates.

TABLE 4

| Compound | EC50 |
| --- | --- |
| Example 24 | ~265 nM |
| Example 28 | ~156 nM |
| Example 27 | ~193 nM |
| Example 35 | ~8 nM (CAP example) |

Table 5 shows percent cell kill (washout protocol) with silicon based conjugates at 48 h.

TABLE 5

| Compound | % Kill (48 h) |
| --- | --- |
| Example 24 | 84 |
| Example 28 | 86 |
| Example 27 | 80 |

Example 54: Synthetic Lethal Payload Combinations

Silicon based conjugates for treating VHL clear cell renal carcinoma via delivery of synthetic lethal payload combinations include:

Ligand—SPACER—

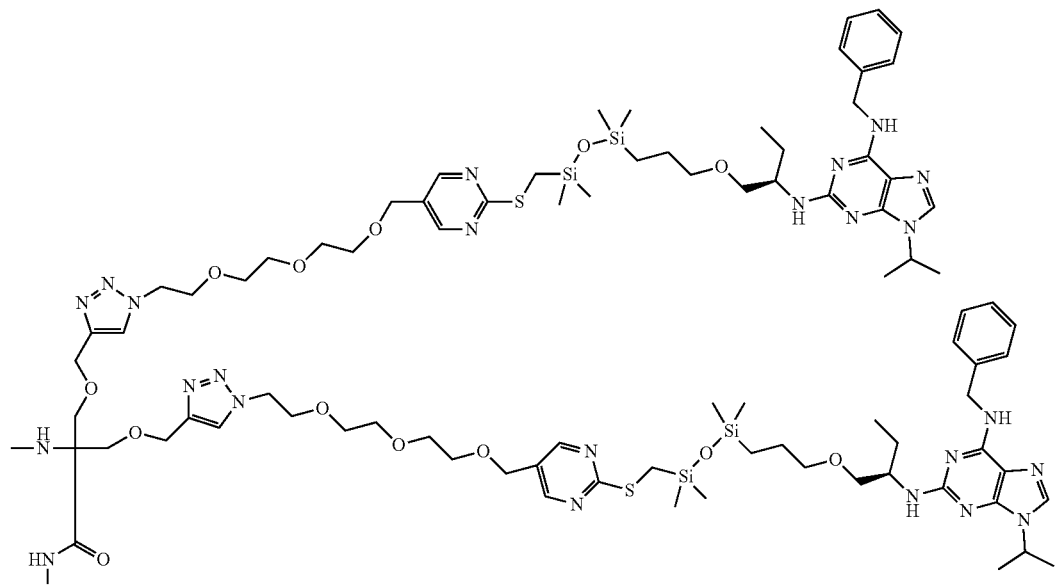

-continued
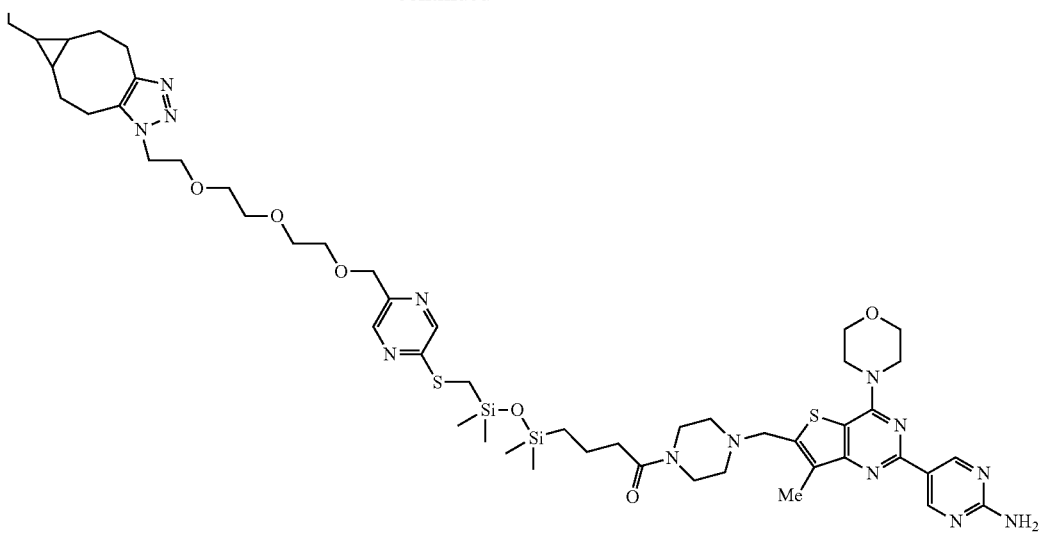
Ligand—SPACER—
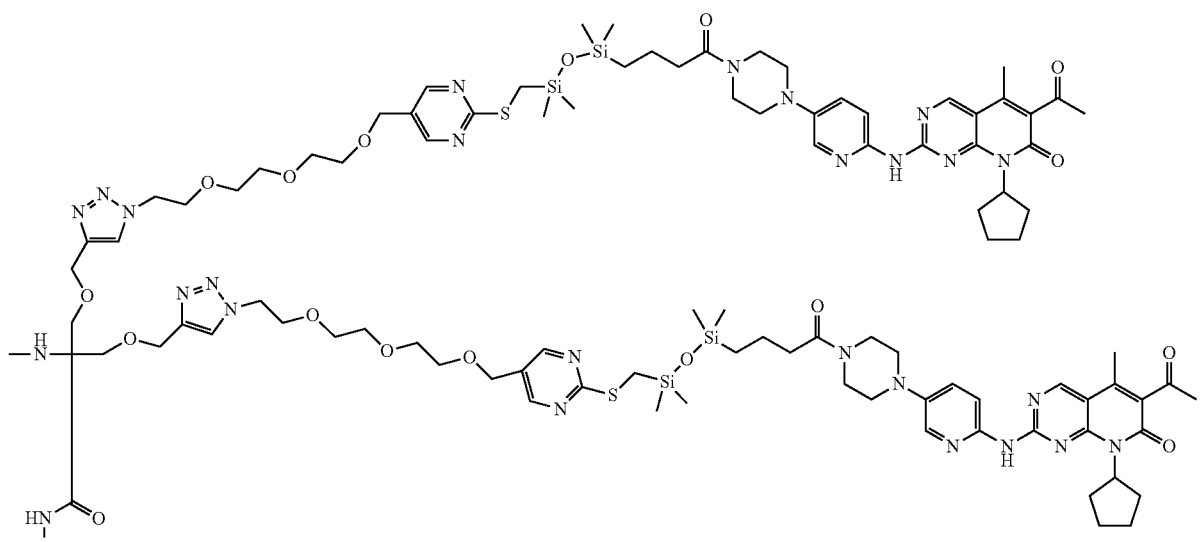
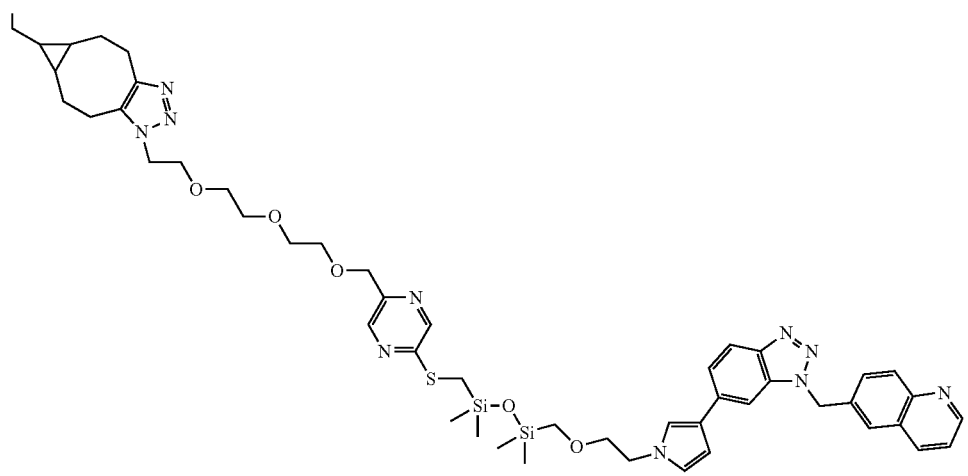

Ligand—SPACER—
-continued
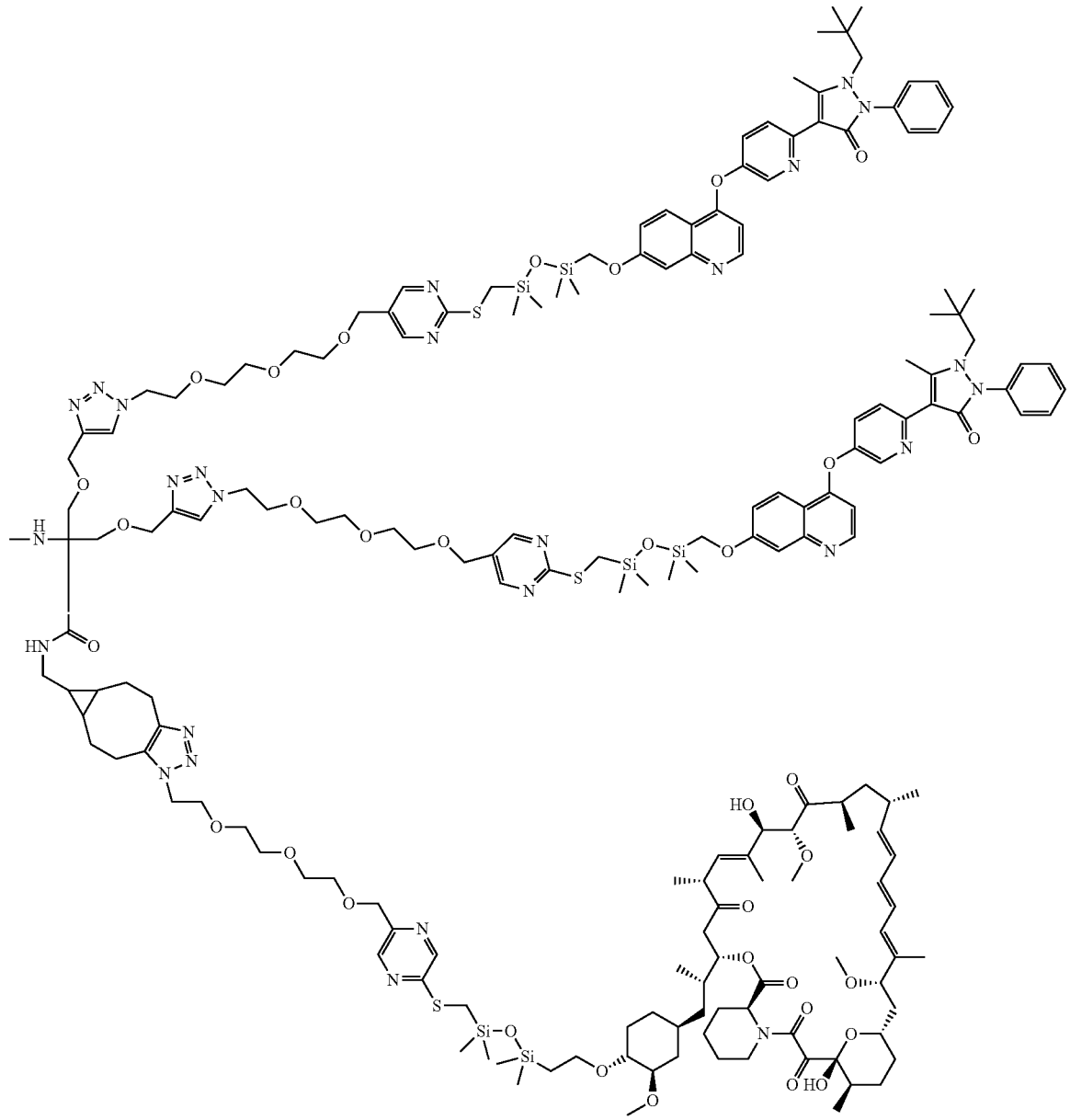
50
Silicon based conjugates for treating triple negative breast cancer via delivery of synthetic lethal payload combinations using folic acid as a targeting ligand include:

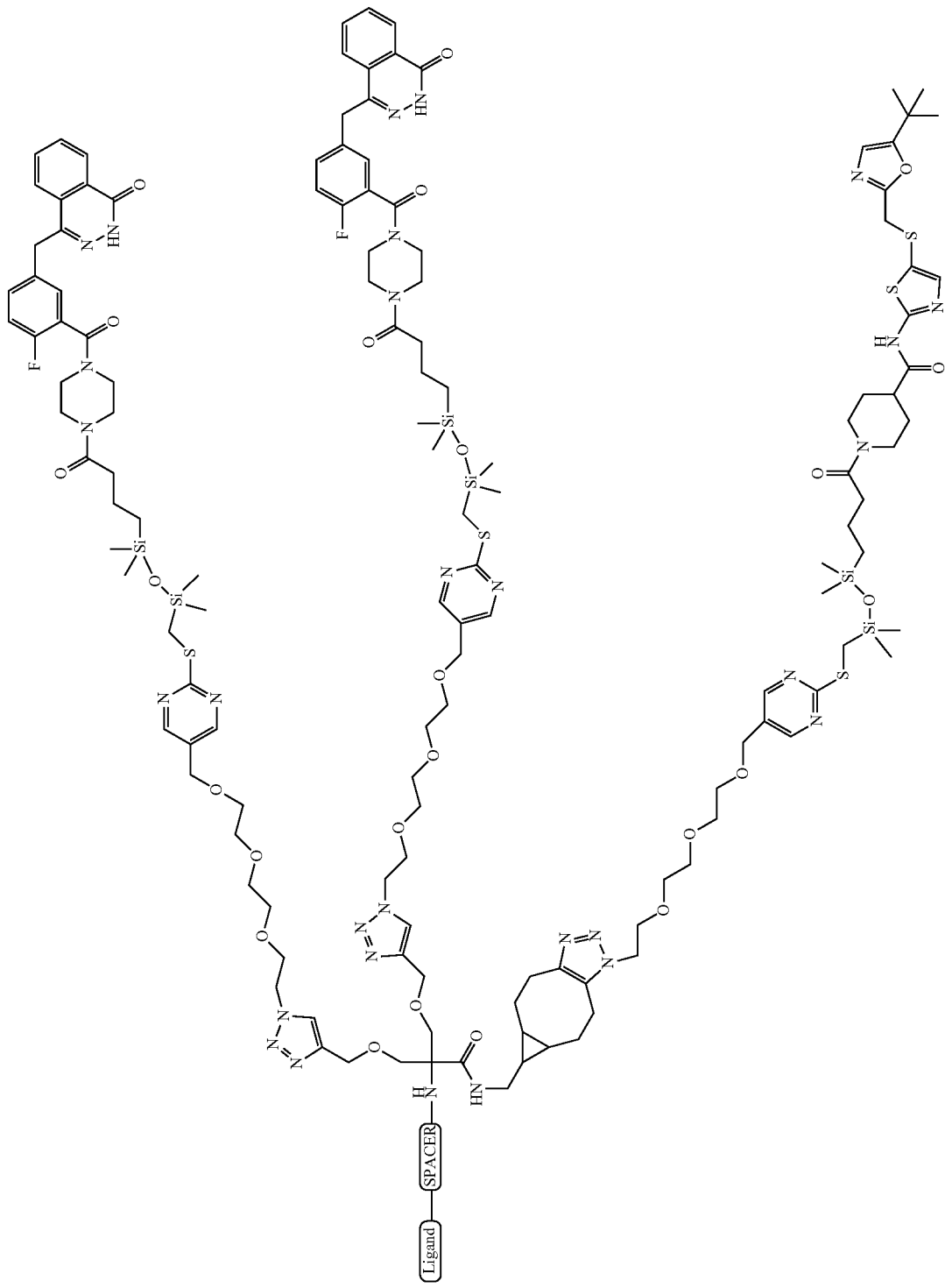

-continued
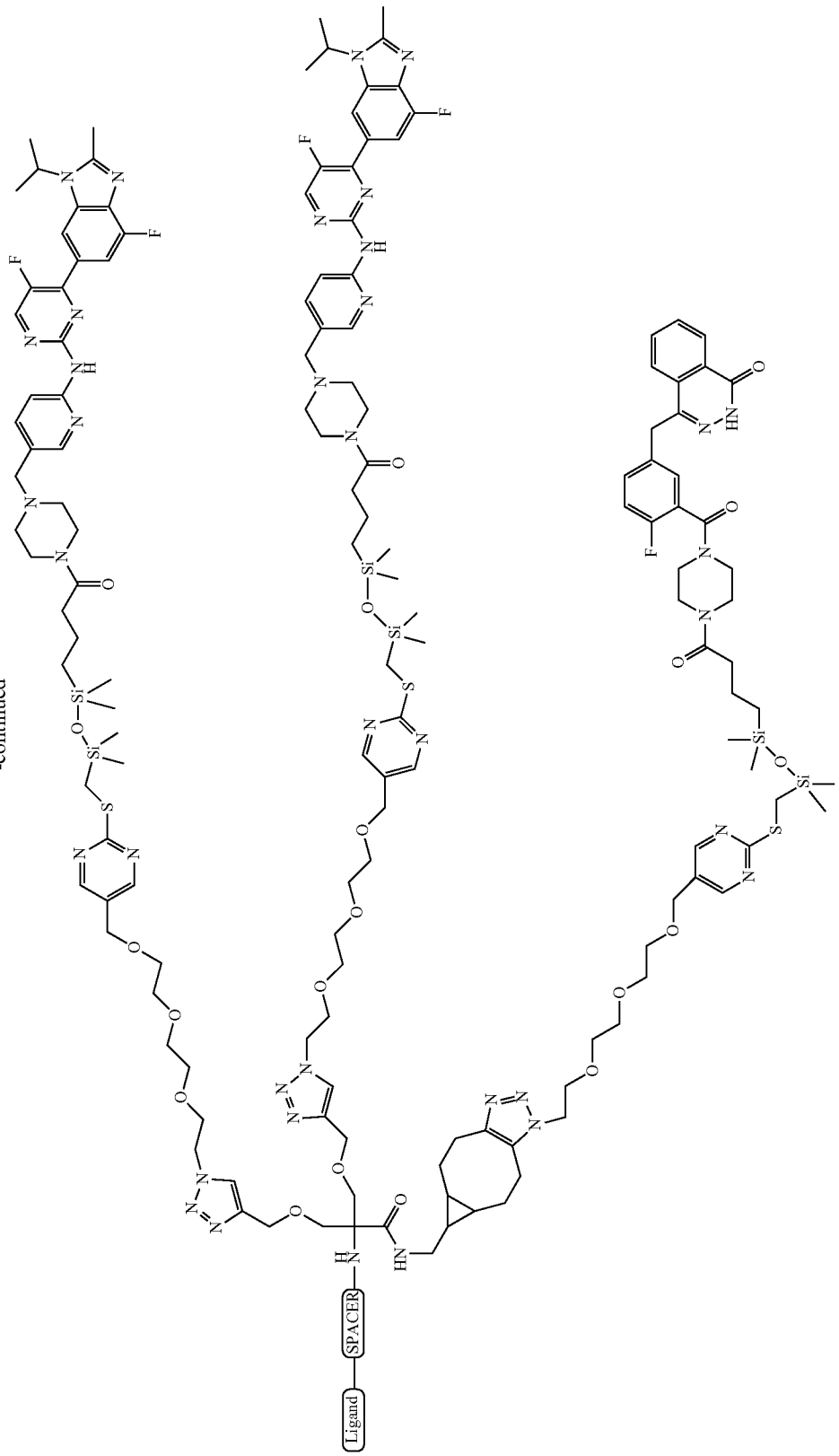

Silicon based conjugates for treating mutant KRAS cancers via an EGFR-targeting approach include (where it can be appreciated that $L_1$ defined above can include

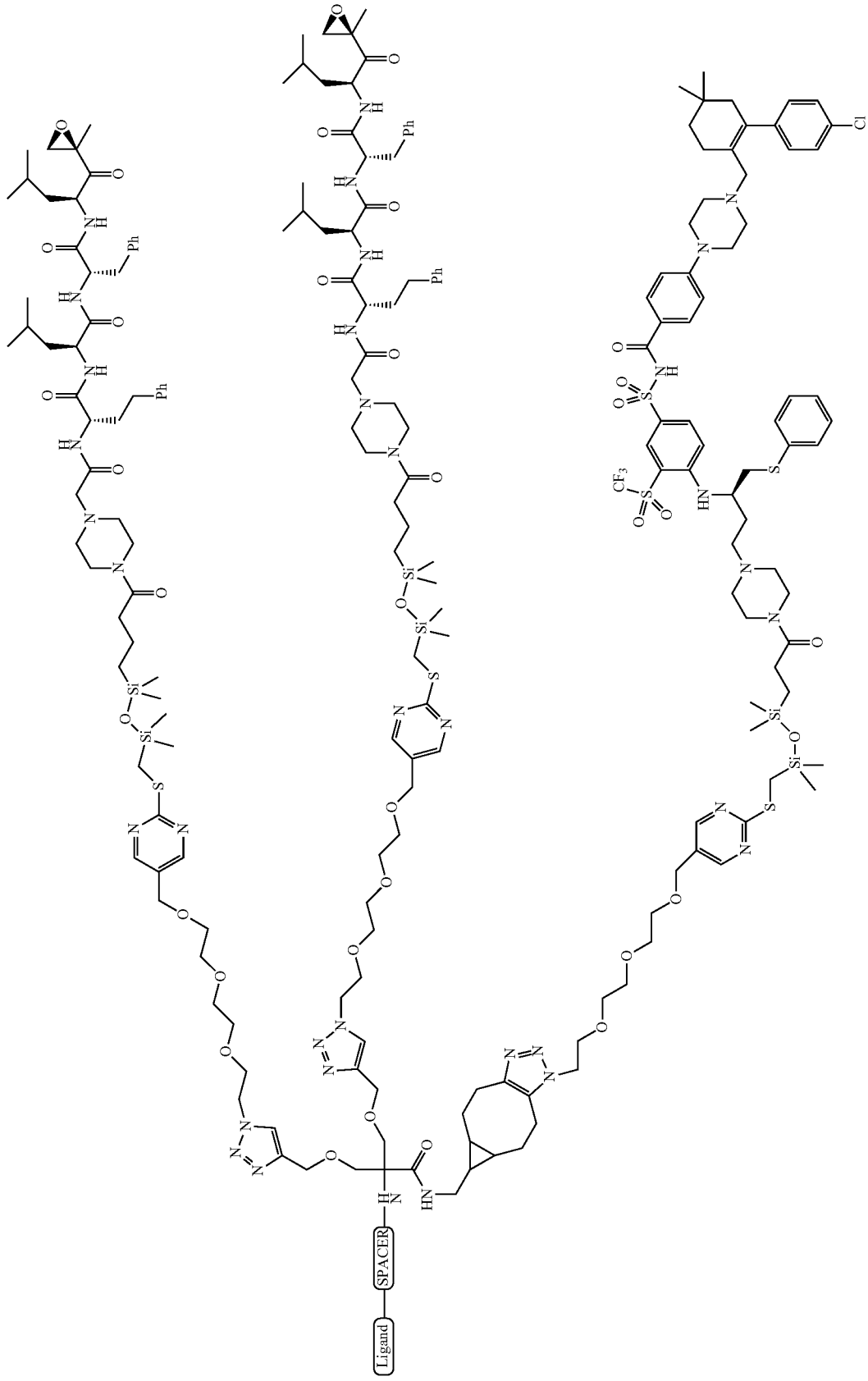

-continued
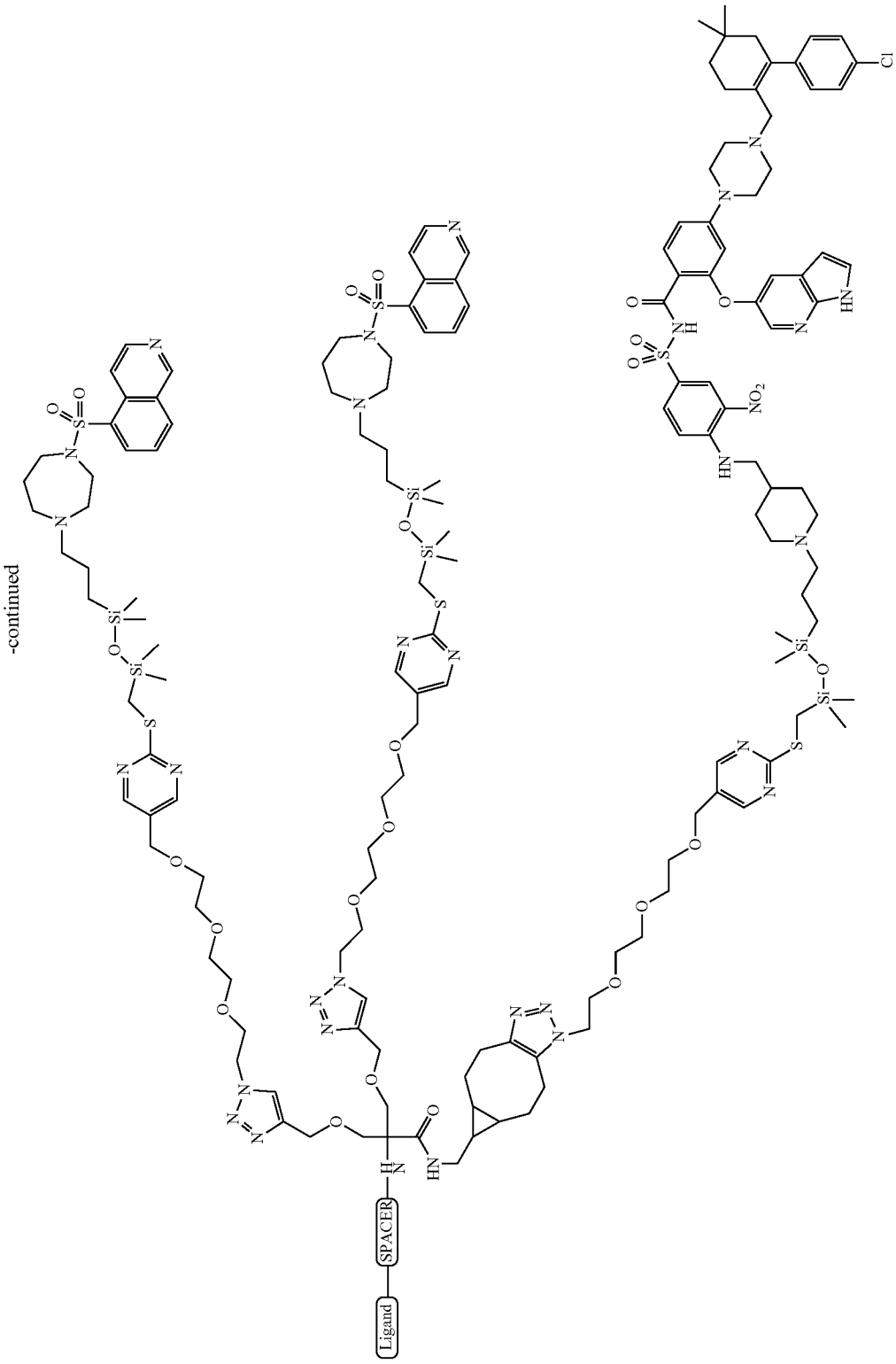

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments have been discussed, the above specification is illustrative and not restrictive. Many variations will become apparent to those skilled in the art upon review of this specification. The full scope of the embodiments should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A silanol drug moiety represented by:

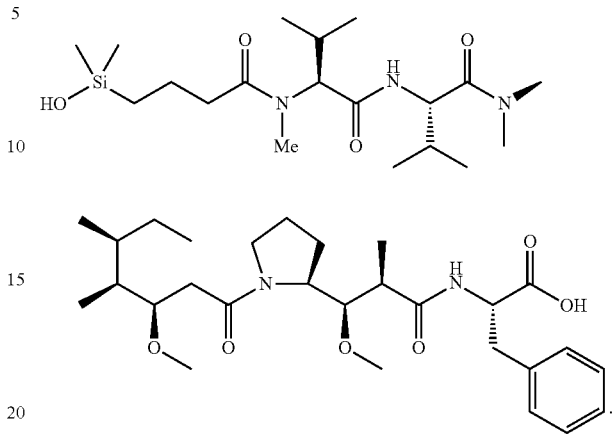

2. The compound of claim 1, formed by contacting a cell or tissue at a pH of less than about 7 at 37° C. with a silicon drug conjugate represented by:

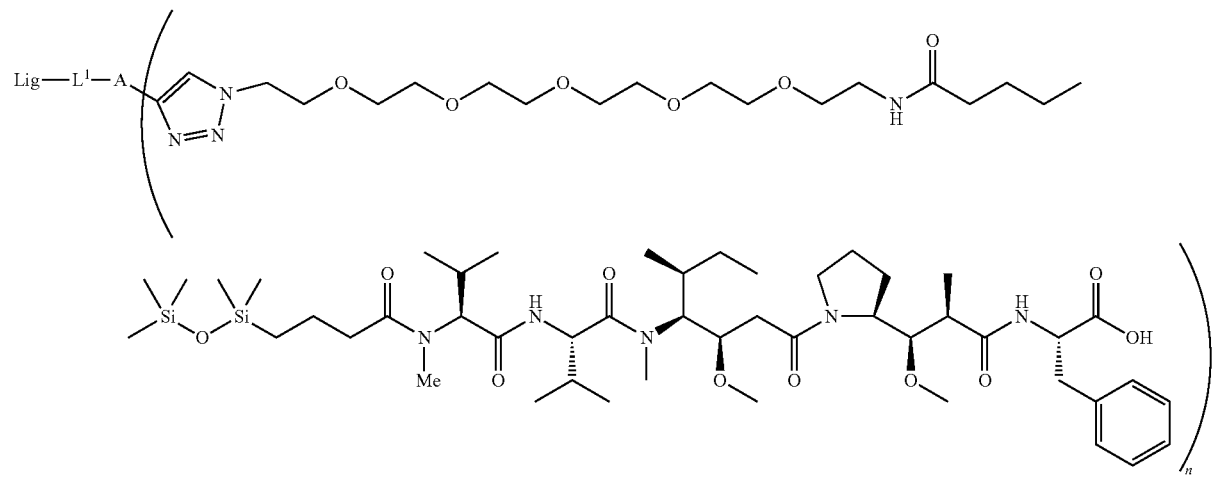

wherein
Lig is a targeting moiety;
$L^1$ is a linker moiety;
A is an adaptor moiety or a bond; and
n is 1, 2, 3, 4, 5, 6 or 7.

* * * * *